(12) United States Patent
Ikeda et al.

(10) Patent No.: US 11,221,557 B2
(45) Date of Patent: *Jan. 11, 2022

(54) RESIST COMPOSITION, METHOD OF FORMING RESIST PATTERN, COMPOUND, AND ACID GENERATOR

(71) Applicant: TOKYO OHKA KOGYO CO., LTD., Kawasaki (JP)

(72) Inventors: Takuya Ikeda, Kawasaki (JP); Masahiro Shiosaki, Kawasaki (JP); Masatoshi Arai, Kawasaki (JP); Yoshitaka Komuro, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 221 days.

This patent is subject to a terminal disclaimer.

(21) Appl. No.: 16/420,961

(22) Filed: May 23, 2019

(65) Prior Publication Data
US 2019/0361345 A1 Nov. 28, 2019

(30) Foreign Application Priority Data

May 28, 2018 (JP) .............................. JP2018-101870
May 28, 2018 (JP) .............................. JP2018-101872
May 28, 2018 (JP) .............................. JP2018-101877

(51) Int. Cl.
*G03F 7/004* (2006.01)
*G03F 7/039* (2006.01)
(Continued)

(52) U.S. Cl.
CPC .......... *G03F 7/0045* (2013.01); *C07C 309/06* (2013.01); *C07C 309/12* (2013.01);
(Continued)

(58) Field of Classification Search
CPC .................................................. C07C 381/12
See application file for complete search history.

(56) References Cited

U.S. PATENT DOCUMENTS 7,301,047 B2 * 11/2007 Yoshida ................... C07C 25/18
430/270.1
8,450,041 B2 * 5/2013 Yamaguchi ........... G03F 7/0045
430/270.1
(Continued)

FOREIGN PATENT DOCUMENTS

JP 08027102 A * 1/1996 ........... G03F 7/0045
JP 2006282652 A * 10/2006
(Continued)

OTHER PUBLICATIONS

Machine translation of JP 2008-290980 (no date).*
Machine translation of JP 2017-102267 (no date).*

Non-Final Office Action dated Apr. 1, 2019, corresponding to U.S. Appl. No. 15/822,999 (now U.S. Pat. No. 10,649,330).
Final Office Action dated Oct. 7, 2019, corresponding to U.S. Appl. No. 15/822,999 (now U.S. Pat. No. 10,649,330).
Office Action in Japanese Patent Application No. 2018-101874 dated Nov. 9, 2021.
(Continued)

*Primary Examiner* — Amanda C. Walke
(74) *Attorney, Agent, or Firm* — Knobbe Martens Olson & Bear LLP

(57) ABSTRACT

A resist composition containing a compound represented by the general formula (bd1-1), (bd1-2) or (bd1-3); in the formula, $Rx^1$ to $Rx^4$ represent a hydrocarbon group or a hydrogen atom or may be mutually bonded to form a ring structure; $Ry^1$ to $Ry^2$ represent a hydrocarbon group or a hydrogen atom or may be mutually bonded to form a ring structure, $Rz^1$ to $Rz^4$ represent a hydrocarbon group or a hydrogen atom or may be mutually bonded to form a ring structure. At least one of $Rx^1$ to $Rx^4$, $Ry^1$ to $Ry^2$ and $Rz^1$ to $Rz^4$ has an anion group, $M_1^{m+}$ represents a sulfonium cation having a sulfonyl group, $R^{001}$ to $R^{003}$ each independently represent a monovalent organic group; provided that at least one of $R^{001}$ to $R^{003}$ is an organic group having an acid dissociable group; and $M_3^{m+}$ represents an m-valent organic cation having an electron-withdrawing group.

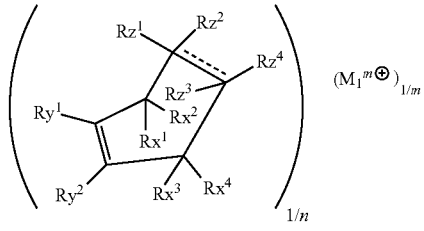

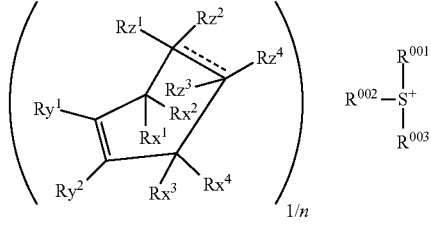

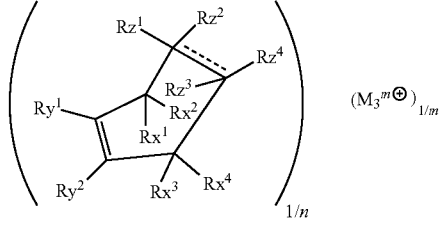

37 Claims, No Drawings

(51) Int. Cl.
  *C07C 309/06* (2006.01)
  *C07D 339/08* (2006.01)
  *C07C 381/12* (2006.01)
  *C07C 309/12* (2006.01)
  *C07D 335/16* (2006.01)
  *C07D 327/08* (2006.01)
  *C07D 333/76* (2006.01)
  *C07D 209/56* (2006.01)
  *G03F 7/038* (2006.01)
  *G03F 7/16* (2006.01)
  *G03F 7/20* (2006.01)
  *G03F 7/38* (2006.01)
  *G03F 7/32* (2006.01)

(52) U.S. Cl.
  CPC .......... *C07C 381/12* (2013.01); *C07D 209/56* (2013.01); *C07D 327/08* (2013.01); *C07D 333/76* (2013.01); *C07D 335/16* (2013.01); *C07D 339/08* (2013.01); *G03F 7/0382* (2013.01); *G03F 7/0392* (2013.01); *C07C 2603/88* (2017.05); *G03F 7/162* (2013.01); *G03F 7/168* (2013.01); *G03F 7/2004* (2013.01); *G03F 7/2037* (2013.01); *G03F 7/322* (2013.01); *G03F 7/38* (2013.01)

(56) References Cited

U.S. PATENT DOCUMENTS

| | | | | |
|---|---|---|---|---|
| 9,023,584 B2* | 5/2015 | Maruyama | ............ | G03F 7/0045 430/270.1 |
| 9,052,592 B2* | 6/2015 | Nakamura | ............ | C07C 381/12 |
| 9,122,154 B2* | 9/2015 | Maruyama | ............ | G03F 7/0045 |
| 9,128,370 B2* | 9/2015 | Maruyama | ............ | C07C 309/06 |
| 9,354,515 B2* | 5/2016 | Nagamine | ............ | C07C 381/12 |
| 9,766,541 B2* | 9/2017 | Yamazaki | ............ | G03F 7/0045 |
| 10,221,131 B2* | 3/2019 | Kaur | ............ | C07D 307/00 |
| 10,649,330 B2* | 5/2020 | Arai | ............ | C07C 309/12 |
| 2009/0162788 A1 | 6/2009 | Hada et al. | | |
| 2010/0086873 A1 | 4/2010 | Seshimo et al. | | |
| 2010/0113818 A1 | 5/2010 | Oh et al. | | |
| 2011/0287362 A1 | 11/2011 | Seshimo et al. | | |
| 2015/0198879 A1 | 7/2015 | Mori et al. | | |
| 2017/0299963 A1* | 10/2017 | Fujiwara | ............ | G03F 7/2006 |
| 2018/0144973 A1 | 5/2018 | Ye et al. | | |
| 2019/0361343 A1 | 11/2019 | Onishi et al. | | |
| 2019/0361346 A1* | 11/2019 | Ikeda | ............ | C08F 220/1812 |

FOREIGN PATENT DOCUMENTS

| | | | |
|---|---|---|---|
| JP | 2008290980 A | * | 12/2008 |
| JP | 2009-014815 A | | 1/2009 |
| JP | 2009-149588 A | | 7/2009 |
| JP | 2010-113334 A | | 5/2010 |
| JP | 2010-250063 A | | 11/2010 |
| JP | 2012-003249 A | | 1/2012 |
| JP | 5149236 B | | 2/2013 |
| JP | 2013-092618 A | | 5/2013 |
| JP | 2014-085515 A | | 5/2014 |
| JP | 2015090457 A | * | 5/2015 |
| JP | 2015-194703 A | | 11/2015 |
| JP | 2017102267 A | * | 6/2017 |
| JP | 2017102267 A | | 6/2017 |
| JP | 2018-028574 A | | 2/2018 |
| JP | 2018-092159 A | | 6/2018 |
| JP | 2019-207297 A | | 12/2019 |
| WO | WO 2017/179727 A1 | | 10/2017 |

OTHER PUBLICATIONS

Office Action in Japanese Patent Application No. 2018-101870 dated Nov. 16, 2021.
Office Action in Japanese Patent Application No. 2018-101872 dated Nov. 16, 2021.
Office Action in Japanese Patent Application No. 2018-101877 dated Nov. 16, 2021.

* cited by examiner

RESIST COMPOSITION, METHOD OF FORMING RESIST PATTERN, COMPOUND, AND ACID GENERATOR

TECHNICAL FIELD

The present invention relates to a resist composition, a method of forming a resist pattern, a compound, and an acid generator.

Priority is claimed on Japanese Patent Application Nos. 2018-101877, 2018-101870 and 2018-101872, all of which were filed May 28, 2018, the contents of which are incorporated herein by reference.

DESCRIPTION OF RELATED ART

In lithography techniques, for example, a resist film formed of a resist material is formed on a substrate, and the resist film is subjected to selective exposure, followed by development, thereby forming a resist pattern having a predetermined shape on the resist film. A resist material with which the exposed portions of the resist film become soluble in a developing solution is called a positive-type, and a resist material with which the exposed portions of the resist film become insoluble in a developing solution is called a negative-tone.

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source.

In particular, ultraviolet radiation typified by g-line and i-line radiation has been used, but nowadays KrF excimer lasers and ArF excimer lasers are used in mass production of semiconductor elements. Furthermore, research is also being conducted into an exposure light source having a wavelength shorter (energy higher) than these excimer lasers, such as extreme ultraviolet radiation (EUV), electron beam (EB), and X-rays.

Resist materials require lithography characteristics such as high resolution capable of reproducing patterns of minute dimensions, and a high level of sensitivity to these types of exposure light sources.

As a resist material that satisfies these requirements, in the related art, a chemically amplified resist composition which includes a base material component of which solubility in a developing solution is changed due to an action of an acid and an acid generator component that generates an acid upon exposure has been used.

For example, as a positive chemically amplified resist composition when the developing solution is an alkali developing solution (alkali development process), a composition which contains a resin component (base resin) of which solubility in an alkali developing solution is increased due to an action of an acid and an acid generator component has been typically used. In a case where a resist film formed using such a resist composition is selectively exposed at the time of forming a resist pattern, in exposed portions, an acid is generated from the acid generator component so that the polarity of the base resin is increased due to the action of the acid, and thus the exposed portions of the resist film become soluble in the alkali developing solution. Accordingly, by conducting alkali development, a positive type pattern in which the unexposed portions of the resist film remain as a pattern is formed.

On the other hand, when such a chemically amplified resist composition is applied to a solvent developing process using a developing solution containing an organic solvent (organic developing solution), the solubility in an organic developing solution decreases as the polarity of the base resin increases, thus the unexposed area of the resist film is dissolved and removed by the organic developing solution to form a negative-tone resist pattern in which the exposed area of the resist film remains as a pattern. Such a solvent developing process for forming a negative-tone resist pattern is also referred to as "negative-tone developing process."

The base resin used in the chemically amplified resist composition generally has a plurality of constitutional units in order to improve the lithography characteristics and the like.

For example, in a case of the resin component of which solubility in an alkali developing solution is increased due to the action of an acid, a constitutional unit containing an acid decomposable group which is decomposed due to the action of an acid generated from an acid generator to increase polarity is used. Additionally, constitutional units containing a lactone-containing cyclic group and constitutional units containing a polar group such as a hydroxyl group are used in combination.

Further, in the formation of a resist pattern, the behavior of an acid generated from the acid generator component upon exposure is one of the factors which has large influence on the lithography properties.

As the acid generator used in a chemically amplified resist composition, various kinds have been proposed. For example, onium salt acid generators such as iodonium salts and sulfonium salts; oxime sulfonate acid generators; diazomethane acid generators; nitrobenzylsulfonate acid generators; iminosulfonate acid generators; and disulfone acid generators are known.

As onium salt acid generators, those which have an onium ion such as triphenylsulfonium in the cation moiety are mainly used. Generally, as the anion moiety for onium salt acid generators, an alkylsulfonate ion or a fluorinated alkylsulfonate ion in which some or all of the hydrogen atoms within the aforementioned alkylsulfonate ion have been substituted with fluorine atoms is typically used.

Further, in order to improve lithography properties in the formation of a resist pattern, an onium salt acid generator having an anion with a specific structure containing an aromatic ring as the anion moiety has been proposed (for example, see Patent Literature 1).

DOCUMENTS OF RELATED ART

Patent Literature

[Patent Literature 1] Japanese Patent No. 5149236

SUMMARY OF THE INVENTION

As lithography technique progress further and miniaturization of resist patterns progress more and more, for example, a target of the lithography performed with an electron beam and EUV is to form fine resist patterns of several tens of nanometers. As the size of a resist pattern decreases accordingly, favorable lithography properties such as high sensitivity, high resolution, defect suppression and low roughness with respect to an exposure light source are required for the resist composition. In addition, a contrast between an exposed portion and an unexposed portion is also required for the resist composition.

However, in the resist composition containing a conventional onium salt acid generator as described above, there is a problem that it is difficult to obtain a desired resist pattern shape and the like when high sensitivity with respect to an exposure light source such as EUV is attempted, and it is difficult to satisfy all of such properties.

The present invention takes the above circumstances into consideration, with an object of providing a novel compound useful as an acid generator for a resist composition, an acid generator using the compound, a resist composition containing the acid generator, and a method of forming a resist pattern using the resist composition.

For solving the above-mentioned problems, the present invention employs the following aspects.

A first aspect of the present invention is a resist composition which generates an acid upon exposure and exhibits changed solubility in a developing solution under the action of an acid, the resist composition including a base component (A) which exhibits changed solubility in a developing solution under the action of an acid, and a compound (BD1-1) having an anion moiety and a cation moiety and which is represented by general formula (bd1-1) shown below.

[Chem. 1]

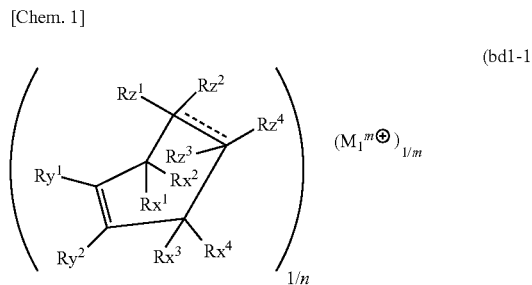

(bd1-1)

In the formula, $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 2]
- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_1^{m+}$ is a cation represented by general formula (ca-0) shown below:

[Chem. 3]

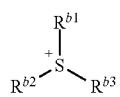

(ca-0)

in the formula, $R^{b1}$ represents an aryl group which may have a substituent; $R^{b2}$ and $R^{b3}$ each independently represent an aryl group which may have a substituent or an alkyl group which may have a substituent;

$Rb^2$ and $Rb^3$ may be mutually bonded to form a ring with the sulfur atom; provided that at least one of $R^{b1}$ to $R^{b3}$ has a substituent containing a sulfonyl group.

A second aspect of the present invention is a method of forming a resist pattern, including: using a resist composition according to the first aspect to form a resist film, exposing the resist film, and developing the exposed resist film to form a resist pattern.

A third aspect of the present invention is a resist composition which generates an acid upon exposure and exhibits changed solubility in a developing solution under the action of an acid, the resist composition including a compound (BD1-2) having an anion moiety and a cation moiety and which is represented by general formula (bd1-2) shown below, and a base component (A) which exhibits changed solubility in a developing solution under the action of an acid.

[Chem. 4]

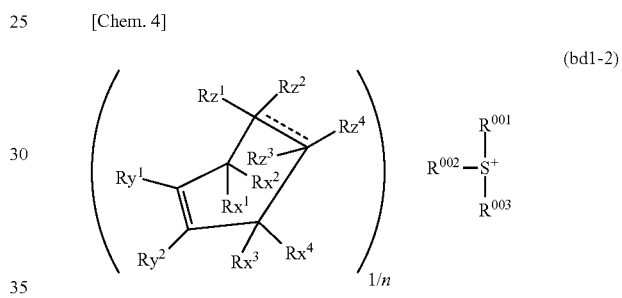

(bd1-2)

In the formula, $R^{001}$ to $R^{003}$ each independently represent a monovalent organic group; provided that at least one of $R^{001}$ to $R^{003}$ represents an organic group having an acid dissociable group; and two or more of $R^{001}$ to $R^{003}$ may be mutually bonded to form a ring with the sulfur atom; $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 5]
- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more.

A fourth aspect of the present invention is a method of forming a resist pattern, including: using a resist composition according to the third aspect to form a resist film, exposing the resist film, and developing the exposed resist film to form a resist pattern.

A fifth aspect of the present invention is a compound having a cation moiety and an anion moiety represented by general formula (bd1-2) shown below.

[Chem. 6]

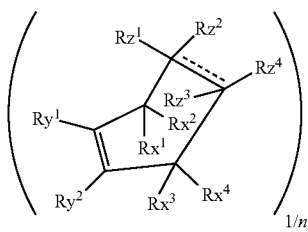 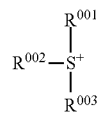

(bd1-2)

A sixth aspect of the present invention is an acid generator including a compound of the fifth aspect.

A seventh aspect of the present invention is a resist composition which generates an acid upon exposure and exhibits changed solubility in a developing solution under action of an acid, the resist composition including a base component (A) which exhibits changed solubility in a developing solution under the action of an acid, and a compound (BD1-3) having an anion moiety and a cation moiety and which is represented by general formula (bd1-3) shown below.

[Chem. 7]

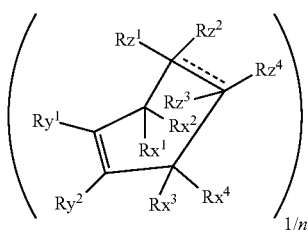 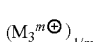

(bd1-3)

In the formula, $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 8]
- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_3^{m+}$ represents an m-valent organic cation having an electron-withdrawing group.

An eighth aspect of the present invention is a method of forming a resist pattern, including: using a resist composition according to the seventh aspect to form a resist film, exposing the resist film, and developing the exposed resist film to form a resist pattern.

A ninth aspect of the present invention is a compound having a cation moiety and an anion moiety represented by general formula (bd1-3) shown below.

[Chem. 9]

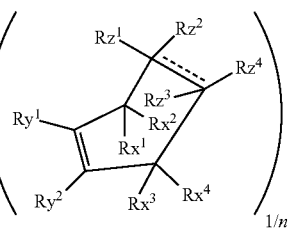 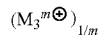

(bd1-3)

In the formula, $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 10]
- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_3^{m+}$ represents an m-valent organic cation having an electron-withdrawing group.

A tenth aspect of the present invention is an acid generator including a compound of the ninth aspect.

According to the present invention, it is possible to provide a resist composition having favorable lithography properties and a method of forming a resist pattern using the resist composition.

In addition, according to the present invention, it is possible to provide a novel compound that is useful as an acid generator for a resist composition, an acid generator using the compound, a resist composition containing the acid generator, and a method of forming a resist pattern using the resist composition.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbons, unless otherwise specified. The same applies for the alkyl group within an alkoxy group.

The term "alkylene group" includes linear, branched or cyclic, divalent saturated hydrocarbons, unless otherwise specified.

A "halogenated alkyl group" is a group in which some or all of the hydrogen atoms of an alkyl group are substituted with halogen atoms. Examples of the halogen atom include a fluorine atom, a chlorine atom, a bromine atom and an iodine atom.

A "fluorinated alkyl group" or a "fluorinated alkylene group" is a group in which some or all of the hydrogen atoms of an alkyl group or an alkylene group have been substituted with a fluorine atom.

The term "structural unit" refers to a monomer unit that contributes to the formation of a polymeric compound (resin, polymer, copolymer).

The case of a description including "may have a substituent" includes both of the case where a hydrogen atom (—H) is substituted with a monovalent group and the case where a methylene group (—$CH_2$—) is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2$=CH—COOH) has been substituted with an organic group.

The acrylate ester may have a hydrogen atom bonded to the carbon atom at the α-position substituted with a substituent. The substituent ($R^\alpha$) that substitutes a hydrogen atom bonded to the carbon atom at the α-position is an atom other than hydrogen or a group, and examples thereof include an alkyl group of 1 to 5 carbon atoms and a halogenated alkyl group of 1 to 5 carbon atoms. Further, an acrylate ester having a hydrogen atom bonded to the carbon atom at the α-position substituted with a substituent ($R^\alpha$) in which the substituent has been substituted with a substituent containing an ester bond (e.g., an itaconic acid diester), or an acrylic acid having a hydrogen atom bonded to the carbon atom at the α-position substituted with a substituent ($R^\alpha$) in which the substituent has been substituted with a hydroxyalkyl group or a group in which the hydroxy group within a hydroxyalkyl group has been modified (e.g., α-hydroxyalkyl acrylate ester) can be mentioned as an acrylate ester having a hydrogen atom bonded to the carbon atom at the α-position substituted with a substituent. A carbon atom at the α-position of an acrylate ester refers to the carbon atom bonded to the carbonyl group, unless specified otherwise.

Hereafter, an acrylate ester having a hydrogen atom bonded to the carbon atom at the α-position substituted with a substituent is sometimes referred to as "α-substituted acrylate ester". Further, acrylate esters and α-substituted acrylate esters are collectively referred to as "(α-substituted) acrylate ester".

A "structural unit derived from acrylamide" refers to a structural unit that is formed by the cleavage of the ethylenic double bond of acrylamide.

The acrylamide may have a hydrogen atom bonded to the carbon atom at the α-position substituted with a substituent, and may have either or both terminal hydrogen atoms on the amino group of acrylamide substituted with a substituent. A carbon atom at the α-position of an acrylamide refers to the carbon atom bonded to the carbonyl group, unless specified otherwise.

As the substituent which substitutes a hydrogen atom at the α-position of acrylamide, the same substituents as those described above for the substituent ($R^\alpha$) at the α-position of the aforementioned α-position of the aforementioned α-substituted acrylate ester can be mentioned.

A "structural unit derived from hydroxystyrene" refers to a structural unit that is formed by the cleavage of the ethylenic double bond of hydroxystyrene. A "structural unit derived from a hydroxystyrene derivative" refers to a structural unit that is formed by the cleavage of the ethylenic double bond of a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and which may have a hydrogen atom at the α-position substituted with a substituent; and hydroxystyrene which has a substituent other than a hydroxy group bonded to the benzene ring and may have a hydrogen atom at the α-position substituted with a substituent. Here, the α-position (carbon atom at the α-position) refers to the carbon atom having the benzene ring bonded thereto, unless specified otherwise.

As the substituent which substitutes a hydrogen atom at the α-position of hydroxystyrene, the same substituents as those described above for the substituent at the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and which may have a hydrogen atom at the α-position substituted with a substituent; and benzoic acid which has a substituent other than a hydroxy group and a carboxy group bonded to the benzene ring and may have a hydrogen atom at the α-position substituted with a substituent. Here, the α-position (carbon atom at the α-position) refers to the carbon atom having the benzene ring bonded thereto, unless specified otherwise.

The term "styrene derivative" includes compounds in which the hydrogen atom at the α-position of styrene has been substituted with another substituent such as an alkyl group or a halogenated alkyl group; and derivatives thereof. Examples of the derivatives thereof include hydroxystyrene which has a substituent other than a hydroxy group bonded to the benzene ring and may have a hydrogen atom at the α-position substituted with a substituent. Here, the α-position (carbon atom at the α-position) refers to the carbon atom having the benzene ring bonded thereto, unless specified otherwise.

A "structural unit derived from styrene" or "structural unit derived from a styrene derivative" refers to a structural unit that is formed by the cleavage of the ethylenic double bond of styrene or a styrene derivative.

As the alkyl group as a substituent at the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent at the α-position include groups in which some or all of the hydrogen atoms of the aforementioned "alkyl group as the substituent at the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent at the α-position include groups in which some or all of the hydrogen atoms of the aforementioned "alkyl group as the substituent at the α-position" are substituted with a hydroxy group. The number of hydroxy groups within the hydroxyalkyl group is preferably 1 to 5, and most preferably 1.

In the present specification and claims, some structures represented by chemical formulae may have an asymmetric carbon, such that an enantiomer or a diastereomer may be present. In such a case, one formula represents all isomers. The isomers may be used individually, or in the form of a mixture.

(First Aspect: Resist Composition)

The resist composition according to a first aspect of the present invention is a resist composition which generates an acid upon exposure and exhibits changed solubility in a developing solution under the action of an acid, the resist composition including a base component (A) which exhibits changed solubility in a developing solution under action of an acid (hereafter, also referred to as "component (A)"), and a compound (BD1-1) represented by general formula (bd1-1) (hereafter, also referred to as "component (BD1-1)").

Regarding one embodiment of such a resist composition, a resist composition containing the component (A) and an acid-generator component (B) that generates an acid due upon exposure (hereinafter referred to as a "component (B)") may be exemplified. Preferable examples thereof also include a resist composition that further contains a base component (hereinafter referred to as a "component (D)") that traps an acid generated from the component (B) upon exposure (that is, controls acid diffusion) in addition to the component (A) and the component (B).

In the resist composition of the present embodiment, the component (BD1-1) can be used as the component (B) or the component (D) by selecting an anion group in the molecule.

When a resist film is formed using the resist composition according to the present embodiment and the formed resist film is subjected to a selective exposure, an acid is generated at exposed portions, and the generated acid acts on the component (A) to change the solubility of the component (A) in a developing solution, whereas the solubility of the component (A) in a developing solution is not changed at unexposed portions, thereby generating a difference in solubility in a developing solution between exposed portions and unexposed portions. Therefore, by subjecting the resist film to development, the exposed portions of the resist film are dissolved and removed to form a positive-tone resist pattern in the case of a positive resist, whereas the unexposed portions of the resist film are dissolved and removed to form a negative-tone resist pattern in the case of a negative resist.

In the present specification, a resist composition which forms a positive resist pattern by dissolving and removing the exposed portions of the resist film is called a positive resist composition, and a resist composition which forms a negative resist pattern by dissolving and removing the unexposed portions of the resist film is called a negative resist composition.

The resist composition of the present embodiment may be either a positive resist composition or a negative resist composition. Further, in the present embodiment, the resist composition may be applied to an alkali developing process using an alkali developing solution in the developing treatment, or a solvent developing process using a developing solution containing an organic solvent (organic developing solution) in the developing treatment, and preferably a solvent developing process.

The resist composition of the present embodiment has a function of generating an acid upon exposure, and the component (A) may generate an acid upon exposure, in addition to the component (B).

In the case where the component (A) generates an acid upon exposure, the component (A) is a "base component which generates an acid upon exposure and exhibits changed solubility in a developing solution under the action of an acid".

In the case where the component (A) is a base component which generates an acid upon exposure and exhibits changed solubility in a developing solution under the action of an acid, the component (A1) described later is preferably a polymeric compound which generates an acid upon exposure and exhibits changed solubility in a developing solution under the action of an acid. As the polymeric compound, a resin having a structural unit which generates an acid upon exposure may be mentioned. As the structural unit which generates an acid upon exposure, any conventionally known structural unit may be used.

<Component (A)>

In the resist composition of the present embodiment, the component (A) is a base component that exhibits a changed solubility in a developing solution under the action of acid.

The "base component" in the present embodiment is an organic compound having a film-forming ability, and an organic compound having a molecular weight of 500 or more is preferably used. When the organic compound has a molecular weight of 500 or more, the film-forming ability is improved, and a nano-level resist pattern can be easily formed.

Organic compounds used as the base component are broadly classified into non-polymers and polymers.

In general, as a non-polymer, any of those which have a molecular weight in the range of 500 to less than 4,000 may be used. Hereafter, a "low-molecular-weight compound" refers to a non-polymer having a molecular weight in the range of 500 to less than 4,000.

As a polymer, any of those which have a molecular weight of 1,000 or more may be generally used. Hereafter, a "resin" or a "polymer" refers to a polymer having a molecular weight of 1,000 or more.

As the molecular weight of the polymer, the weight average molecular weight in terms of the polystyrene equivalent value determined by gel permeation chromatography (GPC) is used.

In the case where the resist composition of the present embodiment is a "negative resist composition for alkali developing process" which forms a negative resist pattern in an alkali developing process, or a "positive resist composition for solvent developing process," as the component (A), a base component (A-2) which is soluble in an alkali developing solution (hereafter, referred to as "component (A-2)") is preferably used, and a cross-linking agent may be blended in. In such a resist composition, for example, when an acid is generated from the component (B) upon exposure, the action of the acid causes cross-linking between the component (A-2) and the cross-linking component. As a result, the solubility of the resist composition in an alkali developing solution is decreased (the solubility of the resist composition in an organic developing solution is increased).

Therefore, in the formation of a resist pattern, by conducting selective exposure of a resist film formed by applying the resist composition to a substrate, the exposed portions of the resist film become insoluble in an alkali developing solution (soluble in an organic developing solution), whereas the unexposed portions of the resist film remain soluble in an alkali developing solution (insoluble in an organic developing solution), and hence, a negative resist pattern is formed by conducting development using an alkali developing solution. Alternatively, in such a case, by developing using an organic developing solution, a positive resist pattern is formed.

As the component (A-2), a resin that is soluble in an alkali developing solution (hereafter, referred to as "alkali-soluble resin") is preferably used.

Examples of the alkali soluble resin include a resin having a structural unit derived from at least one of an α-(hydroxyalkyl)acrylic acid and an alkyl ester of α-(hydroxyalkyl) acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to a carbon atom at the α-position substituted with a substituent or a polycycloolefin resin having a sulfonamide group, as disclosed in U.S. Pat. No. 6,949,325; an acrylic resin which may have the hydrogen atom bonded to a carbon atom at the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to a carbon atom at the α-position having the carboxyl group bonded thereto, and an α-hydroxyalkylacrylic acid in which a hydroxyalkyl group (preferably a hydroxyalkyl group of 1 to 5 carbon atoms) is bonded to a carbon atom at the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range of 1 to 50 parts by mass, relative to 100 parts by mass of the alkali-soluble resin.

In the case where the resist composition of the present embodiment is a "positive resist composition for alkali developing process" which forms a positive resist pattern in an alkali developing process, or a "negative resist composition for solvent developing process," as the component (A), a base component (A-1) which exhibits increased polarity by the action of an acid (hereafter, referred to as "component (A-1)") is preferably used. By using the component (A-1), since the polarity of the base component changes prior to and after exposure, an excellent development contrast can be obtained not only in an alkali developing process, but also in a solvent developing process.

More specifically, in the case of applying an alkali developing process, the component (A1) is substantially insoluble in an alkali developing solution prior to exposure, but when an acid is generated from the component (B) upon exposure, the action of this acid causes an increase in the polarity of the base component, thereby increasing the solubility of the component (A1) in an alkali developing solution. Therefore, in the formation of a resist pattern, by conducting selective exposure of a resist film formed by applying the resist composition to a substrate, the exposed portions of the resist film change from an insoluble state to a soluble state in an alkali developing solution, whereas the unexposed portions of the resist film remain insoluble in an alkali developing solution, and hence, a positive resist pattern is formed by alkali developing.

On the other hand, in the case of a solvent developing process, the component (A-1) exhibits high solubility in an organic developing solution prior to exposure, and when an acid is generated from the component (B) upon exposure, the polarity of the component (A-1) is increased by the action of the generated acid, thereby decreasing the solubility of the component (A-1) in an organic developing solution. Therefore, in the formation of a resist pattern, by conducting selective exposure of a resist film formed by applying the resist composition to a substrate, the exposed portions of the resist film change from an soluble state to an insoluble state in an organic developing solution, whereas the unexposed portions of the resist film remain soluble in an organic developing solution. As a result, by conducting development using an organic developing solution, a contrast can be made between the exposed portions and unexposed portions, thereby forming a negative resist pattern.

In the resist composition of the present embodiment, as the component (A), one kind of compound may be used, or two or more kinds thereof may be used in combination.

In the resist composition of the present embodiment, the component (A) is preferably a component (A-1). That is, the resist composition of the present embodiment is preferably a resist composition which forms a positive pattern in an alkali developing process (i.e, a positive resist compound for alkali developing process) or a resist composition which forms a negative pattern in a solvent developing process (i.e., a negative type resist composition for solvent developing process). In the component (A), at least one of a high-molecular-weight compound and a low-molecular-weight compound can be used.

In the case where the component (A) is a component (A-1), the component (A-1) preferably contains a resin component (A1) (hereafter, referred to as "component (A1)").

Component (A1)

The component (A1) is a resin component preferably containing a polymeric compound having a structural unit (a1) containing an acid decomposable group that exhibits increased polarity by the action of acid.

The component (A1) preferably has, in addition to the structural unit (a1), a structural unit (a10) containing a hydroxystyrene skeleton.

Further, the component (A1) may have, in addition to the structural unit (a1), a structural unit (a2) containing a lactone-containing cyclic group, an —$SO_2$— containing cyclic group or a carbonate-containing cyclic group.

Further, the component (A1) may have, in addition to the structural unit (a1), a structural unit (a3) containing a polar group-containing aliphatic hydrocarbon group (provided that the structural units that fall under the definition of structural units (a1) and (a2) are excluded).

The component (A1) may further include a structural unit other than the structural units (a1), (a2), (a3) and (a10).

<<Structural Unit (a1)>>

The structural unit (a1) is a structural unit containing an acid decomposable group that exhibits increased polarity by the action of acid.

The term "acid decomposable group" refers to a group in which at least a part of the bonds within the structure thereof are cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—$SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group be a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

Examples of the acid dissociable group include groups which have been proposed as acid dissociable groups for the base resin of a conventional chemically amplified resist composition.

Specific examples of acid dissociable groups for the base resin of a conventional chemically amplified resist composition include the "acetal-type acid dissociable group," "tertiary alkyl ester-type acid dissociable group" and "tertiary alkyloxycarbonyl acid dissociable group" described below.

Acetal-Type Acid Dissociable Group

Examples of the acid dissociable group for protecting the carboxy group or hydroxy group as a polar group include the acid dissociable group represented by general formula (a1-r-1) shown below (hereafter, referred to as "acetal-type acid dissociable group").

[Chem. 11]

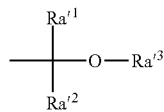

(a1-r-1)

In the formula, $Ra'^1$ and $Ra'^2$ each independently represent a hydrogen atom or an alkyl group; $Ra'^3$ represents a hydrocarbon group, provided that $Ra'^3$ may be bonded to $Ra'^1$ or $Ra'^2$ to form a ring.

In the formula (a1-r-1), it is preferable that at least one of $Ra'^1$ and $Ra'^2$ represent a hydrogen atom, and it is more preferable that both of $Ra'^1$ and $Ra'^2$ represent a hydrogen atom.

In the case where $Ra'^1$ or $Ra'^2$ is an alkyl group, as the alkyl group, the same alkyl groups as those described above for the substituent which may be bonded to a carbon atom at the α-position of the aforementioned α-substituted acrylate ester can be mentioned, and an alkyl group of 1 to 5 carbon atoms is preferable. Specific examples include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In formula (a1-r-1), examples of the hydrocarbon group for $Ra'^3$ include a linear or branched alkyl group and a cyclic hydrocarbon group.

The linear alkyl group preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra'^3$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

When the monovalent hydrocarbon group for $Ra'^3$ is an aromatic hydrocarbon group, the aromatic hydrocarbon group is a hydrocarbon group having at least one aromatic ring.

The aromatic ring is not particularly limited, as long as it is a cyclic conjugated compound having (4n+2) π-electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms.

Examples of the aromatic ring include aromatic hydrocarbon rings, such as benzene, naphthalene, anthracene and phenanthrene; and aromatic hetero rings in which some of the carbon atoms constituting the aforementioned aromatic hydrocarbon rings have been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Ra'^3$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

The cyclic hydrocarbon group for $Ra'^3$ may have a substituent. Examples of the substituent include $-R^{P1}$, $-R^{P2}-O-R^{P1}$, $-R^{P2}-CO-R^{P1}$, $-R^{P2}-CO-OR^{P1}$, $R^{P2}-O-CO-R^{P1}$, $-R^{P2}-OH$, $-R^{P2}-CN$ or $-R^{P2}-COOH$ (hereafter, these substituents are sometimes collectively referred to as "$Ra^{0.5}$").

Here, $R^{P1}$ is a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, a portion or all of the hydrogen atoms having the chain saturated hydrocarbon group, the aliphatic cyclic saturated hydrocarbon group, and the aromatic hydrocarbon group for $R^{P1}$ and $R^{P2}$ may be substituted with a fluorine atom. The aliphatic cyclic hydrocarbon group may have 1 or more substituents of 1 kind, or 1 or more substituents of a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.02,6]decanyl group, a tricyclo[3.3.1.13,7]decanyl group, a tetracyclo[6.2.1.13,6.02,7]dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

In the case where $Ra'^3$ is bonded to $Ra'^1$ or $Ra'^2$ to form a ring, the cyclic group is preferably a 4- to 7-membered ring, and more preferably a 4- to 6-membered ring. Specific examples of the cyclic group include a tetrahydropyranyl group and a tetrahydrofuranyl group.

Tertiary Alkyl Ester-Type Acid Dissociable Group

Examples of the acid dissociable group for protecting the carboxy group as a polar group include the acid dissociable group represented by general formula (a1-r-2) shown below.

Among the acid dissociable groups represented by general formula (a1-r-2), for convenience, a group which is constituted of alkyl groups is referred to as "tertiary ester-type acid dissociable group".

[Chem. 12]

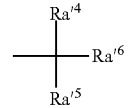

(a1-r-2)

In the formula, $Ra'^4$ to $Ra'^6$ each independently represent a hydrocarbon group, provided that $Ra'^5$ and $Ra'^6$ may be mutually bonded to form a ring.

Examples of the hydrocarbon group for $Ra'^4$ include a linear or branched alkyl group, a chain or cyclic alkenyl group, and a cyclic hydrocarbon group.

The linear or branched alkyl group and the cyclic hydrocarbon group (monocyclic aliphatic hydrocarbon group, polycyclic aliphatic hydrocarbon group or aromatic hydrocarbon group) for $Ra'^4$ are the same as defined for $Ra'^3$.

The chain or cyclic alkenyl group for $Ra'^4$ is preferably an alkenyl group having 2 to 10 carbon atoms.

The hydrocarbon group for $Ra'^5$ and $Ra'^6$ is the same as defined for $Ra'^3$.

In the case where $Ra'^5$ and $Ra'^6$ are mutually bonded to form a ring, a group represented by general formula (a1-r2-1) shown below, a group represented by general formula (a1-r2-2) shown below, and a group represented by general formula (a1-r2-3) shown below may be given as preferable examples.

On the other hand, in the case where $Ra'^4$ to $Ra'^6$ are not mutually bonded and independently represent a hydrocarbon group, the group represented by general formula (a1-r2-4) shown below may be given as a preferable example.

[Chem. 13]

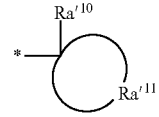

(a1-r2-1)

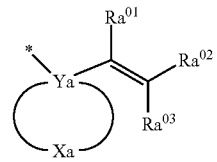

(a1-r2-2)

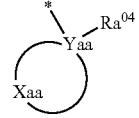

(a1-r2-3)

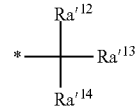

(a1-r2-4)

In formula (a1-r2-1), $Ra'^{10}$ represents an alkyl group of 1 to 10 carbon atoms, or a group represented by general formula (a1-r2-r1) shown below; $Ra'^{11}$ is a group which forms an aliphatic cyclic group together with a carbon atom having $Ra'^{10}$ bonded thereto. In formula (a1-r2-2), Ya represents a carbon atom; Xa represents a group which forms a cyclic hydrocarbon group together with Ya, provided that some or all of the hydrogen atoms of the cyclic hydrocarbon group may be substituted; $Ra^{01}$ to $Ra^{03}$ each independently represent a hydrogen atom, a monovalent saturated chain hydrocarbon group of 1 to 10 carbon atoms or a monovalent saturated aliphatic cyclic hydrocarbon group of 3 to 20 carbon atoms, provided that some or all of the hydrogen atoms of the saturated chain hydrocarbon or the saturated aliphatic cyclic hydrocarbon may be substituted; and two or more of $Ra^{01}$ to $Ra^{03}$ may be mutually bonded to form a cyclic structure. In formula (a1-r2-3), Yaa represents a carbon atom; Xaa represents a group which forms an aliphatic cyclic group together with Yaa; and $Ra^{04}$ represents an aromatic hydrocarbon group which may have a substituent. In formula (a1-r2-4), $Ra'^{12}$ and $Ra'^{13}$ each independently represent a hydrogen atom or a monovalent saturated hydrocarbon group of 1 to 10 carbon atoms, provided that some or all of the hydrogen atoms of the saturated hydrocarbon group may be substituted; $Ra'^{14}$ represents a hydrocarbon group which may have a substituent; and * represents a valence bond (the same definition hereafter).

[Chem. 14]

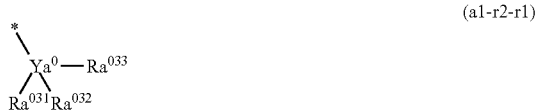

(a1-r2-r1)

In the formula, $Ya^0$ represents a quaternary carbon atom; and $Ra^{031}$, $Ra^{032}$ and $Ra^{033}$ each independently represent a hydrocarbon group which may have a substituent; provided that at least one of $Ra^{031}$, $Ra^{032}$ and $Ra^{033}$ are a hydrocarbon group having at least one polar group].

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable. $Ra'^{10}$ is preferably an alkyl group of 1 to 5 carbon atoms.

In formula (a1-r2-r1), $Ya^0$ represents a quaternary carbon atom. That is, the number of carbon atoms bonded to $Ya^0$ (carbon atom) is 4.

In formula (a1-r2-r1), $Ra^{031}$, $Ra^{032}$ and $Ra^{033}$ each independently represent a hydrocarbon group which may have a substituent. Examples of the hydrocarbon group for $Ra^{031}$, $Ra^{032}$ and $Ra^{033}$ include a linear or branched alkyl group, a chain or cyclic alkenyl group, and a cyclic hydrocarbon group.

The linear alkyl group for $Ra^{031}$, $Ra^{032}$ and $Ra^{033}$ preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group for $Ra^{031}$, $Ra^{032}$ and $Ra^{033}$ preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

The chain or cyclic alkenyl group for $Ra^{031}$, $Ra^{032}$ and $Ra^{033}$ is preferably an alkenyl group having 2 to 10 carbon atoms.

The cyclic hydrocarbon group for $Ra^{031}$, $Ra^{032}$ and $Ra^{033}$ may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group for $Ra^{031}$, $Ra^{032}$ and $Ra^{033}$ is a hydrocarbon group having at least one aromatic ring. The aromatic ring is not particularly limited, as long as it is a cyclic conjugated compound having (4n+2) π-electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which some of the carbon atoms constituting the aforementioned aromatic hydrocarbon rings have been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring. Specific examples of the aromatic hydrocarbon group include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

In the case where the hydrocarbon group for $Ra^{031}$, $Ra^{032}$ and $Ra^{033}$ is substituted, examples of the substituent include a hydroxy group, a carboxy group, a halogen atom (such as a fluorine atom, a chlorine atom or a chlorine atom), an alkoxy group (such as a methoxy group, an ethoxy group, a propoxy group or a butoxy group), and an alkyloxycarbonyl group.

Among these examples, as the hydrocarbon group (which may have a substituent) for $Ra^{031}$, $Ra^{032}$ and $Ra^{033}$, a linear or branched alkyl group which may have a substituent is preferable, and a linear alkyl group is more preferable.

However, at least one of $Ra^{031}$, $Ra^{032}$ and $Ra^{033}$ is a hydrocarbon group having a polar group.

The "hydrocarbon group having a polar group" includes a group in which a methylene group (—$CH_2$—) constituting the hydrocarbon group is substituted with a polar group, and a group in which at least one hydrogen atom constituting the hydrocarbon group has been substituted with a polar group.

Examples of the "hydrocarbon group having a polar group" include a functional group represented by general formula (a1-p1) shown below.

[Chem. 15]

In the formula, $Ra^{07}$ represents a divalent hydrocarbon group having 2 to 12 carbon atoms; $Ra^{08}$ represents a divalent linking group containing a hetero atom; $Ra^{06}$ represents a monovalent hydrocarbon group having 1 to 12 carbon atoms;

and $n_{p0}$ represents an integer of 1 to 6.

In formula (a1-p1), $Ra^{07}$ represents a divalent hydrocarbon group having 2 to 12 carbon atoms.

$Ra^{07}$ has 2 to 12 carbon atoms, preferably 2 to 8 carbon atoms, more preferably 2 to 6 carbon atoms, still more preferably 2 to 4 carbon atoms, and most preferably 2 carbon atoms.

The hydrocarbon group for $Ra^{07}$ is preferably a chain or cyclic aliphatic hydrocarbon group, and more preferably a chain hydrocarbon group.

Examples of $Ra^{07}$ include a linear alkanediyl group, such as an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group; a branched alkanediyl group, such as a propane-1,2-diyl group, a 1-methylbutane-1,3-diyl group, a 2-methylpropane-1,3-diyl group, a pentane-1,4-diyl group, and a 2-methylbutane-1,4-diyl group; a cycloalkanediyl group, such as a cyclobutane-1,3-diyl group, a cyclopentane-1,3-diyl group, a cyclohexane-1,4-diyl group, and a cyclooctane-1,5-diyl group; and a polycyclic divalent alicyclic hydrocarbon group, such as a norbornane-1,4-diyl group, a norbornane-2,5-diyl group, an adamantane-1,5-diyl group, and an adamantane-2,6-diyl group.

Among these examples, an alkanediyl group is preferable, and a linear alkanediyl group is more preferable.

In formula (a1-p1), $Ra^{08}$ represents a divalent linking group containing a hetero atom.

Examples of $Ra^{08}$ include —O—, —C(=O)—O—, —C(=O)—, —O—C(=O)—O—, —C(=O)—NH—, —NH—, —NH—C(=NH)— (H may be substituted with a substituent such as an alkyl group or an acyl group), —S—, —S(=O)$_2$—, and —S(=O)$_2$—O—.

Among these examples, in terms of solubility in a developing solution, —O—, —C(=O)—O—, —C(=O)—, or —O—C(=O)—O— are preferable, and —O— or —C(=O)— is most preferable.

In formula (a1-p1), $Ra^{06}$ represents a monovalent hydrocarbon group having 1 to 12 carbon atoms.

$Ra^{06}$ has 1 to 12 carbon atoms. In terms of solubility in a developing solution, $Ra^{06}$ preferably has 1 to 8 carbon atoms, more preferably 1 to 5 carbon atoms, still more preferably 1 to 3 carbon atoms, still more preferably 1 or 2 carbon atoms, and most preferably 1 carbon atom.

Examples of the hydrocarbon group for $Ra^{06}$ include a chain hydrocarbon group, a cyclic hydrocarbon group, and a combination of a chain hydrocarbon group and a cyclic hydrocarbon group.

Examples of the chain hydrocarbon group include a methyl group, an ethyl group, an n-propyl group, an isopropyl group, an n-butyl group, a sec-butyl group, a tert-butyl group, an n-pentyl group, an n-hexyl group, an n-heptyl group, a 2-ethylhexyl group, an n-octyl group, an n-nonyl group, an n-decyl group, an n-undecyl group and an n-dodecyl group.

The cyclic hydrocarbon group may be an alicyclic hydrocarbon group or an aromatic hydrocarbon group.

The alicyclic hydrocarbon group may be monocyclic or polycyclic. Examples of monocyclic alicyclic hydrocarbon groups include cycloalkyl groups, such as a cyclopropyl group, a cyclobutyl group, a cyclopentyl group, a cyclohexyl group, a dimethylcyclohexyl group, a cycloheptyl group, a cyclooctyl group, a cycloheptyl group, and a cyclodecyl group. Examples of polycyclic alicyclic hydrocarbon groups include a decahydronaphthyl group, an adamantyl group, a 2-alkyladamantan-2-yl group, a 1-(adamantan-1-yl)alkan-1-yl group, a norbornyl group, a methylnorbornyl group, and an isonorbornyl group.

Examples of aromatic hydrocarbon groups include a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, and a 2-methyl-6-ethylphenyl group.

In terms of solubility in a developing solution, $Ra^{06}$ is preferably a chain hydrocarbon group, more preferably an alkyl group, and still more preferably a linear alkyl group.

In formula (a1-p1), $n_{p0}$ is an integer of 1 to 6, preferably an integer of 1 to 3, more preferably 1 or 2, and still more preferably 1.

Specific examples of the hydrocarbon group having a polar group are shown below.

In the following formulae, * represents a valence bond which is bonded to the quaternary carbon atom ($Ya^0$).

[Chem. 16]

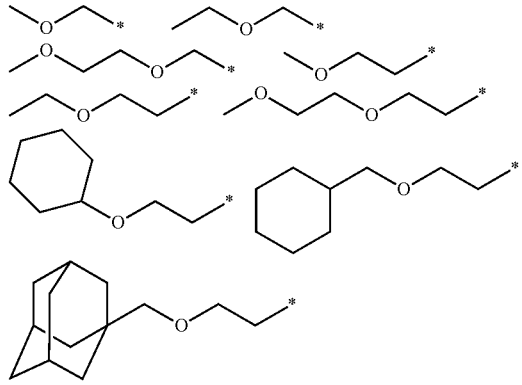

In formula (a1-r2-r1), at least one of $Ra^{031}$, $Ra^{032}$ and $Ra^{033}$ is a hydrocarbon group having a polar group. However, the number of hydrocarbon groups having a polar group may be appropriately selected depending on the solubility in the developing solution used in the formation of a resist pattern. For example, it is preferable that one or two of $Ra^{031}$, $Ra^{032}$ and $Ra^{033}$ be a hydrocarbon group having a polar group, and it is more preferable that one of $Ra^{031}$, $Ra^{032}$ and $Ra^{033}$ be a hydrocarbon group having a polar group.

The hydrocarbon group having a polar group may have a substituent other than a polar group.

Examples of such substituents include a halogen atom (such as a fluorine atom, a chlorine atom or a bromine atom), and a halogenated alkyl group having 1 to 5 carbon atoms.

In formula (a1-r2-1), for the aliphatic cyclic group which is formed by $Ra^{t11}$ together with the carbon atom bonded to $Ra^{t10}$, the same groups as those described above for the monocyclic or polycyclic aliphatic hydrocarbon group for $Ra^{t3}$ in formula (a1-r-1) are preferable.

In formula (a1-r2-2), as the cyclic hydrocarbon group formed by Xa together with Ya, a group in which 1 or more hydrogen atoms have been removed from the monovalent cyclic hydrocarbon group (aliphatic hydrocarbon group) for $Ra^{t3}$ in the aforementioned formula (a1-r-1) may be mentioned.

The cyclic hydrocarbon group which Xa forms with Ya may have a substituent. Examples of substituents include the same substituents as those which the cyclic hydrocarbon group for $Ra^{t3}$ may have.

In formula (a1-r2-2), examples of the monovalent saturated chain hydrocarbon group of 1 to 10 carbon atoms for $Ra^{01}$ to $Ra^{03}$ include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms for $Ra^{01}$ to $Ra^{03}$ include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.0²,⁶]decanyl group, a tricyclo[3.3.1.1³,⁷]decanyl group, a tetracyclo[6.2.1.1³,⁶.0²,⁷]dodecanyl group, and an adamantyl group.

Among these examples, as $Ra^{01}$ to $Ra^{03}$, in terms of ease in synthesis of the monomeric compound which derives the structural unit (a1), a hydrogen atom or a saturated chain hydrocarbon group having 1 to 10 carbon atoms is preferable, a hydrogen atom, a methyl group or an ethyl group is more preferable, and a hydrogen atom is most preferable.

As the substituent for the saturated chain hydrocarbon group or saturated cyclic aliphatic hydrocarbon group represented by $Ra^{01}$ to $Ra^{03}$, for example, the same substituents as those described above for $Ra^{05}$ may be mentioned.

Examples of the group containing a carbon-carbon double bond which is generated by forming a cyclic structure in which two or more of $Ra^{01}$ to $Ra^{03}$ are bonded to each other include a cyclopentenyl group, a cyclohexenyl group, a methylcyclopentenyl group, a methylcyclohexenyl group, a cyclopentylideneethenyl group, and a cyclohexylideneethenyl group. Among these examples, from the viewpoint of the ease of synthesis of the monomer compound which derives the structural unit (a1), a cyclopentenyl group, a cyclohexenyl group, and a cyclopentylideneethenyl group are preferable.

In formula (a1-r2-3), an aliphatic cyclic group which is formed of Xaa together with Yaa is preferably a group exemplified as an aliphatic hydrocarbon group which is a monocyclic group or a polycyclic group of $Ra^{t3}$ in general formula (a1-r-1).

In general formula (a1-r2-3), examples of the aromatic hydrocarbon group for $Ra^{04}$ include a group obtained by removing one or more hydrogen atoms from an aromatic hydrocarbon ring having 5 to 30 carbon atoms. Among these examples, $Ra^{04}$ is preferably a group obtained by removing one or more hydrogen atoms from an aromatic hydrocarbon ring having 6 to 15 carbon atoms, a group obtained by removing one or more hydrogen atoms from benzene, naphthalene, anthracene, or phenanthrene is further preferable, a group obtained by removing one or more hydrogen atoms from benzene, naphthalene, or anthracene is still further preferable, a group obtained by removing one or more hydrogen atoms from benzene and naphthalene is particularly preferable, and a group obtained by removing one or more hydrogen atoms from benzene is most preferable.

Examples of the substituent that $Ra^{04}$ in general formula (a1-r2-3) may have include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

In general formula (a1-r2-4), $Ra^{t12}$ and $Ra^{t13}$ each independently represent a monovalent chain saturated hydrocarbon group having 1 to 10 carbon atoms or a hydrogen atom. With respect to $Ra^{t12}$ and $Ra^{t13}$, examples of the monovalent chain saturated hydrocarbon group having 1 to 10 carbon atoms include the same monovalent chain saturated hydrocarbon group having 1 to 10 carbon atoms as that for $Ra^{01}$ to $Ra^{03}$, provided that some or all of the hydrogen atoms of the saturated hydrocarbon group may be substituted.

Among these examples, as $Ra^{t12}$ and $Ra^{t13}$, a hydrogen atom and an alkyl group having 1 to 5 carbon atoms are preferable, an alkyl group having 1 to 5 carbon atoms is further preferable, a methyl group and an ethyl group are still further preferable, and a methyl group is particularly preferable.

In the case where the chain saturated hydrocarbon group represented by $Ra^{t12}$ and $Ra^{t13}$ is substituted, examples of the substituent include the same groups as that of Re.

In general formula (a1-r2-4), $Ra^{t14}$ is a hydrocarbon group which may have a substituent. Examples of the hydrocarbon group for $Ra^{t14}$ include a linear or branched alkyl group and a cyclic hydrocarbon group.

The linear alkyl group for $Ra^{t14}$ preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group for $Ra^{t14}$ preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra^{t14}$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

As an aromatic hydrocarbon group for Ra'$^{14}$, the same aromatic hydrocarbon groups as those for Ra$^{o4}$ may be exemplified. Among these, Ra'$^{14}$ is preferably a group in which one or more hydrogen atoms are removed from an aromatic hydrocarbon ring having 6 to 15 carbon atoms, more preferably a group in which one or more hydrogen atoms are removed from benzene, naphthalene, anthracene or phenanthrene, still more preferably a group in which one or more hydrogen atoms are removed from benzene, naphthalene or anthracene, particularly preferably a group in which one or more hydrogen atoms are removed from naphthalene or anthracene, and most preferably a group in which one or more hydrogen atoms are removed from naphthalene.

Examples of the substituent that Ra'$^{14}$ may have include the same groups as for the substituent that Ra$^{o4}$ may have.

In the case where Ra'$^{14}$ in general formula (a1-r2-4) is a naphthyl group, a position which is bonded to a tertiary carbon atom in general formula (a1-r2-4) may be 1-position and 2-position of the naphthyl group.

In the case where Ra'$^{14}$ in general formula (a1-r2-4) is an anthryl group, a position which is bonded to a tertiary carbon atom in general formula (a1-r2-4) may be any one of the 1-position, 2-position, and 9-position of the anthryl group.

Specific examples of the group represented by the aforementioned formula (a1-r2-1) are shown below.

[Chem. 17]

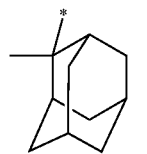
(r-pr-m1)

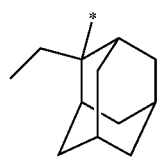
(r-pr-m2)

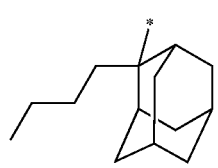
(r-pr-m3)

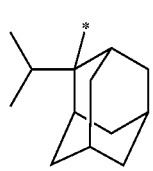
(r-pr-m4)

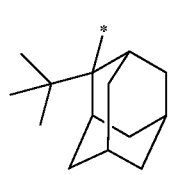
(r-pr-m5)

-continued

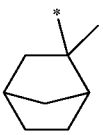
(r-pr-m6)

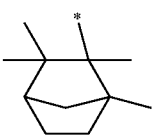
(r-pr-m7)

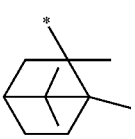
(r-pr-m8)

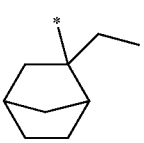
(r-pr-m9)

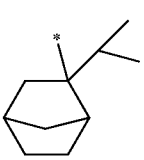
(r-pr-m10)

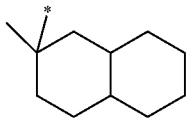
(r-pr-m11)

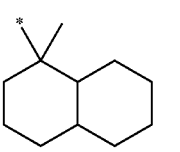
(r-pr-m12)

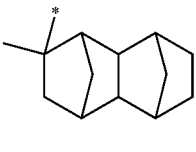
(r-pr-m13)

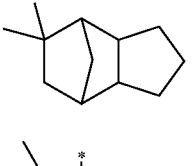
(r-pr-m14)

(r-pr-m15)

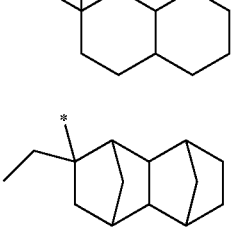
(r-pr-m16)

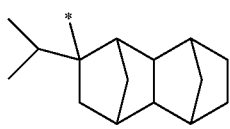
[Chem. 18]
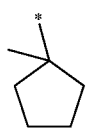 (r-pr-s1)
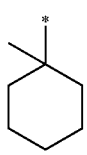 (r-pr-s2)
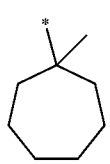 (r-pr-s3)
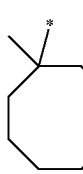 (r-pr-s4)
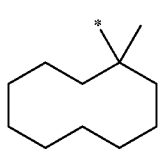 (r-pr-s5)
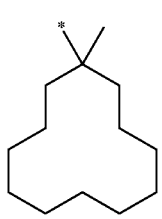 (r-pr-s6)
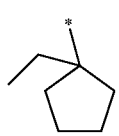 (r-pr-s7)
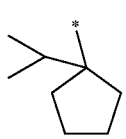 (r-pr-s8)
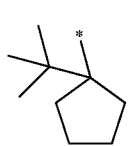 (r-pr-s9)
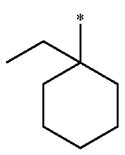 (r-pr-s10)
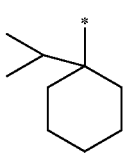 (r-pr-s11)
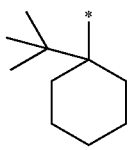 (r-pr-s12)
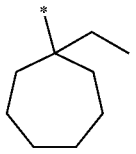 (r-pr-s13)
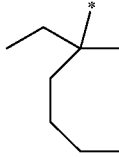 (r-pr-s14)
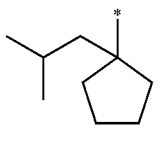 (r-pr-s15)
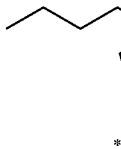 (r-pr-s16)
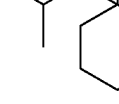 (r-pr-s17)
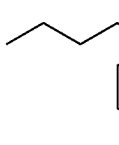 (r-pr-s18)
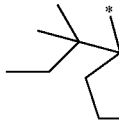 (r-pr-s19)

(r-pr-s20)
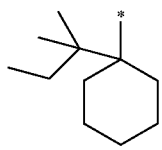
[Chem. 19]
(r-pr-sp1)
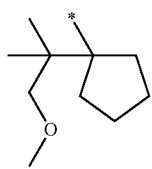
(r-pr-sp2)
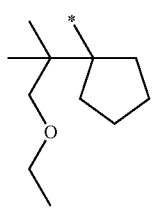
(r-pr-sp3)
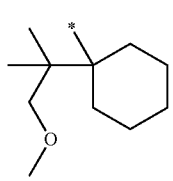
(r-pr-sp4)
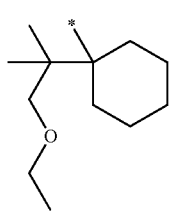
(r-pr-mp1)
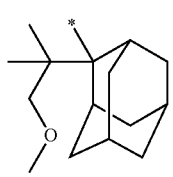
(r-pr-mp2)
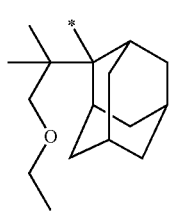
Specific examples of the group represented by the aforementioned formula (a1-r2-2) are shown below.
[Chem. 20]
(r-pr-sv1)
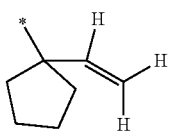
(r-pr-sv2)
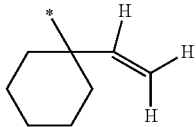
(r-pr-sv3)
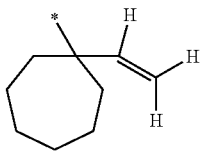
(r-pr-sv4)
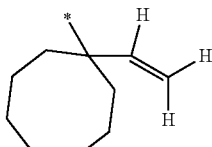
(r-pr-sv5)
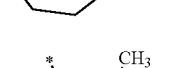
(r-pr-sv6)
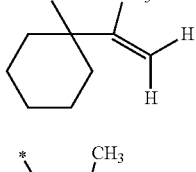
(r-pr-sv7)
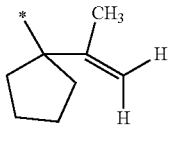
(r-pr-sv8)
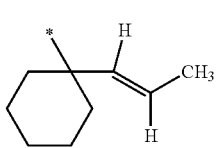
(r-pr-sv9)
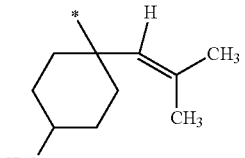
(r-pr-sv10)
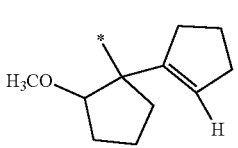

(r-pr-sv11)
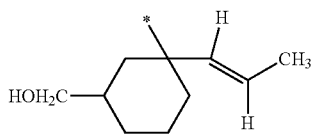
(r-pr-sv12)
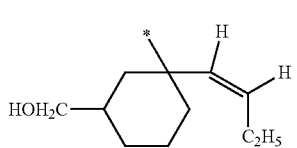
[Chem. 21]
(r-pr-mv1)
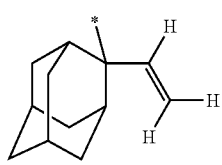
(r-pr-mv2)
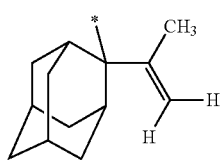
(r-pr-mv3)
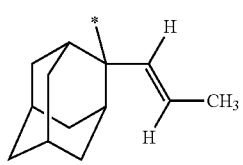
(r-pr-mv4)
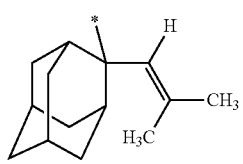
(r-pr-mv5)
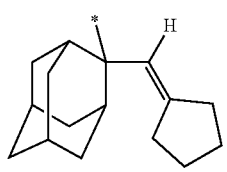
(r-pr-mv6)
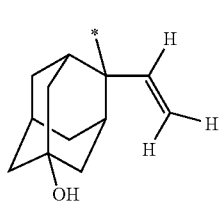
(r-pr-mv7)
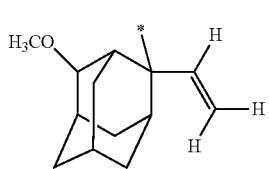
(r-pr-mv8)
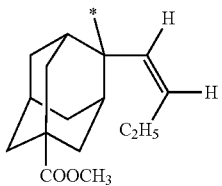
(r-pr-mv9)
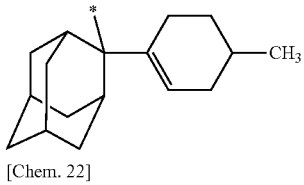
[Chem. 22]
(r-pr-mv10)
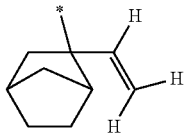
(r-pr-mv11)
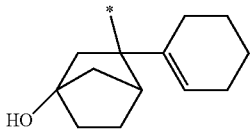
(r-pr-mv12)
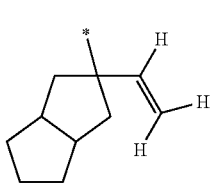
(r-pr-mv13)
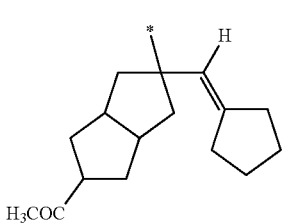
(r-pr-mv14)
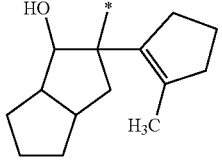
(r-pr-mv15)
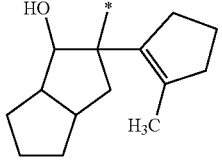
(r-pr-mv16)
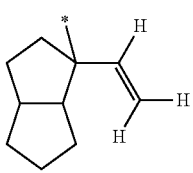

-continued
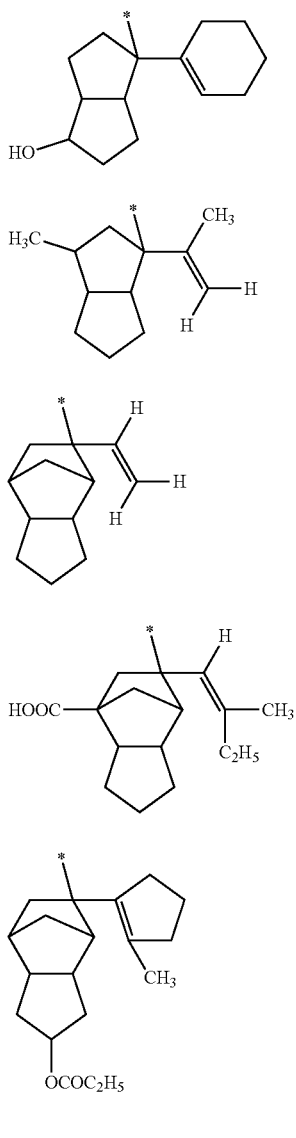
(r-pr-mv17)
(r-pr-mv18)
(r-pr-mv19)
(r-pr-mv20)
(r-pr-mv21)
Specific examples of the group represented by the aforementioned formula (a1-r2-3) are shown below.
[Chem. 23]
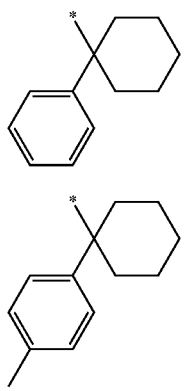
(r-pr-sa1)
(r-pr-sa2)
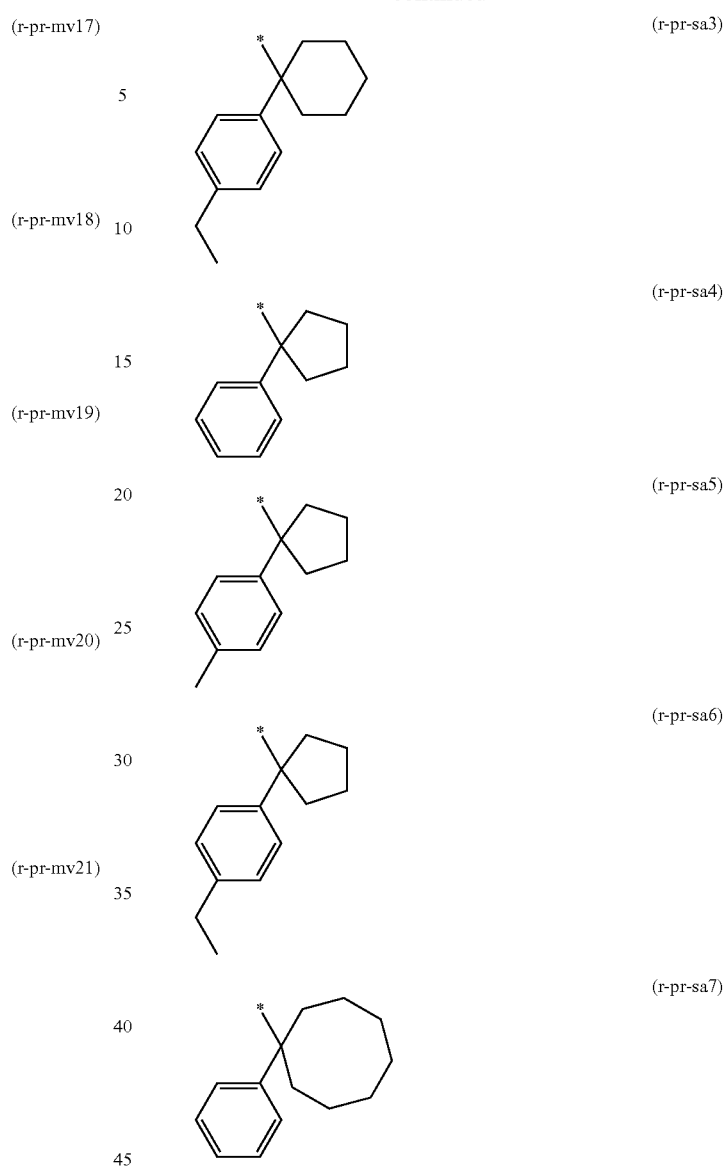
(r-pr-sa3)
(r-pr-sa4)
(r-pr-sa5)
(r-pr-sa6)
(r-pr-sa7)
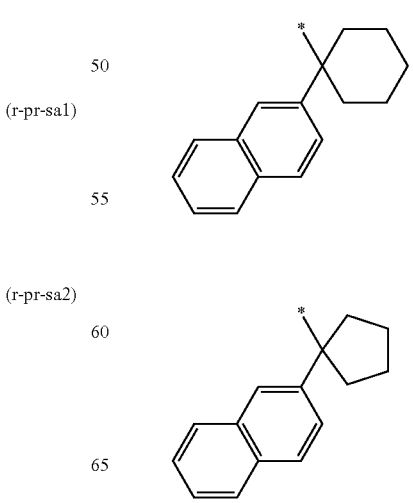
(r-pr-sa8)
(r-pr-sa9)

-continued
(r-pr-ma1)
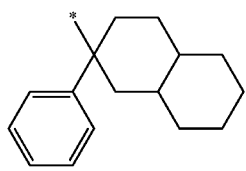
(r-pr-ma2)
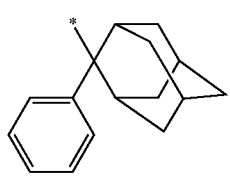
Specific examples of the group represented by the aforementioned formula (a1-r2-4) are shown below.
[Chem. 24]
(r-pr-cm1)
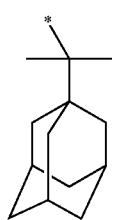
(r-pr-cm2)
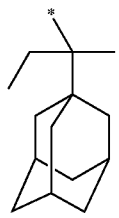
(r-pr-cm3)
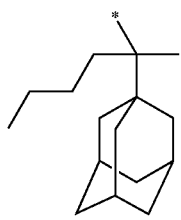
(r-pr-cm4)
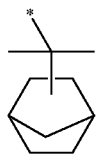
(r-pr-cm5)
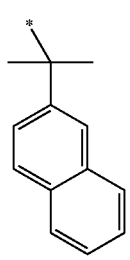
-continued
(r-pr-cm6)
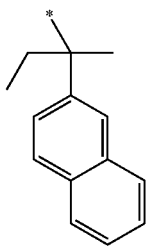
(r-pr-cm7)
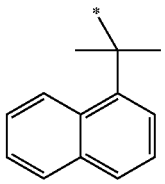
(r-pr-cm8)
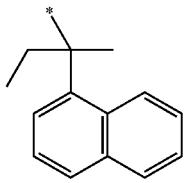
(r-pr-cs1)
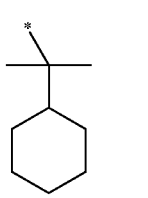
(r-pr-cs2)
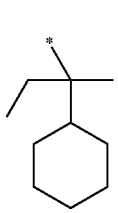
(r-pr-cs3)
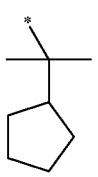
(r-pr-cs4)
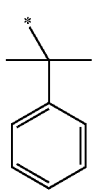
(r-pr-cs5)
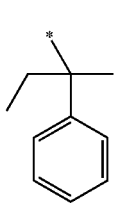

(r-pr-c1)

(r-pr-c2)

(r-pr-c3)

Tertiary Alkyloxycarbonyl Acid Dissociable Group

Examples of the acid dissociable group for protecting a hydroxy group as a polar group include the acid dissociable group represented by general formula (a1-r-3) shown below (hereafter, for convenience, referred to as "tertiary alkyloxy-carbonyl-type acid dissociable group").

[Chem. 25]

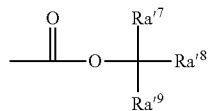

(a1-r-3)

In the formula, $Ra'^7$ to $Ra'^9$ each independently represent an alkyl group.

In formula (a1-r-3), each of $Ra'^7$ to $Ra'^9$ is preferably an alkyl group having 1 to 5 carbon atoms, and more preferably an alkyl group having 1 to 3 carbon atoms. Further, the total number of carbon atoms in the alkyl groups is preferably 3 to 7, more preferably 3 to 5, and still more preferably 3 or 4.

Examples of the structural unit (a1) include a structural unit derived from an acrylate ester which may have the hydrogen atom bonded to a carbon atom at the α-position substituted with a substituent; a structural unit derived from an acrylamide; a structural unit derived from hydroxystyrene or a hydroxystyrene derivative in which at least a part of the hydrogen atoms of the hydroxy group are protected with a substituent containing an acid decomposable group; and a structural unit derived from vinylbenzoic acid or a vinyl-benzoic acid derivative in which at least a part of the hydrogen atoms within —C(=O)—OH are protected with a substituent containing an acid decomposable group.

As the structural unit (a1), a structural unit derived from an acrylate ester which may have a hydrogen atom bonded to a carbon atom at the α-position substituted with a substituent is preferable.

Specific examples of preferable structural units for the structural unit (a1) include structural units represented by general formula (a1-1) or (a1-2) shown below.

[Chem. 26]

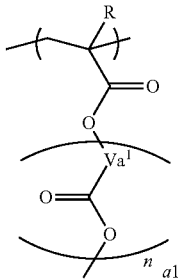

(a1-1)

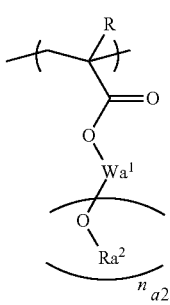

(a1-2)

In the formula, R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; and $Ra^2$ represents an acid dissociable group represented by the aforementioned general formula (a1-r-1) or (a1-r-3).

In the aforementioned formula (a1-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which some or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a1-1), the divalent hydrocarbon group for $V^1$ may be either an aliphatic hydrocarbon group or an aromatic hydrocarbon group.

The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear aliphatic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$-] and a pentamethylene group [—$(CH_2)_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobomane, tricyclodecane and tetracyclododecane.

The aromatic hydrocarbon group as the divalent hydrocarbon group for $Va^1$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which some of the carbon atoms constituting the aforementioned aromatic hydrocarbon rings have been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atoms, more preferably 1 or 2, and most preferably 1.

In formula (a1-1), $Ra^1$ represents an acid dissociable group represented by the aforementioned formula (a1-r-1) or (a1-r-2).

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of a linear or branched aliphatic hydrocarbon group and an aliphatic hydrocarbon group containing a ring in the structure thereof.

The valency of $n_{a2}+1$ is preferably divalent, trivalent or tetravalent, and divalent or trivalent is more preferable.

In formula (a1-2), $Ra^2$ represents an acid dissociable group represented by the aforementioned formula (a1-r-1) or (a1-r-3).

Specific examples of the structural unit represented by formula (a1-1) are shown below. In the formulae shown below, $R^\alpha$ represents a hydrogen atom, a methyl group or a trifluoromethyl group.

[Chem. 27]

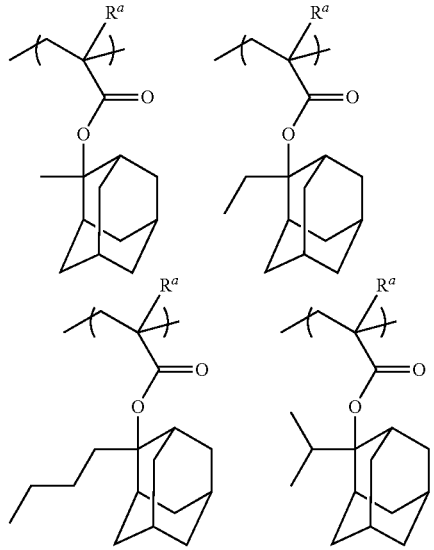

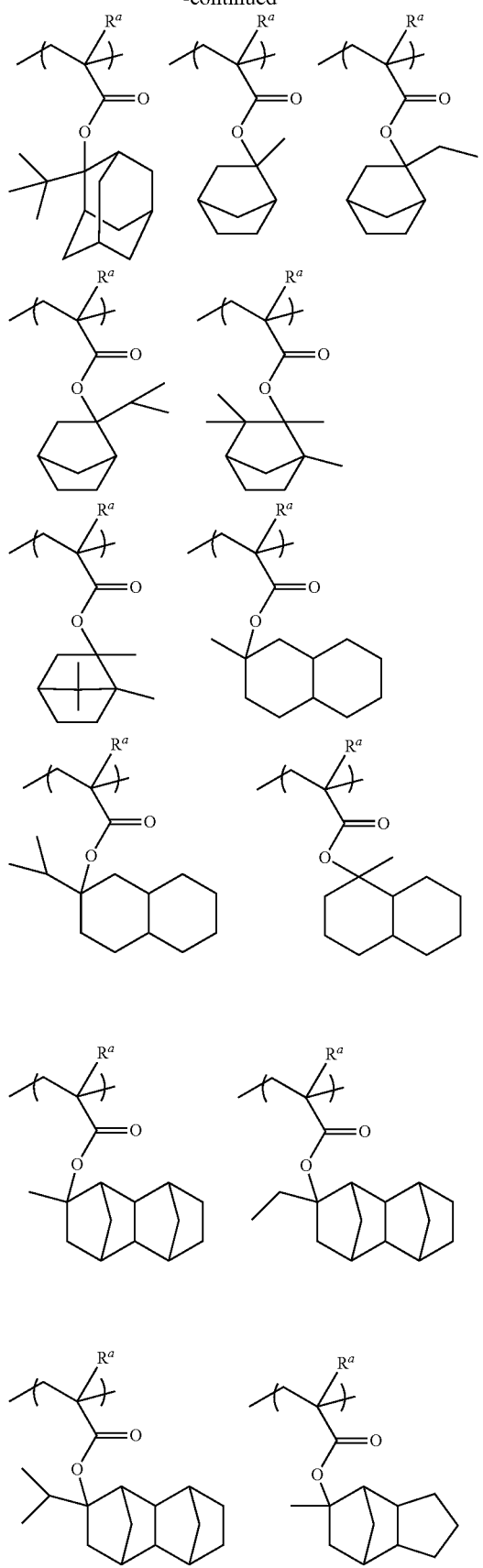
[Chem. 28]
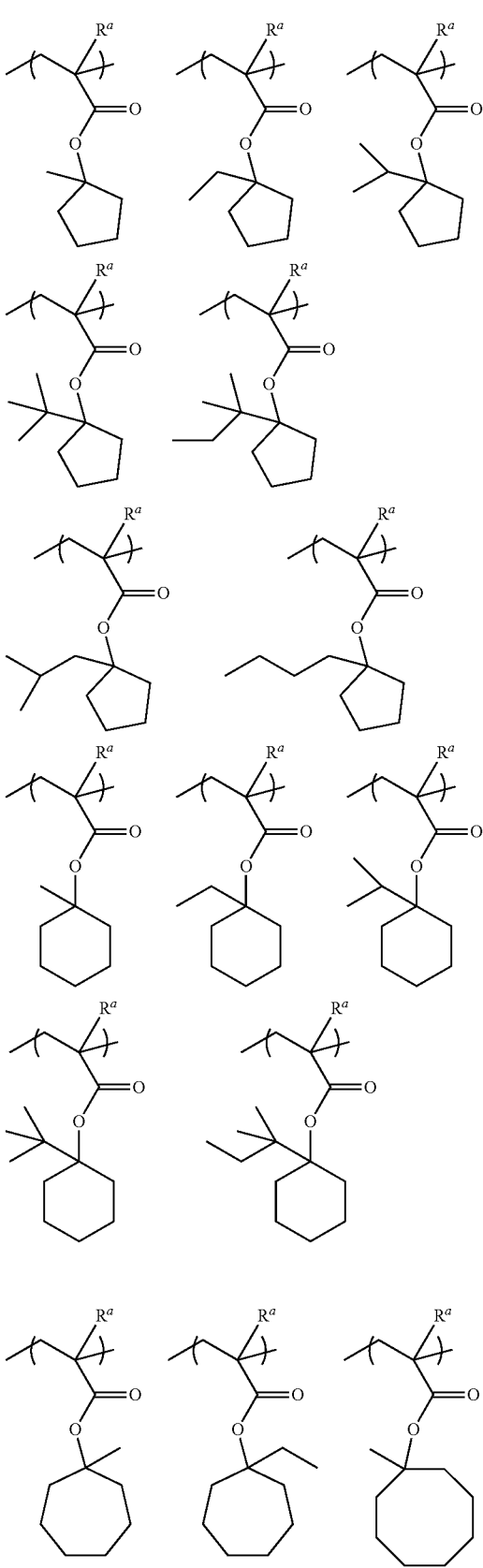

-continued
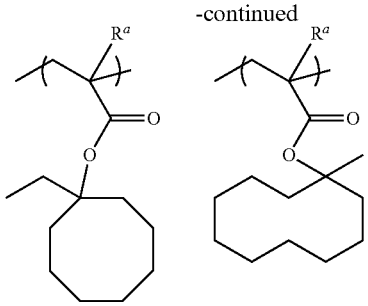
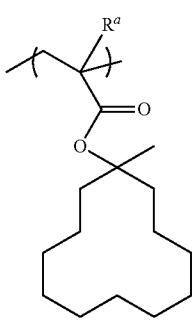
[Chem. 29]
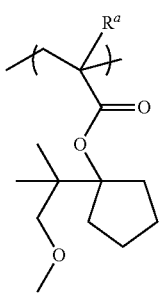 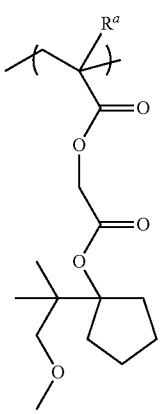 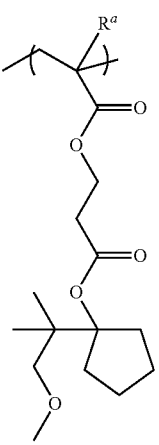
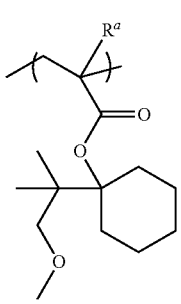 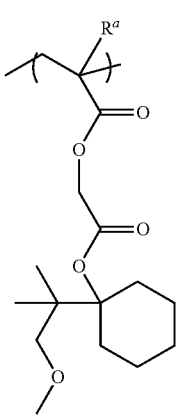
-continued
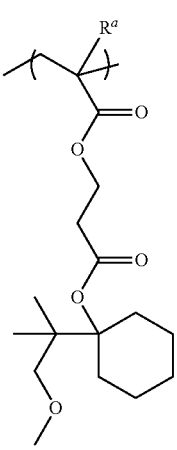
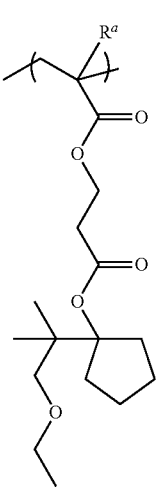 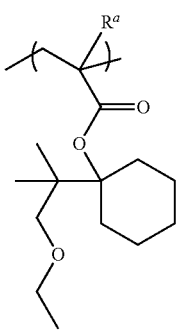
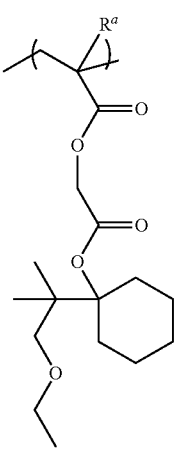 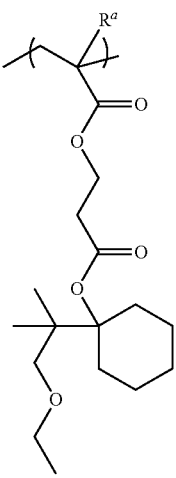

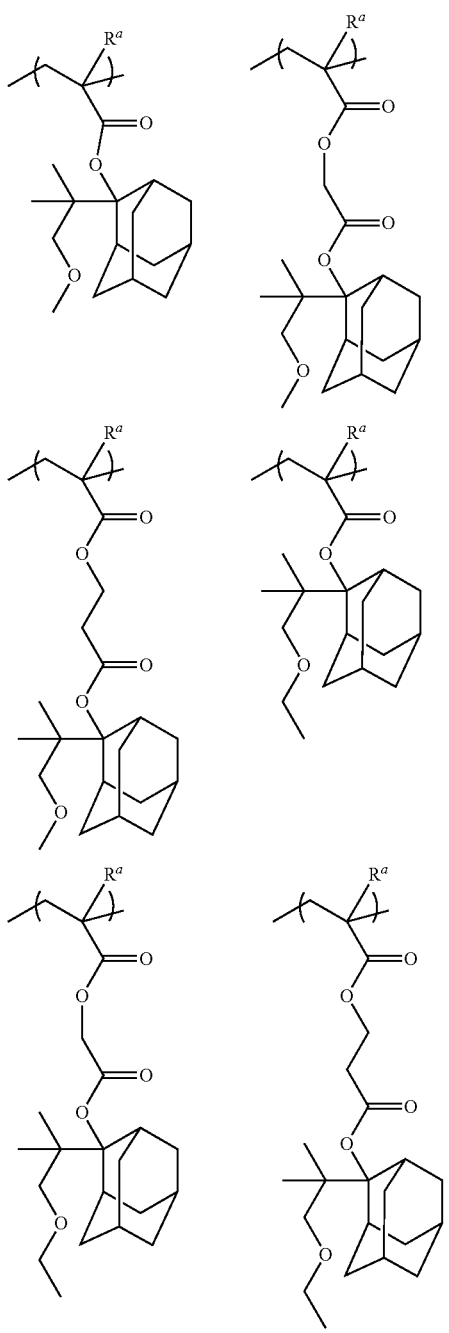
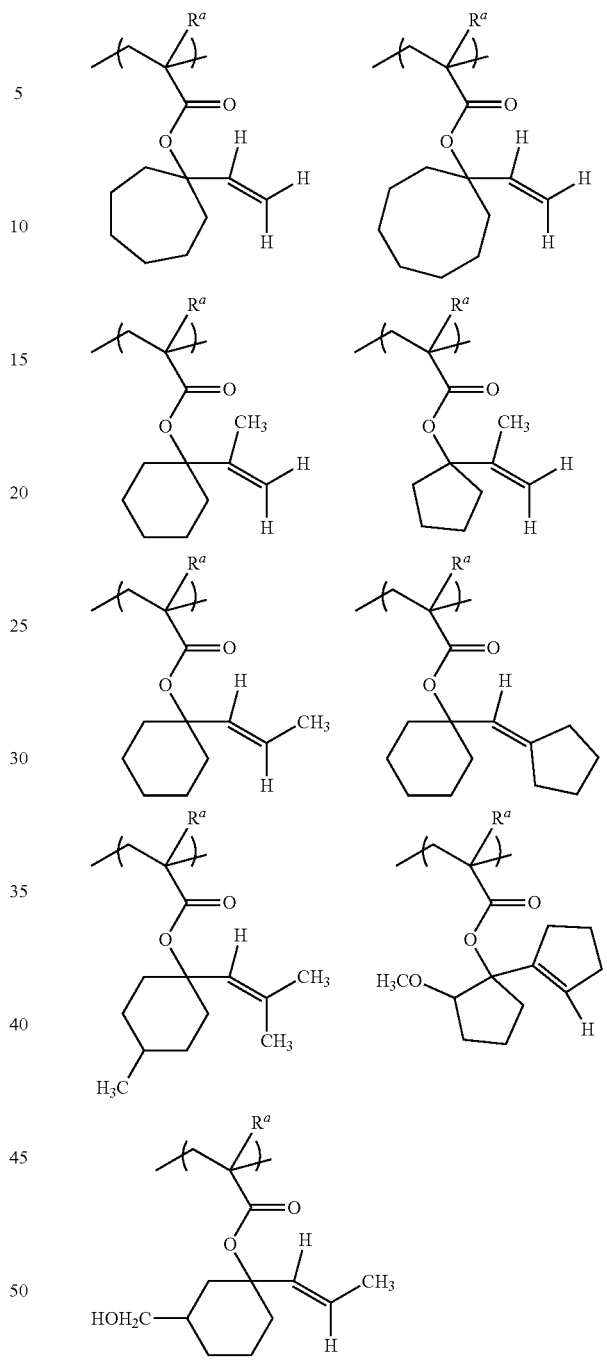
[Chem. 30]
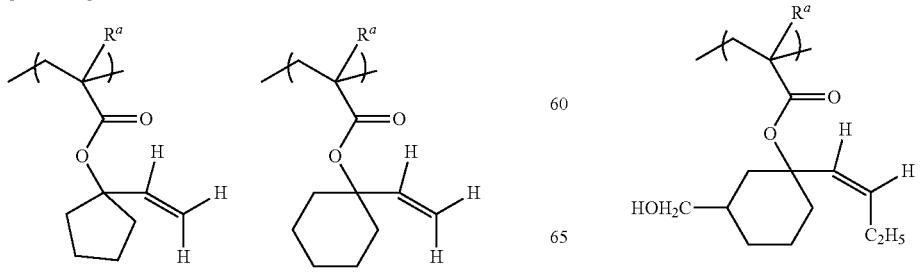

[Chem. 31]
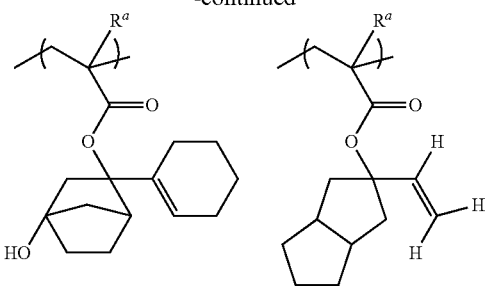
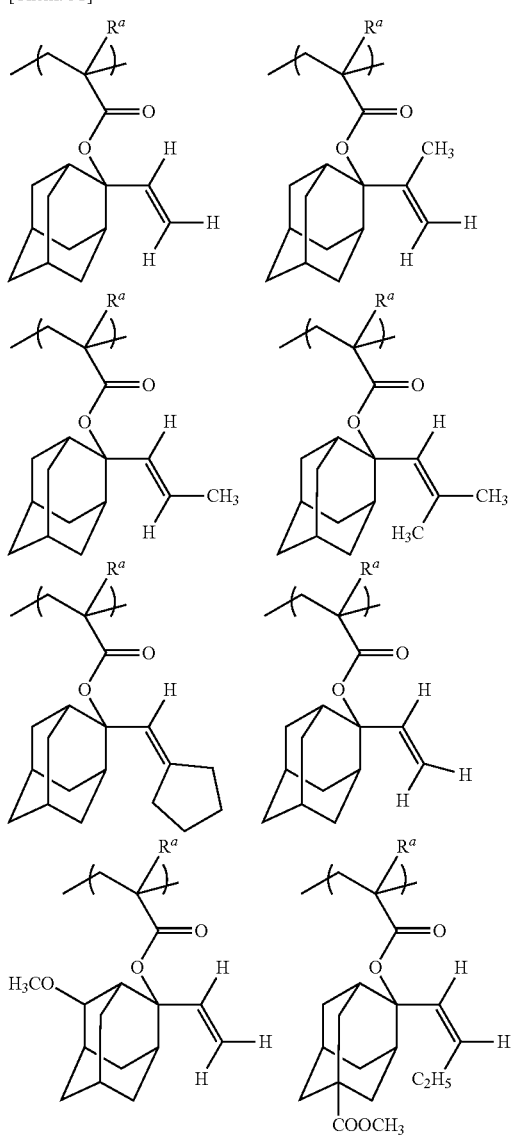
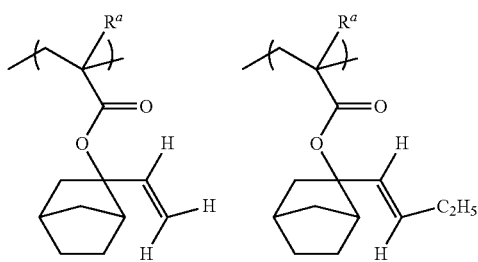
[Chem. 32]

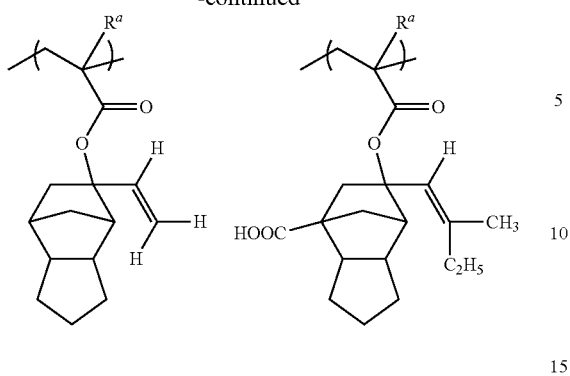
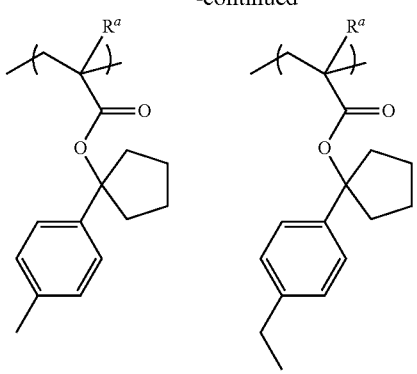
[Chem. 33]
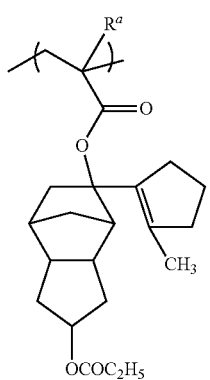
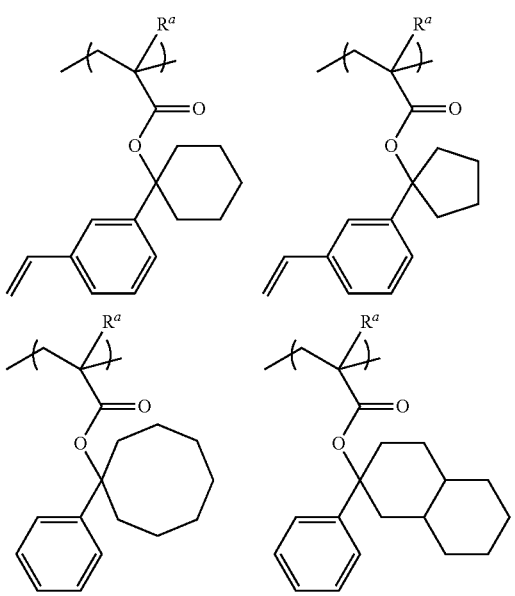
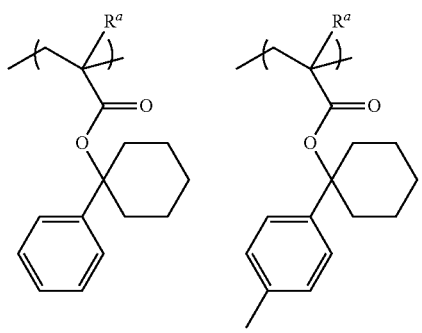
[Chem. 34]
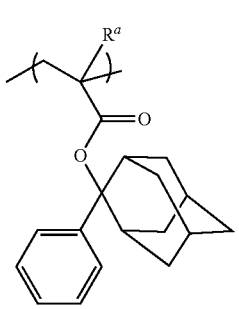
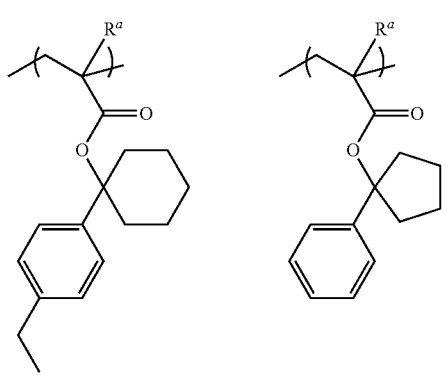
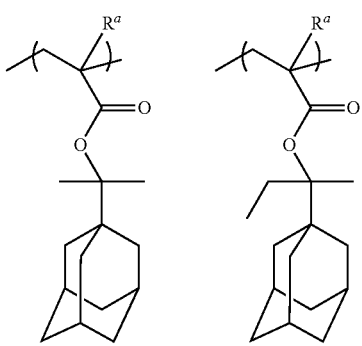

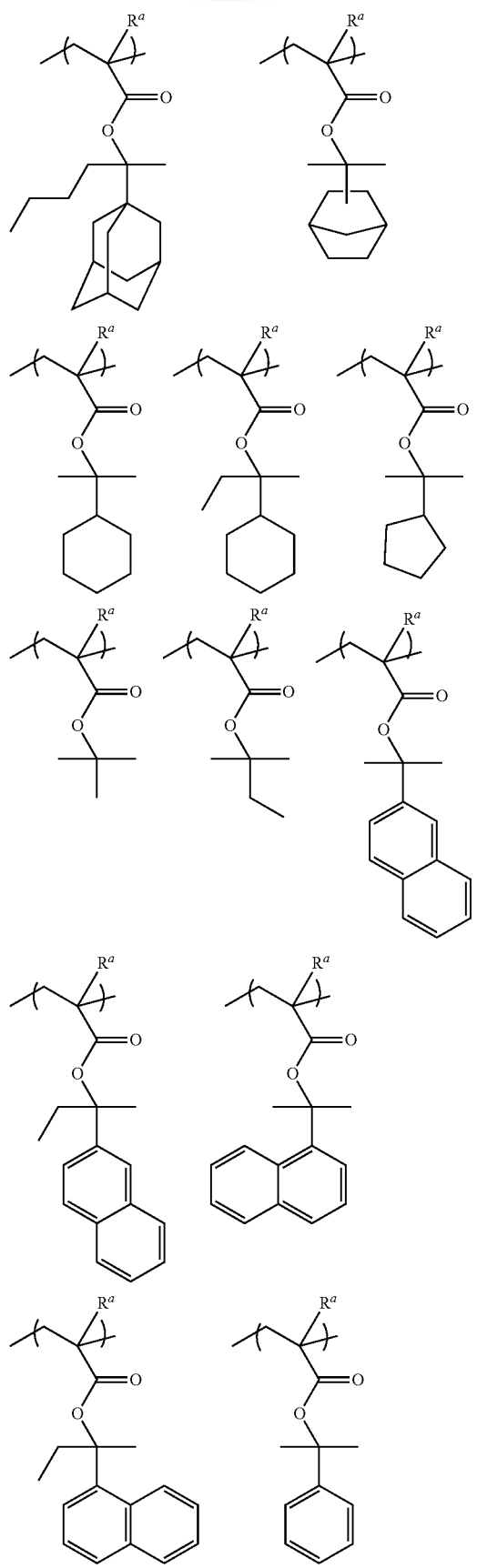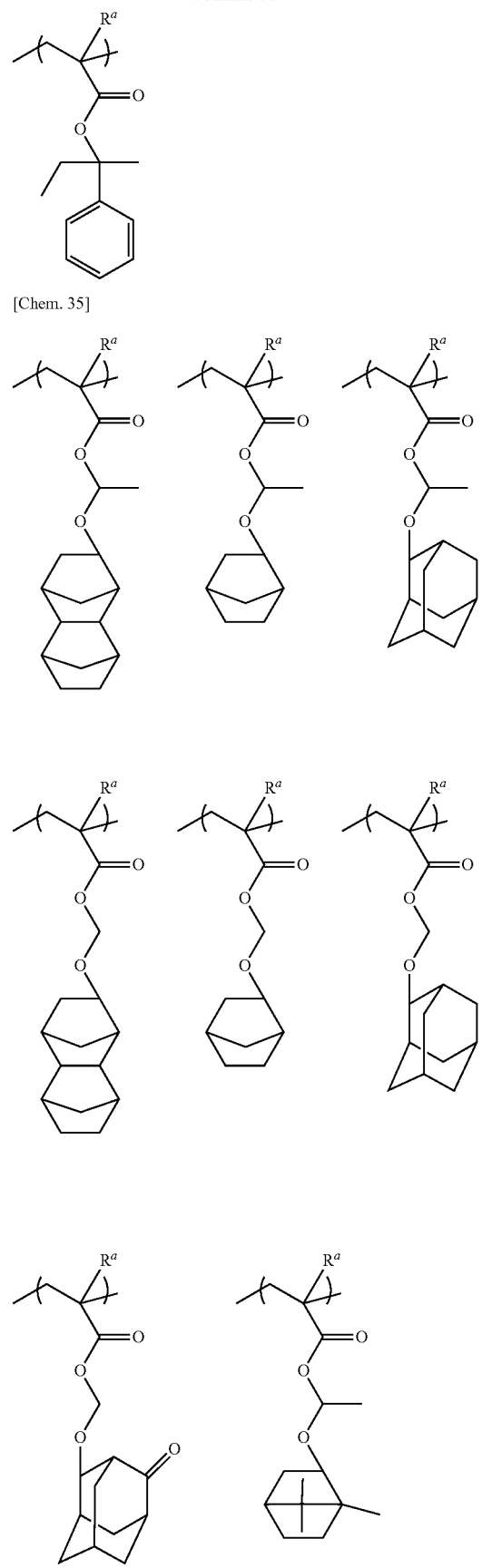

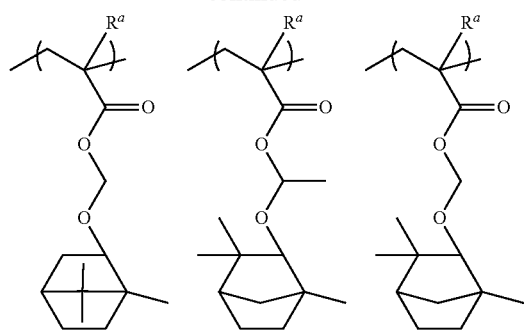
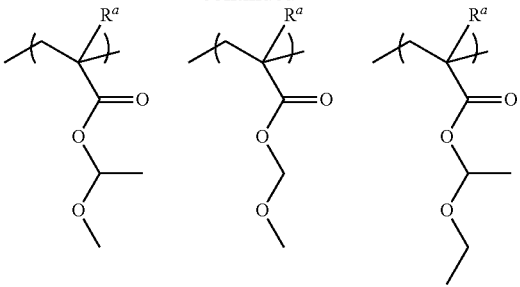
[Chem. 36]
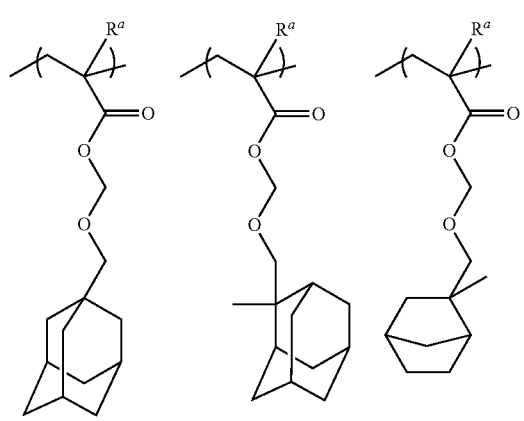
[Chem. 37]
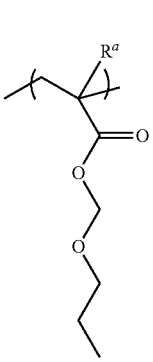
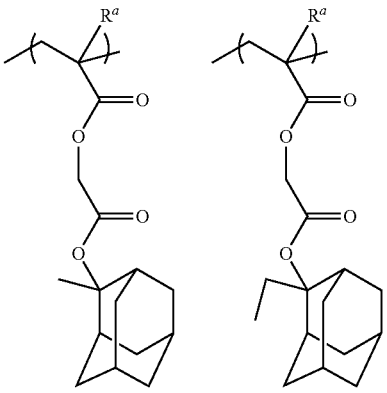
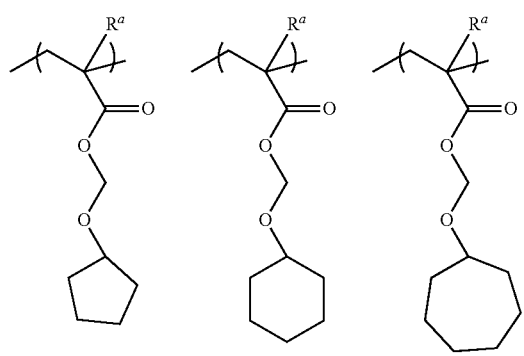
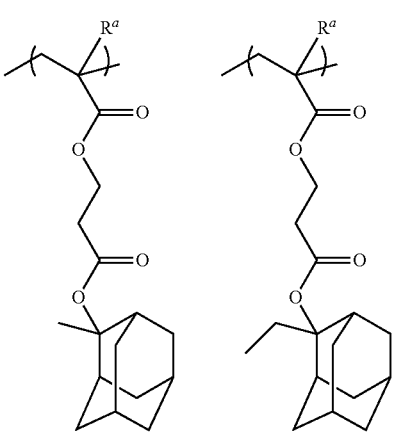
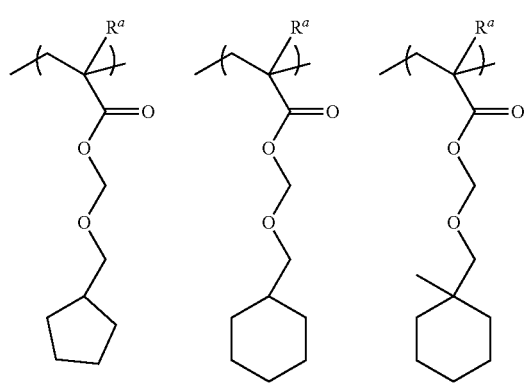

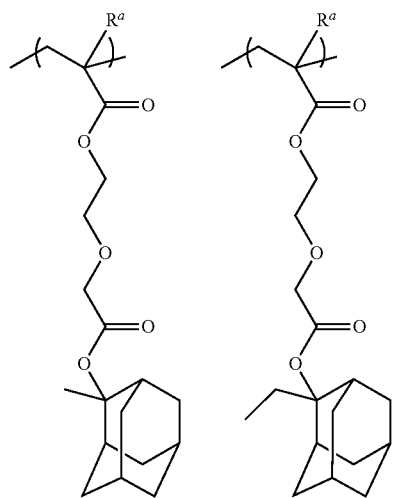
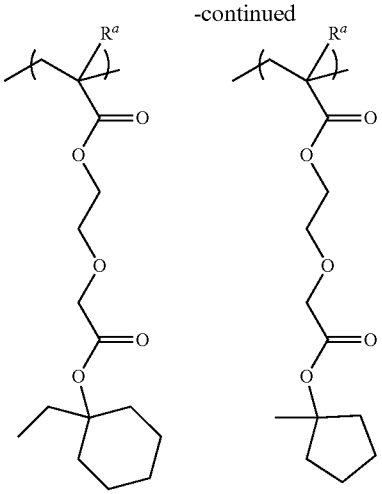
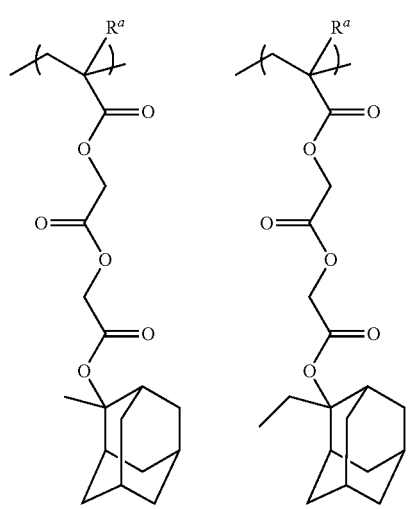
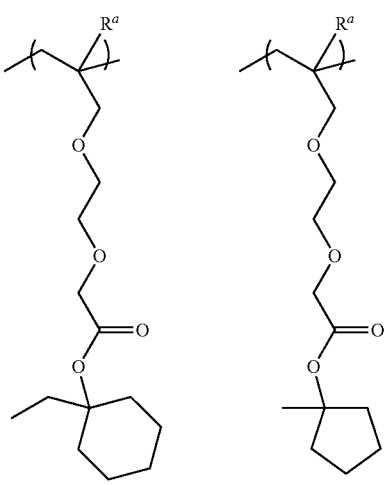
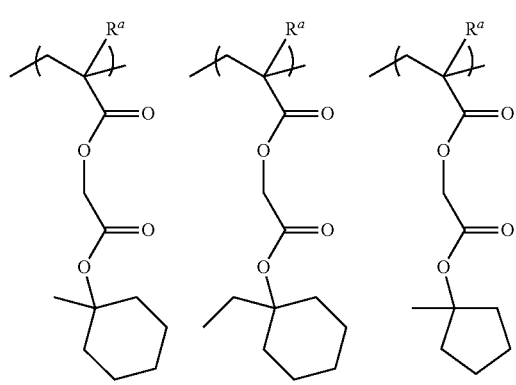
Specific examples of the structural unit represented by formula (a1-2) are shown below.

[Chem. 38]

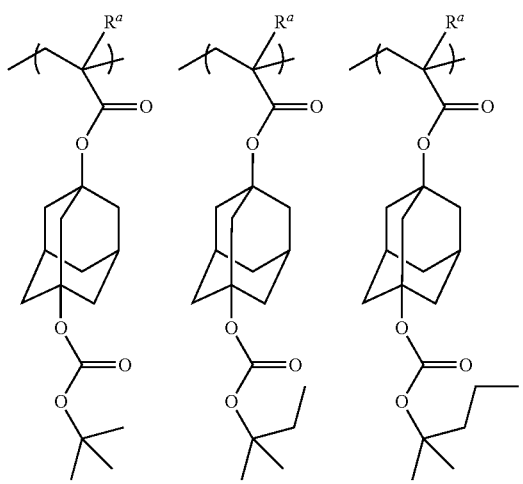 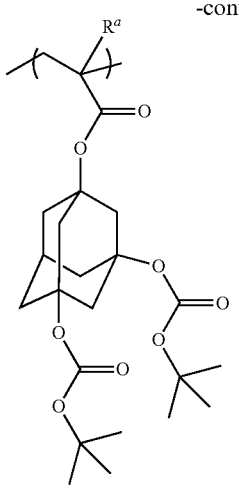 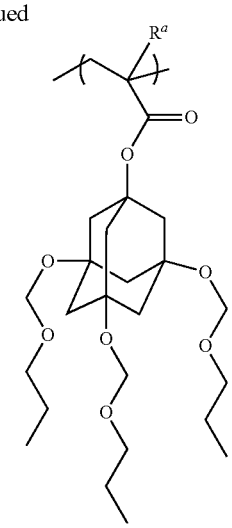

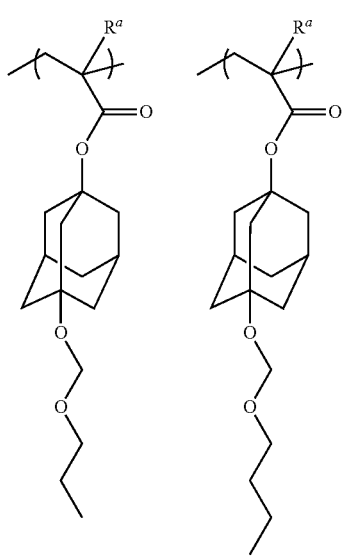

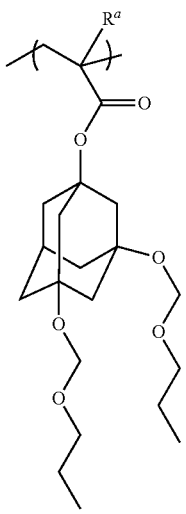

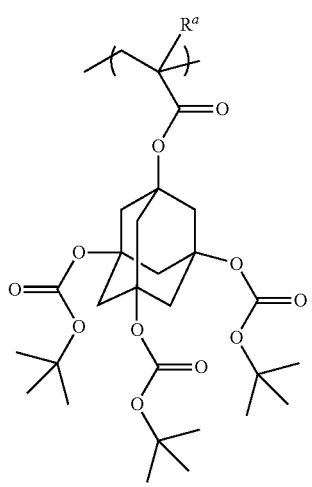

As the structural unit (a1) contained in the component (A1), one type of structural unit may be used, or two or more types thereof may be used in combination.

From the viewpoint that the properties of the lithography (sensitivity, shape, and the like) with an electron beam and EUV are more likely to be enhanced, the structural unit (a1) is further preferably a structural unit represented by general formula (a1-1).

Among these examples, as the structural unit (a1), a structural unit represented by general formula (a1-1-1) is particularly preferable.

[Chem. 39]

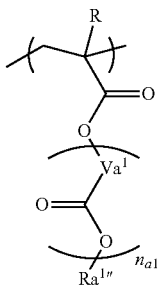

(a1-1-1)

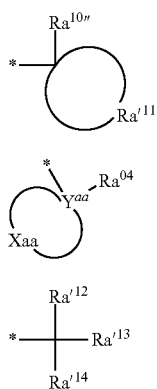

(a1-r2-1)

(a1-r2-3)

(a1-r2-4)

In the formula, $Ra^{1'''}$ is an acid dissociable group represented by general formula (a1-r2-1), (a1-r2-3), or (a1-r2-4).

In general formula (a1-1-1), R, $Va^1$ and $n_{a1}$ are the same as defined for R, $Va^1$ and $n_{a1}$ in general formula (a1-1).

The description of the acid dissociable group represented by general formula (a1-r2-1), (a1-r2-3), or (a1-r2-4) is the same as described above.

In the component (A1), the amount of the structural unit (a1) based on the combined total (100 mol %) of all structural units constituting the component (A1) is preferably 5 to 80 mol %, more preferably 10 to 75 mol %, and still more preferably 30 to 70 mol %.

When the amount of the structural unit (a1) is at least as large as the lower limit of the above-mentioned range, various lithography properties such as sensitivity, resolution and roughness may be improved. On the other hand, when the amount of the structural unit (a1) is no more than the upper limit of the above-mentioned range, a good balance may be achieved with the other structural units, and the lithography properties may be improved.

<<Structural Unit (a10) Containing Hydroxystyrene Skeleton>>

The component (A1) preferably has, in addition to the structural unit (a1), a structural unit (a10) containing a hydroxystyrene skeleton.

Preferable examples of the structural unit (a10) include a structural unit represented by general formula (a10-1) shown below.

[Chem. 40]

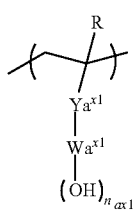

(a10-1)

In the formula, R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of $(n_{ax1}+1)$; and $n_{ax1}$ represents an integer of 1 to 3.

In general formula (a10-1), R represents a hydrogen atom, an alkyl group of 1 to 5 carbon atoms or a halogenated alkyl group of 1 to 5 carbon atoms.

As the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which some or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a10-1), $Ya^{x1}$ represents a single bond or a divalent linking group. Preferable examples of the divalent linking group for $Ya^{x1}$ include a divalent hydrocarbon group which may have a substituent, and a divalent linking group containing a hetero atom.

Divalent Hydrocarbon Group which May have a Substituent:

In the case where $Ya^{x1}$ is a divalent linking group which may have a substituent, the hydrocarbon group may be either an aliphatic hydrocarbon group or an aromatic hydrocarbon group.

Aliphatic Hydrocarbon Group for $Ya^{x1}$

The "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3. As the linear aliphatic hydrocarbon group, a linear alkylene group is preferable.

Specific examples thereof include a methylene group [—$CH_2$—], an ethylene group [—$(CH_2)_2$—], a trimethylene group [—$(CH_2)_3$—], a tetramethylene group [—$(CH_2)_4$-] and a pentamethylene group [—$(CH_2)_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which some or all of the hydrogen atoms within the aforementioned alkyl groups have been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Aromatic Hydrocarbon Group for Ya$^{x1}$

The aromatic hydrocarbon group is a hydrocarbon group having at least one aromatic ring.

The aromatic ring is not particularly limited, as long as it is a cyclic conjugated compound having (4n+2) π-electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Here, the number of carbon atoms within a substituent(s) is not included in the number of carbon atoms of the aromatic hydrocarbon group. Examples of the aromatic ring include aromatic hydrocarbon rings, such as benzene, naphthalene, anthracene and phenanthrene; and aromatic hetero rings in which some of the carbon atoms constituting the aforementioned aromatic hydrocarbon rings have been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, a hydrogen atom within the aromatic hydrocarbon group may be substituted with a substituent. For example, a hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

In the case where Ya$^{x1}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (may be substituted with a substituent such as an alkyl group, an acyl group or the like), —S—, —S(=O)$_2$—, —S(=O)$_2$—O—, and a group represented by general formulae: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$-, —Y$^{21}$—O—C(=O)—Y$^{22}$ or —Y$^{21}$—S(=O)$_2$—O—Y$^{22}$— [in the formulae, Y$^{21}$ and Y$^{22}$ each independently represent a divalent hydrocarbon group which may have a substituent, O represents an oxygen atom, and m' represents an integer of 0 to 3].

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —Y²¹—O—Y²²—, —Y²¹—O—, —Y²¹—C(=O)—O—, —C(=O)—O—Y²¹-, —[Y²¹—C(=O)—O]ₘ„—Y²²—, —Y²¹—O—C(=O)—Y²²— or —Y²¹—S(=O)₂—O—Y²²—, Y²¹ and Y²² each independently represent a divalent hydrocarbon group which may have a substituent. Examples of the divalent hydrocarbon group include the same groups as those described above for the "divalent hydrocarbon group which may have a substituent" in the explanation of the aforementioned divalent linking group.

As Y²¹, a linear aliphatic hydrocarbon group is preferable, a linear alkylene group is more preferable, a linear alkylene group of 1 to 5 carbon atoms is still more preferable, and a methylene group or an ethylene group is particularly desirable.

As Y²², a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[Y²¹—C(=O)—O]ₘ„-Y²²—, m" represents an integer of 0 to 3, preferably an integer of 0 to 2, more preferably 0 or 1, and most preferably 1. Namely, it is particularly desirable that the group represented by the formula —[Y²¹—C(=O)—O]ₘ„-Y²²— is a group represented by the formula —Y²¹—C(=O)—O—Y²²—. Among these, a group represented by the formula —(CH₂)ₐ‚—C(=O)—O—(CH₂)ᵦ‚— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Ya^{x1} preferably represents an ester bond [—C(=O)—O—], an ether bond (—O—), —C(=O)—NH—, a linear or branched alkylene group, a combination of these, or a single bond, and more preferably a single bond.

In formula (a10-1), Wa^{x1} represents an aromatic hydrocarbon group having a valency of (na_{x1}+1).

Examples of the aromatic hydrocarbon group for Wa^{x1} include a group obtained by removing (na_{x1}+1) hydrogen atoms from an aromatic ring. The aromatic ring is not particularly limited, as long as it is a cyclic conjugated compound having (4n+2) π-electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Examples of the aromatic ring include aromatic hydrocarbon rings, such as benzene, naphthalene, anthracene and phenanthrene; and aromatic hetero rings in which some of the carbon atoms constituting the aforementioned aromatic hydrocarbon rings have been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

In formula (a10-1), na_{x1} is an integer of 1 to 3, preferably 1 or 2, and more preferably 1.

Specific examples of the structural unit represented by general formula (a10-1) are shown below.

In the following formulae, R^α represents a hydrogen atom, a methyl group or a trifluoromethyl group.

[Chem. 41]

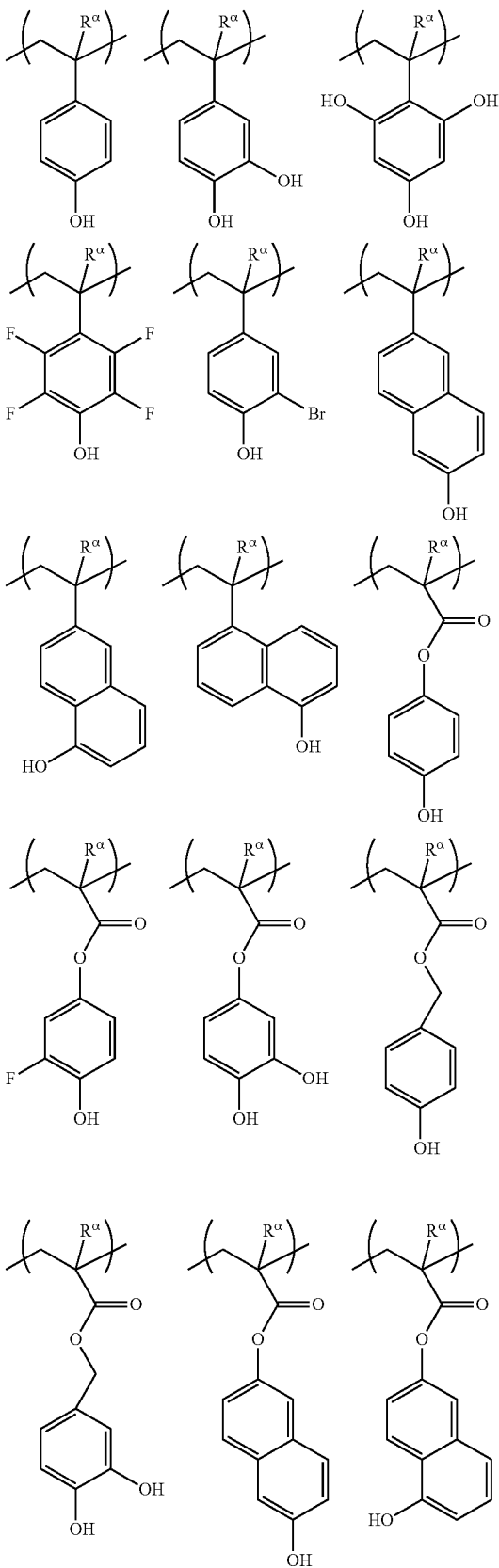

-continued

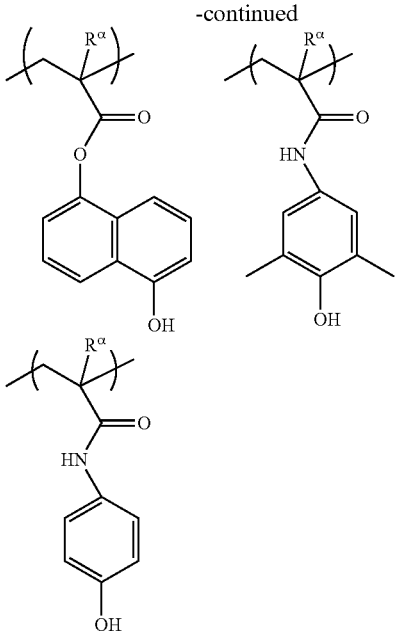

As the structural unit (a10) contained in the component (A1), 1 kind of structural unit may be used, or 2 or more kinds may be used.

In the component (A1), the amount of the structural unit (a10) based on the combined total (100 mol %) of all structural units constituting the component (A1) is, for example, 0 to 80 mol %, preferably 10 to 80 mol %, more preferably 20 to 70 mol %, and still more preferably 30 to 60 mol %.

When the amount of the structural unit (a10) is at least as large as the lower limit of the above-mentioned preferable range, various lithography properties such as sensitivity, resolution and roughness may be improved. On the other hand, when the amount of the structural unit (a1) is no more than the upper limit of the above-mentioned range, a good balance may be achieved with the other structural units, and the lithography properties may be improved.

<<Structural Unit (a2)>>

The component (A1) preferably has, in addition to the structural unit (a1), a structural unit (a2) containing a lactone-containing cyclic group, an —SO$_2$— containing cyclic group or a carbonate-containing cyclic group (provided that structural units which fall under the definition of the structural unit (a1) are excluded).

When the component (A1) is used for forming a resist film, the lactone-containing cyclic group, the —SO$_2$— containing cyclic group or the carbonate-containing cyclic group within the structural unit (a2) is effective in improving the adhesion between the resist film and the substrate. Further, by virtue of including the structural unit (a2), various advantages may be obtained, such as appropriate adjustment of acid diffusion length, enhancement of adhesion of a resist film to a substrate, and appropriate adjustment of solubility of the resist during developing, which may lead to improvement in lithography properties.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include groups represented by general formulae (a2-r-1) to (a2-r-7) shown below.

[Chem. 42]

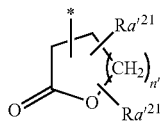
(a2-r-1)

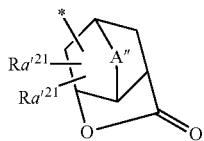
(a2-r-2)

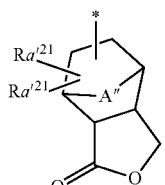
(a2-r-3)

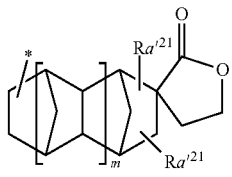
(a2-r-4)

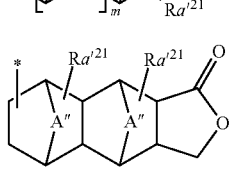
(a2-r-5)

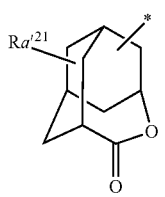
(a2-r-6)

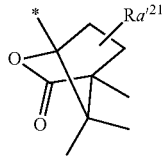
(a2-r-7)

In the formulae, each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO₂— containing cyclic group; A" represents an oxygen atom (—O—), a sulfur atom (—S—) or an alkylene group of 1 to 5 carbon atoms which may contain an oxygen atom or a sulfur atom; n' represents an integer of 0 to 2; and m' represents 0 or 1.

In formulae (a2-r-1) to (a2-r-7), the alkyl group for Ra'²¹ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for Ra'²¹ is preferably an alkoxy group of 1 to 6 carbon atoms.

Further, the alkoxy group is preferably a linear or branched alkoxy group. Specific examples of the alkoxy groups include the aforementioned alkyl groups for Ra'²¹ having an oxygen atom (—O—) bonded thereto.

As examples of the halogen atom for Ra'²¹, a fluorine atom, chlorine atom, bromine atom and iodine atom can be given. Among these, a fluorine atom is preferable.

Examples of the halogenated alkyl group for Ra'²¹ include groups in which some or all of the hydrogen atoms within the aforementioned alkyl group for Ra'²¹ have been substituted with the aforementioned halogen atoms. As the halogenated alkyl group, a fluorinated alkyl group is preferable, and a perfluoroalkyl group is particularly desirable.

With respect to —COOR" and —OC(=O)R" for Ra'²¹, R" represents a hydrogen atom, an alkyl group, a lactone-containing cyclic group, a carbonate-containing cyclic group or an —SO₂— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobomane, tricyclodecane or tetracyclododecane.

Examples of the lactone-containing cyclic group for R" include groups represented by the aforementioned general formulae (a2-r-1) to (a2-r-7).

The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —SO₂— containing cyclic group for R" is the same as defined for the —SO₂— containing cyclic group described later. Specific examples of the —SO₂— containing cyclic group include groups represented by general formulae (a5-r-1) to (a5-r-4).

The hydroxyalkyl group for Ra'²¹ preferably has 1 to 6 carbon atoms, and specific examples thereof include the alkyl groups for Ra'²¹ in which at least one hydrogen atom has been substituted with a hydroxy group.

In formulae (a2-r-2), (a2-r-3) and (a2-r-5), as the alkylene group of 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH₂—, —CH₂—O—CH₂—, —S—CH₂— and —CH₂—S—CH₂—. As A", an alkylene group of 1 to 5 carbon atoms or —O— is preferable, an alkylene group of 1 to 5 carbon atoms is more preferable, and a methylene group is most preferable.

Specific examples of the groups represented by the aforementioned general formulae (a2-r-1) to (a2-r-7) are shown below.

[Chem. 43]

(r-Ic-1-1)

(r-Ic-1-2)

(r-Ic-1-3)

(r-Ic-1-4)

(r-Ic-1-5)

(r-Ic-1-6)

-continued
(r-Ic-1-7)
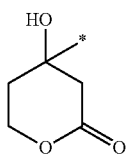
(r-Ic-2-1)
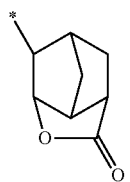
(r-Ic-2-2)
(r-Ic-2-3)
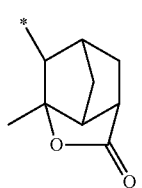
(r-Ic-2-4)
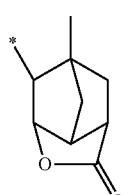
(r-Ic-2-5)
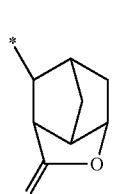
(r-Ic-2-6)
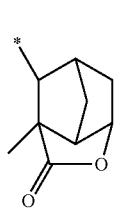
(r-Ic-2-7)
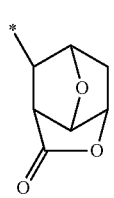
-continued
(r-Ic-2-8)
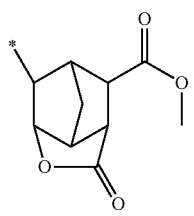
(r-Ic-2-9)
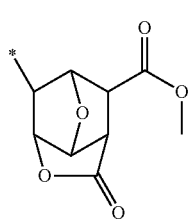
(r-Ic-2-10)
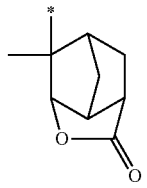
(r-Ic-2-11)
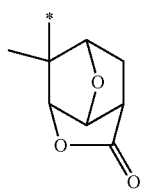
(r-Ic-2-12)
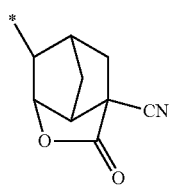
(r-Ic-2-13)
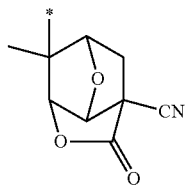
(r-Ic-2-14)
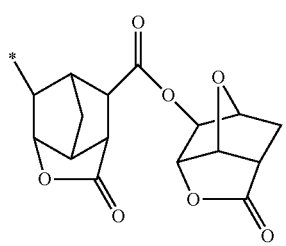

-continued
(r-Ic-2-15)
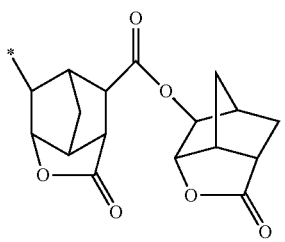
(r-Ic-2-16)
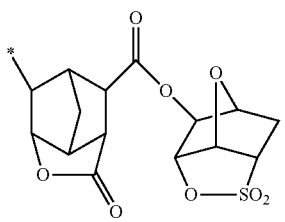
(r-Ic-2-17)
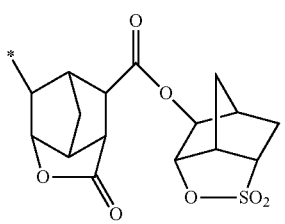
(r-Ic-2-18)
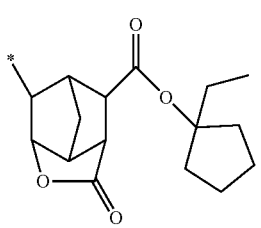
(r-Ic-3-1)
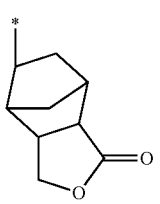
(r-Ic-3-2)
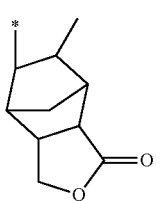
(r-Ic-3-3)
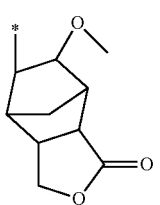
-continued
(r-Ic-3-4)
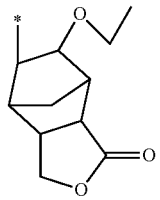
(r-Ic-3-5)
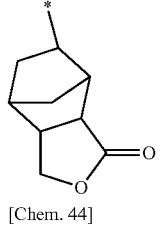
[Chem. 44]
(r-Ic-4-1)
(r-Ic-4-2)
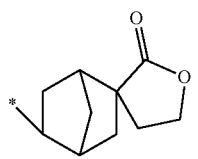
(r-Ic-4-3)
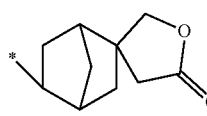
(r-Ic-4-4)
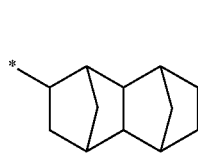
(r-Ic-4-5)
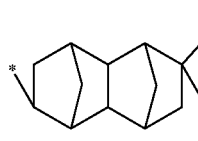
(r-Ic-4-6)
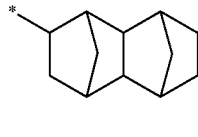
(r-Ic-4-7)
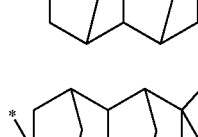
(r-Ic-4-8)
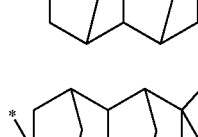

-continued (r-Ic-4-9)
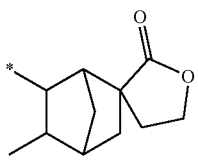

(r-Ic-5-1)
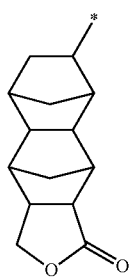

(r-Ic-5-2)
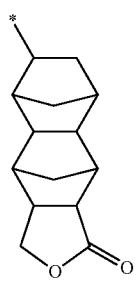

(r-Ic-5-3)
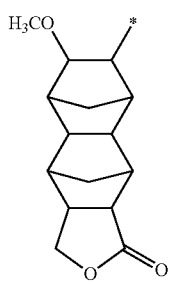

(r-Ic-5-4)
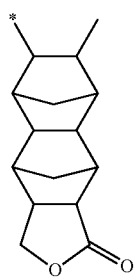

(r-Ic-6-1)
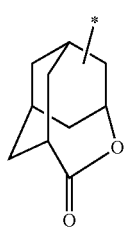

-continued (r-Ic-7-1)
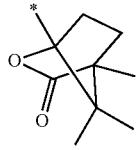

An "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

More specific examples of the —$SO_2$— containing cyclic group include groups represented by general formulas (a5-r-1) to (a5-r-4) shown below.

[Chem. 45]

(a5-r-1)
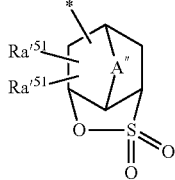

(a5-r-2)
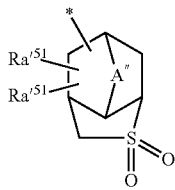

(a5-r-3)
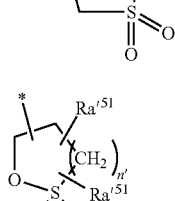

(a5-r-4)
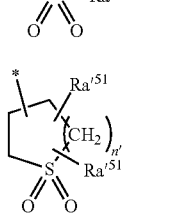

In the formulae, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) and (a5-r-2), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for Ra'$^{51}$ include the same groups as those described above in the explanation of Ra'$^{21}$ in the general formulas (a2-r-1) to (a2-r-7).

Specific examples of the groups represented by the aforementioned general formulae (a5-r-1) to (a5-r-4) are shown below. In the formulae shown below, "Ac" represents an acetyl group.

[Chem. 46]

(r-sl-1-1)

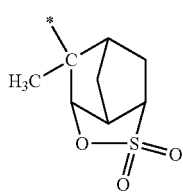
(r-sl-1-2)

(r-sl-1-3)

(r-sl-1-4)

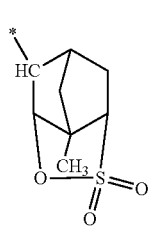
(r-sl-1-5)

(r-sl-1-6)

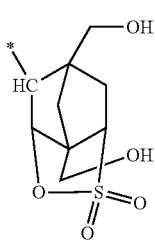
(r-sl-1-7)

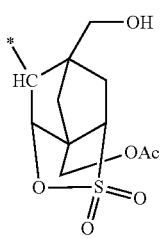
(r-sl-1-8)

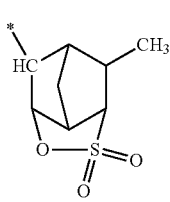
(r-sl-1-9)

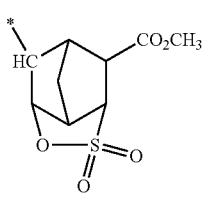
(r-sl-1-10)

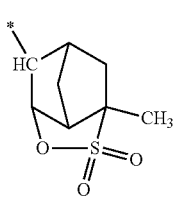
(r-sl-1-11)

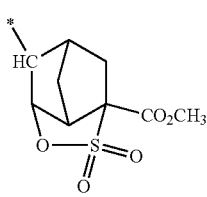
(r-sl-1-12)

-continued
(r-sl-1-13)
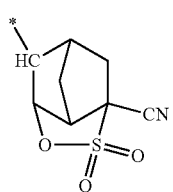
(r-sl-1-14)
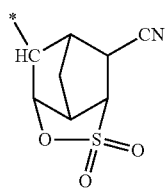
(r-sl-1-15)
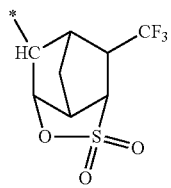
(r-sl-1-16)
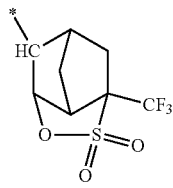
(r-sl-1-17)
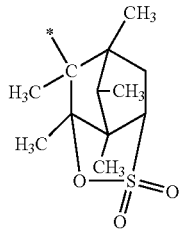
(r-sl-1-18)
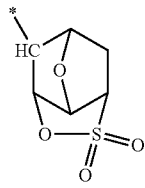
(r-sl-1-19)
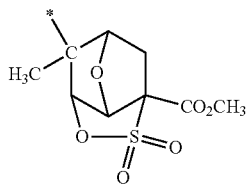
(r-sl-1-20)
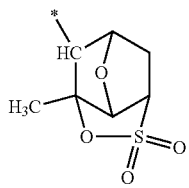
-continued
(r-sl-1-21)
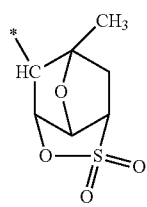
[Chem. 47]
(r-sl-1-22)
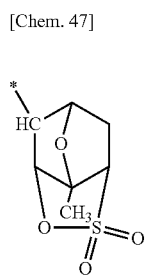
(r-sl-1-23)
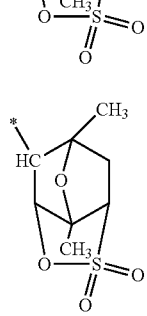
(r-sl-1-24)
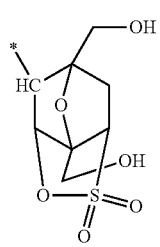
(r-sl-1-25)
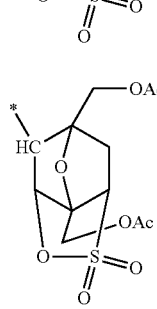
(r-sl-1-26)
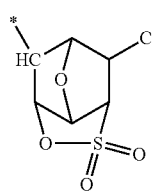
(r-sl-1-27)
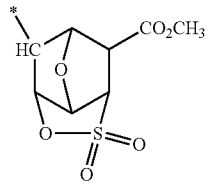

-continued (r-sl-1-28)
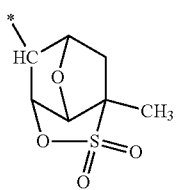

(r-sl-1-29)
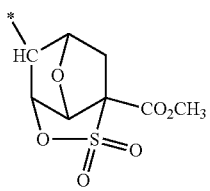

(r-sl-1-30)
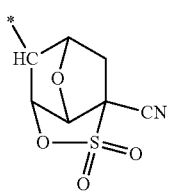

(r-sl-1-31)
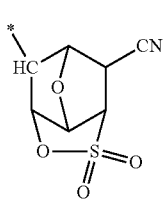

(r-sl-1-32)
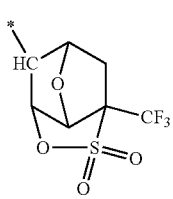

(r-sl-1-33)
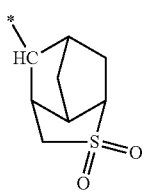

[Chem. 48]

(r-sl-2-1)
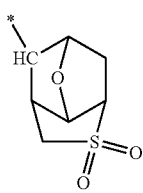

(r-sl-2-2)

-continued (r-sl-3-1)
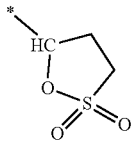

(r-sl-4-1)
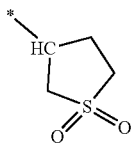

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chem. 49]

(ax3-r-1)

(ax3-r-2)
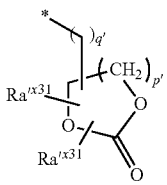

(ax3-r-3)
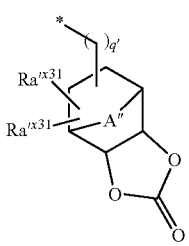

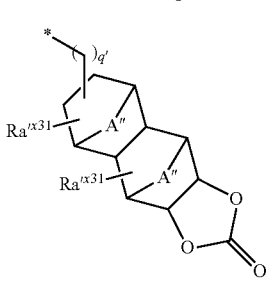

In the formulae, each $Ra'^{x31}$ independently represents a hydrogen atom, an alkyl group, an alkoxy group, a halogen atom, a halogenated alkyl group, a hydroxy group, —COOR″, —OC(=O)R″, a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-2) and (ax3-r-3), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for Ra'$^{31}$ include the same groups as those described above in the explanation of Ra'$^{21}$ in the general formulas (a2-r-1) to (a2-r-7).

Specific examples of the groups represented by the aforementioned general formulae (ax3-r-1) to (ax3-r-3) are shown below.

[Chem. 50]

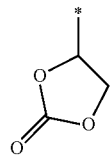
(r-cr-1-1)

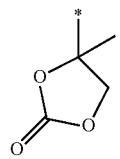
(r-cr-1-2)

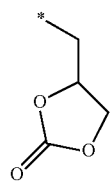
(r-cr-1-3)

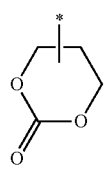
(r-cr-1-4)

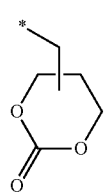
(r-cr-1-5)

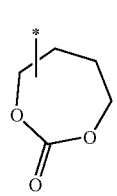
(r-cr-1-6)

-continued

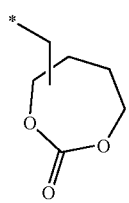
(r-cr-1-7)

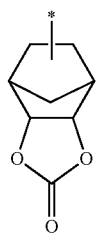
(r-cr-2-1)

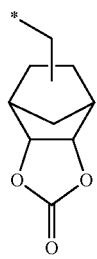
(r-cr-2-2)

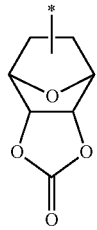
(r-cr-2-3)

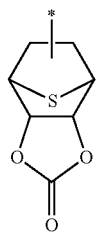
(r-cr-2-4)

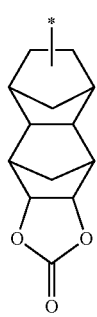
(r-cr-3-1)

-continued (r-cr-3-2)

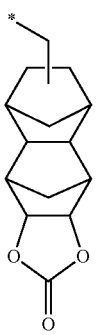

(r-cr-3-3)

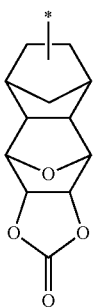

(r-cr-3-4)

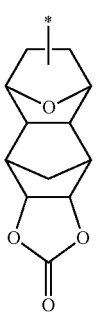

(r-cr-3-5)

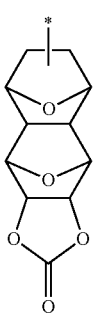

As the structural unit (a2), a structural unit derived from an acrylate ester which may have the hydrogen atom bonded to a carbon atom at the α-position substituted with a substituent is preferable.

The structural unit (a2) is preferably a structural unit represented by general formula (a2-1) shown below.

[Chem. 51]

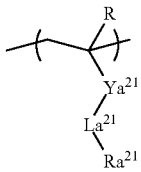

(a2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represent —CO—; and $Ra^{21}$ represents a lactone-containing cyclic group, a carbonate-containing cyclic group or an —$SO_2$— containing cyclic group.

In the formula (a2-1), R is the same as defined above. As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In the formula (a2-1), the divalent linking group for $Ya^{21}$ is not particularly limited, and preferable examples thereof include a divalent hydrocarbon group which may have a substituent and a divalent linking group containing a hetero atom. The divalent hydrocarbon group which may have a substituent and the divalent linking group containing a hetero atom for $Ya^{21}$ are the same as defined for the divalent hydrocarbon group which may have a substituent and the divalent linking group containing a hetero atom described above in relation to $Ya^{x1}$ in general formula (a10-1).

$Ya^{21}$ preferably represents an ester bond [—C(=O)—O—], an ether bond (—O—), a linear or branched alkylene group, a combination of these, or a single bond.

In the formula (a2-1), $Ra^{21}$ represents a lactone-containing cyclic group, an —$SO_2$— containing cyclic group or a carbonate-containing cyclic group.

Preferable examples of the lactone-containing cyclic group, the —$SO_2$— containing cyclic group and the carbonate-containing cyclic group for $Ra^{21}$ include groups represented by general formulae (a2-r-1) to (a2-r-7), groups represented by general formulae (a5-r-1) to (a5-r-4) and groups represented by general formulae (ax3-r-1) to (ax3-r-3).

Among the above examples, a lactone-containing cyclic group or a —$SO_2$-containing cyclic group is preferable, and a group represented by general formula (a2-r-1), (a2-r-2), (a2-r-6) or (a5-r-1) is more preferable. Specifically, a group represented by any of chemical formulae (r-1c-1-1) to (r-1c-1-7), (r-1c-2-1) to (r-1c-2-18), (r-1c-6-1), (r-s1-1-1) and (r-s1-1-18) is still more preferable.

As the structural unit (a2) contained in the component (A1), 1 kind of structural unit may be used, or 2 or more kinds may be used.

When the component (A1) contains the structural unit (a2), the amount of the structural unit (a2) based on the combined total (100 mol %) of all structural units constituting the component (A1) is preferably 1 to 50 mol %, more preferably 5 to 45 mol %, still more preferably 10 to 40 mol %, and most preferably 10 to 30 mol %.

When the amount of the structural unit (a2) is at least as large as the lower limit of the above preferable range, the effect of using the structural unit (a2) can be satisfactorily achieved. On the other hand, when the amount of the structural unit (a2) is no more than the upper limit of the above preferable range, a good balance can be achieved with the other structural units, and various lithography properties and pattern shape can be improved.

<<Structural Unit (a3)>>

The component (A1) may have, in addition to the structural unit (a1), a structural unit (a3) containing a polar group-containing aliphatic hydrocarbon group (provided that the structural units that fall under the definition of structural units (a1) and (a2) are excluded). When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to a carbon atom at the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid.

On the other hand, in the structural unit (a3), when the hydrocarbon group within the polar group-containing aliphatic hydrocarbon group is a polycyclic group, structural units represented by formulas (a3-1), (a3-2), and (a3-3) shown below are preferable.

[Chem. 52]

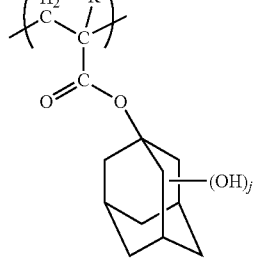

(a3-1)

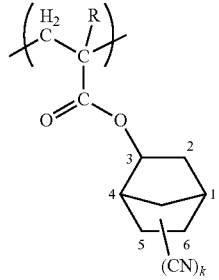

(a3-2)

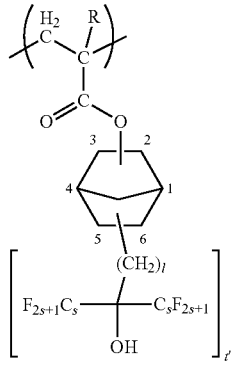

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1.1 is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), one type of structural unit may be used, or two or more types thereof may be used in combination.

When the component (A1) contains the structural unit (a3), the amount of the structural unit (a3) within the component (A1) based on the combined total of all structural units constituting the component (A1) is preferably 1 to 40 mol %, more preferably 2 to 30 mol %, still more preferably 5 to 25 mol %, and still more preferably 5 to 20 mol %.

When the amount of the structural unit (a3) is at least as large as the lower limit of the above preferable range, the effect of using the structural unit (a3) may be satisfactorily achieved. On the other hand, when the amount of the structural unit (a3) is no more than the upper limit of the above preferable range, a good balance may be achieved with the other structural units, and various lithography properties may be improved.

<<Other Structural Units>>

The component (A1) may further include a structural unit other than the structural units (a10), (a1), (a2) and (a3).

Examples of other structural units include a structural unit (a9) represented by general formula (a9-1) described later, a structural unit derived from styrene (provided that the structural units that fall under the definition of structural unit (a10) are excluded).

(Structural Unit (a9)):

The structural unit (a9) is represented by general formula (a9-1) shown below.

[Chem. 53]

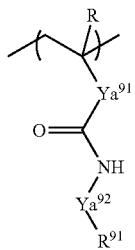

(a9-1)

In the formula, R represents a hydrogen atom, an alkyl group of 1 to 5 carbon atoms or a halogenated alkyl group of 1 to 5 carbon atoms; $Ya^{91}$ represents a single bond or a divalent linking group; $Ya^{92}$ represents a divalent linking group; and $R^{91}$ represents a hydrocarbon group which may have a substituent.

In the general formula (a9-1), R is the same as defined above.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In general formula (a9-1), the divalent linking group for $Ya^{91}$ is the same as defined for the divalent linking group for $Ya^{x1}$ in the aforementioned general formula (a10-1). Among these, $Ya^{91}$ is preferably a single bond.

In general formula (a9-1), the divalent linking group for $Ya^{92}$ is the same as defined for the divalent linking group for $Ya^{x1}$ in the aforementioned general formula (a10-1).

With respect to the divalent linking group for $Ya^{92}$, as the divalent hydrocarbon group which may have a substituent, a linear or branched aliphatic hydrocarbon group is preferable.

In the case where $Ya^{92}$ represents a divalent linking group containing a hetero atom, examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O—, C(=S), a group represented by general formulae —Y$^{21}$—O—Y$^{22}$—, —Y$^{21}$—O—, —Y$^{21}$—C(=O)—O—, —C(=O)—O—Y$^{21}$, —[Y$^{21}$—C(=O)—O]$_{m'}$—Y$^{22}$— or —Y$^{21}$—O—C(=O)—Y$^{22}$-[in the formulae, Y$^{21}$ and Y$^{22}$ each independently represent a divalent hydrocarbon group which may have a substituent, and O represents an oxygen atom; and m' represents an integer of 0 to 3]. Among these examples, —C(=O)— and —C(=S)— are preferable.

In general formula (a9-1), examples of the hydrocarbon group for $R^{91}$ include an alkyl group, a monovalent alicyclic hydrocarbon group, an aryl group and an aralkyl group.

The alkyl group for $R^{91}$ preferably has 1 to 8 carbon atoms, more preferably 1 to 6 carbon atoms, and still more preferably 1 to 4 carbon atoms. The alkyl group may be linear or branched. Specific examples of preferable alkyl groups include a methyl group, an ethyl group, a propyl group, a butyl group, a hexyl group and an octyl group.

The monovalent alicyclic hydrocarbon group for $R^{91}$ preferably has 3 to 20 carbon atoms, and more preferably 3 to 12 carbon atoms. The monovalent alicyclic hydrocarbon group may be polycyclic or monocyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobomane, tricyclodecane and tetracyclododecane.

The aryl group for $R^{91}$ preferably has 6 to 18 carbon atoms, and more preferably 6 to 10 carbon atoms. Specifically, a phenyl group is particularly desirable.

As the aralkyl group for $R^{91}$, an aralkyl group in which an alkylene group having 1 to 8 carbon atoms has been bonded to the aforementioned "aryl group for $R^{91}$" is preferable, an aralkyl group in which an alkylene group of 1 to 6 carbon atoms has been bonded to the aforementioned "aryl group for $R^{91}$" is more preferable, and an aralkyl group in which an alkylene group having 1 to 4 carbon atoms has been bonded to the aforementioned "aryl group for $R^{91}$" is most preferable.

The hydrocarbon group for $R^{91}$ preferably has some or all of the hydrogen atoms within the hydrocarbon group substituted with fluorine, and the hydrocarbon group more preferably has 30 to 100% of the hydrogen atoms substituted with fluorine. Among these, a perfluoroalkyl group in which all of the hydrogen atoms within the alkyl group have been substituted with fluorine atoms is particularly desirable.

The hydrocarbon group for $R^{91}$ may have a substituent. Examples of the substituent include a halogen atom, an oxo group (=O), a hydroxy group (—OH), an amino group (—NH$_2$) and —SO$_2$—NH$_2$. Further, part of the carbon atoms constituting the hydrocarbon group may be substituted with a substituent containing a hetero atom. Examples of the substituent containing a hetero atom include —O—, —NH—, —N=, —C(=O)—O—, —S—, —S(=O)$_2$— and —S(=O)$_2$—O—.

As the hydrocarbon group for $R^{91}$, examples of the hydrocarbon group having a substituent include lactone-containing cyclic groups represented by the aforementioned general formulae (a2-r-1) to (a2-r-7).

Further, as $R^{91}$, examples of the hydrocarbon group having a substituent include —$SO_2$— containing cyclic groups represented by general formulae (a5-r-1) to (a5-r-4); and substituted aryl groups and monocyclic heterocyclic groups represented by chemical formulae shown below.

[Chem. 54]

-continued

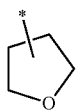 (r-hr-11)

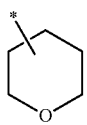 (r-hr-12)

 (r-hr-13)

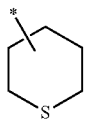 (r-hr-14)

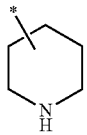 (r-hr-15)

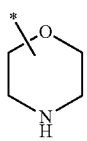 (r-hr-16)

As the structural unit (a9), a structural unit represented by general formula (a9-1) shown below is preferable.

[Chem. 55]

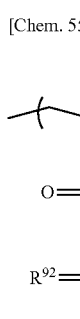 (a9-1-1)

In the formula, R is the same as defined above; $Ya^{91}$ represents a single bond or a divalent linking group; $R^{91}$ represents a hydrocarbon group optionally having a substituent; and $Ya^{92}$ represents an oxygen atom or a sulfur atom.

In general formula (a9-1-1), $Ya^{91}$, $R^{91}$ and R are the same as defined above.

$R^{92}$ represents an oxygen atom or a sulfur atom.

Specific examples of structural units represented by general formula (a9-1) or (a9-1-1) are shown below. In the following formulae, Ra represents a hydrogen atom, a methyl group or a trifluoromethyl group.

[Chem. 56]

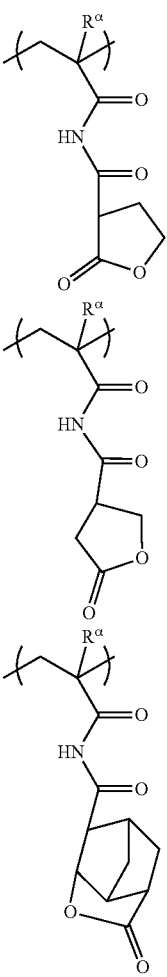

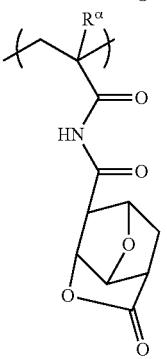

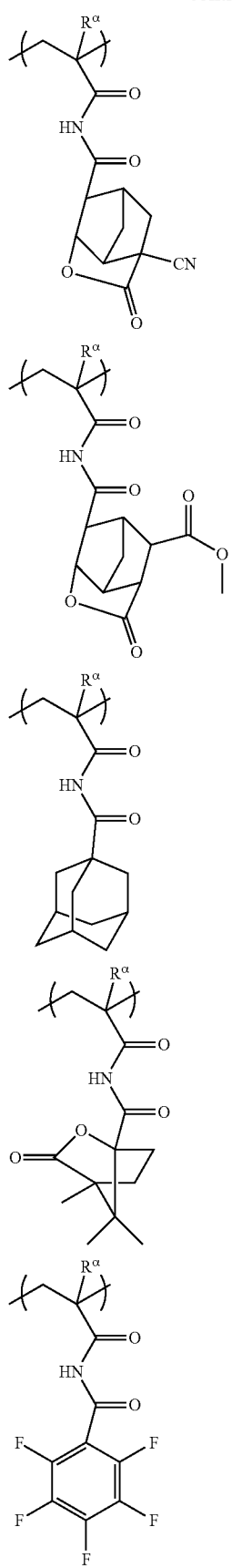
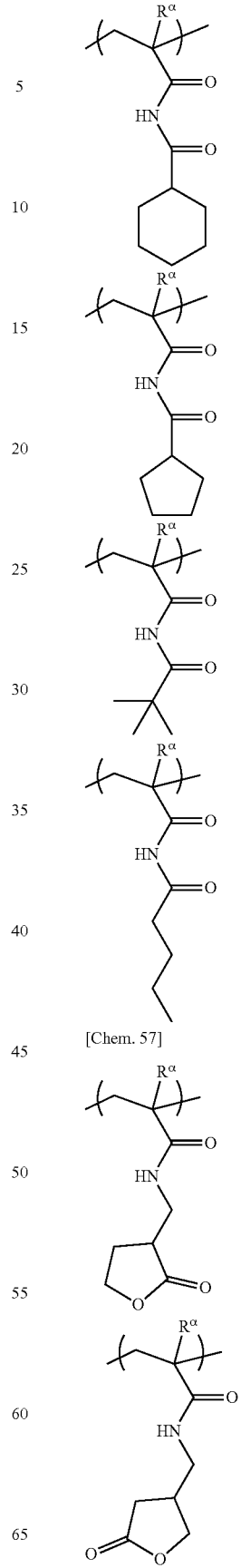
[Chem. 57]

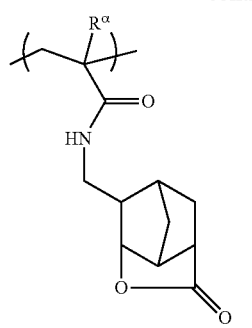
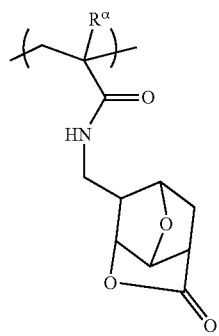
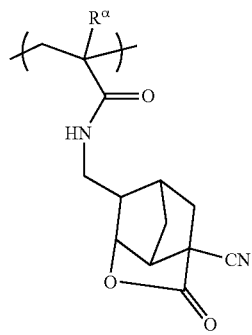
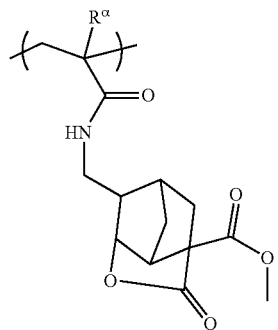
[Chem. 58]
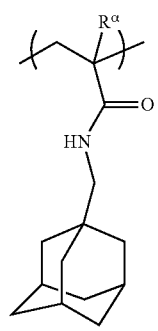
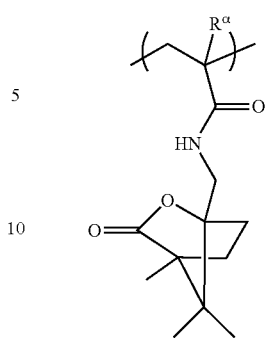
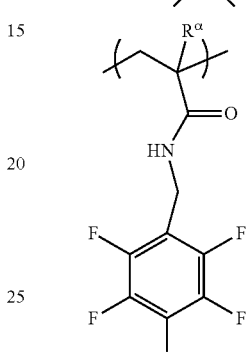
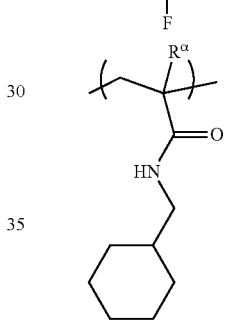
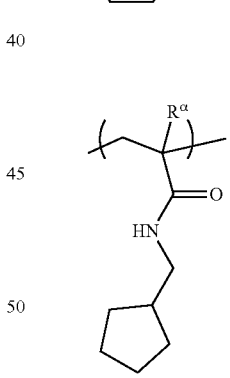
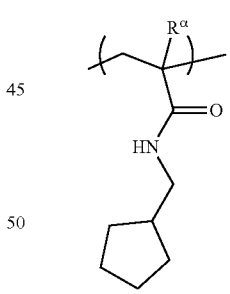

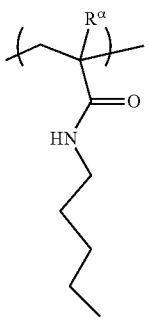

As the structural unit (a9) contained in the component (A1), 1 kind of structural unit may be used, or 2 or more kinds may be used.

When the component (A1) contains the structural unit (a9), the amount of the structural unit (a9) based on the combined total (100 mol %) of all structural units constituting the component (A1) is preferably 1 to 40 mol %, more preferably 3 to 30 mol %, still more preferably 5 to 25 mol %, and most preferably 10 to 20 mol %.

When a proportion of the structural unit (a9) is set to a lower limit or more, for example, effects of appropriately adjusting an acid diffusion length, improving adhesion of a resist film to a substrate, appropriately adjusting solubility during development, improving etching resistance and the like are obtained, and when the proportion thereof is an upper limit or less, a balance with other structural units can be achieved, and various lithography properties become favorable.

In the resist composition, as the component (A), one kind of compound may be used alone, or two or more kinds thereof may be used in combination.

The component (A1) preferably contains a high-molecular-weight compound (A1-1) having a structural unit (a1) (hereinafter referred to as a "component (A1-1)").

Examples of a preferable component (A1-1) include a high-molecular-weight compound having a structure in which a structural unit (a1) and a structural unit (a2) are repeated, and a high-molecular-weight compound having a structure in which a structural unit (a1) and a structural unit (a10) are repeated.

In addition to the combination of the above two structural units, as additional third or more structural units, the structural units described above may be appropriately combined according to a desired effect. Examples of a preferable third structural unit include a structural unit (a3).

The component (A1) can be produced, for example, by dissolving the monomers corresponding to each of the structural units in a polymerization solvent, followed by addition of a radical polymerization initiator such as azobisisobutyronitrile (AIBN) or dimethyl-2,2'-azobisisoutyrate (e.g., V-601). Alternatively, the component (A1) can be produced by dissolving a monomer that derives a structural unit (a1) and a precursor monomer (a monomer with a protected functional group) that derives a structural unit other than the structural unit (a1) as necessary in a polymerization solvent, adding the above radical polymerization initiator thereto for polymerization, and then causing a deprotection reaction. In the polymerization, a chain transfer agent such as HS—$CH_2$—$CH_2$—$CH_2$—$C(CF_3)_2$—OH may be used to introduce a —$C(CF_3)_2$—OH group at the terminal(s) of the polymer. Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography (GPC)) of the component (A1) is not particularly limited, but is preferably 1,000 to 50,000, more preferably 2,000 to 30,000, and still more preferably 3,000 to 20,000.

When the Mw of the component (A1) is no more than the upper limit of the above-mentioned preferable range, the resist composition exhibits a satisfactory solubility in a resist solvent. On the other hand, when the Mw of the component (A1) is at least as large as the lower limit of the above-mentioned preferable range, dry etching resistance and the cross-sectional shape of the resist pattern become satisfactory.

The dispersity (Mw/Mn) of the component (A1) is not particularly limited, but is preferably 1.0 to 4.0, more preferably 1.0 to 3.0, and most preferably 1.1 to 2.0. Here, Mn is the number average molecular weight.

Component (A2)

In the resist composition of the present embodiment, as the component (A), "a base component which exhibits changed solubility in a developing solution under the action of an acid" other than the component (A1) (hereafter, referred to as "component (A2)") may be used in combination.

As the component (A2), there is no particular limitation, and any of the multitude of conventional base resins used within chemically amplified resist compositions may be arbitrarily selected for use.

As the component (A2), one kind of a polymer or a low-molecular-weight compound may be used alone, or two or more thereof may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1-1) is 25% by weight or more, a resist pattern with improved lithography properties such as improvement in roughness may be reliably formed. Such effects are significant in lithography using an electron beam or EUV.

In the resist composition of the present embodiment, the amount of the component (A) may be appropriately adjusted depending on the thickness of the resist film to be formed, and the like.

<Compound (BD1-1)>

In the resist composition of the present embodiment, the component (BD1-1) is a compound having an anion moiety and a cation moiety and which is represented by the following general formula (bd1-1).

[Chem. 59]

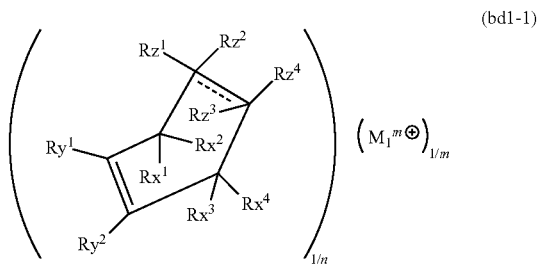

In the formula, $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 60]

----- represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_1^{m+}$ is a cation represented by general formula (ca-0) shown below:

[Chem. 61]

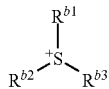

(ca-0)

in the formula, $R^{b1}$ represents an aryl group which may have a substituent; $R^{b2}$ and $R^{b3}$ each independently represent an aryl group which may have a substituent or an alkyl group which may have a substituent; $R^{b2}$ and $R^{b3}$ may be mutually bonded to form a ring with the sulfur atom; provided that at least one of $R^{b1}$ to $R^{b3}$ has a substituent containing a sulfonyl group.

Anion Moiety

In the formula (bd1-1), $Rx^1$ to $Rx^4$ each independently represent a hydrocarbon group or a hydrogen atom which may have a substituent or two or more of $Rx^1$ to $Rx^4$ may be mutually bonded to form a ring structure.

$Ry^1$ to $Ry^2$ each independently represent a hydrocarbon group or a hydrogen atom which may have a substituent or may be mutually bonded to form a ring structure.

$Rz^1$ to $Rz^4$ each independently represent, where valence allows, represent a hydrocarbon group or a hydrogen atom which may have a substituent, or two or more of $Rz^1$ to $Rz^4$ may be mutually bonded to form a ring structure.

The hydrocarbon group for $Rx^1$ to $Rx^4$, $Ry^1$ to $Ry^2$, and $Rz^1$ to $Rz^4$ may be an aliphatic hydrocarbon group, an aromatic hydrocarbon group, a cyclic hydrocarbon group, or a chain-like hydrocarbon group.

Examples of the hydrocarbon group which may have a substituent in $Rx^1$ to $Rx^4$, $Ry^1$ to $Ry^2$, and $Rz^1$ to $Rz^4$ include a cyclic group which may have a substituent, a linear alkyl group which may have a substituent, and a chain-like alkenyl group which may have a substituent.

Cyclic Group which May have a Substituent:

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated. In addition, the cyclic hydrocarbon group for $Rx^1$ to $Rx^4$, $Ry^1$ to $Ry^2$, and $Rz^1$ to $Rz^4$ may contain a hetero atom such as a heterocycle.

The aromatic hydrocarbon group for $Rx^1$ to $Rx^4$, $Ry^1$ to $Ry^2$, and $Rz^1$ to $Rz^4$ is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 10 carbon atoms. Here, the number of carbon atoms within a substituent(s) is not included in the number of carbon atoms of the aromatic hydrocarbon group.

Examples of the aromatic ring of the aromatic hydrocarbon group for $Rx^1$ to $Rx^4$, $Ry^1$ to $Ry^2$, and $Rz^1$ to $Rz^4$ include, specifically, benzene, fluorene, naphthalene, anthracene, phenanthrene, biphenyl, or aromatic heterocycles in which some of carbon atoms constituting such an aromatic ring are substituted with hetero atoms.

Examples of the hetero atom within the aromatic hetero rings include an oxygen atom, a sulfur atom and a nitrogen atom. The aromatic ring of the aromatic hydrocarbon group for $Rx^1$ to $Rx^4$, $Ry^1$ to $Ry^2$, and $Rz^1$ to $Rz^4$ preferably does not contain a hetero atom in consideration of compatibility with the component (A), and aromatic rings such as benzene, fluorene, naphthalene, anthracene, phenanthrene, and biphenyl are more preferable.

Specific examples of the aromatic hydrocarbon group for $Rx^1$ to $Rx^4$, $Ry^1$ to $Ry^2$, and $Rz^1$ to $Rz^4$ include a group in which one hydrogen atom is removed from the aromatic ring (an aryl group: for example, a phenyl group and a naphthyl group), and a group in which one hydrogen atom of the aromatic ring is substituted with an alkylene group (for example, an arylalkyl group such as a benzyl group, a phenethyl group, a 1-naphthylmethyl, group, a 2-naphthylmethyl group, a 1-naphthylethyl group, and a 2-naphthylethyl group). The alkylene group (alkyl chain within the arylalkyl group) preferably has 1 to 4 carbon atoms, more preferably 1 or 2, and most preferably 1.

Examples of the cyclic aliphatic hydrocarbon group for $Rx^1$ to $Rx^4$, $Ry^1$ to $Ry^2$, and $Rz^1$ to $Rz^4$ include an aliphatic hydrocarbon group having a ring in the structure.

As examples of the hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the polycyclic group preferably has 7 to 30 carbon atoms. Among polycycloalkanes, a polycycloalkane having a bridged ring polycyclic skeleton, such as adamantane, norbornane, isobornane, tricyclodecane or tetracyclodpdecane, and a polycycloalkane having a condensed ring polycyclic skeleton, such as a cyclic group having a steroid skeleton are preferable.

Among these, regarding the cyclic aliphatic hydrocarbon group for $Rx^1$ to $Rx^4$, $Ry^1$ to Rye, and $Rz^1$ to $Rz^4$, a group in which one or more hydrogen atoms are removed from a monocycloalkane or polycycloalkane is preferable, a group in which one hydrogen atom is removed from a monocycloalkane is more preferable, and a group in which one hydrogen atom is removed from cyclopentane or cyclohexane is particularly preferable.

The linear aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms. As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$-] and a pentamethylene group [—$(CH_2)_5$—].

The branched aliphatic hydrocarbon group which may be bonded to the alicyclic hydrocarbon group preferably has 2 to 10 carbon atoms, more preferably 3 to 6 carbon atoms, still more preferably 3 or 4 carbon atoms, and most preferably 3 carbon atoms. As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

In addition, examples of the cyclic group for $Rx^1$ to $Rx^4$, $Ry^1$ to $Ry^2$, and $Rz^1$ to $Rz^4$ include —$COOR^{xyz}$ and —$OC(=O)R^{xyz}$ in which $R^{xyz}$ is a lactone-containing cyclic group, a carbonate-containing cyclic group, or a cyclic group containing —$SO_2$—.

Examples of the substituent in the cyclic group for $Rx^1$ to $Rx^4$, $Ry^1$ to $Ry^2$, and $Rz^1$ to $Rz^4$ include an alkyl group, an alkoxy group, a halogen atom, a halogenated alkyl group, a hydroxyl group, a nitro group, and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which some or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

The carbonyl group as the substituent is a group that substitutes a methylene group (—$CH_2$—) constituting the cyclic hydrocarbon group.

Among these, regarding the substituent in the cyclic group for $Rx^1$ to $Rx^4$, $Ry^1$ to $Ry^2$, and $Rz^1$ to $Rz^4$, in consideration of compatibility with the component (A), an alkyl group, a halogen atom, a halogenated alkyl group, and the like are preferable, and an alkyl group is more preferable.

Linear Alkyl Group which May have a Substituent:

The linear alkyl group for $Rx^1$ to $Rx^4$, $Ry^1$ to $Ry^2$, and $Rz^1$ to $Rz^4$ may be linear or branched.

The linear alkyl group preferably has 1 to 20 carbon atoms, more preferably 1 to 15 carbon atoms, and still more preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15 carbon atoms, and still more preferably 3 to 10 carbon atoms. Specific examples thereof include a 1-methylethyl group, a 1,1-dimethylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-Like Alkenyl Group which May have a Substituent:

The chain-like alkenyl group for $Rx^1$ to $Rx^4$, $Ry^1$ to $Ry^2$, $Rz^1$ to $Rz^4$ may be linear or branched, and preferably has 2 to 10 carbon atoms, more preferably has 2 to 5 carbon atoms, still more preferably has 2 to 4 carbon atoms, and particularly preferably has 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

Examples of the substituent in a linear alkyl group or alkenyl group for $Rx^1$ to $Rx^4$, $Ry^1$ to $Ry^2$, and $Rz^1$ to $Rz^4$ include an alkoxy group, a halogen atom (a fluorine atom, a chlorine atom, a bromine atom, an iodine atom, etc.), a halogenated alkyl group, a hydroxyl group, a carbonyl group, a nitro group, an amino group, and the cyclic groups for $Rx^1$ to $Rx^4$, $Ry^1$ to $Ry^2$, and $Rz^1$ to $Rz^4$. Among these, regarding the linear alkyl group or alkenyl group for $Rx^1$ to $Rx^4$, $Ry^1$ to $Ry^2$, and $Rz^1$ to $Rz^4$, in consideration of compatibility with the component (A), a halogen atom, a halogenated alkyl group, groups exemplified as the cyclic groups for $Rx^1$ to $Rx^4$, $Ry^1$ to $Ry^2$, and $Rz^1$ to $Rz^4$, and the like are preferable, and groups exemplified as the cyclic groups for $Rx^1$ to $Rx^4$, $Ry^1$ to $Ry^2$, and $Rz^1$ to $Rz^4$ are more preferable.

Regarding the hydrocarbon group for $Rx^1$ to $Rx^4$, $Ry^1$ to $Ry^2$, and $Rz^1$ to $Rz^4$, a cyclic group which may have a substituent and a linear alkyl group which may have a substituent are preferable among the above hydrocarbon groups.

In the formula (bd1-1), $Ry^1$ to $Ry^2$ may be mutually bonded to form a ring structure.

Such a ring structure formed of $Ry^1$ to $Ry^2$ shares one side (a bond between carbon atoms to which $Ry^1$ and $Ry^2$ are bonded) of a 6-membered ring in the formula (bd1-1), and the ring structure may be an alicyclic hydrocarbon or aromatic hydrocarbon ring. In addition, the ring structure may be a polycyclic structure composed of other ring structures.

An alicyclic hydrocarbon formed of $Ry^1$ to $Ry^2$ may be polycyclic or monocyclic. As a monocyclic alicyclic hydrocarbon, a monocycloalkane is preferable. The monocycloalkane preferably has 3 to 6 carbon atoms, and specific examples thereof include cyclopentane and cyclohexane. As a polycyclic alicyclic hydrocarbon, a polycycloalkane is preferable.

The polycycloalkane preferably has 7 to 30 carbon atoms. Specific examples of the polycycloalkane include a polycycloalkane having a polycyclic skeleton with a bridged ring, such as adamantane, norbornane, isobornane, tricyclodecane or tetracyclododecane; and a polycycloalkane having a polycyclic skeleton with a condensed ring, such as a cyclic ring having a steroid skeleton.

Examples of an aromatic hydrocarbon ring formed of $Ry^1$ to $Ry^2$ include benzene, fluorene, naphthalene, anthracene, phenanthrene, biphenyl, and an aromatic heterocycle in which some of carbon atoms constituting such an aromatic ring are substituted with a hetero atom.

An aromatic hydrocarbon ring formed of $Ry^1$ to $Ry^2$ preferably does not contain a hetero atom in consideration of compatibility with the component (A), and an aromatic ring such as benzene, fluorene, naphthalene, anthracene, phenanthrene, and biphenyl is more preferable.

A ring structure (alicyclic hydrocarbon, aromatic hydrocarbon) formed of $Ry^1$ to $Ry^2$ may have a substituent. Examples of the substituent here include those the same as for the above substituent (for example, an alkyl group, an alkoxy group, a halogen atom, a halogenated alkyl group, a hydroxyl group, a nitro group, and a carbonyl group) for the cyclic group for $Rx^1$ to $Rx^4$, $Ry^1$ to $Ry^2$, and $Rz^1$ to $Rz^4$. Among these, regarding the substituent for the ring structure formed of $Ry^1$ to $Ry^2$, in consideration of compatibility with the component (A), an alkyl group, a halogen atom, a halogenated alkyl group, and the like are preferable, and an alkyl group is more preferable.

Regarding the ring structure formed of $Ry^1$ to $Ry^2$, among these, in consideration of short diffusion of an acid generated upon exposure and an ability to control acid diffusion, an aromatic hydrocarbon which may have a substituent is more preferable.

In the formula (bd1-1), two or more of $Rz^1$ to $Rz^4$ may be mutually bonded to form a ring structure. For example, $Rz^1$ may form a ring structure with any of $Rz^2$ to $Rz^4$. Specifically, a ring structure sharing one side (a bond between a carbon atom to which $Rz^1$ and $Rz^2$ are bonded and a carbon atom to which $Rz^3$ and $Rz^4$ are bonded) of a 6-membered ring in the formula (bd1-1), a ring structure formed by bonding $Rz^1$ and $Rz^2$, a ring structure formed by bonding $Rz^3$ and $Rz^4$, and the like may be exemplified.

Such a ring structure formed of two or more of $Rz^1$ to $Rz^4$ may be an alicyclic hydrocarbon or aromatic hydrocarbon ring, and an aromatic hydrocarbon ring is particularly preferable.

In addition, the ring structure may be a polycyclic structure composed of other ring structures.

An alicyclic hydrocarbon ring formed of two or more of $Rz^1$ to $Rz^4$ may be polycyclic or monocyclic. As a monocyclic alicyclic hydrocarbon, a monocycloalkane is preferable. The monocycloalkane preferably has 3 to 6 carbon atoms, and specific examples thereof include cyclopentane and cyclohexane. As a polycyclic alicyclic hydrocarbon, a polycycloalkane is preferable. The polycycloalkane preferably has 7 to 30 carbon atoms. Specific examples of the polycycloalkane include a polycycloalkane having a polycyclic skeleton with a bridged ring, such as adamantane, norbornane, isobornane, tricyclodecane or tetracyclododecane; and a polycycloalkane having a polycyclic skeleton with a condensed ring, such as a cyclic ring having a steroid skeleton.

A heterocyclic structure in which some of carbon atoms are substituted with a hetero atom may be exemplified, and a nitrogen-containing heterocycle is particularly preferable, and specifically a cyclic imide and the like may be exemplified.

Examples of an aromatic hydrocarbon ring formed of two or more of $Rz^1$ to $Rz^4$ include benzene, fluorene, naphthalene, anthracene, phenanthrene, biphenyl, and an aromatic heterocycle in which some of carbon atoms constituting such an aromatic ring are substituted with a hetero atom. An aromatic hydrocarbon ring formed of two or more of $Rz^1$ to $Rz^4$ preferably does not contain a hetero atom in consideration of compatibility with the component (A), and an aromatic ring such as benzene, fluorene, naphthalene, anthracene, phenanthrene, and biphenyl is more preferable.

A ring structure (alicyclic hydrocarbon, aromatic hydrocarbon) formed of $Rz^1$ to $Rz^4$ may have a substituent. Examples of the substituent here include those the same as for the above substituent (for example, an alkyl group, an alkoxy group, a halogen atom, a halogenated alkyl group, a hydroxyl group, a nitro group, and a carbonyl group) for the cyclic group for $Rx^1$ to $Rx^4$, $Ry^1$ to Rye, and $Rz^1$ to $Rz^4$. Among these, regarding the substituent for the ring structure formed of $Rz^1$ to $Rz^4$, in consideration of compatibility with the component (A), an alkyl group, a halogen atom, a halogenated alkyl group, and the like are preferable, and an alkyl group is more preferable.

Regarding the ring structure formed of two or more of $Rz^1$ to $Rz^4$, among these, in consideration of an ability to control diffusion of an acid generated upon exposure, a ring structure sharing one side (a bond between a carbon atom to which $Rz^1$ and $Rz^2$ are bonded and a carbon atom to which $Rz^3$ and $Rz^4$ are bonded) of a 6-membered ring in the formula (bd1-1) is preferable, and an aromatic ring structure is more preferable.

Here, in the formula (bd1-1), the meaning of "where valence allows" is as follows.

Specifically, when a bond between a carbon atom to which $Rz^1$ and $Rz^2$ are bonded and a carbon atom to which $Rz^3$ and $Rz^4$ are bonded is a single bond, all of $Rz^1$, $Rz^2$, $Rz^3$ and $Rz^4$ are present. When a bond between a carbon atom to which $Rz^1$ and $Rz^2$ are bonded and a carbon atom to which $Rz^3$ and $Rz^4$ are bonded is a double bond, only either $Rz^1$ or $Rz^2$ is present and only either $Rz^3$ or $Rz^4$ is present. In addition, for example, when $Rz^1$ and $Rz^3$ are bonded to form an aromatic ring structure, $Rz^2$ and $Rz^4$ are not present.

In the formula (bd1-1), two or more of $Rx^1$ to $Rx^4$ may be mutually bonded to form a ring structure. For example, $Rx^1$ may form a ring structure with any of $Rx^2$ to $Rx^4$.

Such a ring structure formed of two or more of $Rx^1$ to $Rx^4$ may be an alicyclic hydrocarbon or aromatic hydrocarbon ring. In addition, the ring structure may be a polycyclic structure composed of other ring structures.

An alicyclic hydrocarbon ring formed of two or more of $Rx^1$ to $Rx^4$ may be polycyclic or monocyclic. As a monocyclic alicyclic hydrocarbon, a monocycloalkane is preferable. The monocycloalkane preferably has 3 to 6 carbon atoms, and specific examples thereof include cyclopentane and cyclohexane. As a polycyclic alicyclic hydrocarbon, a polycycloalkane is preferable. The polycycloalkane preferably has 7 to 30 carbon atoms. Specific examples of the polycycloalkane include a polycycloalkane having a polycyclic skeleton with a bridged ring, such as adamantane, norbornane, isobornane, tricyclodecane or tetracyclododecane; and a polycycloalkane having a polycyclic skeleton with a condensed ring, such as a cyclic ring having a steroid skeleton.

Examples of an aromatic hydrocarbon ring formed of two or more of $Rx^1$ to $Rx^4$ include benzene, fluorene, naphthalene, anthracene, phenanthrene, biphenyl, and an aromatic heterocycle in which some of carbon atoms constituting such an aromatic ring are substituted with a hetero atom. An aromatic hydrocarbon ring formed of two or more of $Rx^1$ to $Rx^4$ preferably does not contain a hetero atom in consideration of compatibility with the component (A), and an aromatic ring such as benzene, fluorene, naphthalene, anthracene, phenanthrene, and biphenyl is more preferable.

A ring structure (alicyclic hydrocarbon, aromatic hydrocarbon) formed of $Rx^1$ to $Rx^4$ may have a substituent. Examples of the substituent here include those the same as for the above substituent (for example, an alkyl group, an alkoxy group, a halogen atom, a halogenated alkyl group, a hydroxyl group, a nitro group, and a carbonyl group) for the cyclic group for $Rx^1$ to $Rx^4$, $Ry^1$ to $Ry^2$, and $Rz^1$ to $Rz^4$. Among these, regarding the substituent for the ring structure formed of $Rx^1$ to $Rx^4$, in consideration of compatibility with the component (A), an alkyl group, a halogen atom, a halogenated alkyl group, and the like are preferable, and an alkyl group is more preferable.

Regarding a ring structure formed of two or more of $Rx^1$ to $Rx^4$, among these, in consideration of an ability to control acid diffusion, an alicyclic hydrocarbon ring is preferable.

In addition, regarding a ring structure formed of two or more of $Rx^1$ to $Rx^4$, among these, in consideration of an ability to control acid diffusion, preferably, at least one of $Rx^1$ to $Rx^2$ and at least one of $Rx^3$ to $Rx^4$ are mutually bonded to form a crosslinked ring structure, and the ring structure is more preferably an alicyclic hydrocarbon ring.

When at least one of $Rx^1$ to $Rx^2$ and at least one of $Rx^3$ to $Rx^4$ are mutually bonded to form a ring structure, the number of carbon atoms constituting a bicyclic structure (a ring structure containing carbon atoms to which $Ry^1$, $Ry^2$, $Rz^1$ and $Rz^2$, and $Rz^3$ and $Rz^4$ are bonded) is preferably 7 to 16.

In the formula (bd1-1), at least one of $Rx^1$ to $Rx^4$, $Ry^1$ to $Ry^2$ and $Rz^1$ to $Rz^4$ has an anion group, and the entire anion moiety may be an n-valent anion. n represents an integer of 1 or more;

By selecting an anion group in the molecule, in the resist composition, the component (BD1-1) functions as an acid-generator component (B) that generates an acid that acts on the base component (A) or a base component (D) that traps (controls acid diffusion) an acid that is generated from the component (B) upon exposure.

In the component (BD1-1), $Rx^1$ to $Rx^4$, $Ry^1$ to $Ry^2$, and $Rz^1$ to $Rz^4$ may be the anion group or in the component (BD1-1), when two or more of $Rx^1$ to $Rx^4$ are mutually bonded to form a ring structure, a carbon atom forming the ring structure or a hydrogen atom bonded to the carbon atom may be substituted with the anion group. When two or more of $Ry^1$ to $Ry^2$ are mutually bonded to form a ring structure, a carbon atom forming the ring structure or a hydrogen atom bonded to the carbon atom may be substituted with the anion group. When two or more of $Rz^1$ to $Rz^4$ are mutually bonded to form a ring structure, a carbon atom forming the ring structure or a hydrogen atom bonded to the carbon atom may be substituted with the anion group.

Examples of the anion group for $Rx^1$ to $Rx^4$, $Ry^1$ to $Ry^2$, and $Rz^1$ to $Rz^4$ include those having a sulfonic acid anion structure, a carboxylic acid anion structure, an imide anion structure, a methide anion structure, a carbanion structure, a borate anion structure, a halogen anion structure, a phosphoric acid anion structure, an antimony acid anion structure, an arsenic acid anion structure, or the like.

Among these, those having a sulfonic acid anion structure and those having a carboxylic acid anion structure are preferable.

Preferable examples of the anion group having a carboxylic acid anion structure include *—$V^{10}$—COO ($V^{10}$ is a single bond or an alkylene group having 1 to 20 carbon atoms).

Preferable examples of the anion group having a sulfonic acid anion structure include anion groups represented by *—$V^{11}$—$SO_3$ ($V^{11}$ is a single bond or an alkylene group having 1 to 20 carbon atoms) and the following general formula (bd1-r-an1).

In the formula (bd1-r-an1), the symbol * represents a bond. The symbol * means a bond with a carbon atom to which $Rx^1$ to $Rx^4$, $Ry^1$ to $Ry^2$, and $Rz^1$ to $Rz^4$ are bonded.

[Chem. 62]

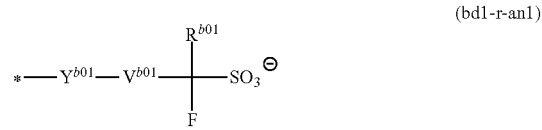

(bd1-r-an1)

In the formula, $R^{b01}$ represents a fluorinated alkyl group of 1 to 5 carbon atoms or a fluorine atom; $V^{b01}$ represents an alkylene group, a fluorinated alkylene group or a single bond; and $Y^{b01}$ represents a divalent linking group or a single bond.

In the formula (bd1-r-an1), $R^{b01}$ represents a fluorinated alkyl group having 1 to 5 carbon atoms or a fluorine atom. $R^{b01}$ is preferably a perfluoroalkyl group of 1 to 5 carbon atoms or a fluorine atom, and is more preferably a fluorine atom.

In the formula (bd1-r-an1), $V^{b01}$ represents an alkylene group, a fluorinated alkylene group or a single bond.

The alkylene group or the fluorinated alkylene group for $V^{b01}$ preferably has 1 to 4 carbon atoms, and more preferably 1 to 3 carbon atoms. Examples of the fluorinated alkyl group for $V^{b01}$ include a group in which some or all of the hydrogen atoms within an alkylene group have been substituted with a fluorine atom. Among these examples, as $V^{b01}$ an alkylene group having 1 to 4 carbon atoms, a fluorinated alkylene group having 1 to 4 carbon atoms or a single bond is preferable.

In the formula (bd1-r-an1), $Y^{b01}$ represents a bivalent linking group or a single bond.

As the divalent linking group for $Y^{b01}$, a divalent linking group containing an oxygen atom may be given as a preferable example.

In the case where $Y^{b01}$ is a divalent linking group containing an oxygen atom, $Y^{b01}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—SO$_2$—) bonded thereto.

Examples of the divalent linking group containing an oxygen atom include divalent linking groups represented by general formulae (y-a1-1) to (y-a1-8) shown below.

[Chem. 63]

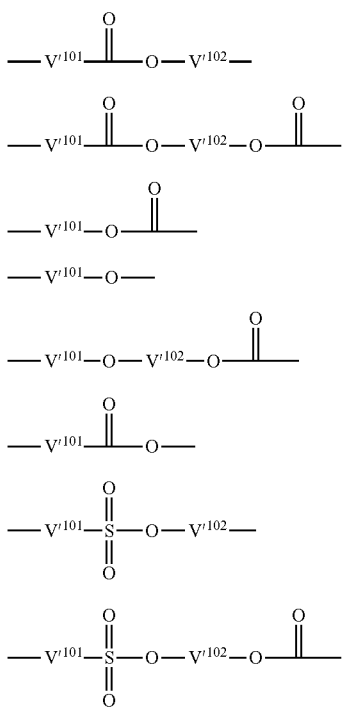

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms, more preferably an alkylene group of 1 to 10 carbon atoms, and still more preferably an alkylene group of 1 to 5 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—CH$_2$—]; an alkylmethylene group, such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; an alkylethylene group, such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; an alkyltrimethylene group, such as CH(CH$_3$)CH$_2$CH$_2$— and —CH$_2$CH(CH$_3$)CH$_2$—; a tetramethylene group [—CH$_2$CH$_2$CH$_2$CH$_2$—]; an alkyltetramethylene group, such as —CH(CH$_3$)CH$_2$CH$_2$CH$_2$—, CH$_2$CH(CH$_3$)CH$_2$CH$_2$—; and a pentamethylene group [—CH$_2$CH$_2$CH$_2$CH$_2$CH$_2$—].

Further, part of the methylene groups within the alkylene groups for $V'^{101}$ and $V'^{102}$ may be substituted with a divalent aliphatic cyclic group of 5 to 10 carbon atoms. The aliphatic cyclic group is preferably a cyclohexylene group, a 1,5-adamantylene group or a 2,6-adamantylene group.

$Y^{b01}$ is preferably a divalent linking group containing an ether bond or a divalent linking group containing an ester bond, and groups represented by the aforementioned formulas (y-a1-1) to (y-a1-6) are preferable.

Specific examples of the anion group represented by the formula (bd1-r-an1) include,
when $Y^{b01}$ is a single bond, —CH$_2$CF$_2$SO$_3$, —CF$_2$CF$_2$SO$_3$, and a fluorinated alkylsulfonate anion such as a trifluoromethanesulfonate anion and a perfluorobutanesulfonate anion.

When $Y^{b01}$ is a bivalent linking group containing an oxygen atom, anion groups represented by any of the following formulae (bd1-r-an11) to (bd1-r-an13) may be exemplified.

[Chem. 64]

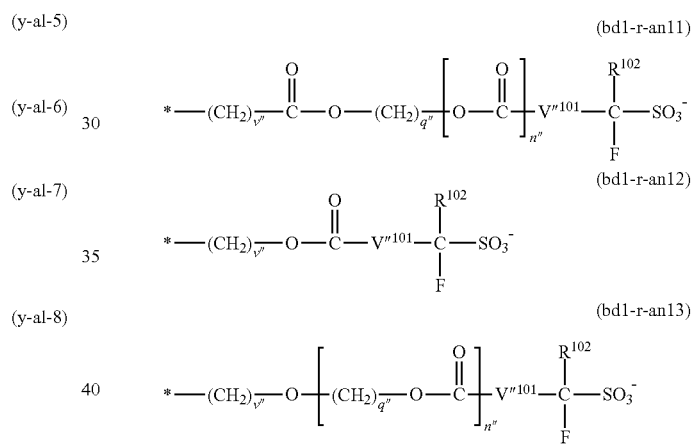

[In the formula, $V'''^{101}$ is a single bond, an alkylene group having 1 to 4 carbon atoms, or a fluorinated alkylene group having 1 to 4 carbon atoms. $R^{102}$ is a fluorine atom or a fluorinated alkyl group having 1 to 5 carbon atoms. v'''s each independently represent an integer of 0 to 3. Each q'' independently represents an integer of 1 to 20; n'' is 0 or 1.

In the formulae (bd1-r-an11) to (bd1-r-an13), $V'''^{101}$ is a single bond, an alkylene group having 1 to 4 carbon atoms, or a fluorinated alkylene group having 1 to 4 carbon atoms. $V'''^{101}$ is preferably a single bond, an alkylene group having 1 carbon atom (a methylene group), or a fluorinated alkylene group having 1 to 3 carbon atoms.

In the formulae (bd1-r-an11) to (bd1-r-an13), $R^{102}$ is a fluorine atom or a fluorinated alkyl group having 1 to 5 carbon atoms. $R^{102}$ is preferably a perfluorinated alkyl group having 1 to 5 carbon atoms or a fluorine atom and more preferably a fluorine atom.

In the formulae (bd1-r-an11) to (bd1-r-an13), v'' is an integer of 0 to 3 and is preferably 0 or 1.

q'' represents an integer of 1 to 20, preferably an integer of 1 to 10, more preferably an integer of 1 to 5, still more preferably 1, 2 or 3, and most preferably 1 or 2.

n'' is 0 or 1, and preferably 0.

The number of anion groups in the component (BD1-1) may be 1 or 2 or more, and 1 is preferable.

In the component (BD1-1), the entire anion moiety may be an n-valent anion. n represents an integer of 1 or more; m represents an integer of 1 or more, preferably 1 or 2, and more preferably 1.

Regarding the anion moiety in the component (BD1-1), in consideration of an ability to control acid diffusion, anions represented by the following general formula (bd1-an1) are preferable.

[Chem. 65]

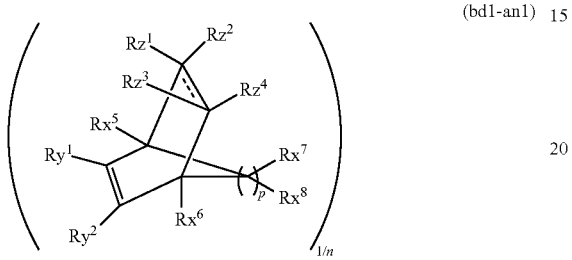

(bd1-an1)

[In the formula, $Rx^5$ to $Rx^6$ each independently represent a hydrocarbon group or a hydrogen atom which may have a substituent. $Rx^7$ to $Rx^8$ each independently represent a hydrocarbon group or a hydrogen atom which may have a substituent or may be mutually bonded to form a ring structure. When p is 1 or 2, and p=2, a plurality of $Rx^7$ to $Rx^8$ may be different from each other. $Ry^1$ to $Ry^2$ each independently represent a hydrocarbon group or a hydrogen atom which may have a substituent or may be mutually bonded to form a ring structure.

[Chem. 66]

- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^5$ to $Rx^8$, $Ry^1$ to $Ry^2$ and $Rz^1$ to $Rz^4$ has an anion group, and the entire anion moiety may be an n-valent anion. n represents an integer of 1 or more.

In the formula (bd1-an1), $Rx^5$ to $Rx^6$ each independently represent a hydrocarbon group or a hydrogen atom which may have a substituent. Description of the hydrocarbon group which may have a substituent for $Rx^5$ to $Rx^6$ is the same as that of the hydrocarbon group which may have a substituent for $Rx^1$ to $Rx^4$ in the above formula (bd1-1).

In the formula (bd1-an1), $Rx^7$ to $Rx^8$ each independently represent a hydrocarbon group or a hydrogen atom which may have a substituent, or may be mutually bonded to form a ring structure. Description of $Rx^7$ to $Rx^8$ is the same as that of $Rx^1$ to $Rx^4$ in the above formula (bd1-1).

In the formula (bd1-an1), when p is 1 or 2, and p=2, a plurality of $Rx^7$ to $Rx^8$ may be different from each other. The anion represented by the general formula (bd1-an1) has a bicycloheptane ring structure when p=1, and a bicyclooctane ring structure when p=2.

In the formula (bd1-an1), $Ry^1$ to $Ry^2$ each independently represent a hydrocarbon group or a hydrogen atom which may have a substituent, or may be mutually bonded to form a ring structure. Such $Ry^1$ to $Ry^2$ are the same as $Ry^1$ to $Ry^2$ in the above formula (bd1-1).

$Rz^1$ to $Rz^4$ each independently, where valence allows, represent a hydrocarbon group or a hydrogen atom which may have a substituent or two or more thereof may be mutually bonded to form a ring structure. Such $Rz^1$ to $Rz^4$ are the same as $Rz^1$ to $Rz^4$ in the above formula (bd1-1).

However, in the formula (bd1-an1), at least one of $Rx^5$ to $Rx^8$, $Ry^1$ to $Ry^2$, and $Rz^1$ to $Rz^4$ has an anion group, and the entire anion moiety may be an n-valent anion. n represents an integer of 1 or more;

Among the above examples, in consideration of an ability to control acid diffusion, the anion moiety in the component (BD1-1) is an anion represented by p=2 in the formula (bd1-an1), that is, an anion represented by the following general formula (bd1-an2) is more preferable.

[Chem. 67]

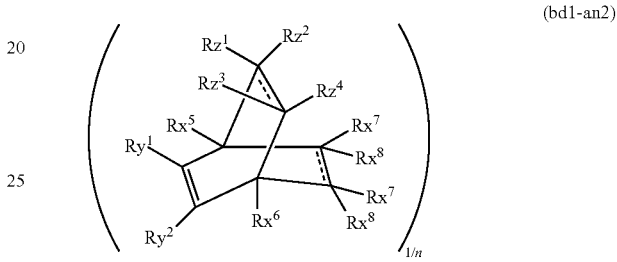

(bd1-an2)

[In the formula, $Rx^5$ to $Rx^6$ each independently represent a hydrocarbon group or a hydrogen atom which may have a substituent. A plurality of $Rx^7$ to $Rx^8$ each independently represent a hydrocarbon group or a hydrogen atom which may have a substituent, or two or more thereof may be mutually bonded to form a ring structure. $Ry^1$ to $Ry^2$ each independently represent a hydrocarbon group or a hydrogen atom which may have a substituent, or may be mutually bonded to form a ring structure.

[Chem. 68]

- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^5$ to $Rx^8$, $Ry^1$ to $Ry^2$, and $Rz^1$ to $Rz^4$ has an anion group, and the entire anion moiety may be an n-valent anion. n represents an integer of 1 or more.

In the formula (bd1-an2), $Rx^5$ to $Rx^6$, $Rx^7$ to $Rx^8$, $Ry^1$ to $Ry^2$, and $Rz^1$ to $Rz^4$ are the same as $Rx^5$ to $Rx^6$, $Rx^7$ to $Rx^8$, $Ry^1$ to $Ry^2$, and $Rz^1$ to $Rz^4$ in the above formula (bd1-1).

Here, in the formula (bd1-an2), at least one of $Rx^5$ to $Rx^8$, $Ry^1$ to $Ry^2$ and $Rz^1$ to $Rz^4$ has an anion group, and the entire anion moiety may be an n-valent anion. represents an integer of 1 or more;

In the formula (bd1-1), formula (bd1-an1), and formula (bd1-an2), in consideration of short diffusion of an acid generated upon exposure and an ability to control acid diffusion, preferably, $Ry^1$ to $Ry^2$ are mutually bonded to form a ring structure, and a ring structure to be formed is more preferably an aromatic hydrocarbon (aromatic ring, aromatic heterocycle) ring which may have a substituent.

In the formula (bd1-1), formula (bd1-an1), and formula (bd1-an2), $Rz^1$ to $Rz^4$ are preferably mutually bonded to form a ring structure in consideration of an ability to control diffusion of an acid generated upon exposure, and regarding the ring structure to be formed, a ring structure sharing one side (a bond between a carbon atom to which $Rz^1$ and $Rz^2$ are bonded and a carbon atom to which $Rz^3$ and $Rz^4$ are bonded) of a 6-membered ring in the formula is preferable, and an aromatic hydrocarbon ring (aromatic ring, aromatic heterocycle) which may have a substituent is more preferable.

In the formula (bd1-an1) and formula (bd1-an2), in consideration of short diffusion of an acid generated upon exposure and an ability to control acid diffusion, preferably, $Rx^7$ to $Rx^8$ are mutually bonded to form a ring structure, and a ring structure to be formed is more preferably an aromatic hydrocarbon ring (aromatic ring, aromatic heterocycle) which may have a substituent.

In the formula (bd1-an2), regarding a ring structure formed in $Rx^7$ to $Rx^8$, a ring structure sharing one side (a bond between the same carbon atoms to which $Rx^7$ and $Rx^8$ are bonded) of a 6-membered ring in the formula is preferable, and an aromatic hydrocarbon ring (aromatic ring, aromatic heterocycle) which may have a substituent is more preferable.

In all anions represented by the above formula (bd1-an2), the number of ring structures formed by mutually bonding $Rx^7$ to $Rx^8$, $Ry^1$ to $Ry^2$, and $Rz^1$ to $Rz^4$ may be one, two or more, and preferably two or three.

In particular, regarding the anion moiety in the component (BD1-1), anions represented by the following general formula (bd1-an3) are preferable examples thereof.

[Chem. 69]

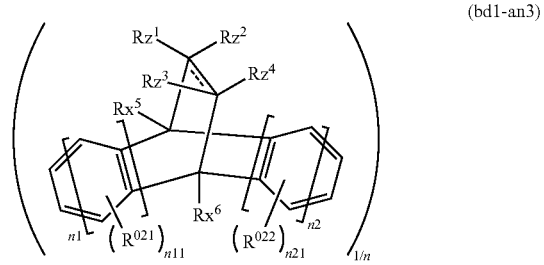

(bd1-an3)

[In the formula, $Rx^5$ to $Rx^6$ each independently represent a hydrocarbon group or a hydrogen atom which may have a substituent.

[Chem. 70]

- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^5$ to $Rx^6$ and $Rz^1$ to $Rz^4$ has an anion group, and the entire anion moiety may be an n-valent anion. n represents an integer of 1 or more; $R^{021}$ is an alkyl group, an alkoxy group, halogen atom, a halogenated alkyl group, a hydroxyl group, a carbonyl group or a nitro group. n represents an integer of 1 to 3; n11 represents an integer of 0 to 8; $R^{022}$ is an alkyl group, an alkoxy group, a halogen atom, a halogenated alkyl group, a hydroxyl group, a carbonyl group or a nitro group. n2 represents an integer of 1 to 3; and n21 represents an integer of 0 to 8.

In the formula (bd1-an3), $Rx^5$ to $Rx^6$, and $Rz^1$ to $Rz^4$ are the same as $Rx^5$ to $Rx^6$, and $Rz^1$ to $Rz^4$ in the formula (bd1-an1).

In the formula (bd1-an3), $R^{021}$ is an alkyl group, an alkoxy group, a halogen atom, a halogenated alkyl group, a hydroxy group, a carbonyl group or a nitro group.

The alkyl group for $R^{021}$ is preferably an alkyl group having 1 to 5 carbon atoms, and most preferably a methyl group, an ethyl group, a propyl group, an n-butyl group, or a tert-butyl group.

The alkoxy group for $R^{021}$ is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for $R^{021}$ include a fluorine atom, a chlorine atom, a bromine atom, and an iodine atom, and a fluorine atom is preferable.

Examples of the halogenated alkyl group for $R^{021}$ include an alkyl group having 1 to 5 carbon atoms, for example, a group in which some or all of hydrogen atoms are substituted with a halogen atom such as a methyl group, an ethyl group, a propyl group, an n-butyl group, and a tert-butyl group.

Among these, in consideration of compatibility with the component (A), $R^{021}$ is preferably an alkyl group, a halogen atom, a halogenated alkyl group or the like, and more preferably an alkyl group.

In the formula (bd1-an3), n1 is an integer of 1 to 3, preferably 1 or 2, and particularly preferably 1.

In the formula (bd1-an3), n11 is an integer of 0 to 8, preferably an integer of 0 to 4, more preferably 0, 1 or 2, and particularly preferably 0 or 1.

In the formula (bd1-an3), $R^{022}$ is an alkyl group, an alkoxy group, a halogen atom, a halogenated alkyl group, a hydroxy group, a carbonyl group or a nitro group, and those the same as $R^{021}$ may be exemplified. Among these, in consideration of compatibility with the component (A), $R^{022}$ is preferably an alkyl group, a halogen atom, a halogenated alkyl group or the like, and more preferably an alkyl group.

In the formula (bd1-an3), n2 is an integer of 1 to 3, preferably 1 or 2, and particularly preferably 1.

In the formula (bd1-an3), n21 is an integer of 0 to 8, preferably an integer of 0 to 4, more preferably 0, 1 or 2, and particularly preferably 0 or 1.

Here, in the formula (bd1-an3), at least one of $Rx^5$ to $Rx^6$ and $Rz^1$ to $Rz^4$ has an anion group, and the entire anion moiety may be an n-valent anion. n represents an integer of 1 or more;

Regarding the anion group, the above anion group represented by $*-V^{10}-COO$ ($V^{10}$ is a single bond or an alkylene group having 1 to 5 carbon atoms), and anions represented by general formula (bd1-r-an1) are preferable examples thereof.

In the formula (bd1-1), formula (bd1-an1), formula (bd1-an2), and formula (bd1-an3), in consideration of excellent effects of the present embodiment, at least one of $Rz^1$ to $Rz^4$ preferably has an anion group. When two or more of $Rz^1$ to $Rz^4$ are mutually bonded to form a ring structure, a carbon atom forming the ring structure or a hydrogen atom bonded to the carbon atom may be substituted with the anion group.

Alternatively, in the formula (bd1-an1), formula (bd1-an2), and formula (bd1-an3), in consideration of excellent effects of the present embodiment, at least one of $Rx^5$ to $Rx^6$ preferably has an anion group.

Alternatively, in the formula (bd1-an1), formula (bd1-an2), and formula (bd1-an3), in consideration of excellent effects of the present embodiment, at least one of $Rx^5$ to $Rx^6$ and $Rz^1$ to $Rz^4$ preferably has an anion group.

Specific examples of the anion moiety in the compound (BD1-1) will be described below.
[Chem. 71]
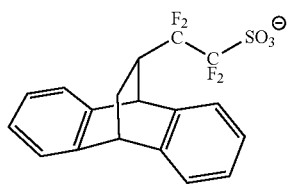
(bd1-an3-1)
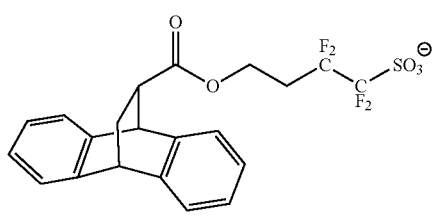
(bd1-an3-2)
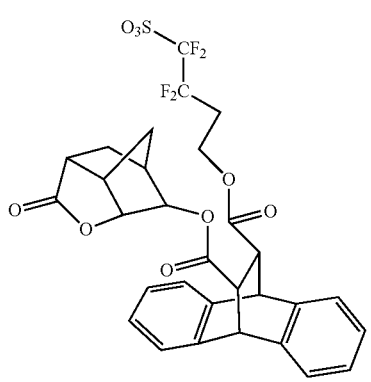
(bd1-an3-3)
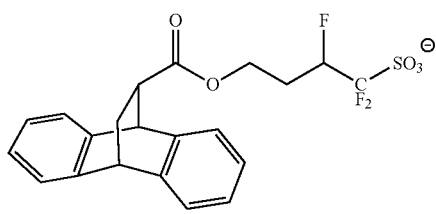
(bd1-an3-4)
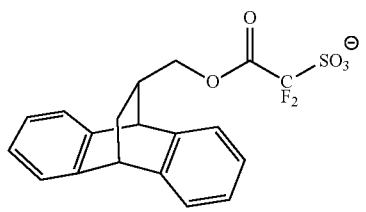
(bd1-an3-5)
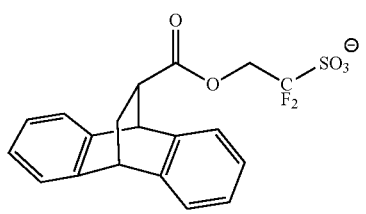
(bd1-an3-6)
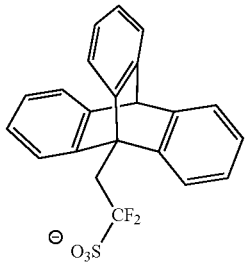
(bd1-an3-7)
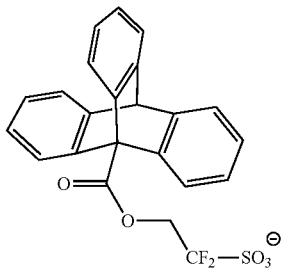
(bd1-an3-8)
[Chem. 72]
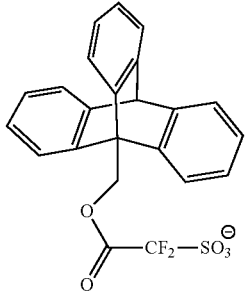
(bd1-an3-9)
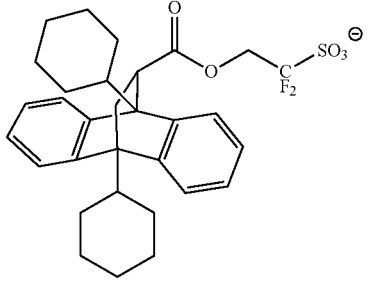
(bd1-an3-10)
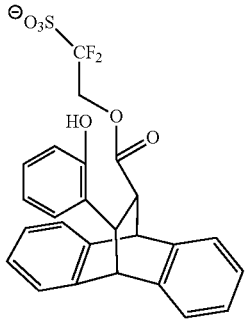
(bd1-an3-11)

-continued

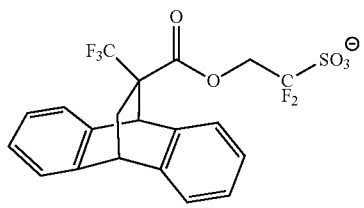
(bd1-an3-12)

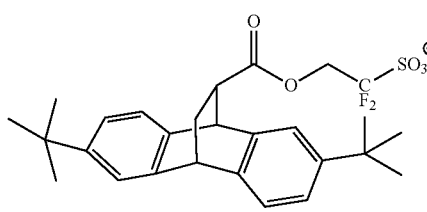
(bd1-an3-13)

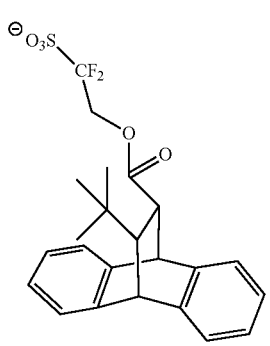
(bd1-an3-14)

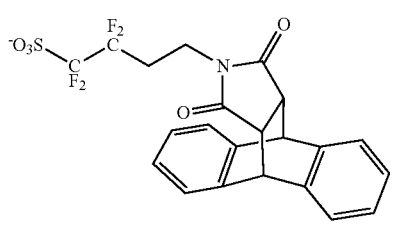
(bd1-an3-15)

[Chem. 73]

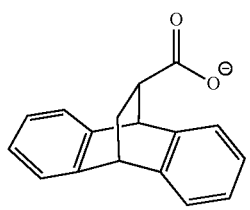
(bd1-an3-21)

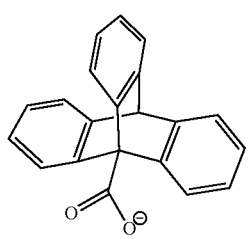
(bd1-an3-22)

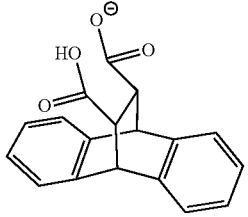
(bd1-an3-23a)

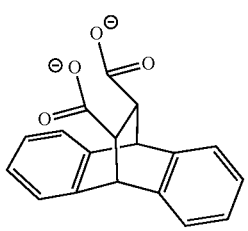
(bd1-an3-23b)

(bd1-an3-24)

Regarding the cation moiety $((M_1^{m+})_{l/m})$, in the formula (bd1-1), $M_1^{m+}$ represents a cation represented by the following general formula (ca-0). m represents an integer of 1 or more.

[Chem. 74]

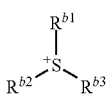
(ca-0)

In the formula, $R^{b1}$ represents an aryl group which may have a substituent; $R^{b2}$ and $R^{b3}$ each independently represent an aryl group which may have a substituent or an alkyl group which may have a substituent;

$R^{b2}$ and $R^{b3}$ may be mutually bonded to form a ring with the sulfur atom; provided that at least one of $R^{b1}$ to $R^{b3}$ has a substituent containing a sulfonyl group.

In the formula (ca-0), examples of the aryl group for $R^{b1}$ to $R^{b3}$ include a group in which one hydrogen atom is removed from an aromatic hydrocarbon ring such as benzene, naphthalene, anthracene, phenanthrene, biphenyl, and fluorene.

Among these, the aryl group for $R^{b1}$ to $R^{b3}$ is preferably a group (a phenyl group or a naphthyl group) in which one hydrogen atom is removed from benzene or naphthalene and more preferably a group (a phenyl group) in which one hydrogen atom is removed from benzene.

In the formula (ca-0), the alkyl group for $R^{b2}$ to $R^{b3}$ may be linear, branched or cyclic.

Chain Alkyl Group which May have a Substituent:

The linear alkyl group for $R^{b2}$ to $R^{b3}$ may be linear or branched.

The linear alkyl group preferably has 1 to 20 carbon atoms, more preferably 1 to 15 carbon atoms, and still more preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15 carbon atoms, and still more preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Cyclic Alkyl Group which May have a Substituent:

The cyclic alkyl group for $R^{b2}$ to $R^{b3}$ preferably has 3 to 15 carbon atoms, more preferably has 4 to 12 carbon atoms, and most preferably 5 to 10 carbon atoms.

Specifically, for example, a group in which one or more hydrogen atoms are removed from a monocycloalkane; a group in which one or more hydrogen atoms are removed from a polycycloalkane such as a bicycloalkane, a tricycloalkane, and a tetracycloalkane and the like may be exemplified. The monocycloalkane preferably has 3 to 6 carbon atoms, and specific examples thereof include cyclopentane and cyclohexane. Examples of the polycycloalkane include adamantane, norbornane, isobornane, tricyclodecane, and tetracyclododecane.

In the formula (ca-0), at least one of $R^{b2}$ to $R^{b3}$ is preferably an aryl group which may have a substituent and more preferably all of them are an aryl group which may have a substituent.

In the formula (ca-0), when $R^{b2}$ to $R^{b3}$ are mutually bonded to form a ring together with a sulfur atom in the formula, they may be bonded via a hetero atom such as a sulfur atom, an oxygen atom, and a nitrogen atom or a functional group such as a carbonyl group, —SO—, —COO—, —CONH—, or —N(RN)— (RN is an alkyl group having 1 to 5 carbon atoms). The ring containing the sulfur atom in the skeleton thereof is preferably a 3- to 10-membered ring, and most preferably a 5- to 7-membered ring. Specific examples of the ring formed include a thiophene ring, a thiazole ring, a benzothiophene ring, a thianthrene ring, a dibenzothiophene ring, a 9H-thioxanthene ring, a phenoxathiin ring, a tetrahydrothiophenium ring, and a tetrahydrothiopyranium ring.

In the formula (ca-0), at least one of $R^{b1}$ to $R^{b3}$ has a substituent containing a sulfonyl group.

Examples of the substituent containing a sulfonyl group include a monovalent group represented by —SO$_2$— $R^{b4}$ ($R^{b4}$ is a linear or branched linear alkyl group which may have a substituent, an alicyclic hydrocarbon group which may have a substituent, or an aromatic hydrocarbon group which may have a substituent).

When the substituent containing a sulfonyl group is a monovalent group represented by —SO$_2$— $R^{b4}$ ($R^{b4}$ is a linear or branched linear alkyl group which may have a substituent, an alicyclic hydrocarbon group which may have a substituent, or an aromatic hydrocarbon group which may have a substituent) and is bonded to an aryl group for $R^{b1}$, a substitution position is not particularly limited, and preferably in consideration of production, a meta position and/or a para position is preferable. Here, similarly, in the case in which $R^{b2}$ to $R^{b3}$ are an aryl group which may have a substituent, a substitution position is not particularly limited, but in consideration of production, a meta position and/or a para position is preferable.

Examples of the linear or branched linear alkyl group for $R^{b4}$ include a methyl group, an ethyl group, a propyl group, an isopropyl group, an n-butyl group, an isobutyl group, a tert-butyl group, a pentyl group, an isopentyl group, and an neopentyl group, and a methyl group or an ethyl group is preferable, and an methyl group is more preferable.

Examples of the substituent that the linear or branched linear alkyl group for $R^{b4}$ may have include a halogen atom, a halogenated alkyl group having 1 to 5 carbon atoms, an alkoxy group having 1 to 5 carbon atoms, a hydroxy group, a carbonyl group, and a carboxy group.

The alicyclic hydrocarbon group for $R^{b4}$ preferably has 3 to 20 carbon atoms, more preferably has 3 to 12 carbon atoms, and may be polycyclic or monocyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

Examples of the substituent that the alicyclic hydrocarbon group for $R^{b4}$ may have include the same groups as those for the above Re.

Examples of the aromatic hydrocarbon group for $R^{b4}$ include a group in which one hydrogen atom is removed from an aromatic hydrocarbon ring such as benzene, naphthalene, anthracene, phenanthrene, biphenyl, and fluorene.

Among these, the aryl group for $R^{b1}$ to $R^{b3}$ is preferably a group (a phenyl group or a naphthyl group) in which one hydrogen atom is removed from benzene or naphthalene, and more preferably a group (a phenyl group) in which one hydrogen atom is removed from benzene.

Examples of the substituent that the aromatic hydrocarbon group for $R^{b4}$ may have include the same groups as for the above Re.

Among these, $R^{b4}$ is preferably a linear or branched linear alkyl group or an aromatic hydrocarbon group, and more preferably a methyl group or a phenyl group.

The sulfonyl group that the cation represented by the general formula (ca-0) has may be a bivalent sulfonyl group in which one carbon atom of a ring formed of $R^{b2}$ to $R^{b3}$ that are mutually bonded to form a ring together with a sulfur atom in the formula is substituted. The bivalent sulfonyl group may be —SO$_2$—, and may be a bivalent group bonded via a functional group other than the sulfonyl group (—SO$_2$—) or an atom such as —SO$_3$—, —SO$_2$NH—, and —SO$_2$N(RN)—. In this case, a ring formed by mutually bonding $R^{b2}$ to $R^{b3}$ together with a sulfur atom in the formula is not particularly limited, and may or not have an aromatic ring. When no aromatic ring is contained, examples of a ring to be formed include a 1,4-dithiane 1,1-dioxide cyclic structure. When an aromatic ring is contained, a fused two-ring system or a fused three-ring system containing one or more benzene rings is preferable. In the case of the fused two-ring system, for example, a fused two-ring system having a benzo[1,3]dithiol 1,1-dioxide skeleton is preferable. In the case of the fused three-ring system, for example, a fused three-ring system having a thianthrene 5, 5-dioxide skeleton and the like are preferable.

In the formula (ca-0), at least one of $R^{b1}$ to $R^{b3}$ is preferably an aryl group having a substituent containing a sulfonyl group as the substituent.

In the formula (ca-0), at least one of $R^{b1}$ to $R^{b3}$ is an aryl group having a substituent containing a sulfonyl group as the substituent at the meta position and/or para position or an aryl group in which $R^{b2}$ to $R^{b3}$ may have a substituent, and preferably includes a bivalent sulfonyl group in which one carbon atom of a ring formed by mutually bonding $R^{b2}$ to $R^{b3}$ together with a sulfur atom in the formula is substituted.

In the formula (ca-0), the aryl group for $R^{b1}$ to $R^{b3}$ may have a substituent other than the substituent containing a sulfonyl group.

Examples of the substituent include an alkyl group having 1 to 5 carbon atoms, a halogen atom (a fluorine atom, a bromine atom, and a chlorine atom), a halogenated alkyl group having 1 to 5 carbon atoms, a carbonyl group, a cyano group, an amino group, an aryl group having 6 to 20 carbon atoms, and groups represented by the following formulae (ca-r-1) to (ca-r-7).

In formula (ca-0), a substituent other than the substituent containing a sulfonyl group that the aryl group for $R^{b1}$ to $R^{b3}$ may have is preferably a halogen atom or a halogenated alkyl group having 1 to 5 carbon atoms, and more preferably a fluorine atom or a trifluoromethyl group.

The number of sulfonyl groups that the cation represented by the general formula (ca-0) has is not particularly limited, and is preferably 1 to 4, more preferably 1 to 3, and most preferably 1 or 2. When the number of substituents containing a sulfonyl group is 2 or more, one of $R^{b1}$ to $R^{b3}$ may have a substituent containing 2 or more sulfonyl groups, and more preferably, each of $R^{b1}$ to $R^{b3}$ is substituted with a substituent containing a sulfonyl group.

In addition, in the formula (ca-0), the number of substituents other than the substituent containing a sulfonyl group that the aryl group for $R^{b1}$ to $R^{b3}$ may have is preferably 0 to 8, more preferably 0 to 6, and most preferably 0 to 4.

Specific examples of a suitable cation represented by the formula (ca-0) include cations represented by the following formulae (ca-O-1) to (ca-O-10).

[Chem. 75]

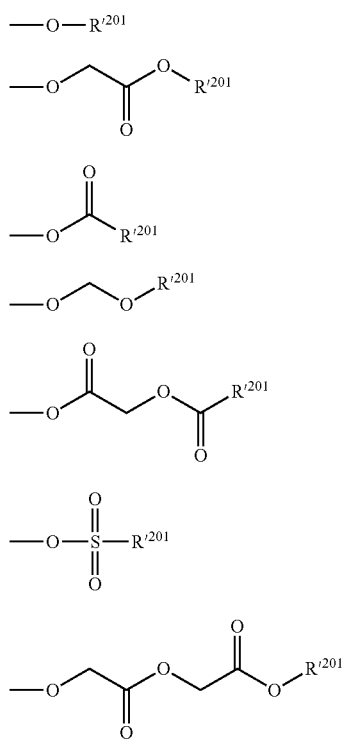

[ca-r-1]
[ca-r-2]
[ca-r-3]
[ca-r-4]
[ca-r-5]
[ca-r-6]
[ca-r-7]

[Chem. 76]

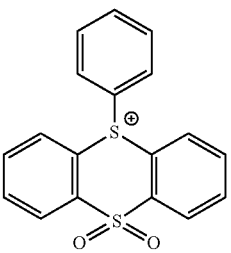

(ca-O-1)

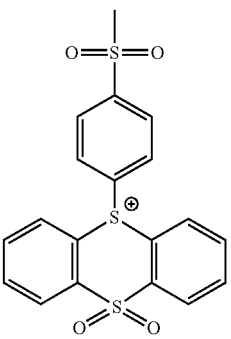

(ca-O-2)

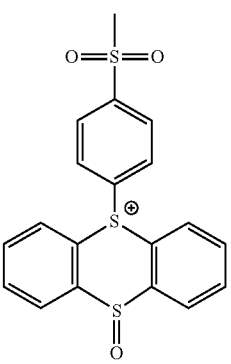

(ca-O-3)

In the formulae, each $R'^{2''}$ independently represents a hydrogen atom, a cyclic group which may have a substituent, a chain-like alkyl group which may have a substituent, or a chain-like alkenyl group which may have a substituent.

In the formulae (ca-r-1) to (ca-r-7), descriptions of a cyclic group which may have a substituent for $R'^{2''}$, a linear alkyl group which may have a substituent, or a chain-like alkenyl group which may have a substituent are the same as description of a hydrocarbon group which may have a substituent (a cyclic group which may have a substituent, a linear alkyl group which may have a substituent, or a chain-like alkenyl group which may have a substituent) for $Rx^1$ to $Rx^4$, $Ry^1$ to $Rye$, $Rz^1$ to $Rz^4$ (hereinafter referred to as "$Rx^1$ to $Rx^4$ and the like") in the formula (bd1-1).

(ca-0-4) 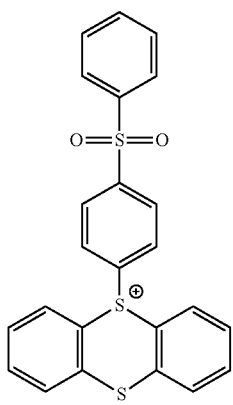

(ca-0-5) 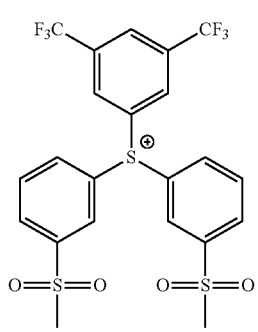

(ca-0-6) 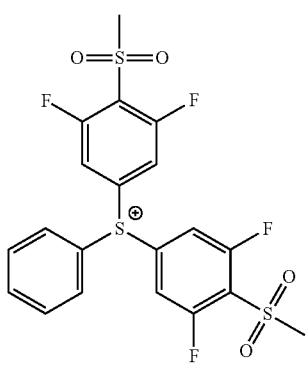

(ca-0-7) 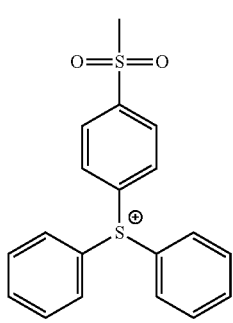

(ca-0-8) 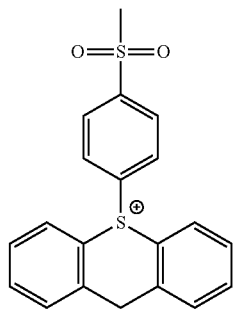

(ca-0-9) 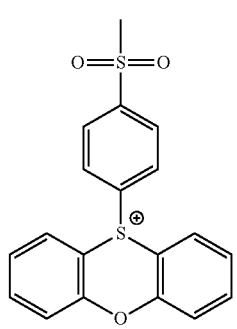

(ca-0-10) 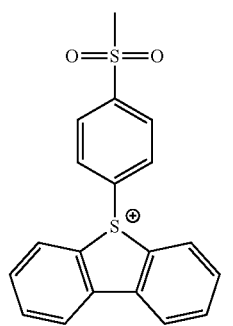

Among the components (BD1-1) described above, regarding compounds suitable as an acid-generator component (B) (hereinafter referred to as a "component (B1a)") that generates an acid acting on the component (A), various combinations of anions represented by the formulae (bd1-an1) to (bd1-an3) which are anions (most preferably, an anion represented by any of (bd1-an3-1) to (bd1-an3-15)) having an anion group represented by the general formula (bd1-r-an1) (more preferably an anion group represented by any of the formulae (bd1-r-an11) to (bd1-r-an13)) and a cation represented by the formula (ca-0) (more preferably, a cation represented by any of (ca-O-1) to (ca-O-10)) may be exemplified. Specific examples of the component (B1a) are shown below, but the component (B1a) is not limited thereto.

[Chem. 77]
(B1a-1)
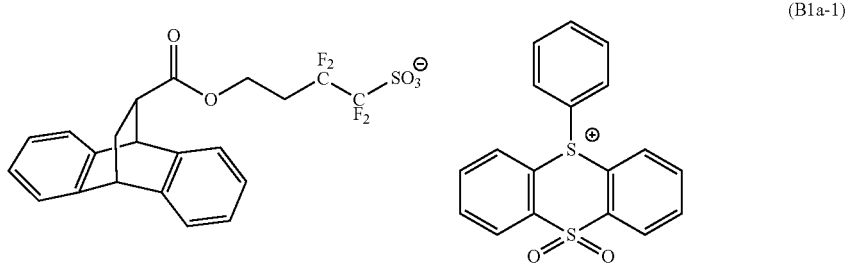
(B1a-2)
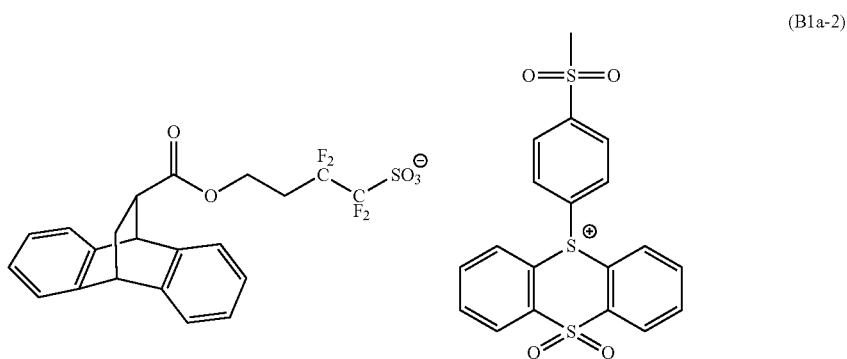
(B1a-3)
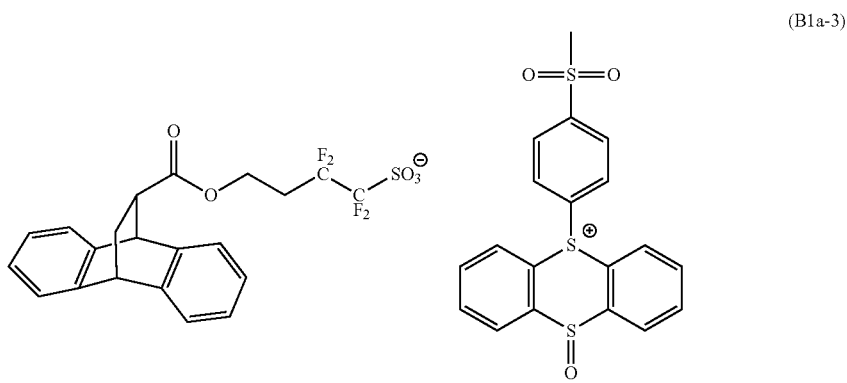
(B1a-4)
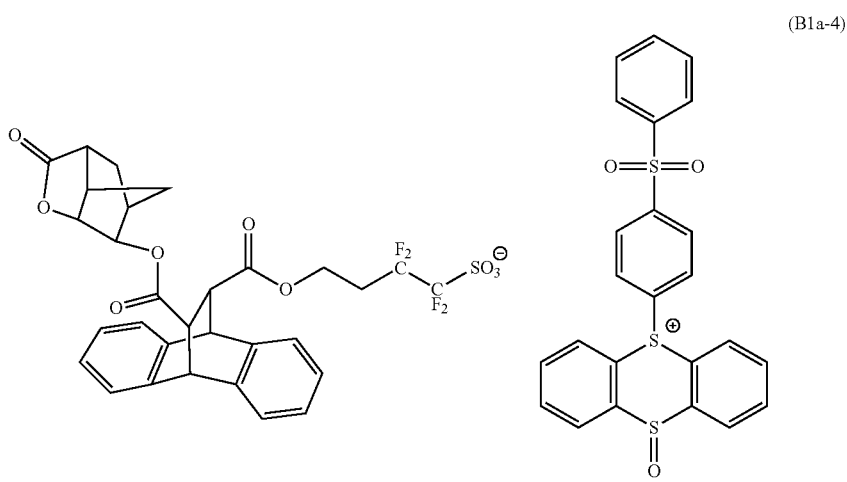

-continued
(B1a-5)
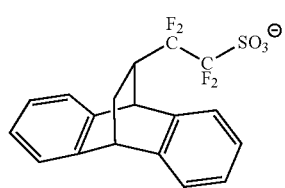 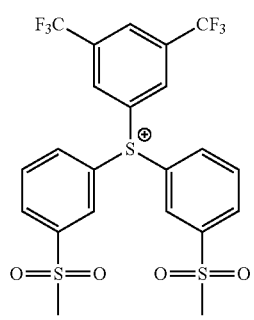
(B1a-6)
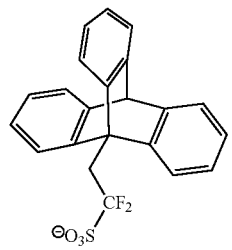 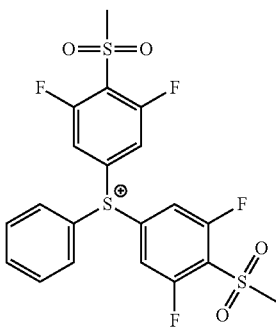
[Chem. 78]
(B1a-7)
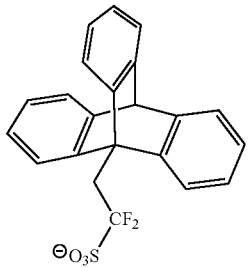 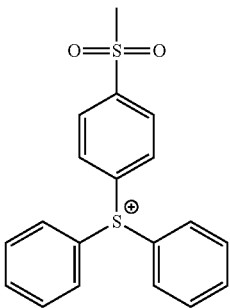
(B1a-8)
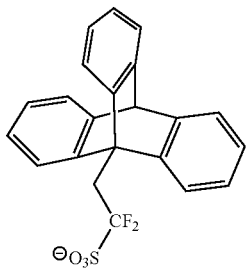 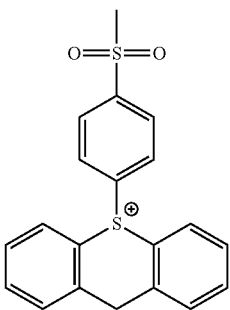

-continued
(B1a-9)
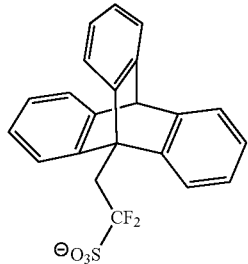 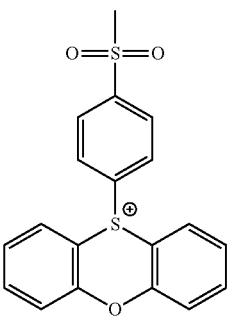
(B1a-10)
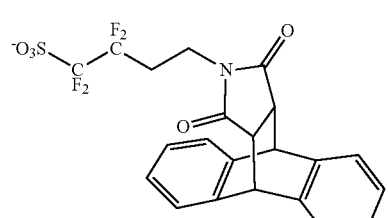 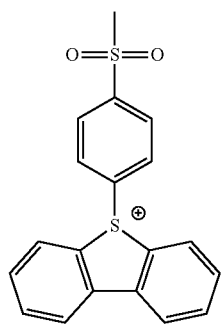
(B1a-11)
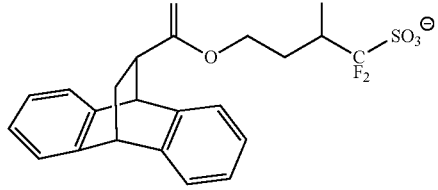 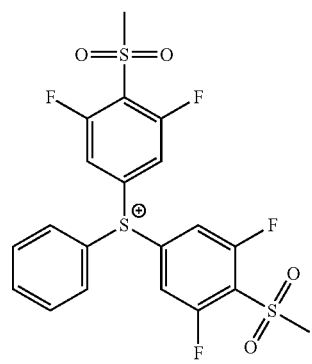
[Chem. 79]
(B1a-12)
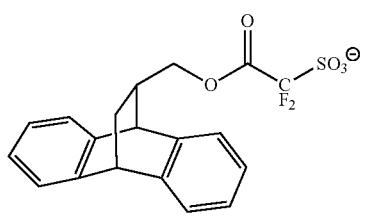 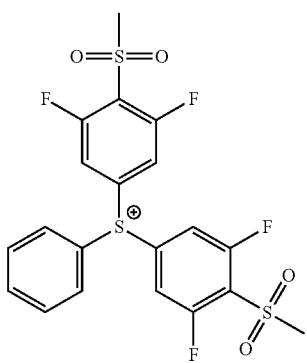

-continued

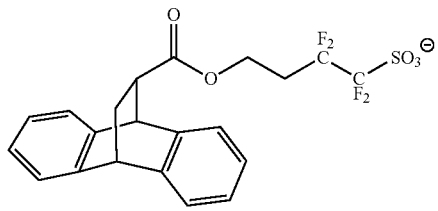
(B1a-13)

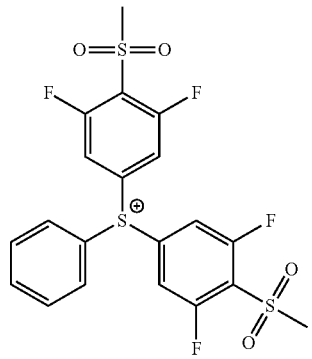

In the resist composition of the present embodiment, one type of the component (B1a) may be used alone or two or more thereof may be used in combination.

In the resist composition of the present embodiment, an amount of the component (B1a) is preferably 5 to 65 parts by mass, more preferably 5 to 55 parts by mass, still more preferably 10 to 45 parts by mass, and particularly preferably 15 to 40 parts by mass with respect to 100 parts by mass of the component (A). When an amount of the component (B1a) is equal to or more than a lower limit of the preferable range, in the resist pattern formation, lithography properties such as sensitivity, resolution performance, defect reduction, line-wise roughness (LWR) reduction, a shape, and the like are further improved.

On the other hand, if the amount thereof is equal to or less than an upper limit of the preferable range, when components of the resist composition are dissolved in an organic solvent, a homogeneous solution is easily obtained, and storage stability for the resist composition is further improved.

In addition, among the components (BD1-1) described above, examples of compounds suitable as a base component (D) (hereinafter referred to as a "component (D1a)") that traps (controls acid diffusion) an acid generated from the component (B) upon exposure may include various combinations of the above anions represented by the formulae (bd1-an1) to (bd1-an3) which are anions (more preferably an anion represented by any of (bd1-an3-21) to (bd1-an3-24)) having an anion group represented by *—$V'^{10}$—COO ($V'^{10}$ is a single bond or an alkylene group having 1 to 20 carbon atoms) or *—$V'^{11}$—$SO_3$ ($V'^{11}$ is a single bond or an alkylene group having 1 to 20 carbon atoms) and a cation represented by the formula (ca-0) (more preferably a cation represented by any of (ca-O-1) to (ca-O-10)).

Specific examples of the component (D1a) are shown below, but the component (D1a) is not limited thereto.

[Chem. 80]

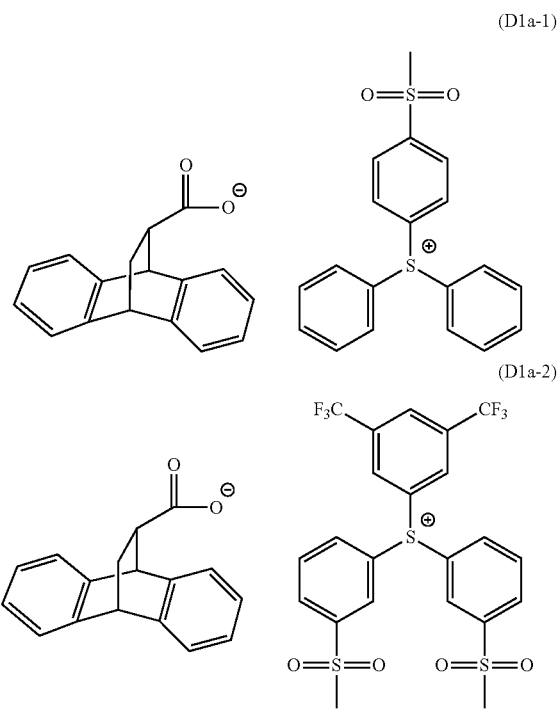

In the resist composition of the present embodiment, one type of the component (D1a) may be used alone or two or more thereof may be used in combination.

In the resist composition of the present embodiment, an amount of the component (D1a) is preferably 1 to 35 parts by mass, more preferably 2 to 25 parts by mass, and most preferably 3 to 20 parts by mass with respect to 100 parts by mass of the component (A).

When an amount of the component (D1a) is equal to or more than a lower limit of the preferable range, favorable lithography properties and resist pattern shapes are easily obtained. On the other hand, when the amount thereof is equal to or less than an upper limit of the preferable range, a balance with other components can be achieved, and various lithography properties become favorable.

<Optional Components>

The resist composition of the present embodiment may further contain components (optional components) other than the component (A) and the compound (BD1-1) (the component (B1a), and the component (D1a)) described above.

Examples of such optional components include a component (B2a), a component (D2a), a component (D3), a component (E), a component (F), and a component (S) shown below.

<<Component (B2a)>>

The resist composition of the present embodiment may contain an acid generator other than the component (B1a) (hereafter, referred to as "component (B2a)"), as long as the effects of the present invention are not impaired.

As the component (B2a), there is no particular limitation, and any of the known acid generators used in conventional chemically amplified resist compositions may be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be mentioned. However, the component (b-1) does not include compounds which fall under the category of the component (B1a).

[Chem. 81]

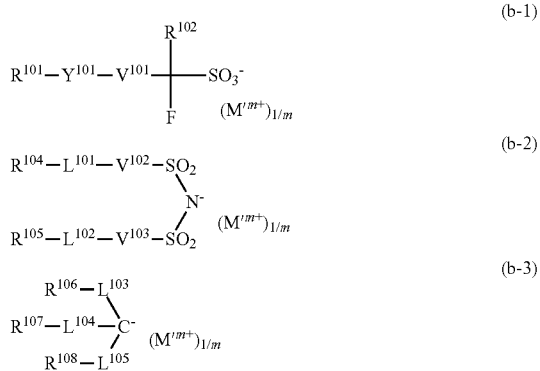

In the formulae, $R^{101}$ and $R^{104}$ to $R^{108}$ each independently represent a cyclic group which may have a substituent, a chain-like alkyl group which may have a substituent or a chain-like alkenyl group which may have a substituent, provided that $R^{104}$ and $R^{105}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represent a single bond, an alkylene group or a fluorinated alkylene group; $L^{101}$ and $L^{102}$ each independently represent a single bond or an oxygen atom; $L^{103}$ to $L^{105}$ each independently represent a single bond, —CO— or —SO$_2$—; and m represents an integer of 1 or more; and $M'^{m+}$ represents an m-valent onium cation.

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent. Description of such $R^{101}$ is the same as description of a hydrocarbon group which may have a substituent (a cyclic group which may have a substituent, a linear alkyl group which may have a substituent, or a chain-like alkenyl group which may have a substituent) for $Rx^1$ to $Rx^4$, $Ry^1$ to Rye, and $Rz^1$ to $Rz^4$ (hereinafter referred to as "$Rx^1$ to $Rx^4$ and the like") in the formula (bd1-1).

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formulae (a2-r-1), and (a2-r-3) to (a2-r-7), and an —SO$_2$— containing cyclic group represented by any one of the aforementioned formulae (a5-r-1) to (a5-r-4). In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of the divalent linking group containing an oxygen atom include divalent linking groups represented by the aforementioned general formulae (y-a1-1) to (y-a1-8).

$Y^{101}$ is preferably a divalent linking group containing an ether bond or a divalent linking group containing an ester bond, and groups represented by the aforementioned formulas (y-a1-1) to (y-a1-5) are preferable.

In formula (b-1), $V^{101}$ represents a single bond, an alkylene group or a fluorinated alkylene group. The alkylene group and the fluorinated alkylene group for $V^{101}$ preferably have 1 to 4 carbon atoms. Examples of the fluorinated alkylene group for $V^{101}$ include a group in which some or all of the hydrogen atoms within the alkylene group for $V^{101}$ have been substituted with fluorine atoms. Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As a specific example of the anion moiety for the component (b-1), in the case where $Y^{101}$ is a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chem. 82]

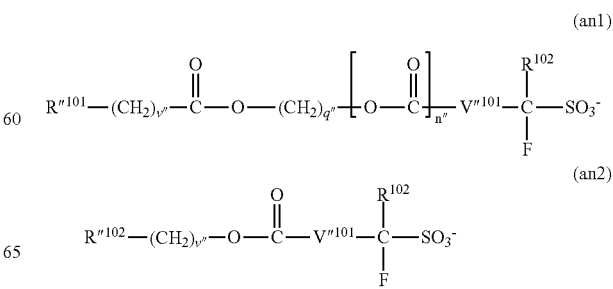

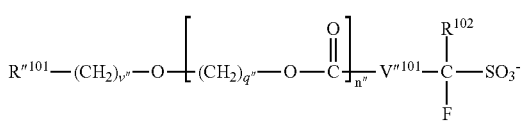

(an3)

[In the formula, $R'''^{101}$ is an aliphatic cyclic group which may have a substituent, a monovalent heterocyclic group represented by each of the chemical formulae (r-hr-1) to (r-hr-6), or a linear alkyl group which may have a substituent. $R'''^{102}$ is an aliphatic cyclic group which may have a substituent, a lactone-containing cyclic group represented by each of the general formulae (a2-r-1), (a2-r-3) to (a2-r-7), or a —$SO_2$— containing cyclic group represented by each of the general formulae (a5-r-1) to (a5-r-4). $R'''^{103}$ is an aromatic cyclic group which may have a substituent, an aliphatic cyclic group which may have a substituent, or a chain-like alkenyl group which may have a substituent.

$V'''^{101}$ is an alkylene group having 1 to 4 carbon atoms or a fluorinated alkylene group having 1 to 4 carbon atoms. $R^{102}$ is a fluorine atom or a fluorinated alkyl group having 1 to 5 carbon atoms. $v'''$'s each independently represent an integer of 0 to 3, $q'''$'s each independently represent an integer of 1 to 20, and $n''$ is 0 or 1].

As the aliphatic cyclic group for $R'''^{101}$, $R'''^{102}$ and $R'''^{103}$ which may have a substituent, the same groups as the cyclic aliphatic hydrocarbon groups for $Rx^1$ to $Rx^4$ in formula (bd1-1) described above are preferable. Examples of the substituent include the same substituents as those described above for the cyclic aliphatic hydrocarbon group for $Rx^1$ to $R^4$ in formula (bd1-1).

As the aromatic cyclic group for $R'''^{103}$ which may have a substituent, the same groups as the aromatic hydrocarbon groups for the cyclic hydrocarbon group represented by $Rx^1$ to $Rx^4$ in formula (bd1-1) described above are preferable. Examples of the substituent include the same substituents that may substitute the aromatic hydrocarbon group for $Rx^1$ to $Rx^4$ and the like in the formula (bd1-1).

As the chain-like alkyl group for $R'''^{101}$ which may have a substituent, the same groups as those described above for $Rx^1$ to $Rx^4$ in the aforementioned formula (bd1-1) are preferable. A chain-like alkenyl group which may have a substituent for $R'''^{103}$ is preferably a group exemplified as a chain-like alkenyl group for $Rx^1$ to $Rx^4$ and the like in the formula (bd1-1).

Anion Moiety of Component (b-2)

In formula (b-2), $R^{104}$ and $R^{105}$ each independently represent a cyclic group which may have a substituent, a chain-like alkyl group which may have a substituent or a chain-like alkenyl group which may have a substituent, and are the same as defined for a cyclic group which may have a substituent, a chain-like alkyl group which may have a substituent or a chain-like alkenyl group which may have a substituent for $Rx^1$ to $Rx^4$ in the aforementioned formula (bd1-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms be as large as possible because the acid strength increases. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represent a single bond, an alkylene group or a fluorinated alkylene group, and are the same as defined for $V^{101}$ in formula (b-1).

In formula (b-2), $L^{101}$ and $L^{102}$ each independently represent a single bond or an oxygen atom.

Anion Moiety of Component (b-3)

In formula (b-3), $R^{106}$ to $R^{108}$ each independently represent a cyclic group which may have a substituent, a chain-like alkyl group which may have a substituent or a chain-like alkenyl group which may have a substituent, and are the same as defined for a cyclic group which may have a substituent, a chain-like alkyl group which may have a substituent or a chain-like alkenyl group which may have a substituent for $Rx^1$ to $Rx^4$ in the aforementioned formula (bd1-1).

$L^{103}$ to $L^{105}$ each independently represent a single bond, —CO— or —$SO_2$—.

{Cation Moiety}

In the formulae (b-1), (b-2), and (b-3), m is an integer of 1 or more, $M^{m+}$ is an m-valent onium cation, and a sulfonium cation and an iodonium cation are preferably exemplified.

Preferable examples of the cation moiety $((M^{m+})_{l/m})$ include an organic cation represented by any of general formulae (ca-1) to (ca-4) shown below.

[Chem. 83]

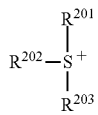

(ca-1)

(ca-2)

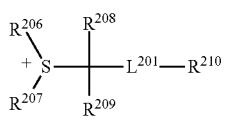

(ca-3)

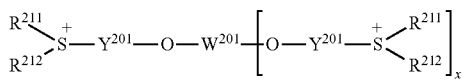

(ca-4)

In the formulae, $R^{201}$ to $R^{207}$, $R^{211}$ and $R^{212}$ each independently represent an aryl group which may have a substituent, an alkyl group which may have a substituent, or an alkenyl group which may have a substituent. $R^{201}$ to $R^{203}$, $R^{206}$ and $R^{207}$, and $R^{211}$ and $R^{212}$ may be mutually bonded to form a ring with the sulfur atom. $R^{208}$ and $R^{209}$ each independently represent a hydrogen atom or an alkyl group of 1 to 5 carbon atoms. $R^{210}$ represents an aryl group which may have a substituent, an alkyl group which may have a substituent, an alkenyl group which may have a substituent, or an —$SO_2$— containing cyclic group which may have a substituent. $L^{201}$ represents —C(=O)— or —C(=O)—O—. Each $Y^{201}$ independently represents an arylene group, an alkylene group or an alkenylene group. x represents 1 or 2. $W^{201}$ represents an (x+1)-valent linking group.

The aryl group for $R^{201}$ to $R^{207}$, and $R^{211}$ to $R^{212}$ is the same as the aryl group for $R^{b1}$ in the formula (ca-0).

The alkyl group for $R^{201}$ to $R^{207}$, and $R^{211}$ to $R^{212}$ is the same as the alkyl group for $R^{b2}$ to $R^{b3}$ in the formula (ca-0).

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by the aforementioned general formulae (ca-r-1) to (ca-r-7).

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(RN)— (wherein RN represents an alkyl group of 1 to 5 carbon atoms). The ring containing the sulfur atom in the skeleton thereof is preferably a 3- to 10-membered ring, and most preferably a 5- to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represent a hydrogen atom or an alkyl group of 1 to 5 carbon atoms, preferably a hydrogen atom or an alkyl group of 1 to 3 carbon atoms, and when $R^{208}$ and $R^{209}$ each represent an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, an "—SO$_2$— containing polycyclic group" is preferable, and a group represented by the aforementioned general formula (a5-r-1) is more preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b1-a1).

Examples of the alkylene group and alkenylene group for $Y^{201}$ include groups in which one hydrogen atom has been removed from the chain-like alkyl group or the chain-like alkenyl group given as an example of $R^{101}$ in the aforementioned formula (b1-a1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups (which may have a substituent) as those described above for $Y_a^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Examples of a specific suitable cation represented by the formula (ca-1) include cations represented by the following formulae (ca-1-1) to (ca-1-71) in addition to (ca-0-1) to (ca-0-10).

[Chem. 84]

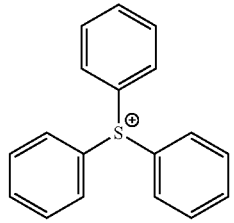

(ca-1-1)

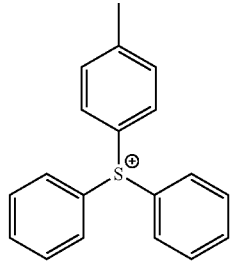

(ca-1-2)

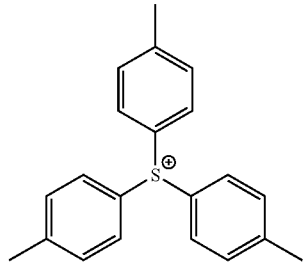

(ca-1-3)

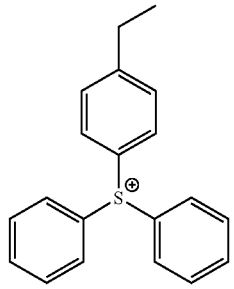

(ca-1-4)

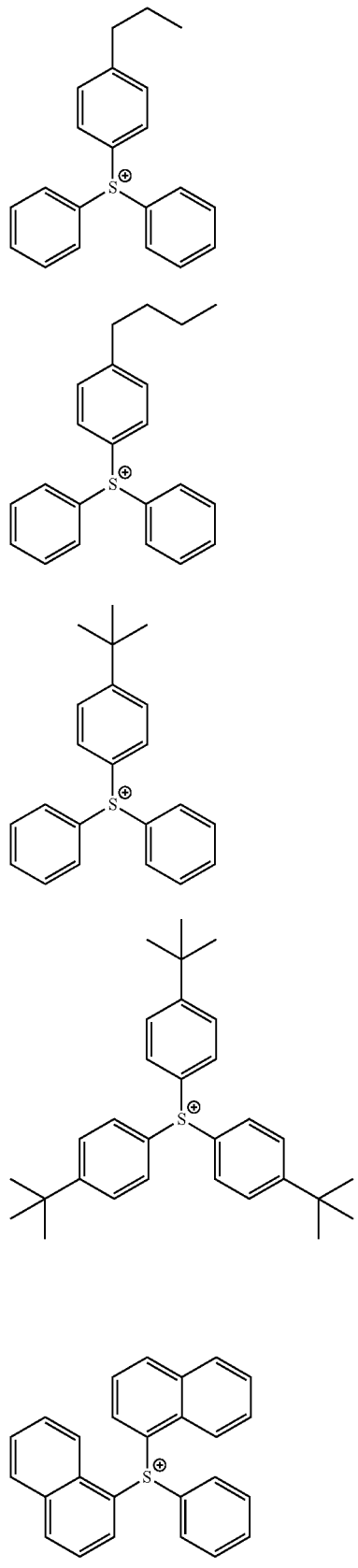
(ca-1-5)
(ca-1-6)
(ca-1-7)
(ca-1-8)
(ca-1-9)
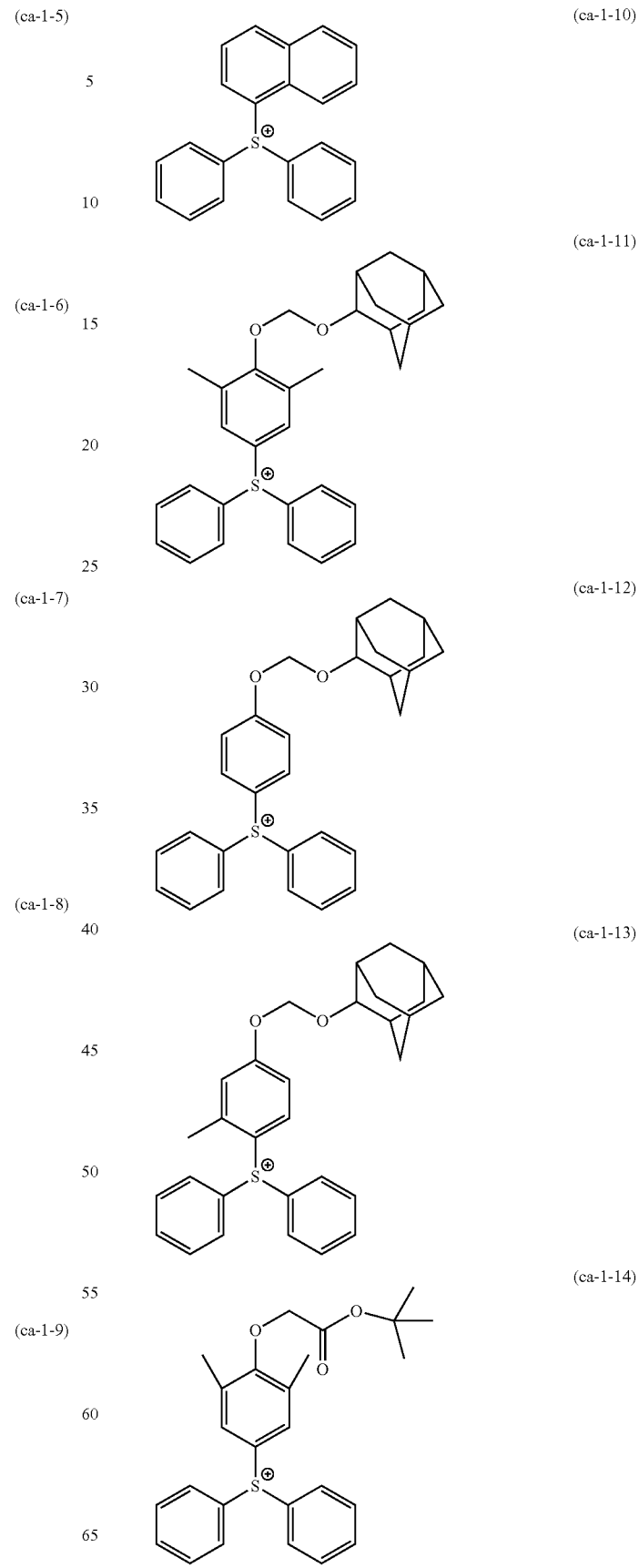
(ca-1-10)
(ca-1-11)
(ca-1-12)
(ca-1-13)
(ca-1-14)

(ca-1-15)
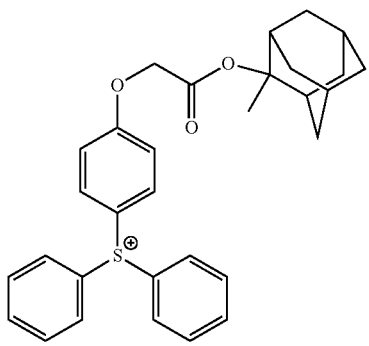
(ca-1-16)
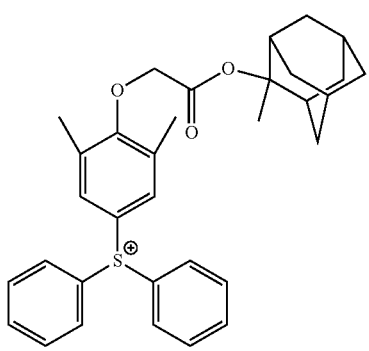
[Chem. 85]
(ca-1-17)
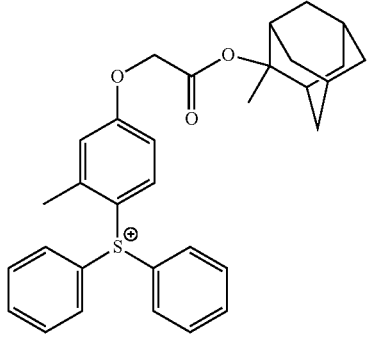
(ca-1-18)
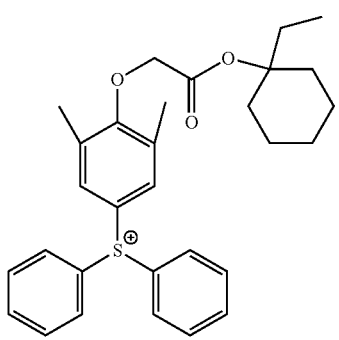
(ca-1-19)
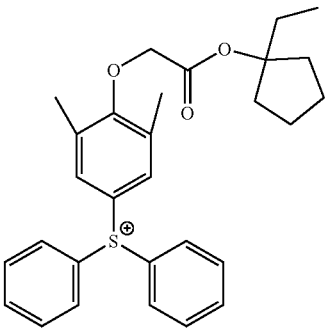
(ca-1-20)
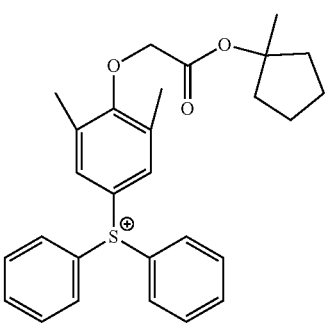
(ca-1-21)
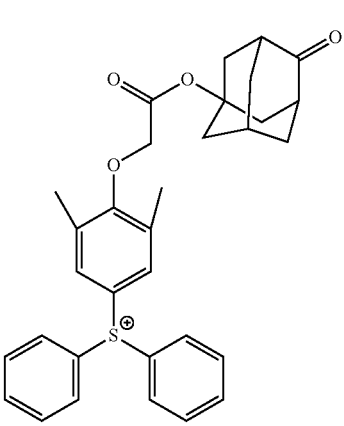
(ca-1-22)
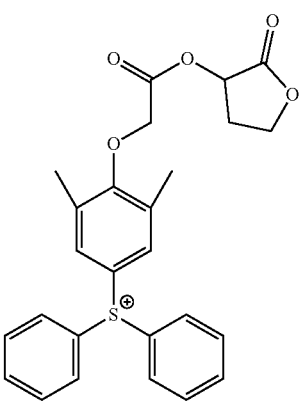

(ca-1-23)
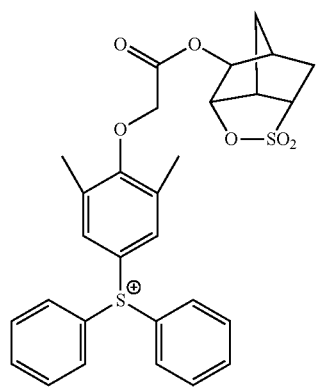
(ca-1-24)
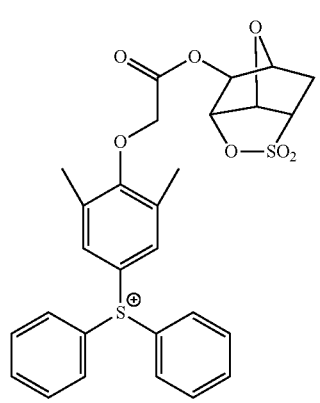
(ca-1-25)
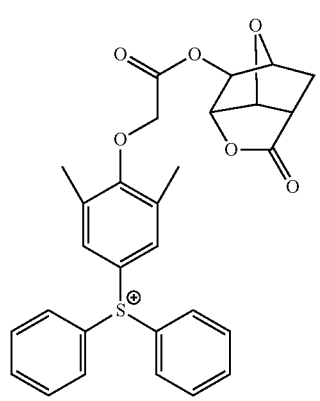
(ca-1-26)
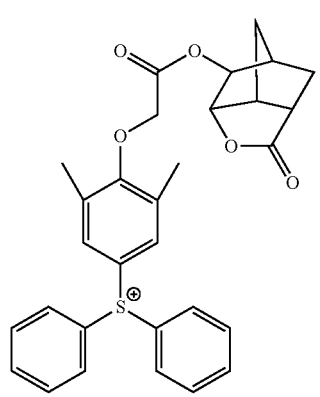
(ca-1-27)
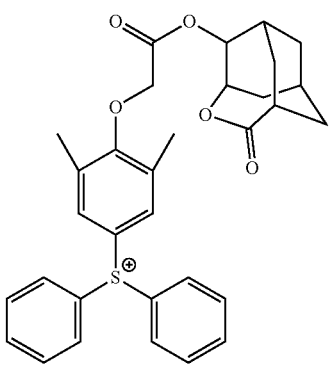
(ca-1-28)
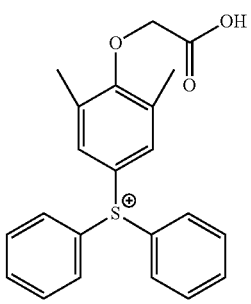
(ca-1-29)
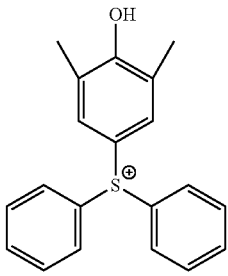
(ca-1-30)
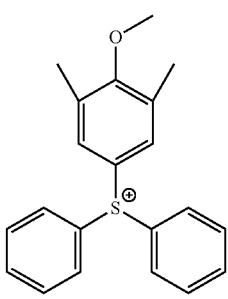
(ca-1-31)
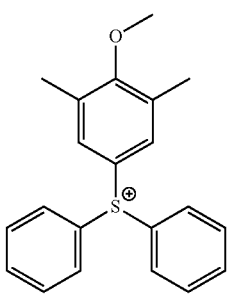

(ca-1-32) 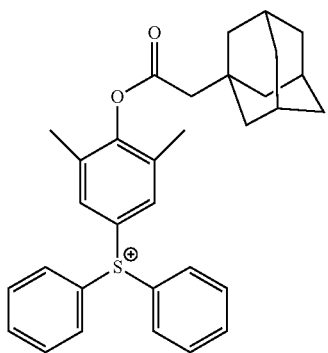
(ca-1-33) 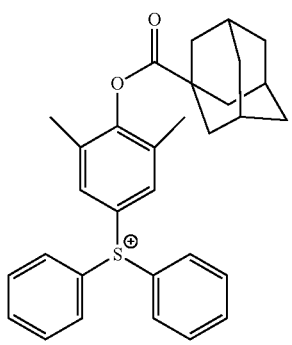
[Chem. 86]
(ca-1-34)
(ca-1-35)
(ca-1-36) 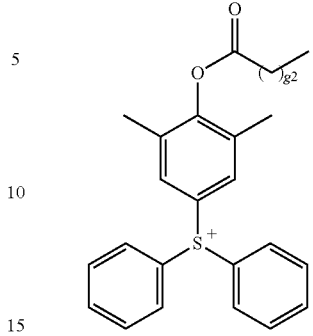
(ca-1-37) 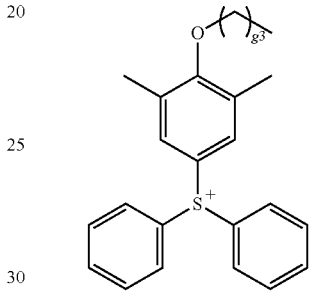
(ca-1-38) 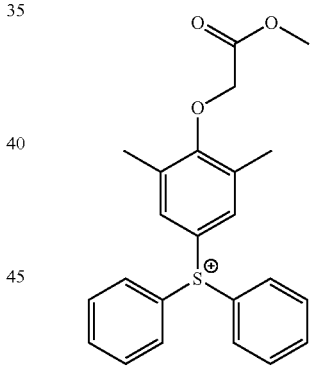
(ca-1-39) 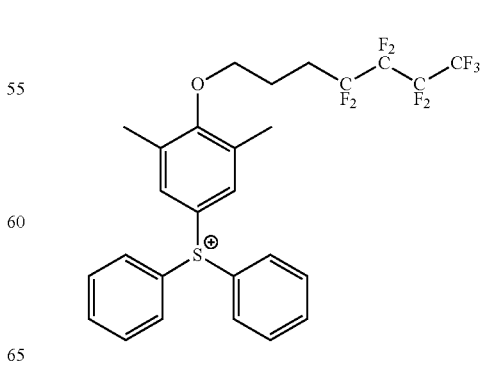

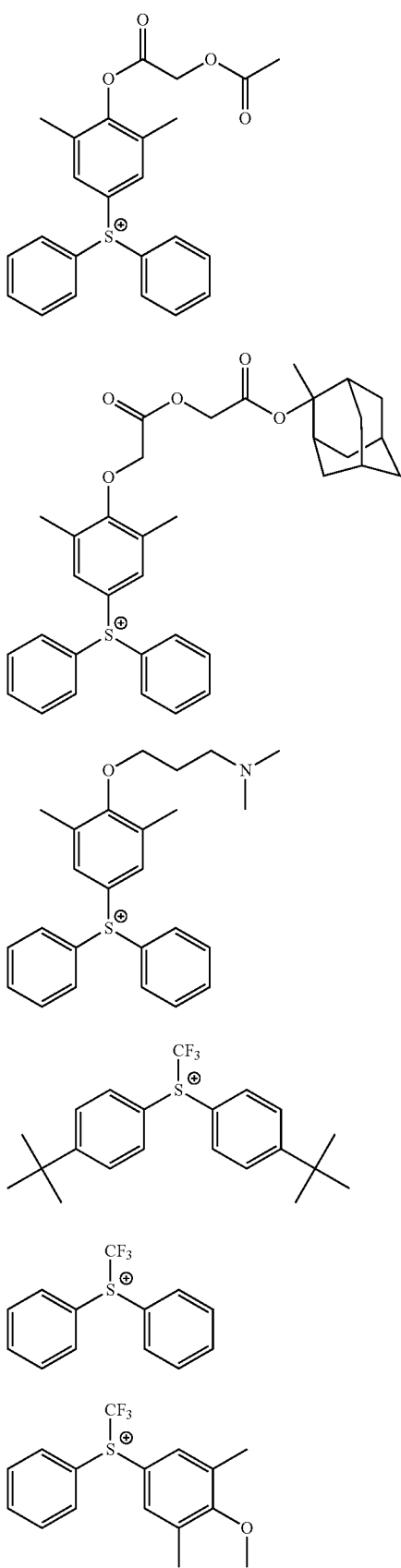
(ca-1-40)
(ca-1-41)
(ca-1-42)
(ca-1-43)
(ca-1-44)
(ca-1-45)
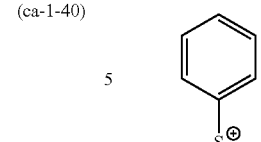 (ca-1-46)
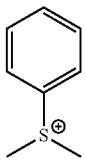 (ca-1-47)
 (ca-1-48)
 (ca-1-49)
 (ca-1-50)
 (ca-1-51)
In the formulae, g1, g2 and g3 represent a number of repetitions, wherein g1 is an integer of 1 to 5, g2 is an integer of 0 to 20, and g3 is an integer of 0 to 20.

[Chem. 87]
(ca-1-52)
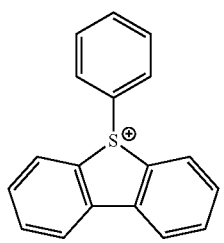
(ca-1-53)
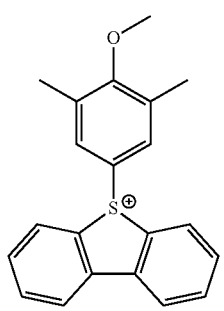
(ca-1-54)
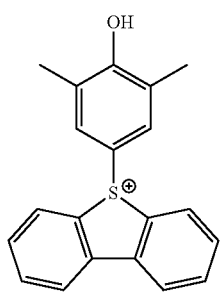
(ca-1-55)
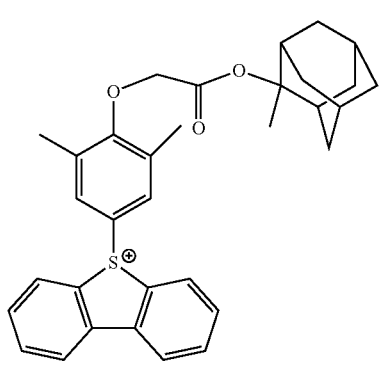
(ca-1-56)
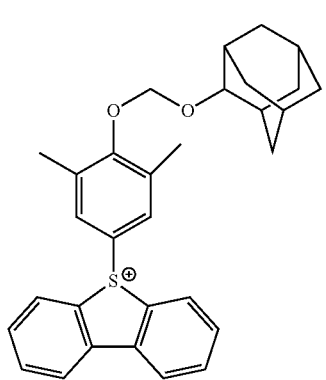
(ca-1-57)
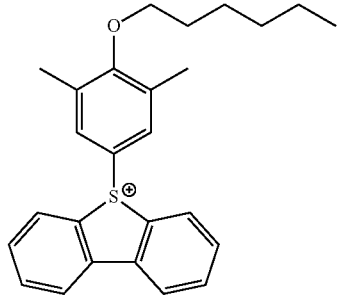
(ca-1-58)
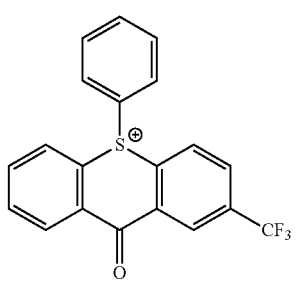
(ca-1-59)
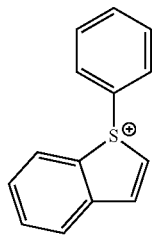
(ca-1-60)
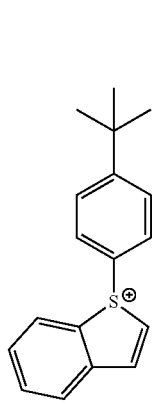
(ca-1-61)
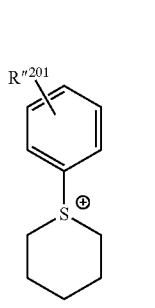

-continued
(ca-1-62) 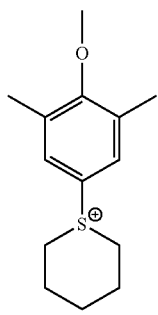
(ca-1-63) 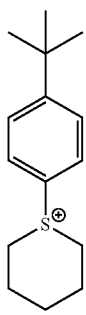
(ca-1-64) 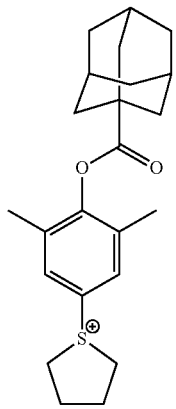
(ca-1-65) 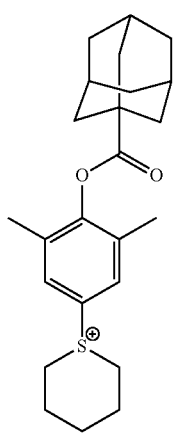
-continued
(ca-1-66) 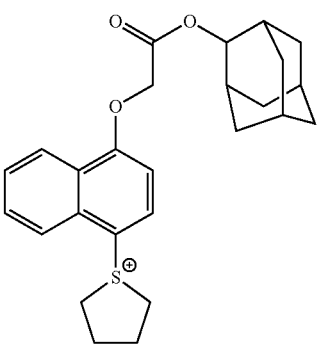
(ca-1-67) 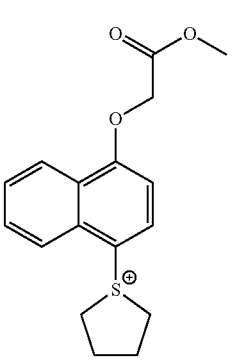
[Chem. 88]
(ca-1-68) 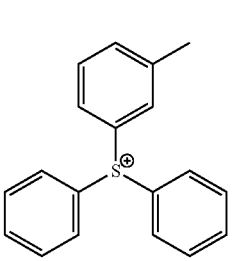
(ca-1-69) 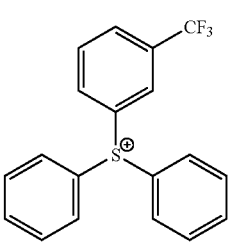
(ca-1-70) 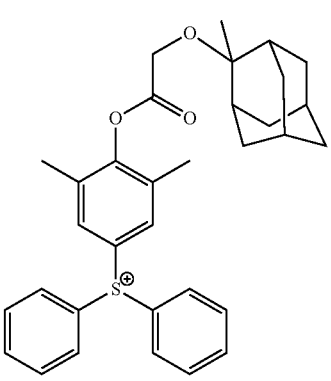

-continued (ca-1-71)

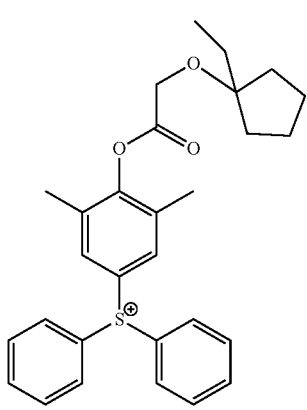

In the formulae, R"²⁰¹ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by the formula (ca-2) include a dihphenyliodonium cation and a bis(4-tert-butylphenyl)iodonium cation.

Specific examples of preferable cations represented by formula (ca-3) include cations represented by formulae (ca-3-1) to (ca-3-6) shown below.

[Chem. 189]

(ca-3-1)

(ca-3-2)

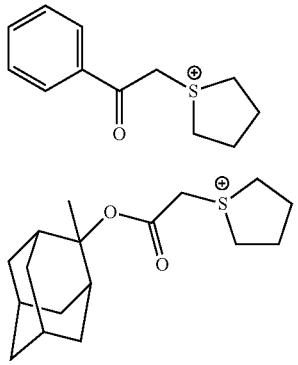

(ca-3-3)

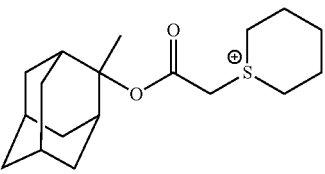

(ca-3-4)

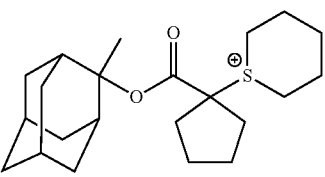

(ca-3-5)

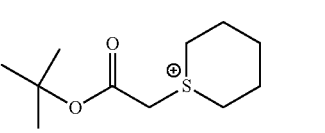

(ca-3-6)

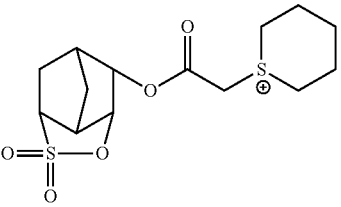

Specific examples of preferable cations represented by formula (ca-4) include cations represented by formulae (ca-4-1) and (ca-4-2) shown below.

[Chem. 90]

(ca-4-1)

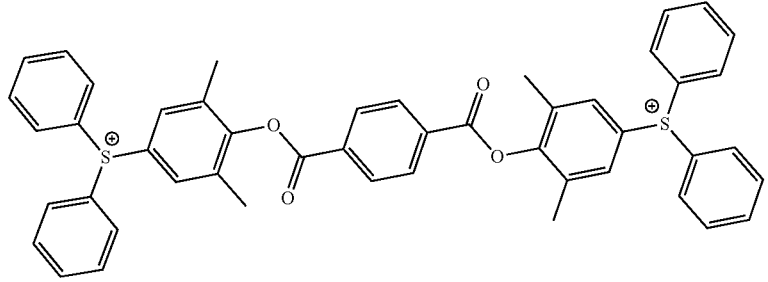

(ca-4-2)

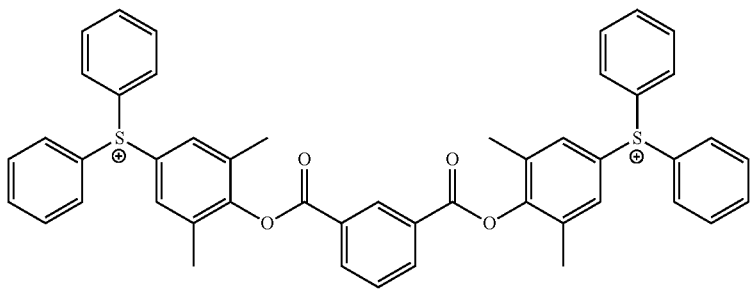

Among the above examples, as the cation moiety (($M^{m+}$)$_{l/m}$), a cation represented by general formula (ca-1) is preferable, and a cation represented by any one of formulae (ca-1-1) to (ca-1-71) is more preferable.

In the resist composition of the present embodiment, as the component (B2a), one kind of compound may be used alone, or two or more thereof may be used in combination.

When the resist composition contains the component (B2a), the amount of the component (B2a) relative to 100 parts by mass of the component (A) is preferably 50 parts by mass or less, more preferably 1 to 40 parts by mass, and still more preferably 5 to 30 parts by mass.

When an amount of the component (B2a) is set to be within the above range, pattern formation is sufficiently performed.

<<Component (D2a)>>

The component (D2a) is a basic component, and is a photodecomposable base which is decomposed upon exposure and then loses the ability to control acid diffusion (provided that the component (D1a) is excluded).

When a resist pattern is formed using a resist composition containing the component (D2a), the contrast between exposed portions and unexposed portions of the resist film is further improved.

The component (D2a) is not particularly limited as long as it is decomposed upon exposure and loses an ability to control acid diffusion, and one or more compounds selected from the group consisting of a compound represented by the following general formula (d2-1) (hereinafter referred to as a "component (d2-1)"), a compound represented by the following general formula (d2-2) (hereinafter referred to as a "component (d2-2)") and a compound represented by the following general formula (d2-3) (hereinafter referred to as a "component (d2-3)") are preferable.

The components (d2-1) to (d2-3) decompose in an exposed portion of the resist film and lose an ability to control acid diffusion (basic) and thus do not act as a quencher, but act as a quencher in an unexposed portion of the resist film.

[Chem. 91]

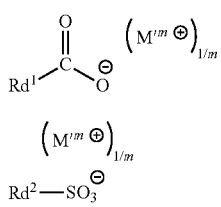

(d2-1)

(d2-2)

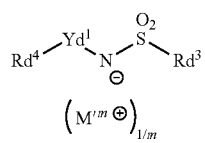

(d2-3)

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in general formula (d2-2) has no fluorine atom bonded thereto; $Yd^1$ represents a single bond or a divalent linking group; m represents an integer of 1 or more, and each $M^{'m+}$ independently represents an onium cation having a valency of m.

{Component (d2-1)}
Anion Moiety

In formula (d1-2), $Rd^1$ represents a cyclic group which may have a substituent, a chain-like alkyl group which may have a substituent or a chain-like alkenyl group which may have a substituent, and is the same groups as those defined above for $Rx^1$ to $Rx^4$ in the aforementioned formula (bd1-1).

Among these, as the group for $Rd^1$, an aromatic hydrocarbon group which may have a substituent, an aliphatic cyclic group which may have a substituent and a chain-like alkyl group which may have a substituent are preferable.

Examples of the substituent for these groups include a hydroxy group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of the aforementioned formulae (y-a1-1) to (y-a1-5) is preferable as the substituent.

Regarding the aromatic hydrocarbon group, a polycyclic structure having a phenyl group, a naphthyl group, and a bicyclooctane skeleton (for example, a polycyclic structure composed of a bicyclooctane skeleton ring structure and other ring structures) are preferably exemplified.

Examples of the aliphatic cyclic group include groups in which one or more hydrogen atoms have been removed from a polycycloalkane such as adamantane, norbomane, isobomane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having fluorine atoms or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a sulfur atom and a nitrogen atom.

As $Rd^1$, a fluorinated alkyl group in which some or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is particularly desirable.

Specific examples of preferable anion moieties for the component (d2-1) are shown below.

[Chem. 92]

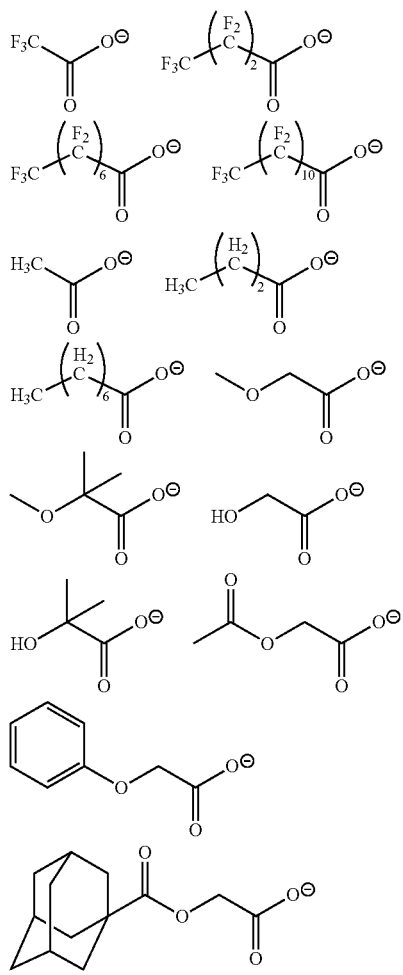

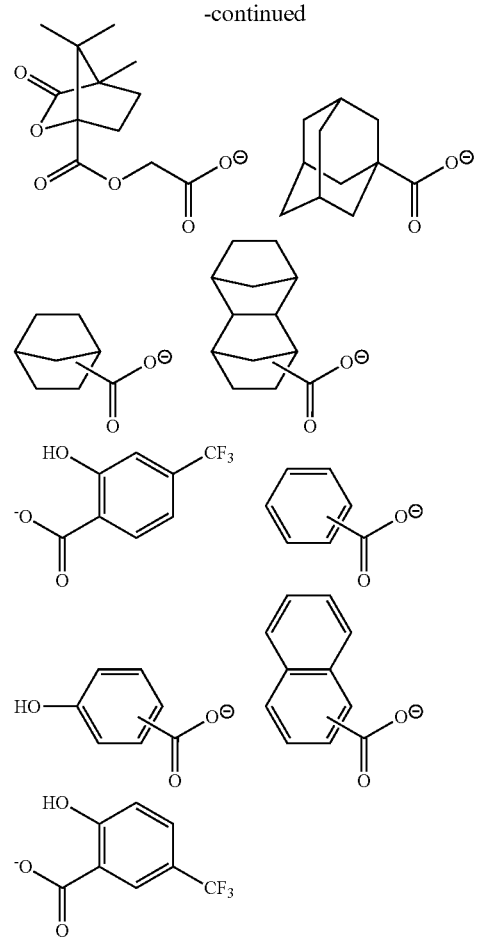

Cation Moiety

In the formula (d2-1), $M^{m+}$ is an m-valent onium cation. Examples of onium cations for $M^{m+}$ include those the same as in the general formulae (ca-1) to (ca-4).

As the component (d2-1), one kind of compound may be used alone, or two or more kinds thereof may be used in combination.

{Component (d2-2)}

Anion Moiety

In formula (d2-2), $Rd^2$ represents a cyclic group which may have a substituent, a chain-like alkyl group which may have a substituent or a chain-like alkenyl group which may have a substituent, and is the same groups as those defined above for $Rx^1$ to $Rx^4$ in the aforementioned formula (bd1-1).

However, the carbon atom adjacent to the sulfur atom within the $Rd^2$ has no fluorine atom bonded thereto. Accordingly, the anion of the component (d2-2) becomes an appropriate weak acid anion, and a quenching ability for the component (D2a) is improved.

As $Rd^2$, a chain-like alkyl group which may have a substituent or an aliphatic cyclic group which may have a substituent is preferable. The chain-like alkyl group preferably has 1 to 10 carbon atoms, and more preferably 3 to 10 carbon atoms. As the aliphatic cyclic group, a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic cyclic group, chain-like alkyl group) for $Rd^1$ in the formula (d2-1) can be mentioned.

Specific examples of preferable anion moieties for the component (d2-2) are shown below.

[Chem. 93]

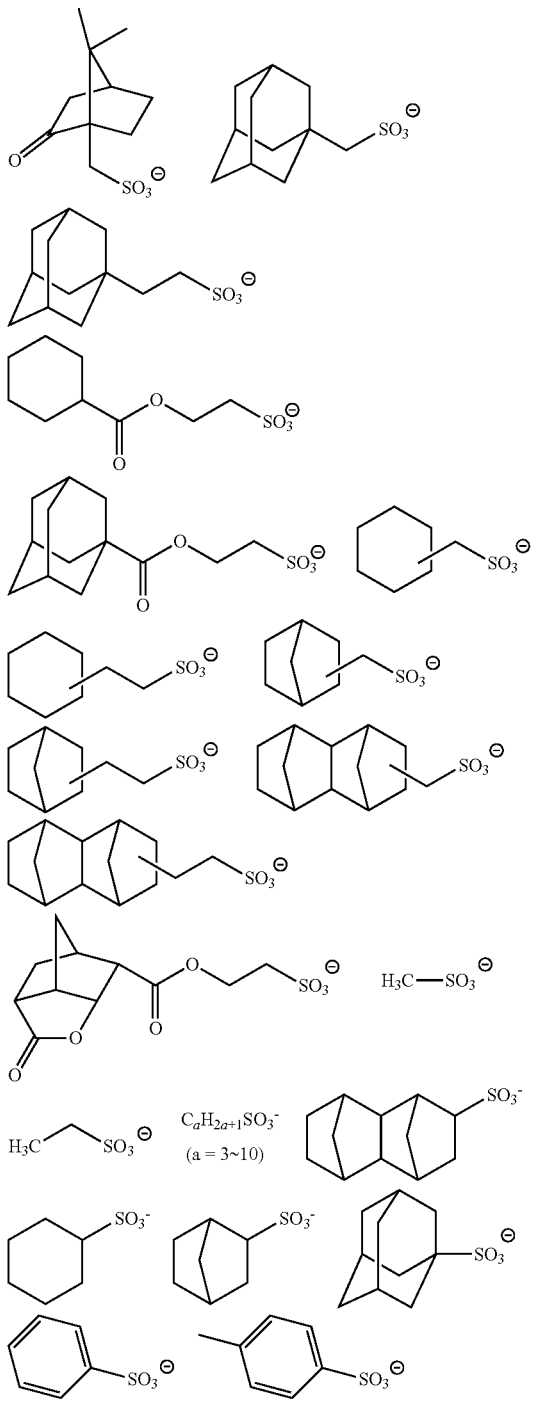

Cation Moiety

In formula (d2-2), $M'^{m+}$ is an m-valent onium cation, and is the same as defined for $M'^{m+}$ in the aforementioned formula (d2-1).

As the component (d2-2), one kind of compound may be used alone, or two or more thereof may be used in combination.

{Component (d2-3)}

Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $Rx^1$ to $Rx^4$ in the aforementioned formula (bd1-1), and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d2-3), $Rd^4$ represents a cyclic group which may have a substituent, a chain-like alkyl group which may have a substituent or a chain-like alkenyl group which may have a substituent, and is the same groups as those defined above for $Rx^1$ to $Rx^4$ in the aforementioned formula (bd1-1).

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $Rx^1$ to $Rx^4$ in the aforementioned formula (bd1-1) can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $Rx^1$ to $Rx^4$ in the aforementioned formula (bd1-1) can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. In the case where $Rd^4$ is an aliphatic cyclic group, the resist composition satisfactorily dissolves in an organic solvent, and the lithography properties are improved. Further, in the case where $Rd^4$ is an aromatic group, in a lithography process using EUV or the like as the exposure source, the light absorption efficiency of the resist composition is improved, and the sensitivity and the lithography properties become satisfactory.

In formula (d2-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. The divalent linking groups are the same as defined for the divalent hydrocarbon group which may have a substituent and the divalent linking group containing a hetero atom explained above for the divalent linking group for $Ya^{x1}$ in the aforementioned formula (a10-1).

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d2-3) are shown below.

[Chem. 94]

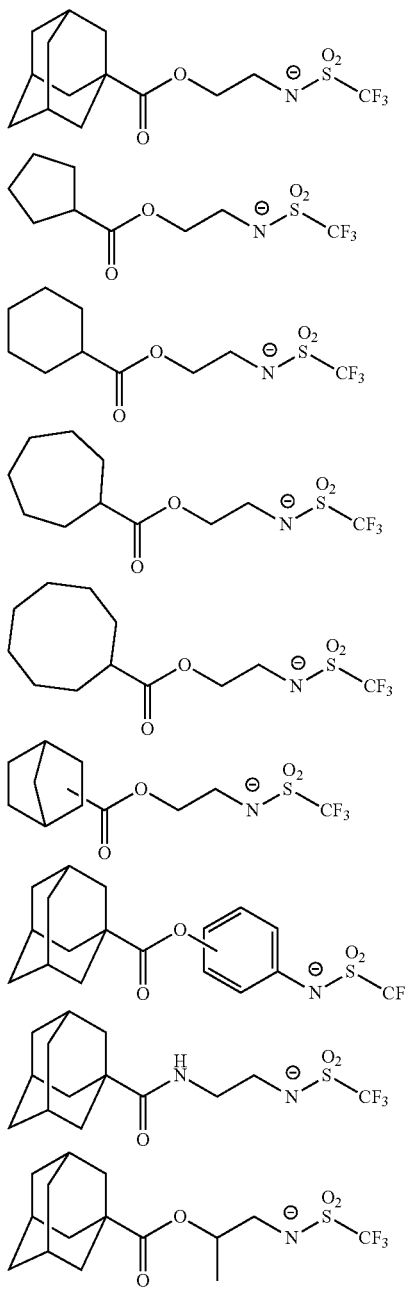

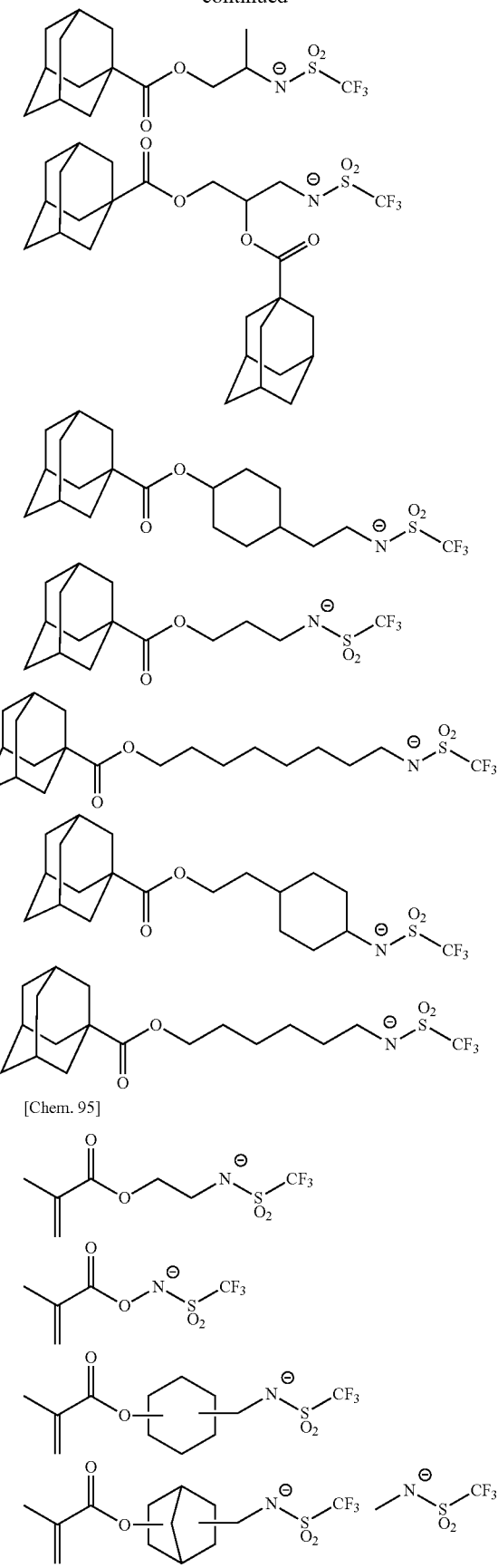

[Chem. 95]

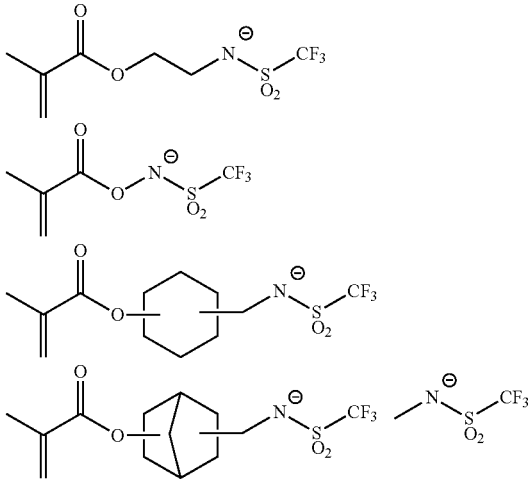

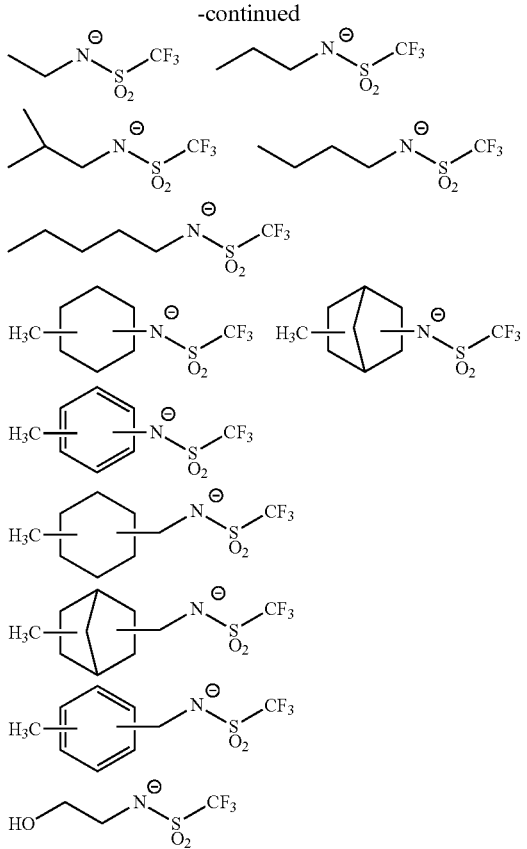

Cation Moiety

In formula (d2-3), $M'^{m+}$ is an m-valent onium cation, and is the same as defined for $M'^{m+}$ in the aforementioned formula (d2-1).

As the component (d2-3), one kind of compound may be used alone, or two or more thereof may be used in combination.

As the component (D2a), one kind of the above components (d1-1) to (d1-3), or at least two kinds thereof may be used in combination.

In the case where the resist composition contains the component (D2a), the amount of the component (D2a) relative to 100 parts by mass of the component (A) is preferably within a range of 0.5 to 10 parts by mass, more preferably from 0.5 to 8 parts by mass, and still more preferably from 1 to 6 parts by mass.

In addition, when the resist composition contains the component (D2a), in the resist composition, the amount of the component (D2a) within the entire base component (D) that traps (controls acid diffusion) an acid generated from the component (B) upon exposure is not particularly limited, but may be appropriately adjusted to be within a range of 0 mass % or more to 100 mass %.

When the amount of the component (D2a) is at least as large as the lower limit of the above-mentioned range, excellent lithography properties and excellent resist pattern shape can be more reliably obtained. On the other hand, a balance with other components can be achieved, and various lithography properties become favorable.

Production Method of Component (D2a):

The production methods of the components (d2-1) and (d2-2) are not particularly limited, and the components (d2-1) and (d2-2) can be produced by conventional methods.

Further, the production method of the component (d2-3) is not particularly limited, and the component (d1-3) can be produced in the same manner as disclosed in US2012-0149916.

<<Component (D3)>>

The component (D3) is a base component, and is a nitrogen-containing organic compound component that acts as an acid diffusion control agent (except for those corresponding to the component (D1a) and the component (D2a)) in the resist composition.

The component (D3) is not particularly limited as long as it acts as an acid diffusion control agent and does not correspond to the component (D1a) or the component (D2a), and examples thereof include a compound having an anion moiety and a cation moiety, and an aliphatic amine.

In the component (D3), regarding a compound having an anion moiety and a cation moiety, those in which a cation moiety in the components (d2-1) to (d2-3) is an ammonium cation may be exemplified. Examples of the ammonium cation here include cations (primary to quaternary ammonium cations) in which $NH_4$, or H bonded to a nitrogen atom thereof is substituted with a hydrocarbon group which may have a hetero atom or cyclic cations forming a ring together with a nitrogen atom thereof.

Among these aliphatic amines, a secondary aliphatic amine and a tertiary aliphatic amine are preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkylalcoholamines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy) ethyl}amine, tris {2-(2-methoxyethoxymethoxy) ethyl}amine, tris {2-(1-methoxyethoxy)ethyl}amine, tris {2-(1-ethoxyethoxy)ethyl}amine, tris{2-(1-ethoxypropoxy)

ethyl}amine, tris[2-{2-(2-hydroxyethoxy)ethoxy}ethyl]amine and triethanolamine triacetate, and triethanolamine triacetate is preferable.

Further, as the component (D3), an aromatic amine may be used.

Examples of aromatic amines include 4-dimethylaminopyridine, pyrrole, indole, pyrazole, imidazole and derivatives thereof, as well as tribenzylamine, 2,6-diisopropylaniline and N-tert-butoxycarbonylpyrrolidine.

As the component (D3), one kind of compound may be used alone, or two or more thereof may be used in combination.

When the resist composition contains the component (D3), the amount of the component (D3) is typically used in an amount within a range of 0.01 to 5 parts by mass, relative to 100 parts by mass of the component (A). Within the above range, a balance with other components can be achieved, and various lithography properties become favorable.

<<Component (E): At Least One Compound Selected from the Group Consisting of Organic Carboxylic Acids, and Phosphorus Oxo Acids and Derivatives Thereof>>

In the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof may be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

In the resist composition of the present embodiment, as the component (E), one kind of compound may be used alone, or two or more thereof may be used in combination.

When the resist composition contains the component (E), the amount of the component (E) is typically used in an amount within a range of 0.01 to 5 parts by mass, relative to 100 parts by mass of the component (A).

<<Component (F): Fluorine Additive>>

In the present embodiment, the resist composition may further include a fluorine additive (hereafter, referred to as "component (F)") for imparting water repellency to the resist film, or improving lithography properties.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of the structural unit (f1) and the aforementioned structural unit (a1); and a copolymer of the structural unit (f1), a structural unit derived from acrylic acid or methacrylic acid and the aforementioned structural unit (a1) are preferable. As the structural unit (a1) to be copolymerized with the structural unit (f1), a structural unit derived from 1-ethyl-1-cyclooctyl (meth)acrylate or a structural unit derived from 1-methyl-1-adamantyl (meth)acrylate is preferable.

[Chem. 96]

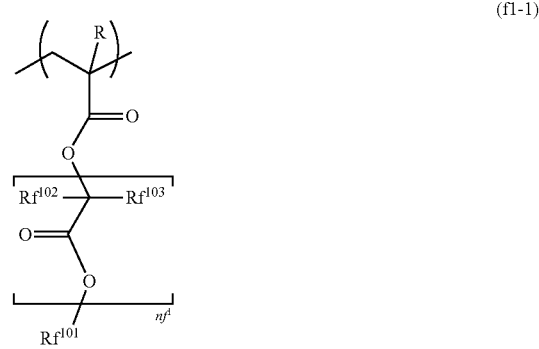

(f1-1)

In the formula, R is the same as defined above; $Rf^{102}$ and $Rf^{103}$ each independently represent a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to a carbon atom at the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl groups of 1 to 5 carbon atoms as those described above for R, and a methyl group or an ethyl group is preferable. Specific examples of the halogenated alkyl group of 1 to 5 carbon atoms represented by $Rf^{102}$ or $Rf^{103}$ include groups in which some or all of the hydrogen atoms of the aforementioned alkyl groups of 1 to 5 carbon atoms have been substituted with halogen atoms.

Examples of the halogen atom include a fluorine atom, a chlorine atom, a bromine atom and an iodine atom, and a fluorine atom is particularly desirable. Among these examples, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), nf¹ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having fluorine atoms have 25% or more of the hydrogen atoms within the hydrocarbon group fluorinated, more preferably 50% or more, and most preferably 60% or more, as the hydrophobicity of the resist film during immersion exposure is then enhanced.

Among these, as $Rf^{101}$, a fluorinated hydrocarbon group of 1 to 6 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight is equal to or less than the upper limit of this range, solubility in the resist solvent used for the resist becomes sufficient, and when the weight is equal to or more than the lower limit of this range, water repellency of the resist film becomes favorable.

Further, the dispersity (Mw/Mn) of the component (F) is preferably 1.0 to 5.0, more preferably 1.0 to 3.0, and most preferably 1.2 to 2.5.

In the resist composition of the present embodiment, as the component (F), one kind of compound may be used, or two or more thereof may be used in combination.

When the resist composition contains the component (F), the component (F) is used in an amount within a range of 0.5 to 10 parts by mass, relative to 100 parts by mass of the component (A).

<<Component (S): Organic Solvent>>

The resist composition of the present embodiment may be prepared by dissolving the resist materials for the resist composition in an organic solvent (hereafter, referred to as "component (S)").

The component (S) may be any organic solvent which can dissolve the respective components to give a homogeneous solution, and any organic solvent can be appropriately selected from those which are conventionally known as solvents for a chemically amplified resist composition.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

In the resist composition of the present embodiment, as the component (S), one kind of solvent may be used, or two or more thereof may be used in combination as a mixed solvent.

Among these, PGMEA, PGME, γ-butyrolactone, EL and cyclohexanone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably 2:8 to 8:2.

Specifically, when EL or cyclohexanone is mixed in as the polar solvent, the PGMEA:EL or cyclohexanone weight ratio is preferably from 1:9 to 9:1, and more preferably from 2:8 to 8:2. Alternatively, when PGME is mixed in as the polar solvent, the PGMEA:PGME weight ratio is preferably from 1:9 to 9:1, more preferably from 2:8 to 8:2, and still more preferably 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. In this case, regarding a mixing ratio, a mass ratio between the former and the latter is preferably 70:30 to 95:5.

The amount of the component (S) is not particularly limited, and is appropriately adjusted to a concentration which enables coating of a coating solution to a substrate. In general, the component (S) is used so that a solid content concentration of the resist composition is in a range of 0.1 to 20 mass %, and preferably in a range of 0.2 to 15 mass %.

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

After dissolving the resist materials in the organic solvent (S), the resist composition of the present embodiment may have impurities or the like removed by using a polyimide porous film, a polyamide-imide porous film, or the like. For example, the resist composition may be subjected to filtration using a filter formed of a polyimide porous membrane, a filter formed of a polyamide-imide porous film, or a filter formed of a polyimide porous membrane and a polyamide-imide porous film. Examples of the polyimide porous membrane and the polyamide-imide porous film include those described in Japanese Unexamined Patent Application, First Publication No. 2016-155121.

The resist composition of the present embodiment may contain the above component (A) and component (BD1-1), and as necessary, the above optional components.

For example, when the component (BD1-1) is used as the component (B1a), a resist composition containing the component (A), the component (B1a), the component (D2a) or the component (D3) is preferably exemplified. For example, when the component (BD1-1) is used as the component (D1a), a resist composition containing the component (A), the component (B2a), and the component (D1a) is preferably exemplified.

In addition, for example, when the component (BD1-1) is used as the component (B1a) and the component (D1a), a resist composition containing the component (A), the component (B1a), and the component (D1a) is preferably exemplified.

The resist composition of the present embodiment described above contains the compound (BD1-1) represented by the general formula (bd1-1). The component (BD1-1) has a relatively high hydrophobicity because it has a specific structure (bulky structure) in which the anion moiety is mainly composed of hydrocarbons. Therefore, the compatibility between the compound (BD1-1) and the base component (A) is improved, solubility in an organic solvent becomes favorable, and acid diffusivity in the resist film is appropriately controlled.

In addition, the component (BD1-1) has a cation moiety represented by the general formula (ca-0). The cation moiety represented by the general formula (ca-0) has a substituent containing a sulfonyl group, and thus the reactivity is improved. In addition, developing properties are favorable. It is speculated that, when the component (BD1-1) having such an anion moiety and cation moiety is contained, lithography properties (roughness reduction, defect reduction, and the like) are further improved and the sensitivity is enhanced according to the resist composition of the embodiment.

In addition, when the resist composition of the embodiment is used, since the uniformity of the compound (BD1-1) is improved in the resist film to be formed, it is possible to easily form a resist pattern having a high resolution and a favorable shape with reduced roughness.

(Second Aspect: Method of Forming Resist Pattern)

The method of forming a resist pattern according to the second aspect of the present invention includes: using a resist composition according to the first aspect to form a resist film on a substrate; exposing the resist film; and developing the exposed resist film to form a resist pattern.

The method for forming a resist pattern according to the present embodiment can be performed, for example, as follows.

Firstly, a resist composition of the first aspect is applied to a substrate using a spinner or the like, and a baking treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, a baking treatment (post baking) can be conducted following the developing.

In this manner, a resist pattern can be formed.

The substrate is not specifically limited and a conventionally known substrate can be used. For example, substrates for electronic components, such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

Multilayer resist methods are broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (triple-layer resist method).

The wavelength used for exposure is not particularly limited, and radiation using an ArF excimer laser, a KrF excimer laser, an $F_2$ excimer laser, extreme ultraviolet (EUV), vacuum ultraviolet (VUV), an electron beam (EB), X-rays, soft X-rays, or the like can be performed. The resist composition of the present embodiment is effective with an KrF excimer laser, an ArF excimer laser, an EB and EUV, and more effective with an ArF excimer laser, an EB and EUV, and most effective with an EB and EUV. That is, the method of forming a resist pattern of the present embodiment is a particularly useful method when a step of exposing a resist film includes an operation of exposing the resist film with extreme ultraviolet (EUV) or an electron beam (EB).

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range of 70 to 180° C. and preferably 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, the environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of conventional organic solvents which are capable of dissolving the component (A) (prior to exposure) can be used. Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group in the structure thereof. An "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterize the aforementioned solvents within the structure thereof. In such a case, the organic solvent can be classified as any solvent type having the characteristic functional group. For example, diethylene glycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of the ester-based solvent include methyl acetate, butyl acetate, ethyl acetate, isopropyl acetate, amyl acetate, isoamyl acetate, methoxyethyl acetate, ethoxyethyl acetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl 3-ethoxypropionate, and propyl-3-methoxypropionate. Among these examples, as an ester solvent, butyl acetate is preferable.

Examples of the nitrile-based solvent include acetonitrile, propionitrile, valeronitrile, and butyronitrile.

If desired, the organic developing solution may have a conventional additive blended in. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution which hardly dissolve the resist pattern can be used. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, at least one solvent selected from the group consisting of alcohol solvents and ester solvents is more preferable, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

As the organic solvent, one kind of solvent may be used alone, or two or more thereof may be used in combination. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended in. Examples of the additive include surfactants. As the surfactant, the same surfactants as those described above can be mentioned, a non-ionic surfactant is preferable, and a non-ionic fluorine surfactant or a non-ionic silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

In the method of forming a resist pattern of the present embodiment described above, since the resist composition according to the first aspect described above is used, when the resist pattern is formed, it is possible to form a resist pattern having high sensitivity and more favorable lithography properties (roughness reduction and the like).

(Method of Producing Compound)

A method of producing a compound (BD1-1) having an anion moiety and a cation moiety represented by the general formula (bd1-1) includes a step of oxidizing a compound represented by the following general formula (bp-1) (hereinafter referred to as a "compound (bp-1)") to obtain a compound represented by the following general formula (b1-1) (hereinafter referred to as a "compound (b1-1)").

[Chem. 97]

[In the formula, $R^{p1}$ is an aryl group which may have a substituent, $R^{p2}$ to $R^{p3}$ each independently represent an aryl group which may have a substituent or an alkyl group which may have a substituent.

$R^{p2}$ to $R^{p3}$ may be mutually bonded to form a ring together with a sulfur atom in the formula. Here, at least one of $R^{p1}$ to $R^{p3}$ is an aryl group or alkyl group having a group represented by —$SR^{p4}$ as the substituent. $R^{p4}$ is an alkyl group. Xp is a counter anion].

[Chem. 98]

[In the formula, $R^{b11}$ is an aryl group which may have a substituent, $R^{b12}$ to $R^{b13}$ each independently represent an aryl group which may have a substituent or an alkyl group which may have a substituent. $R^{b12}$ to $R^{b13}$ may be mutually bonded to form a ring together with a sulfur atom in the formula. Here, at least one of $R^{b11}$ to $R^{b13}$ is an aryl group or alkyl group having a group represented by —$SO_2$—$R^{p4}$ as the substituent. $R^{p4}$ is an alkyl group. Xp is a counter anion].

In the compound (bp-1), description of an aryl group which may have a substituent for $R^{p1}$ is the same as description of an aryl group which may have a substituent for $R^{b1}$ in the formula (ca-0).

Description of an aryl group which may have a substituent or an alkyl group which may have a substituent for $R^{p2}$ to $R^{p3}$ in the formula (bp-1) is the same as description of an aryl group which may have a substituent or an alkyl group which may have a substituent for $R^{b2}$ to $R^{b3}$ in the formula (ca-0).

In the formula (bp-1), at least one of $R^{p1}$ to $R^{p3}$ is an aryl group or alkyl group having a group represented by —$SR^{p4}$ as a substituent. $R^{p4}$ is an alkyl group.

In the group represented by —$SR^{p4}$, an alkyl group for $R^{p4}$ is preferably a linear or branched linear alkyl group. Specific examples of the linear or branched linear alkyl group include a methyl group, an ethyl group, a propyl group, an isopropyl group, an n-butyl group, an isobutyl group, a tert-butyl group, a pentyl group, an isopentyl group, and a neopentyl group, and a methyl group or an ethyl group is preferable, and a methyl group is more preferable.

In addition, in the group represented by —$SR^{p4}$, when $R^{p2}$ to $R^{p3}$ are mutually bonded to form a ring together with a sulfur atom in the formula and additionally to form a ring together with the group represented by —$SR^{p4}$, the group represented by —$SR^{p4}$ may form a ring as a bivalent group in which one hydrogen atom is removed from an alkyl group for $R^{p4}$ or a bivalent group for —S— (that is, as —$SR^{p4'}$— ($R^{p4'}$ is an alkylene group or a single bond)).

In the formula (bp-1), examples of the counter anion for Xp include a halogen anion (Cl, Br, I), a carboxylic acid anion (acetate anion, and the like), and $RpSO_3$.

Rp is an alkyl group having 1 to 5 carbon atoms (a methyl group, an ethyl group, a propyl group, an isopropyl group, an n-butyl group, an isobutyl group, a tert-butyl group, a pentyl group, an isopentyl group, a neopentyl group) or a fluorinated alkyl group having 1 to 5 carbon atoms, and a trifluoromethyl group is preferable.

In the formula (b1-1), description of an aryl group which may have a substituent for $R^{b11}$ is the same as the description for an aryl group which may have a substituent for $R^{b11}$ in the formula (ca-0).

In the formula (b1-1), description of an aryl group which may have a substituent or an alkyl group which may have a substituent for $R^{b12}$ to $R^{b13}$ is the same as the description for an aryl group which may have a substituent or an alkyl group which may have a substituent for $R^{b2}$ to $R^{b3}$ in the formula (ca-0).

In the formula (b1-1), at least one of $Rb^1$ to $R^{b13}$ is an aryl group or alkyl group having a group represented by —$SO_2$—$R^{p4}$ as a substituent.

Description of a substituent containing a halogen atom for $R^{b11}$ to $R^{b13}$ is the same as the description for a substituent containing a halogen atom for $R^{b1}$ to $R^{b3}$ in the formula (ca-0).

In the group represented by —$SO_2$—$R^{p4}$, description of an alkyl group for $R^{p4}$ is the same as an alkyl group for $R^{p4}$ in the "group represented by —$SR^{p4}$" for $R^{p1}$ to $R^{p3}$ in the formula (bp-1).

In the formula (b1-1), description of a counter anion for Xp is the same as the description for a counter anion for Xp in the formula (bp-1).

A method of oxidizing the compound (bp-1) is not particularly limited, and examples thereof include an oxidation reaction (for example, oxidation with oxone) in which the compound (bp-1) is reacted with potassium persulfate monosulfate (2$KHSO_5$·$KHSO_4$·$K_2SO_4$).

A solvent used for an oxidation reaction is not particularly limited, and examples thereof include water or at least one selected from alcohol solvents such as methanol, ethanol, and isopropanol.

A reaction temperature of the oxidation reaction is not particularly limited, and it is preferably 0 to 50° C. and more preferably 5 to 40° C.

A reaction time of the oxidation reaction is not particularly limited, and it is preferably 1 to 72 hours and more preferably 2 to 60 hours.

Regarding the compound (bp-1), those commercially available may be used or those synthesized by a known production method may be used.

Regarding the compound (b1-1), for example, according to a salt exchange reaction with a precursor such as an ammonium salt having a desired anion (a precursor having an anion moiety in the general formula (bd1-1)), the compound (BD1-1) having the anion can be obtained.

Here, for example, the precursor such as an ammonium salt having the desired anion (a precursor having an anion moiety in the general formula (bd1-1)) can be produced as follows.

For example, as shown in the following reaction formula, a method using a Diels-Alder reaction in which an alkene or alkyne ((1) in the following reaction formula) is added to a conjugated diene ((2) in the following reaction formula) to form a ring structure ((3) in the following reaction formula) may be exemplified.

Specifically, when a desired anion group is introduced into a product (intermediate) according to a Diels-Alder reaction to obtain a precursor, and then a desired cation is introduced according to a salt exchange reaction, a desired component (BD1-1) is obtained. In addition, a Diels-Alder reaction using an alkene, alkyne or conjugated diene containing a substituent derived from a desired anion group (a substituent that can introduce a desired anion group) may be performed and an intermediate obtained, and a desired anion group is then introduced, and thereby a precursor can be obtained.

The conjugated diene is appropriately selected according to a desired compound (the component (BD1-1)), and for example, anthracene or derivatives thereof, and triptycene or derivatives thereof may be used.

Examples of a method of introducing an anion group include a method using an esterification reaction; a method using a reaction between an ammonium salt having an anion group into which a tosyl group is introduced and a lithium compound having a ring structure with an anion moiety skeleton (derived due to a Diels-Alder reaction) and a method of sulfinating an intermediate containing a halogen atom to obtain a sulfonate, and then performing oxidation to obtain a sulfonate.

When an esterification reaction is used for a method of introducing an anion group, examples of a method of producing a compound represented by the general formula (bd1-1) [a compound having an anion group represented by the general formula (bd1-r-an1), $Y^{b01}$=—C(=O)—O—] include a production method of an embodiment including the following Steps 1 and 2.

Here, an anion group represented by the general formula (bd1-r-an1), which is $Y^{b01}$=—C(=O)—O—, is referred to as "an anion group represented by the general formula (b1-r-an10)." A desired compound produced according to the production method of the embodiment including such Steps 1 and 2 is set as a compound (B 1-0).

As the compounds used in each step, commercially available compounds may be used, or the compounds may be synthesized.

As the organic solvent used in steps 1 and 2, any solvent capable of dissolving compounds used in each step and which does not react with the compounds may be used. Examples of the solvent include dichloromethane, dichloroethane, chloroform, tetrahydrofuran, N,N-dimethylformamide, dimethylacetamide, dimethylsulfoxide, acetonitrile, and propionitrile.

Step 1

In Step 1, an intermediate and the compound (I) are dissolved in an organic solvent (dichloromethane and the like), and a reaction occurs in the presence of a base. Then, filtration, concentration or the like is conducted to obtain a precursor (Bpre).

[Chem. 99]

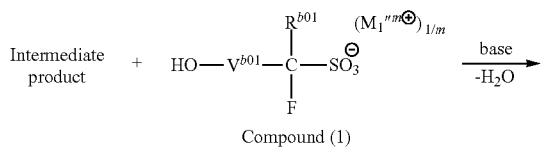

Compound (1)

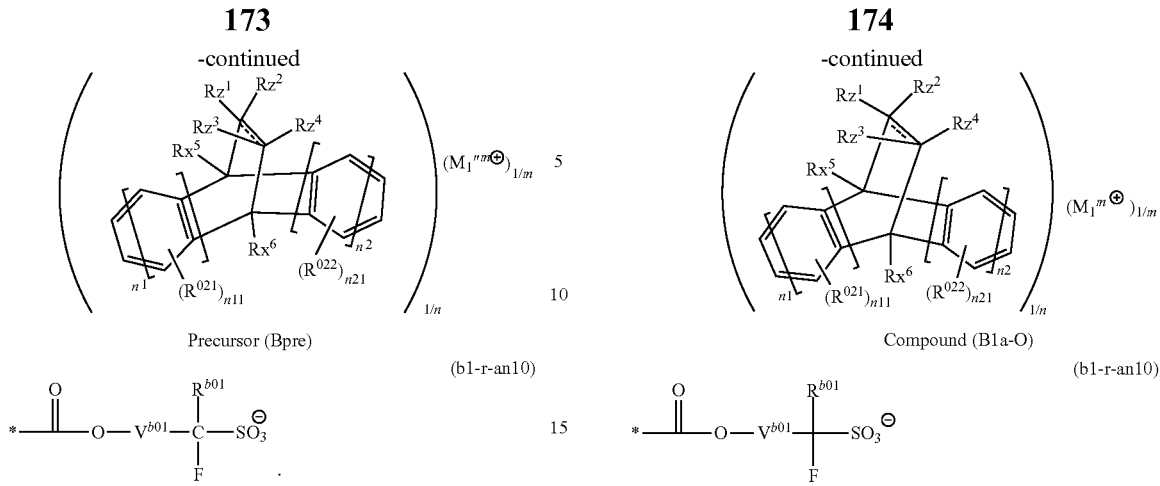

Precursor (Bpre)

Compound (B1a-O)

(b1-r-an10)

(b1-r-an10)

[In the formula, $R^{b01}$ and $V^{b01}$ are the same as $R^{b01}$ and $V^{b01}$ in the formula (bd1-r-an1). $(M_1^{''m\oplus})_{1/m}$ represents an ammonium cation; and $Rx^5$, $Rx^6$, $Rz^1$ to $Rz^4$, $R^{021}$, n1, n11, $R^{022}$, n2 and n21 are the same as $Rx^5$, $Rx^6$, $Rz^1$ to $Rz^4$, $R^{021}$, n1, n11, $R^{022}$, n2 and n21 in the formula (bd1-an3). Here, at least one of $Rx^5$ to $Rx^6$ and $Rz^1$ to $Rz^4$ has an anion group represented by the general formula (b1-r-an10), and the entire anion moiety may be an n-valent anion. n represents an integer of 1 or more.

Examples of the base added in step 1 include an organic base, such as triethylamine, 4-dimethylaminopyridine, pyridine, ethyldiisopropylaminocarbodiimide hydrochloride (EDCI), dicyclohexylcarboxyimide (DCC), diisopropylcarbodiimide and carbodiimidazole; and an organic base, such as sodium hydride, $K_2CO_3$, and $Cs_2CO_3$.

The cation moiety of the compound (I) may be an ammonium cation derived from an aliphatic amine, or an ammonium cation derived from an aromatic amine.

The amount of the compound (I) used, relative to the intermediate product is preferably within a range of 1 to 3 equivalents, and more preferably 1 to 2 equivalents.

The reaction temperature is preferably within the range of 0 to 50° C., and more preferably 5 to 40° C.

Step 2

In Step 2, a precursor (Bpre) and a compound (IIa) for salt exchange (specifically, for example, the compound (b1-1)) are reacted in a solvent such as water, dichloromethane, acetonitrile, or chloroform, and a desired compound (B1a-O) is obtained according to salt exchange between the precursor (Bpre) and an organic cation in the compound (IIa).

[Chem. 100]

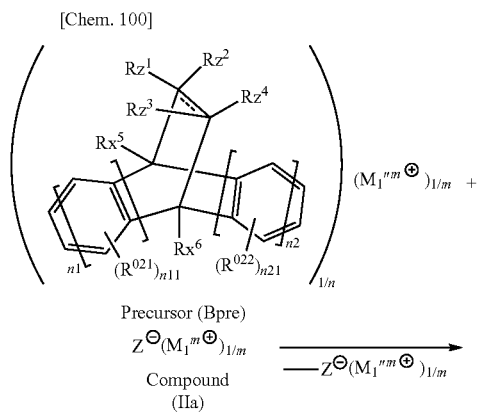

Precursor (Bpre)

$Z^{\ominus}(M_1^{m\oplus})_{1/m}$ Compound (IIa) ⟶ $-Z^{\ominus}(M_1^{''m\oplus})_{1/m}$

[In the formula, $R^{b01}$ and $V^{b01}$ are the same as $R^{b01}$ and $V^{b01}$ in the formula (b1-r-an10). $(M_1^{''m+})_{1/m}$ represents an ammonium cation; and $Rx^5$, $Rx^6$, $Rz^1$ to $Rz^4$, $R^{021}$, n1, n11, $R^{022}$, n2 and n21 are the same as $Rx^5$, $Rx^6$, $Rz^1$ to $Rz^4$, $R^{021}$, n1, n11, $R^{022}$, n2 and n21 in the formula (bd1-an3). Here, at least one of $Rx^5$ to $Rx^6$ and $R^z$ to $Rz^4$ has an anion group represented by the general formula (b1-r-an10), and the entire anion moiety may be an n-valent anion. n represents an integer of 1 or more; Z represents a non-nucleophilic ion. $(M_1^{m+})_{1/m}$ is an m-valent organic cation, and here it is the same as the cation represented by the formula (ca-0)].

Examples of Z include a halogen ion such as a bromine ion and a chloride ion; an ion that can act as an acid with less acidity than the precursor (Bpre), $BF_4$, $AsF_6$, $SbF_6$, $PF_6$ or $ClO_4$.

The reaction temperature is preferably 0 to 100° C., and more preferably 0 to 50° C.

The reaction time varies, depending on the reactivity of the precursor (Bpre) and the compound (II) for salt exchange, the reaction temperature, and the like. However, in general, the reaction time is preferably 10 minutes to 24 hours, more preferably 10 minutes to 12 hours.

After the salt exchange reaction, the compound in the reaction liquid may be separated and purified. The separation and purification can be conducted by a conventional method. For example, any of concentration, solvent extraction, distillation, crystallization, re-crystallization and chromatography may be used.

The structure of the compound obtained in the manner described above can be identified by a general organic analysis method such as [1]H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The intermediate is appropriately selected according to the desired compound (B1-0), and examples thereof include a product represented by the following reaction formula according to a Diels-Alder reaction. For a (starting material 1) in the following reaction formula, anthracene or derivatives thereof can be used. For a (starting material 2) in the following reaction formula, a compound having an ethylenic double bond such as an acrylic ester can be used.

In addition, examples of the intermediate include triptycene and derivatives thereof.

[Chem. 101]

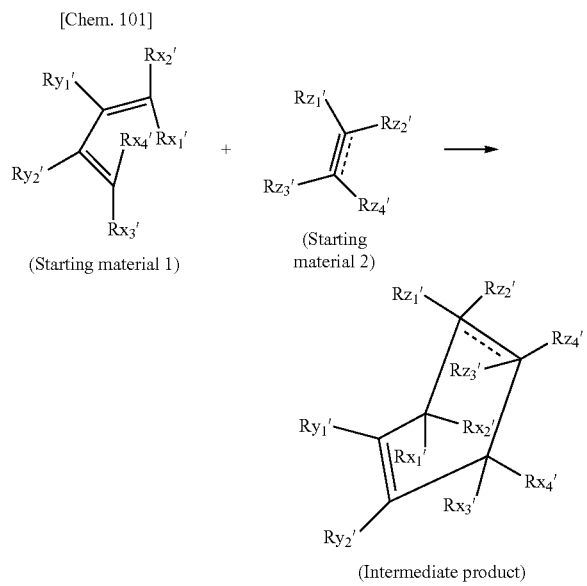

(Starting material 1)    (Starting material 2)

(Intermediate product)

[In the formula, $Rx_1'$ to $Rx_4'$ are the same as $Rx^1$ to $Rx^4$. $Ry_1'$ to $Ry_2'$ are the same as $Ry^1$ to $Ry^2$.

[Chem. 102]

───── is a triple bond or a double bond.

[Chem. 103]

─ ─ ─ ─ ─ is a double bond or a single bond. $Rz_1'$ to $Rz_4'$ are the same as $Rz^1$ to $Rz^4$. Here, at least one of $Rx_1'$ to $Rx_4'$, $Ry_1'$ to $Ry_2'$ and $Rz_1'$ to $Rz_4'$ is a group containing a leaving group that can introduce the anion group].

Examples of the group containing a leaving group that can introduce an anion group include groups containing a halogen atom, a group containing a halogen atom, and a dehydration-condensable substituent (a hydroxyl group, a carboxy group, and the like).

Regarding a method of introducing an anion group, when an esterification reaction is used, examples of the group containing a leaving group include a dehydration-condensable substituent. For example, the intermediate in the reaction formula shown in Step 1 preferably has a dehydration-condensable substituent (such as a hydroxyl group or a carboxy group). An esterification reaction occurs in Step 1, and a sulfonic acid ammonium salt as a precursor (Bpre) is obtained.

Regarding a method of introducing an anion group, when a reaction between an ammonium salt having an anion group into which a tosyl group is introduced and a lithium compound having a ring structure of an anion moiety skeleton (derived from a Diels-Alder reaction) is used, examples of the group containing a leaving group include a halogen atom and a group containing a halogen atom, and a bromine atom is preferable. An intermediate containing a halogen atom (preferably, a bromine atom) is converted into Li to obtain a Li compound, and then reacted with an ammonium salt having an anion group into which a tosyl group is introduced, and thereby a sulfonic acid ammonium salt as a precursor is obtained.

Regarding a method of introducing an anion group, when a method of sulfinating an intermediate containing a halogen atom to obtain a sulfonate and then performing oxidation to obtain a sulfonate is used, examples of the group containing a leaving group include a halogen atom and a group containing a halogen atom, and a bromine atom is preferable. An intermediate containing a halogen atom (preferably, a bromine atom) is converted into a sulfinate ammonium salt using a sulfinating agent in the presence of an amine and additionally reacted with an oxidizing agent, and thereby a sulfonic acid ammonium salt as a precursor is obtained.

When the above salt exchange in Step 2 is performed on the respective sulfonic acid ammonium salts as precursors, a desired compound (the component (BD1-1)) can be obtained.

(Third Aspect: Resist Composition)

A resist composition according to a third aspect of the present invention generates an acid upon exposure and contains the compound (BD1-2) that exhibits a changed solubility in a developing solution under the action of acid, and is represented by the general formula (bd1-2) (hereinafter referred to as a "component (BD1-2)") and the base component (A) (hereinafter referred to as a "component (A)") that exhibits a changed solubility in a developing solution under the action of acid.

Regarding one embodiment of such a resist composition, a resist composition containing the component (A) and an acid-generator component (B) that generates an acid upon exposure (hereinafter referred to as a "component (B)") may be exemplified. Preferable examples include those further containing a base component (hereinafter referred to as a "component (D)") that traps (that is, controls acid diffusion) an acid generated from the component (B) upon exposure in addition to the component (A) and the component (B).

In the resist composition of the present embodiment, the component (BD1-2) can be used as the component (B) or the component (D) by selecting an anion group in the molecule.

<Compound (BD1-2)>

In the resist composition of the present embodiment, component (BD1-2) is a compound having an anion moiety and a cation moiety represented by the following general formula (bd1-2).

[Chem. 104]

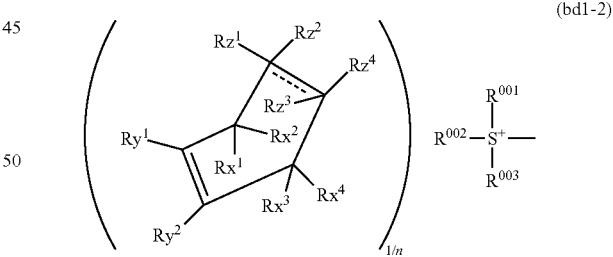

(bd1-2)

In the formula, $R^{001}$ to $R^{003}$ each independently represent a monovalent organic group; provided that at least one of $R^{001}$ to $R^{003}$ represents an organic group having an acid dissociable group; and two or more of $R^{001}$ to $R^{003}$ may be mutually bonded to form a ring with the sulfur atom; $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 105]

----- represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more.

Anion Moiety

Regarding an anion moiety in the formula (bd1-2), the same anion moiety as in the formula (bd1-1) described above may be exemplified.

Cation Moiety $[S^+(R^{001})(R^{002})(R^{003})]$

In the formula (bd1-2), $R^{001}$ to $R^{003}$ each independently represent a monovalent organic group; provided that at least one of $R^{001}$ to $R^{003}$ represents an organic group having an acid dissociable group; and two or more of $R^{001}$ to $R^{003}$ may be mutually bonded to form a ring with the sulfur atom;

The monovalent organic group for $R^{001}$ to $R^{003}$ may be an aliphatic hydrocarbon group which may have a substituent or an aromatic hydrocarbon group which may have a substituent. The aliphatic hydrocarbon group may be saturated or unsaturated. In addition, the aliphatic hydrocarbon group and the aromatic hydrocarbon group for $R^{001}$ to $R^{003}$ may contain a hetero atom.

Examples of the monovalent organic group for $R^{001}$ to $R^{003}$ include an aryl group which may have a substituent, an alkyl group which may have a substituent, and an alkenyl group which may have a substituent.

The aryl group for $R^{001}$ to $R^{003}$ is a hydrocarbon group having an aromatic ring, preferably has 3 to 30 carbon atoms, more preferably 5 to 30 carbon atoms, still more preferably 6 to 20 carbon atoms, particularly preferably 6 to 15 carbon atoms, and most preferably 6 to 10 carbon atoms. Here, the number of carbon atoms within a substituent(s) is not included in the number of carbon atoms of the aromatic hydrocarbon group.

Specific examples of the aromatic ring contained in the aromatic hydrocarbon group for $R^{001}$ to $R^{003}$ include benzene, fluorene, naphthalene, anthracene, phenanthrene, biphenyl, and an aromatic heterocycle in which some of carbon atoms constituting such an aromatic ring are substituted with a hetero atom. Examples of the hetero atom within the aromatic hetero rings include an oxygen atom, a sulfur atom and a nitrogen atom.

Among these, regarding the aryl group for $R^{001}$ to $R^{003}$, an aryl group having 6 to 20 carbon atoms is preferable, and a phenyl group, and a naphthyl group are particularly preferable.

The alkyl group for $R^{001}$ to $R^{003}$ may be linear or cyclic.

The linear alkyl group may be linear or branched. The linear alkyl group preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group. The branched linear alkyl group preferably has 3 to 20 carbon atoms, more preferably 3 to 15 carbon atoms, and most preferably 3 to 10 carbon atoms. Specifically, for example, a 1-methylethyl group, a 1,1-dimethylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, a 4-methylpentyl group, and the like may be exemplified.

The alkenyl group for $R^{001}$ to $R^{003}$ may be linear or branched, and preferably has 2 to 10 carbon atoms, more preferably 2 to 5 carbon atoms, still more preferably 2 to 4 carbon atoms, and particularly preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

The cyclic alkyl group may be polycyclic or monocyclic. Regarding the monocyclic group, a group in which one or more hydrogen atoms are removed from a monocycloalkane is preferable. The monocycloalkane preferably has 3 to 6 carbon atoms, and specific examples thereof include cyclopentane and cyclohexane. Regarding the polycyclic group, a group in which one or more hydrogen atoms are removed from a polycycloalkane is preferable. The polycycloalkane preferably has 7 to 12 carbon atoms, and specifically, adamantane, norbornane, isobomane, tricyclodecane, tetracyclododecane, and the like may be exemplified.

Here, in the formula (bd1-2), at least one of $R^{001}$ to $R^{003}$ is an organic group having an acid dissociable group.

Regarding the acid dissociable group, those the same as in the above component (A) may be exemplified, and an "acetal type acid dissociable group," a "tertiary alkyl ester type acid dissociable group," a "tertiary alkyl ester type acid dissociable group," and the like may be exemplified.

Among the above examples, in consideration of diffusion control, an acid dissociable group contained in at least one of $R^{001}$ to $R^{003}$ is preferably a group having a cyclic structure, and more preferably a group having an alicyclic structure. The alicyclic structure may be monocyclic or polycyclic.

Alternatively, an acid dissociable group contained in at least one of $R^{001}$ to $R^{003}$ is preferably a group having a tertiary alkyl ester structure and more preferably a group having a tertiary alkyl ester structure with 5 or more carbon atoms in order to easily improve dissolution contrast during development.

Regarding an organic group containing an acid dissociable group for $R^{001}$ to $R^{003}$, for example, a group represented by the following general formula (Rca-0) is preferably exemplified. The symbol * in the formula indicates a bond that bonds to a sulfur atom.

[Chem. 106]

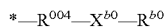
$*—R^{004}—X^{b0}—R^{b0}$ (Rca-0)

[In the formula, $R^{004}$ represents a bivalent organic group. $X^{b0}$ represents $—Y^{b0}—C(=O)—O—$, or $—O—$. $Y^{b0}$ represents an alkylene group. $R^{b0}$ represents an acid dissociable group represented by the following general formula (a1-r-1), (a1-r-2) or (a1-r-3)].

In the formula (Rca-0), a bivalent organic group for $R^{004}$ may be an aliphatic hydrocarbon group which may have a substituent or an aromatic hydrocarbon group which may have a substituent. The aliphatic hydrocarbon group may be saturated or unsaturated. In addition, the aliphatic hydrocarbon group and the aromatic hydrocarbon group for $R^{004}$ may contain a hetero atom.

Examples of the bivalent organic group for $R^{004}$ include an arylene group which may have a substituent, an alkylene group which may have a substituent, and an alkenylene group which may have a substituent. Examples of the arylene group, the alkylene group, and the alkenylene group for $R^{004}$ include groups in which one hydrogen atom is additionally removed from the aryl group, the alkyl group, and the alkenyl group for $R^{001}$ to $R^{003}$.

The alkylene group for $Y^{b0}$ preferably has 1 to 10 carbon atoms, more preferably 1 to 8 carbon atoms, still more preferably 1 to 5 carbon atoms, and particularly preferably 1 to 2 carbon atoms.

In the formula (Rca-0), when $X^{b0}$ is —$Y^{b0}$—C(=O)—O—, $R^{b0}$ is an acid dissociable group represented by the general formula (a1-r-1) or (a1-r-2). When $X^{b0}$ is —O—, $R^{b0}$ is an acid dissociable group represented by the general formula (a1-r-1) or (a1-r-3).

Examples of the substituent (except for an acid dissociable group) contained in the aliphatic hydrocarbon group (an alkyl group, an alkenyl group) or the aromatic hydrocarbon group (an aryl group) for $R^{001}$ to $R^{003}$ include an alkyl group, a halogen atom, a halogenated alkyl group, a carbonyl group, a cyano group, an amino group, an aryl group, and groups represented by the following general formulae (ca-r-1) to (ca-r-7).

In addition, in the formula (bd1-2), two or more of $R^{001}$ to $R^{003}$ may be mutually bonded to form a ring together with a sulfur atom in the formula.

When two or more of $R^{001}$ to $R^{003}$ are mutually bonded to form a ring together with a sulfur atom in the formula, they may be bonded via a hetero atom such as a sulfur atom, an oxygen atom, and a nitrogen atom, or a functional group such as a carbonyl group, —SO—, —$SO_2$—, —$SO_3$—, —COO—, —CONH— or —N(RN)— (RN is an alkyl group having 1 to 5 carbon atoms). The ring containing the sulfur atom in the skeleton thereof is preferably a 3- to 10-membered ring, and most preferably a 5- to 7-membered ring. Specific examples of a ring to be formed include, for example a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

Specific examples of cations suitable for a cation moiety in the component (BD1-2) include cations represented by the following formulae (ca-1-1b) to (ca-1-34b), and (ca-3-1b) to (ca-3-4b).

[Chem. 107]

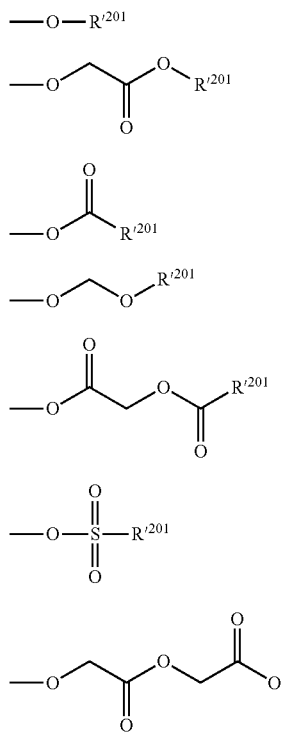

[ca-r-1]
[ca-r-2]
[ca-r-3]
[ca-r-4]
[ca-r-5]
[ca-r-6]
[ca-r-7]

[Chem. 108]

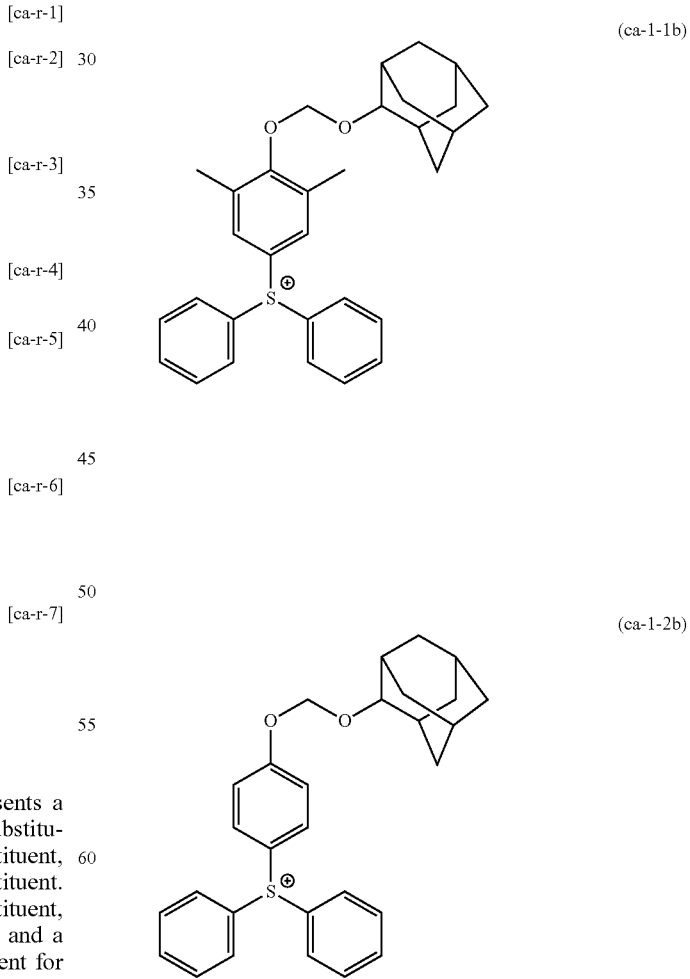

(ca-1-1b)

(ca-1-2b)

In the formulae, each $R'^{201}$ independently represents a hydrogen atom, a cyclic group which may have a substituent, a chain-like alkyl group which may have a substituent, or a chain-like alkenyl group which may have a substituent.

Regarding a cyclic group which may have a substituent, a linear alkyl group which may have a substituent, and a chain-like alkenyl group which may have a substituent for $R'^{201}$, those the same as described for $R^{001}$ to $R^{003}$ described above (an aryl group, a cyclic alkyl group, a linear alkyl group, and an alkenyl group) may be exemplified.

-continued
(ca-1-3b)
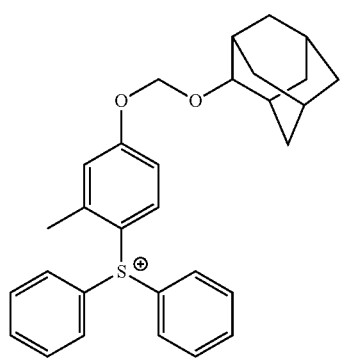
(ca-1-4b)
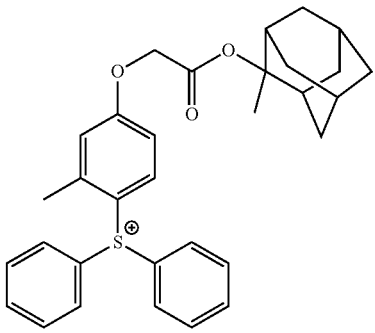
(ca-1-5b)
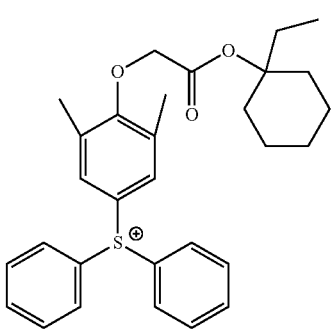
(ca-1-6b)
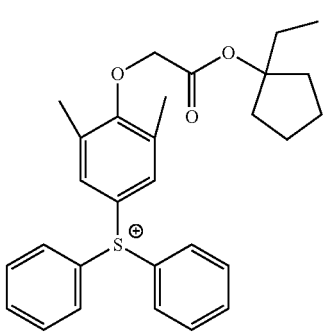
-continued
(ca-1-7b)
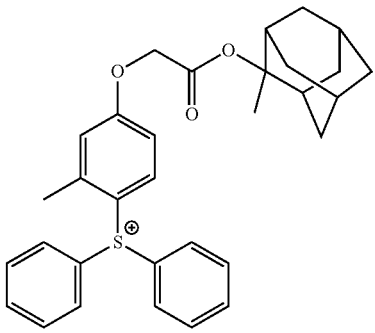
(ca-1-8b)
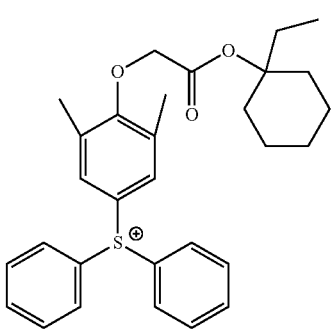
(ca-1-9b)
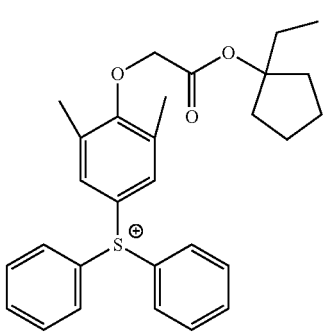
(ca-1-10b)
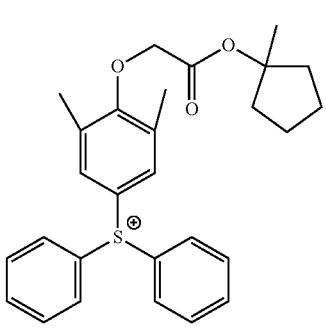
(ca-1-11b)
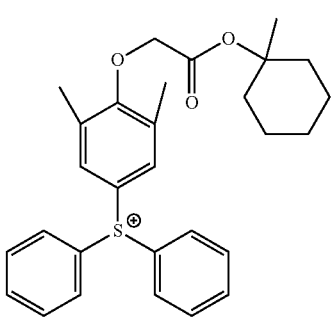

[Chem. 109]
(ca-1-12b)
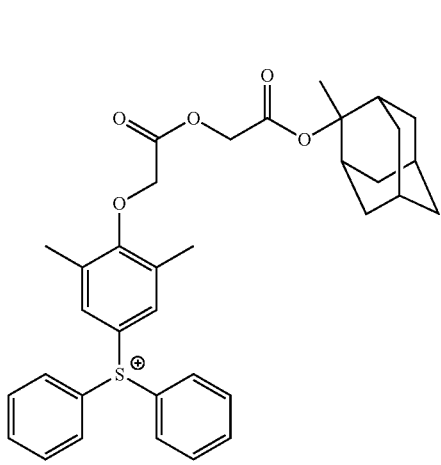
(ca-1-13b)
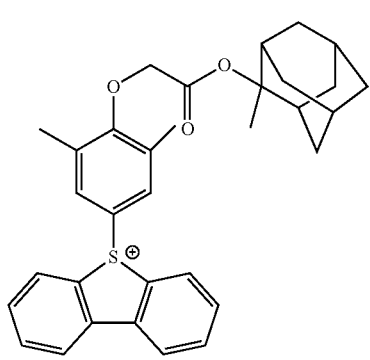
(ca-1-14b)
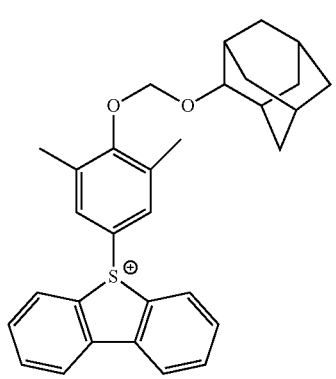
[Chem. 110]
(ca-1-15b)
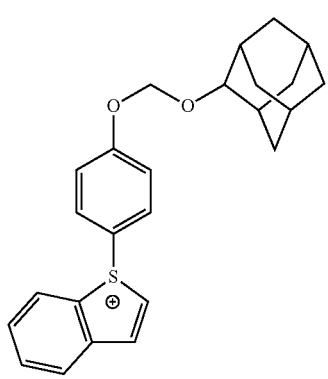
(ca-1-16b)
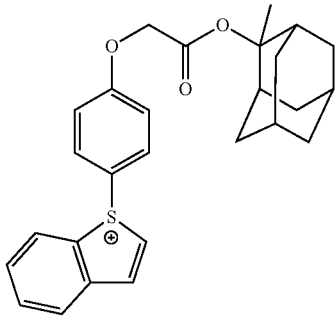
(ca-1-17b)
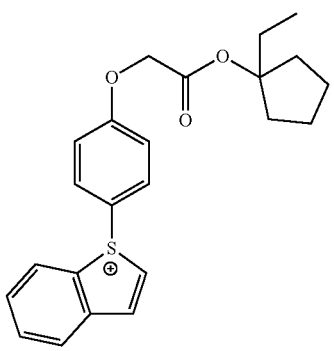
(ca-1-18b)
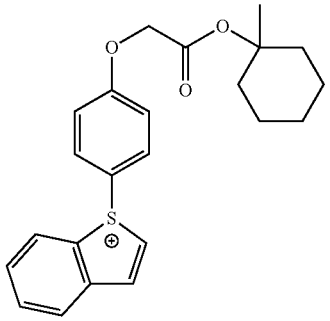
[Chem. 111]
(ca-1-19b)
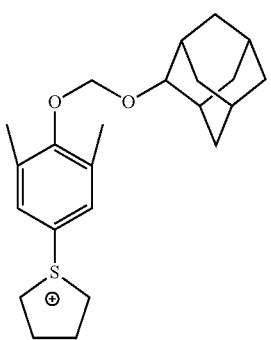

(ca-1-20b)
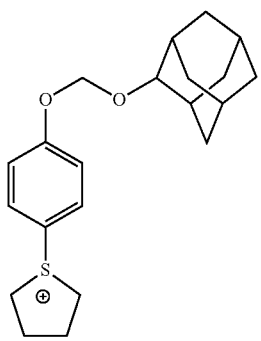
(ca-1-21b)
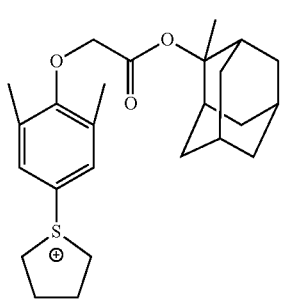
(ca-1-22b)
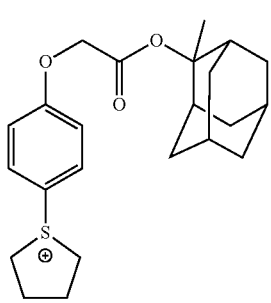
(ca-1-23b)
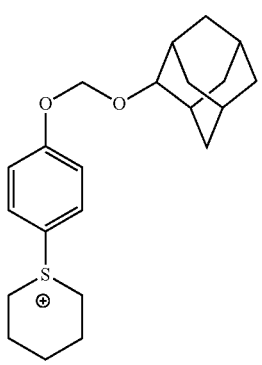
(ca-1-24b)
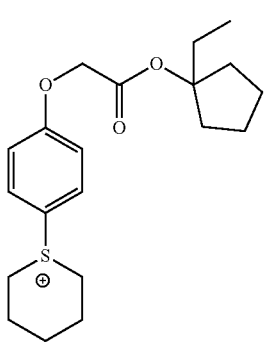
(ca-1-25b)
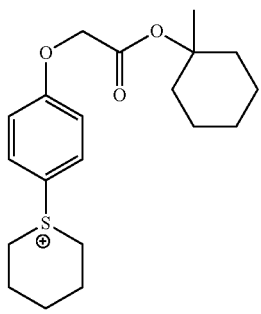
(ca-1-26b)
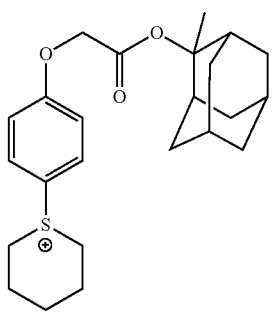
[Chem. 112]
(ca-1-27b)
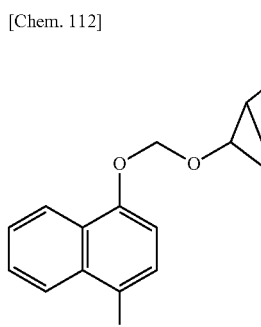
(ca-1-28b)
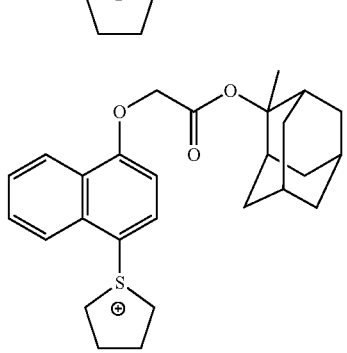
(ca-1-29b)
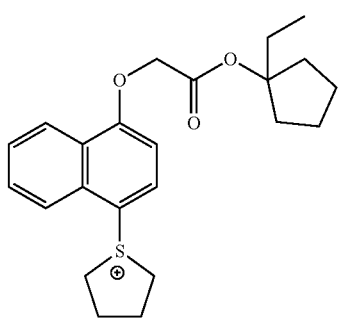

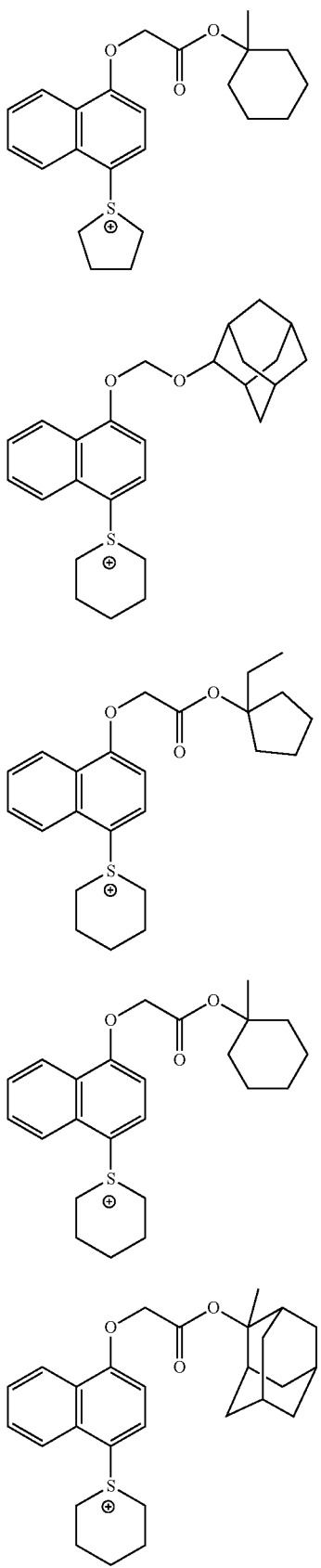

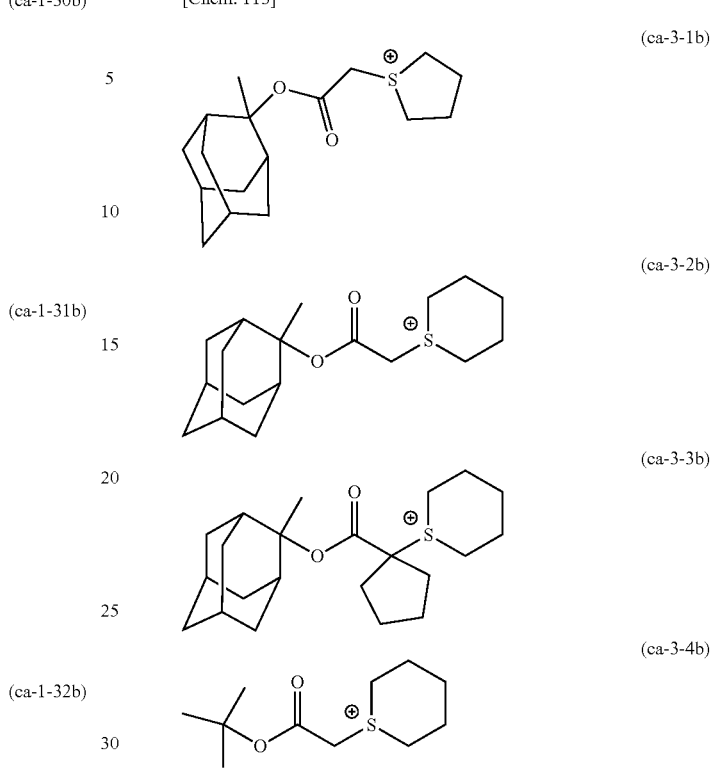

Among the above examples, the cation moiety of the component (BD1-2) which has a cyclic structure and a cation represented by any of the chemical formulae (ca-1-1b) to (ca-1-3b), (ca-1-5b) to (ca-1-14b), and (ca-3-1b) to (ca-3-3b) having a tertiary alkyl ester structure having 5 or more carbon atoms is preferable. Among these, a cation represented by any of chemical formulae (ca-1-6b) to (ca-1-12b) is more preferable.

Among the components (BD1-2) described above, regarding an acid-generator component (B) (hereinafter referred to as a "component (B1b)") that generates an acid acting on the component (A), various combinations of anions represented by the formulae (bd1-an1) to (bd1-an3) described above which are anions (most preferably, an anion represented by any of (bd1-an3-1) to (bd1-an3-15)) having an anion group (more preferably, an anion group represented by any of the formulae (bd1-r-an11) to (bd1-r-an13)) represented by the general formula (bd1-r-an1) and a cation represented by any of the chemical formulae (ca-1-1b) to (ca-1-3b), (ca-1-5b) to (ca-1-34b), and (ca-3-1b) to (ca-3-3b) may be exemplified as suitable compounds. While specific combination examples are shown below, the combinations are not limited thereto.

[Chem. 114]

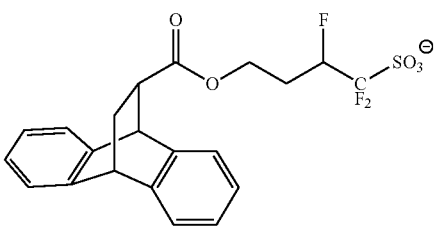

189
-continued
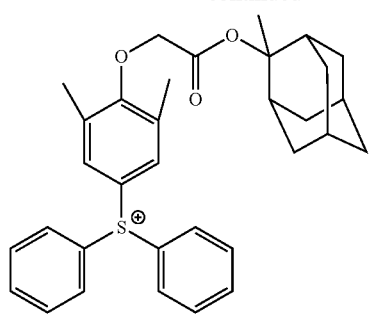
(B1b-2)
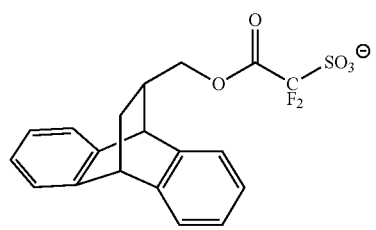
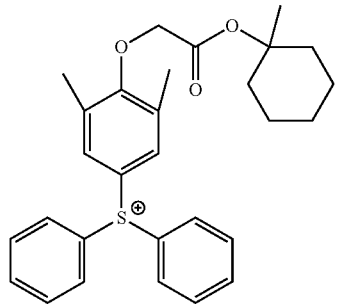
(B1b-3)
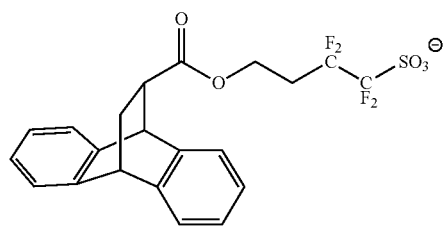
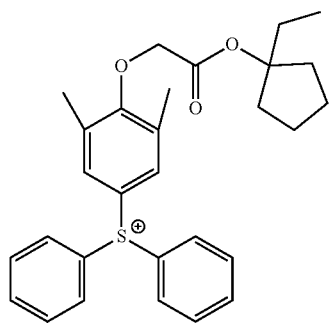
(B1b-4)
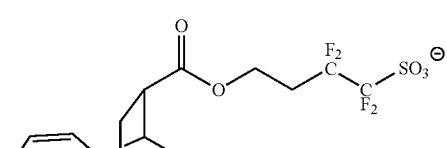
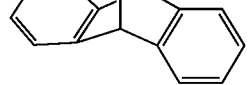
190
-continued
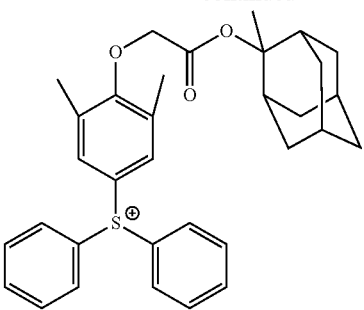
(B1b-5)
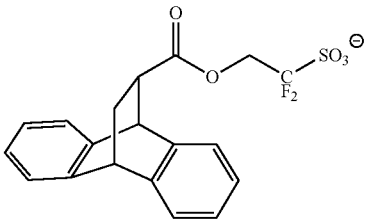
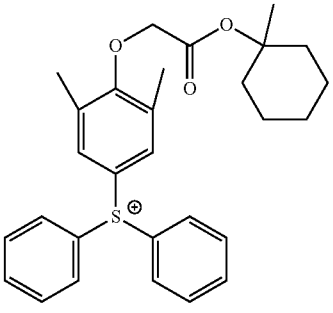
(B1b-6)
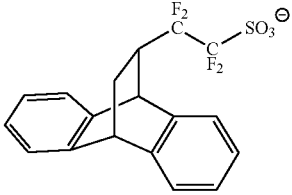
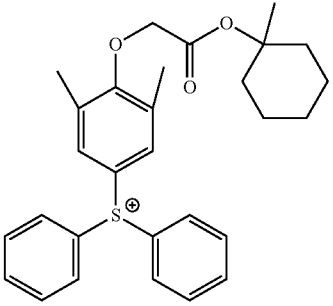 [SMILES: Cc1cc([S+](c2ccccc2)c2ccccc2)cc(C)c1OCC(=O)OC1(C)CCCCC1]
(B1b-7)
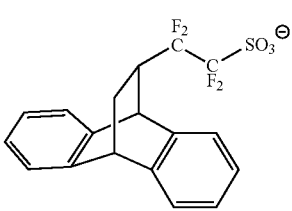

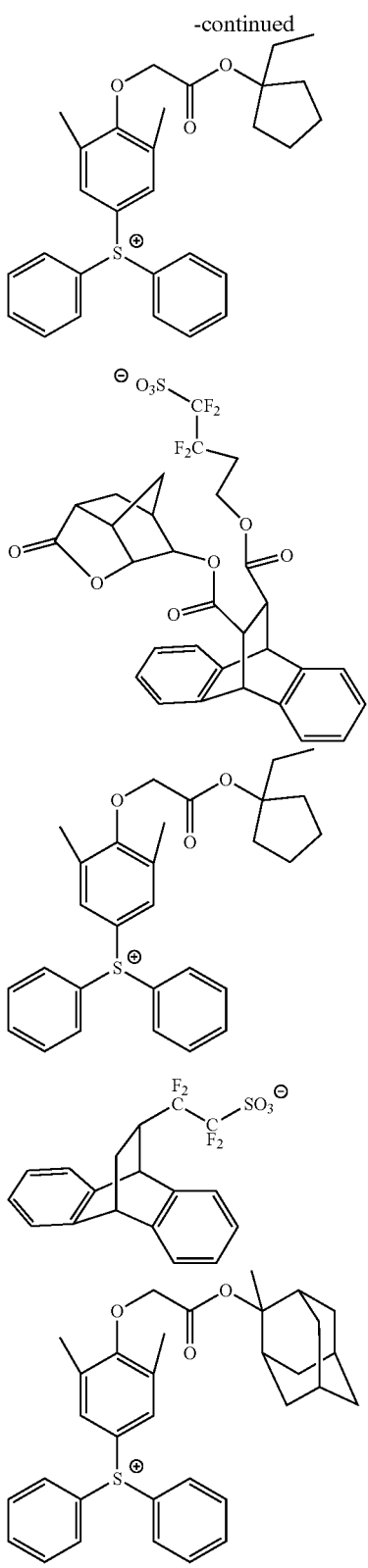

(B1b-8)

(B1b-9)

preferably 10 to 45 parts by mass, and particularly preferably 10 to 40 parts by mass with respect to 100 parts by mass of the component (A).

In the resist composition, within the entire acid-generator component (B) that generates an acid acting on the component (A), a proportion of the component (B1b) is, for example, 50 mass % or more, preferably 70 mass % or more, and most preferably 95 mass % or more. Here, the proportion may be 100 mass %.

If an amount of the component (B1b) is equal to or more than a lower limit of the preferable range, in the resist pattern formation, lithography properties such as sensitivity, resolution performance, line-wise roughness (LWR) reduction, and the shape are further improved. On the other hand, if the amount thereof is equal to or less than an upper limit of the preferable range, when components in the resist composition are dissolved in an organic solvent, a homogeneous solution is easily obtained, and storage stability for the resist composition is further improved.

In addition, when the resist composition contains the component (B1b) and the component (D) (at least one of the component (D1b), the component (D2b) and the component (D3)), a ratio thereof (molar ratio) is, for example, (B1b):(D)=100:0 to 50:50, more preferably (B1b):(D)=99:1 to 51:49, and most preferably (B1b):(D)=90:10 to 60:40 because then favorable lithography properties and resist pattern shape are easily obtained.

In addition, among the components (BD1-2) described above, regarding compounds suitable as a base component (D) (hereinafter referred to as a "component (D1b)") that traps (controls acid diffusion) an acid generated from the component (B) upon exposure, various combinations of the above anions represented by the formula (bd1-an1) to (bd1-an3) which are anions (more preferably, an anion represented by any of (bd1-an3-21) to (bd1-an3-24)) having an anion group represented by *—$V^{10}$—COO ($V^{10}$ is a single bond or an alkylene group having 1 to 20 carbon atoms) or *—$V^{11}$—$SO_3$ ($V^{11}$ is a single bond or an alkylene group having 1 to 20 carbon atoms) and a cation represented by any of the chemical formulae (ca-1-1b) to (ca-1-3b), (ca-1-5b) to (ca-1-34b), and (ca-3-1b) to (ca-3-3b) may be exemplified. Specific examples of the component (D b) are shown below, but the component (D b) is not limited thereto.

[Chem. 115]

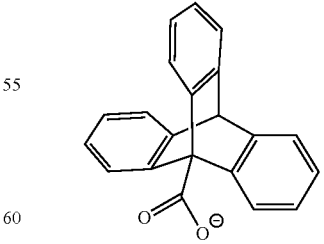

(D1-1b)

In the resist composition of the present embodiment, the component (B1b) may be used alone or two or more thereof may be used in combination.

In the resist composition of the present embodiment, an amount of the component (B1b) is preferably 5 to 65 parts by mass, more preferably 5 to 55 parts by mass, still more

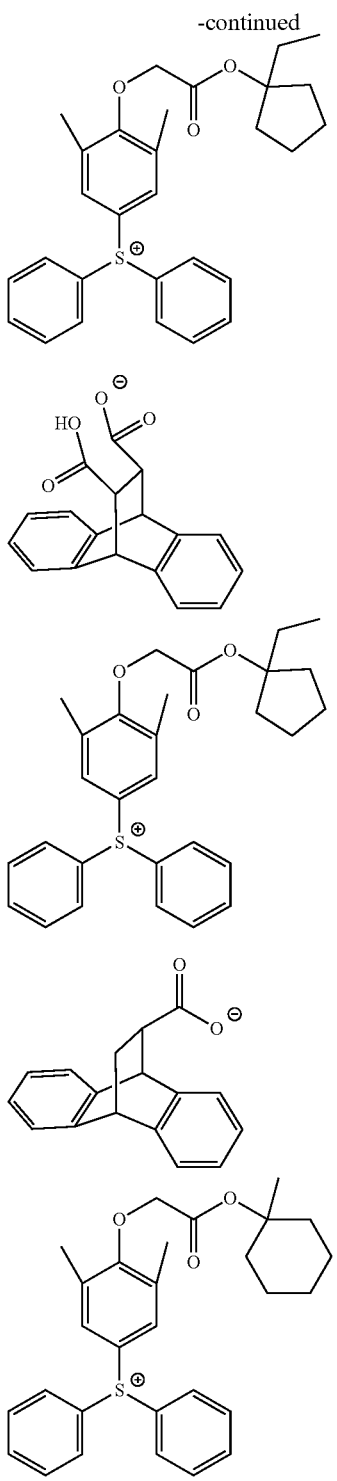

(D1-2b)

(D1-3b)

In the resist composition of the present embodiment, the component (D1b) may be used alone or two or more thereof may be used in combination.

In the resist composition of the present embodiment, an amount of the component (D1b) is preferably 1 to 35 parts by mass, more preferably 2 to 25 parts by mass, still more preferably 3 to 20 parts by mass, and particularly preferably 4 to 15 parts by mass with respect to 100 parts by mass of the component (A).

In the resist composition, within the entire base component (D) that traps (controls acid diffusion) an acid generated from the component (B) upon exposure, a proportion of the component (D1b) is, for example, 50 mass % or more, preferably 70 mass % or more, and more preferably 95 mass % or more. Here, the proportion may be 100 mass %. In addition, within the entire component (D) when the resist composition contains the component (B1b), a proportion of the component (D1b) is not particularly limited, and it may be appropriately adjusted to be within a range of 0 mass % or more and 100 mass % or less.

If an amount of the component (D b) is equal to or more than a lower limit of the preferable range, favorable lithography properties and resist pattern shape are easily obtained. On the other hand, if the amount thereof is equal to or less than an upper limit of the preferable range, a balance with other components can be achieved, and various lithography properties become favorable.

In addition, when the resist composition contains the component (D1b) and the component (B) (at least one of the components (B1b) and (B2b)), a ratio thereof (molar ratio) is, for example, (B):(D1b)=100:0 to 50:50, more preferably (B):(D1b)=99:1 to 51:49, and most preferably (B):(D1b)= 90:10 to 60:40 because then favorable lithography properties and resist pattern shape are easily obtained.

<Component (A)>

In the present embodiment, regarding the component (A), those the same as described in the resist composition according to the first aspect described above may be exemplified.

In the resist composition of the present embodiment, when the component (A) is a component (A-1), regarding the component (A-1), those containing a resin component (A1) are preferable.

Component (A1)

The component (A1) is a resin component preferably containing a polymeric compound having a structural unit (a1) containing an acid decomposable group that exhibits increased polarity by the action of acid.

The component (A1) preferably has, in addition to the structural unit (a1), a structural unit (a10) containing a hydroxystyrene skeleton.

Further, the component (A1) may have, in addition to the structural unit (a1), a structural unit (a2) containing a lactone-containing cyclic group, an —SO$_2$— containing cyclic group or a carbonate-containing cyclic group.

Further, the component (A1) may have, in addition to the structural unit (a1), a structural unit (a3) containing a polar group-containing aliphatic hydrocarbon group (provided that the structural units that fall under the definition of structural units (a1) and (a2) are excluded).

The component (A1) may further include a structural unit other than the structural units (a1), (a2), (a3) and (a10).

<Optional Components>

The resist composition of the present embodiment may further contain components (optional components) other than the component (A) and the compound (BD1-2) described above.

Examples of such optional components include a component (B2b), a component (D2b), a component (D3), a component (E), a component (F), and a component (S).

Here, the component (B2b) is an acid-generator component other than the component (B1b) described above, and examples thereof include those in which a component corresponding to the component (B1b) is removed from those exemplified for the component (B1a) and component (B2a) described above.

In addition, the component (D2b) is a base component other than the component (D1b) described above, and is a photodecomposable base which is decomposed upon exposure and loses an ability to control acid diffusion. Specifically, those in which a component corresponding to the component (D1b) is removed from those exemplified for the component (D1a) and the component (D2a) may be exemplified.

Regarding the component (D3), the component (E), the component (F), and the component (S), those the same as described in the resist composition according to the first aspect described above may be exemplified.

The resist composition of the present embodiment contains the component (A) and the component (BD1-2) described above, and as necessary the above optional components.

For example, when the component (BD1-2) is used as a component (B1b), a resist composition containing the component (A), the component (B1b), and the component (D2b) or the component (D3) is preferably exemplified. For example, when the component (BD1-2) is used as a component (D1b), a resist composition containing the component (A), the component (B2b), and the component (D1b) is preferably exemplified.

In addition, for example, when the component (BD1-2) is used as the component (B1b) or the component (D1b), a resist composition containing the component (A), the component (B1b), and the component (D1b) is preferably exemplified.

The resist composition of the present embodiment described above contains the compound (BD1-2) represented by the general formula (bd1-2). The component (BD1-2) has a relatively high hydrophobicity because it has a specific structure (bulky structure) in which the anion moiety is mainly composed of hydrocarbons.

Therefore, the compatibility between the compound (BD1-2) and the base component (A) is improved, and acid diffusivity in the resist film is appropriately controlled. In addition, regarding the component (BD1-2), the cation moiety has an acid dissociable group. It is speculated that, when the component (BD1-2) having such an anion moiety and cation moiety is contained, contrast between the exposed portion and the unexposed portion, and lithography properties (resolution, roughness reduction, and the like) are further improved and the sensitivity is enhanced according to the resist composition of the embodiment.

In addition, when the resist composition of the embodiment is used, since uniformity of the compound (BD1-2) in the resist film to be formed is improved, it is possible to easily form a resist pattern having a high resolution and a favorable shape with reduced roughness.

(Fourth Aspect: Method of Forming a Resist Pattern)

A method of forming a resist pattern according to a fourth aspect of the present invention is a method including a step of forming a resist film on a support using the resist composition according to the third aspect described above, a step of exposing the resist film, and a step of developing the exposed resist film to form a resist pattern.

Regarding one embodiment of the method of forming a resist pattern, the same method of forming a resist pattern according to the second embodiment described above except that the resist composition according to the third aspect is used may be exemplified.

(Fifth Aspect: Compound)

A compound according to a fifth aspect of the present invention has an anion moiety and a cation moiety and is represented by the following general formula (bd1-2).

[Chem. 116]

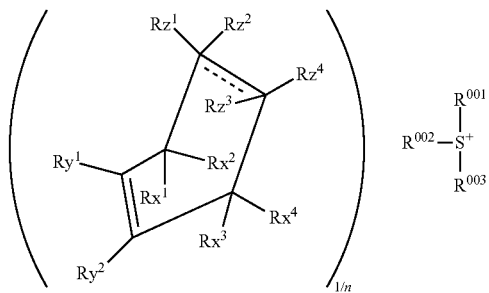

(bd1-2)

In the formula, $R^{001}$ to $R^{003}$ each independently represent a monovalent organic group; provided that at least one of $R^{001}$ to $R^{003}$ represents an organic group having an acid dissociable group; and two or more of $R^{001}$ to $R^{003}$ may be mutually bonded to form a ring with the sulfur atom; $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 117]

- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more.

The compound represented by the general formula (bd1-2) is the same compound as the component (BD1-2) described in the resist composition of the embodiment described above.

[Method of Producing Compound (BD1-2)]

Examples of a method of producing the component (BD1-2) include the same method as that of producing the component (BD1-1) described above. Specifically, a method in which an intermediate is obtained using a Diels-Alder reaction, a desired anion group is then introduced to obtain a precursor, a desired cation is introduced according to a salt exchange reaction, and thus a desired compound (B1b-0) is obtained may be exemplified.

[Chem. 118]

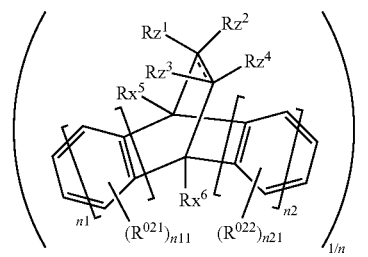

Precursor (Bpre)

-continued

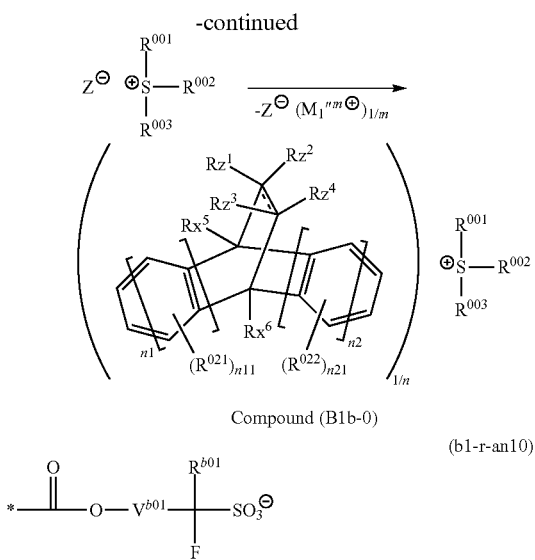

Compound (B1b-0)

(b1-r-an10)

(Sixth Aspect: Acid Generator)

An acid generator according to a sixth aspect of the present invention includes the compound according to the fifth aspect described above.

The acid generator is useful as an acid-generator component for a chemically amplified resist composition. When such an acid-generator component is used for a chemically amplified resist composition, in the resist pattern formation, lithography properties such as roughness reduction are improved, the pattern shape is favorably maintained and the sensitivity is enhanced. When such an acid-generator component is used, in particular, high sensitivity with respect an EB or EUV light source is easily obtained. In addition, according to a chemically amplified resist composition containing such an acid generator component, resolution performance is further improved.

(Seventh Aspect: Resist Composition)

A resist composition according to a seventh aspect of the present invention generates an acid upon exposure and exhibits a changed solubility in a developing solution under the action of acid, and contains a base component (A) (hereinafter referred to as a "component (A)") that exhibits a changed solubility in a developing solution under the action of an acid and a compound (BD1-3) (hereinafter referred to as a "component (BD1-3)") represented by the general formula (bd1-3).

Regarding one embodiment of such a resist composition, a resist composition containing the component (A) and an acid-generator component (B) (hereinafter referred to as a "component (B)") that generates an acid upon exposure may be exemplified. Preferable examples include a resist composition further containing a base component (hereinafter referred to as a "component (D)") that traps (that is, controls acid diffusion) an acid generated from the component (B) upon exposure in addition to the component (A) and the component (B).

In the resist composition of the present embodiment, the component (BD1-3) can be used as the component (B) or the component (D) by selecting an anion group in the molecule.

<Component (A)>

In the present embodiment, regarding the component (A), those the same as described in the resist composition according to the first aspect described above may be exemplified.

In the resist composition of the present embodiment, when the component (A) is the component (A-1), regarding the component (A-1), those containing a resin component (A1) are preferable.

Component (A1)

The component (A1) is a resin component preferably containing a polymeric compound having a structural unit (a1) containing an acid decomposable group that exhibits increased polarity by the action of acid.

The component (A1) preferably has, in addition to the structural unit (a1), a structural unit (a10) containing a hydroxystyrene skeleton.

Further, the component (A1) may have, in addition to the structural unit (a1), a structural unit (a2) containing a lactone-containing cyclic group, an —$SO_2$— containing cyclic group or a carbonate-containing cyclic group.

Further, the component (A1) may have, in addition to the structural unit (a1), a structural unit (a3) containing a polar group-containing aliphatic hydrocarbon group (provided that the structural units that fall under the definition of structural units (a1) and (a2) are excluded).

The component (A1) may further include a structural unit other than the structural units (a1), (a2), (a3) and (a10).

<Compound (BD1-3)>

In the resist composition of the present embodiment, the component (BD1-3) is a compound that is represented by the following general formula (bd1-3) and has an anion moiety and a cation moiety.

[Chem. 119]

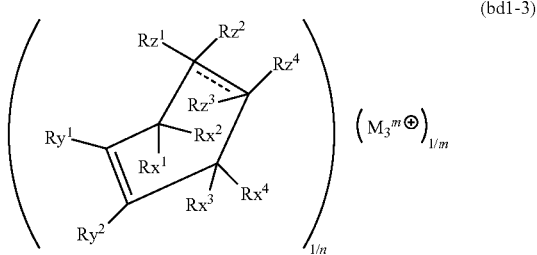

(bd1-3)

In the formula, $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 120]

----- represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_3^{m+}$ represents an m-valent organic cation having an electron-withdrawing group.

Anion Moiety

Regarding the anion moiety in the formula (bd1-3), the same anion moieties as those for the formula (bd1-1) described above may be exemplified.

Cation Moiety $((M_3^{m+})_{l/m})$

In the formula (bd1-3), $M_3^{m+}$ represents an m-valent organic cation having an electron-withdrawing group. m represents an integer of 1 or more.

An electron-withdrawing group contained in an $M_3^{m+}$ organic cation which is a cation moiety may be, for example, an electron-withdrawing group of a monovalent substituent or an electron-withdrawing group of a bivalent substituent. Specifically, an oxygen atom (—O—), a carbonyl group, a methanesulfonyl group (mesyl group), a halogen atom, a halogenated alkyl group, a halogenated alkoxy group, a halogenated aryloxy group, a halogenated alkylamino group, a halogenated alkylthio group, an alkyloxycarbonyl group, an aryloxycarbonyl group, a cyano group, a nitro group, a dialkylphosphono group, a diarylphosphono group, an alkylsulfonyl group, an arylsulfonyl group, a sulfonyloxy group, an acylthio group, a sulfamoyl group, a thiocyanate group, and a thiocarbonyl group may be exemplified.

As the halogenated alkyl group, a halogenated alkyl group of 1 to 10 carbon atoms is preferable. The halogenated alkyl group of 1 to 10 carbon atoms represented by R is a group in which some or all of the hydrogen atoms of the aforementioned alkyl group of 1 to 10 carbon atoms have been substituted with halogen atoms. Examples of the halogen atom include a fluorine atom, a chlorine atom, a bromine atom and an iodine atom, and a fluorine atom is particularly desirable.

Among the above examples, in consideration of high sensitivity, an oxygen atom (—O—), a carbonyl group, a methanesulfonyl group (mesyl group), a halogen atom or a halogenated alkyl group is preferable, and a halogen atom or a halogenated alkyl group is more preferable in consideration of solubility of the component (BD1-3) in the component (S) to be described below.

Among these, a fluorine atom, or a fluorinated alkyl group is more preferable, and a fluorine atom, or a trifluoromethyl group is particularly preferable.

When the electron-withdrawing group is a fluorine atom or a fluorinated alkyl group, the number of fluorine atoms in the cation moiety $((M_3^{m+})_{l/m})$ is preferably 1 to 9, more preferably 2 to 6, and most preferably 3 or 4.

When the number of fluorine atoms increases, the sensitivity becomes favorable, and when the number thereof is equal to or less than an upper limit of the preferable range, the compatibility with components in the resist composition is maintained, and the occurrence of roughness is easily prevented.

Regarding an $M_3^{m+}$ organic cation, a sulfonium cation or an iodonium cation is preferable. In addition, when the component (BD1-3) is used as the base component (D), an ammonium cation and the like may be exemplified.

Examples of a preferable cation moiety $((M_3^{m+})_{l/m})$ include organic cations represented by the following general formulae (ca0-1) to (ca0-4).

[Chem. 121]

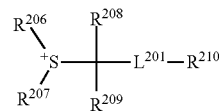
(ca0-1)

$R^{204}$—I$^+$—$R^{205}$
(ca0-2)

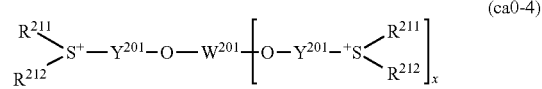

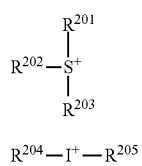
(ca0-4)

[In the formula, $R^{201}$ to $R^{207}$ and $R^{211}$ to $R^{212}$ each independently represent an aryl group which may have a substituent, an alkyl group which may have a substituent, or an alkenyl group which may have a substituent. $R^{201}$ to $R^{203}$, $R^{206}$ to $R^{207}$, and $R^{211}$ to $R^{212}$ may be mutually bonded to form a ring together with a sulfur atom in the formula. $R^{208}$ to $R^{209}$ each independently represent a hydrogen atom or an alkyl group having 1 to 5 carbon atoms or they may be mutually bonded to form a ring together with a sulfur atom in the formula. $R^{210}$ is an aryl group which may have a substituent, an alkyl group which may have a substituent, an alkenyl group which may have a substituent, or an —SO$_2$-containing cyclic group which may have a substituent. Here, at least one of $R^{201}$ to $R^{203}$ at least one of $R^{204}$ and $R^{205}$, at least one of $R^{206}$ and $R^{207}$, and at least one of $R^{211}$ and $R^{212}$ has an electron-withdrawing group as a substituent. $L^{201}$ represents —C(=O)— or —C(=O)—O—. A plurality of $Y^{201}$'s each independently represent an arylene group, an alkylene group or an alkenylene group. x is 1 or 2. $W^{201}$ represents an (x+1)-valent linking group].

Regarding the aryl group for $R^{201}$ to $R^{207}$ and $R^{211}$ to $R^{212}$, an aryl group having 6 to 20 carbon atoms may be exemplified, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$ and $R^{211}$ to $R^{212}$ preferably has 2 to 10 carbon atoms.

Examples of the substituent that $R^{201}$ to $R^{207}$ and $R^{211}$ to $R^{212}$ may have include an alkyl group, a halogen atom, a halogenated alkyl group, a carbonyl group, a cyano group, an amino group, an aryl group, and groups represented by the following general formulae (ca-r-1) to (ca-r-7).

[Chem. 122]

—O—R$^{'201}$
[ca-r-1]

[ca-r-2]

[ca-r-3]

[ca-r-4]

[ca-r-5]

-continued

[ca-r-6]

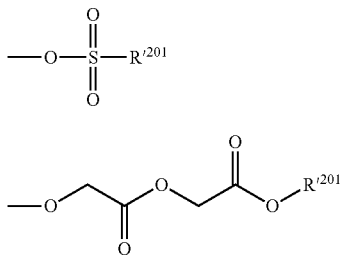

[ca-r-7]

In the formulae, each $R'^{201}$ independently represents a hydrogen atom, a cyclic group which may have a substituent, a chain-like alkyl group which may have a substituent, or a chain-like alkenyl group which may have a substituent.

Regarding a cyclic group which may have a substituent, a linear alkyl group which may have a substituent, or a chain-like alkenyl group which may have a substituent for $R'^{201}$, those the same as described for $Rx^1$ to $Rx^4$, $Ry^1$ to $Ry^2$, $Rz^1$ to $Rz^4$ in the above formula (bd1-3) may be exemplified, and regarding a cyclic group which may have a substituent or a linear alkyl group which may have a substituent, those the same as the acid dissociable group represented by the above formula (a1-r-2) may be exemplified.

$R^{201}$ to $R^{203}$, $R^{206}$ to $R^{207}$, and $R^{211}$ to $R^{212}$ may be mutually bonded to form a ring together with a sulfur atom in the formula.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(RN)— (wherein RN represents an alkyl group of 1 to 5 carbon atoms). The ring containing the sulfur atom in the skeleton thereof is preferably a 3- to 10-membered ring, and most preferably a 5- to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ to $R^{209}$ each independently represent a hydrogen atom or an alkyl group having 1 to 5 carbon atoms, and are preferably a hydrogen atom or an alkyl group having 1 to 3 carbon atoms, and when $R^{208}$ to $R^{209}$ are an alkyl group, they are mutually bonded to form a ring together with a sulfur atom in the formula.

$R^{210}$ is an aryl group which may have a substituent, an alkyl group which may have a substituent, an alkenyl group which may have a substituent, or a —SO$_2$-containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, an "—SO$_2$— containing polycyclic group" is preferable, and a group represented by the aforementioned general formula (a5-r-1) is more preferable.

Here, at least one of $R^{201}$ to $R^{203}$, at least one of $R^{204}$ and $R^{205}$, at least one of $R^{206}$ and $R^{207}$, and at least one of $R^{211}$ and $R^{212}$ have an electron-withdrawing group as a substituent.

Here, having an electron-withdrawing group as a substituent means that an electron-withdrawing group as a substituent is bonded to an aryl group, an alkyl group or an alkenyl group for $R^{201}$ to $R^{207}$ and $R^{211}$ to $R^{212}$ in the above general formulae (ca0-1) to (ca0-4). In addition, when $R^{201}$ to $R^{203}$, $R^{206}$ to $R^{207}$, and $R^{211}$ to $R^{212}$ are mutually bonded to form a ring together with a sulfur atom in the formula, its ring structure has an electron-withdrawing group.

Each $Y^{201}$ independently represents an arylene group, an alkylene group or an alkenylene group.

Regarding an arylene group for $Y^{201}$, groups in which one hydrogen atom is additionally removed from an aryl group exemplified as an aromatic hydrocarbon group for $Rx^1$ to $Rx^4$, $Ry^1$ to $Ry^2$, and $Rz^1$ to $Rz^4$ in the above formula (bd1-3) may be exemplified.

Regarding an alkylene group and an alkenylene group for $Y^{201}$, groups in which one hydrogen atom is additionally removed from groups exemplified as a linear alkyl group or a chain-like alkenyl group for $Rx^1$ to $Rx^4$, $Ry^1$ to $Ry^2$, and $Rz^1$ to $Rz^4$ in the above formula (bd1-3) may be exemplified.

In the formula (ca-04), x is 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups (which may have a substituent) as those described above for $Ya^{x1}$ in the general formula (a10-1) may be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of a suitable cation represented by the formula (ca0-1) include cations represented by the following formulae (ca-1-1c) to (ca-1-78c).

[Chem. 123]

(ca-1-1c)

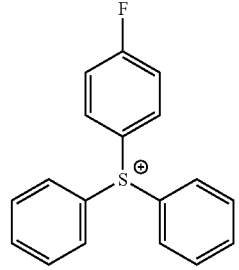

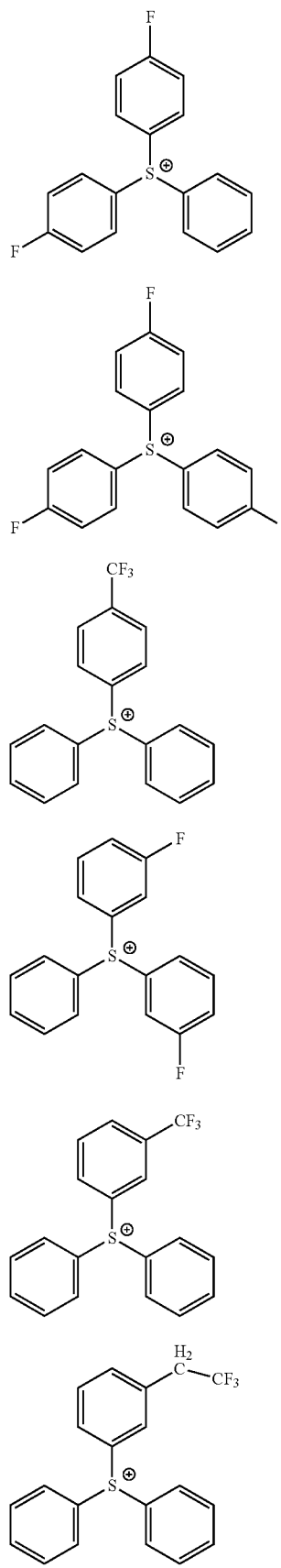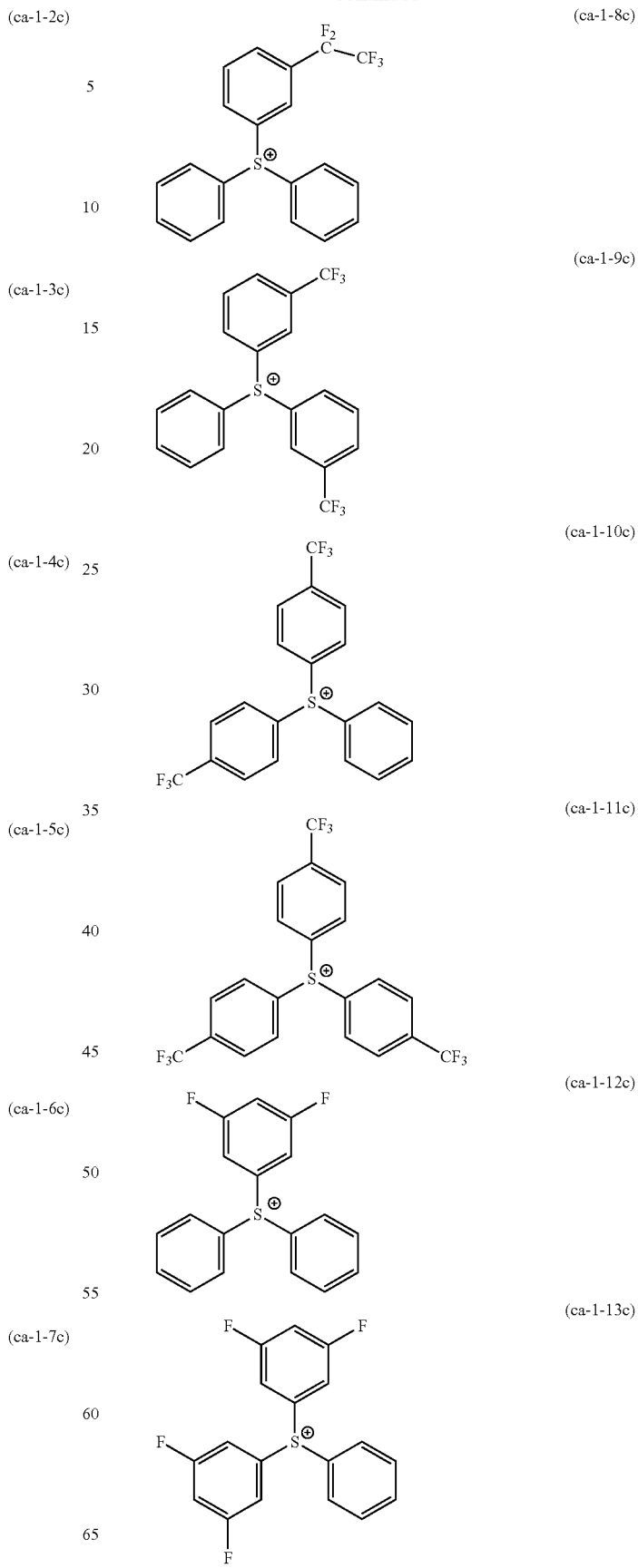

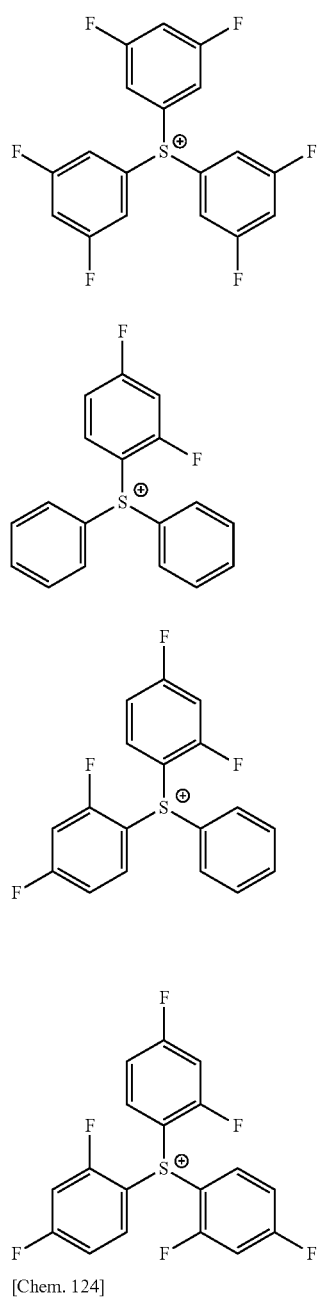
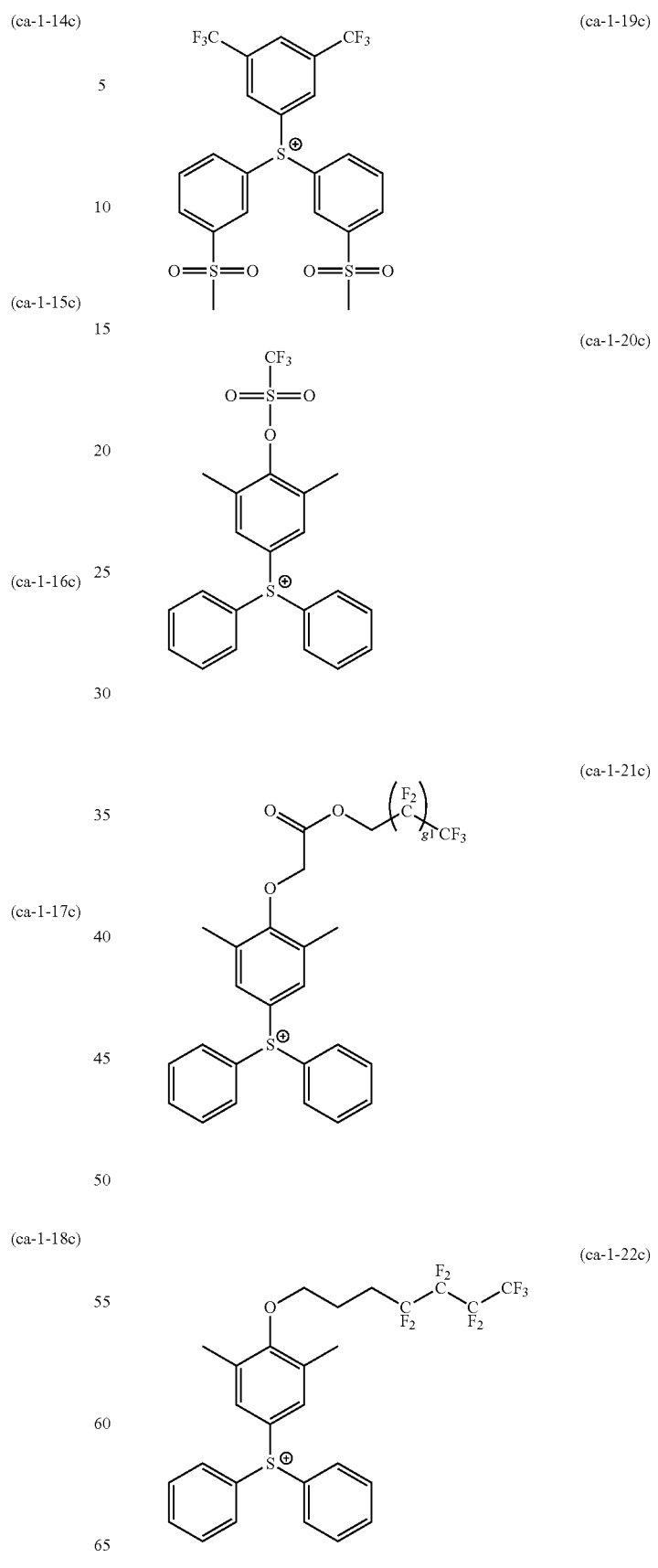

(ca-1-23c)
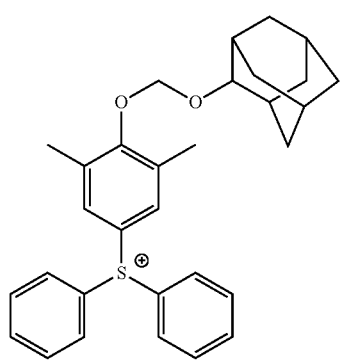
(ca-1-24c)
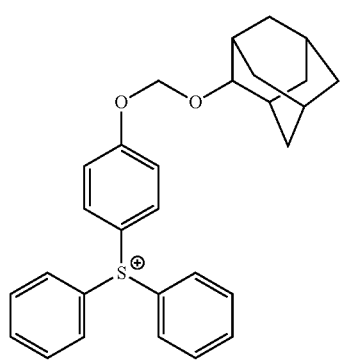
(ca-1-25c)
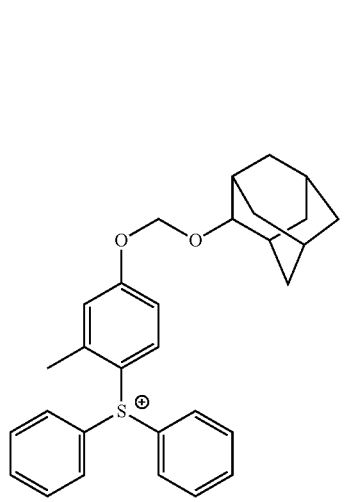
(ca-1-26c)
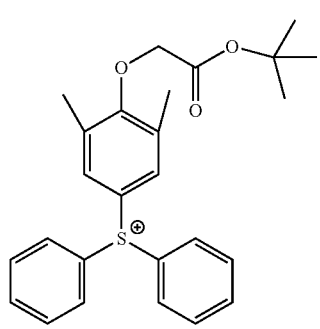
(ca-1-27c)
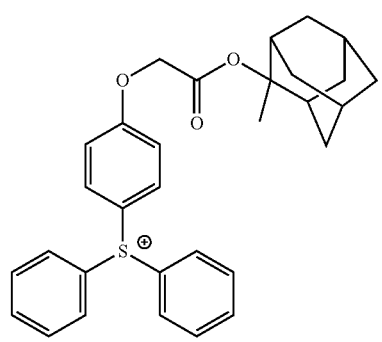
(ca-1-28c)
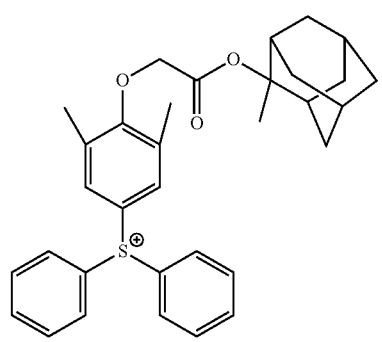
(ca-1-29c)
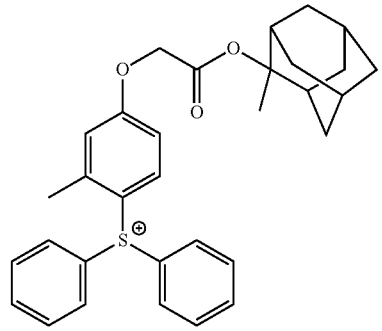
[In the formula, g1 represents a number of repetitions, and g1 is an integer of 1 to 5].
[Chem. 125]
(ca-1-30c)
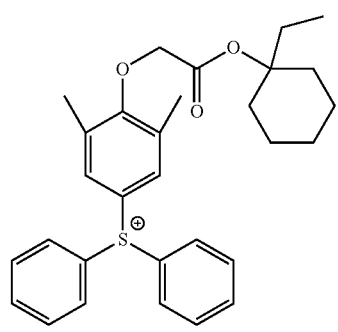

(ca-1-31c)
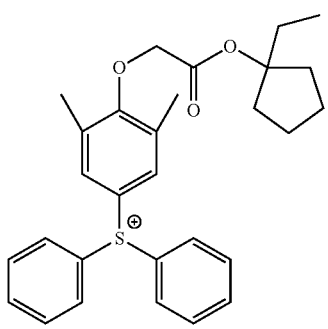
(ca-1-32c)
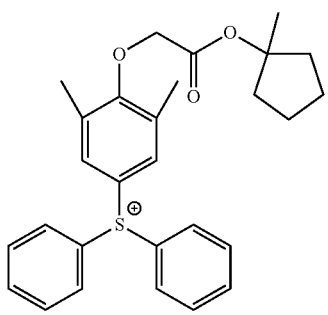
(ca-1-33c)
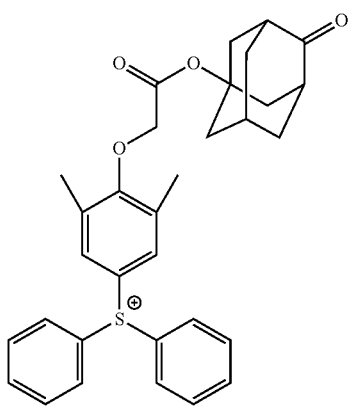
(ca-1-34c)
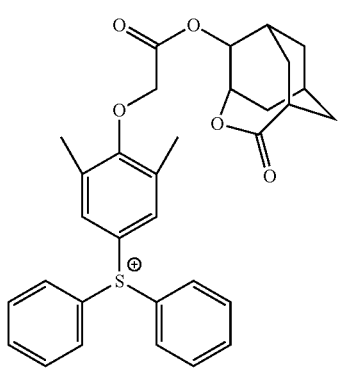
(ca-1-35c)
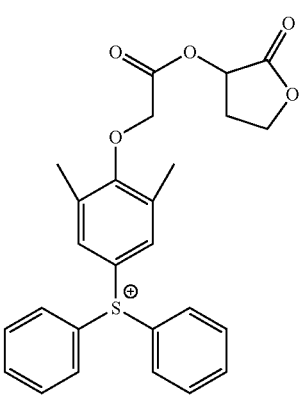
(ca-1-36c)
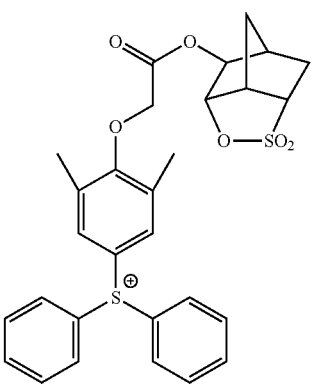
(ca-1-37c)
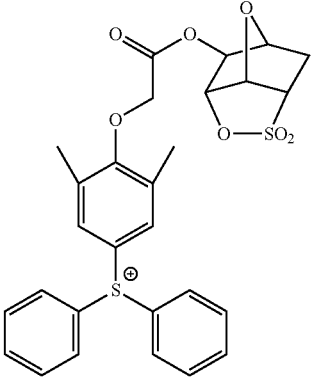
(ca-1-38c)
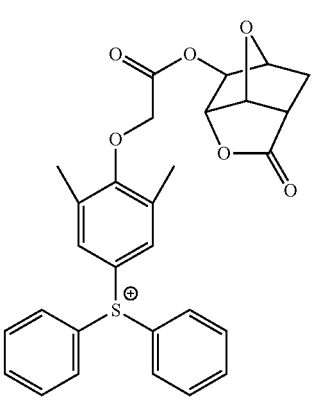

(ca-1-39c)
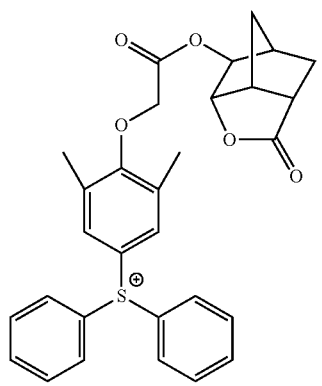
(ca-1-40c)
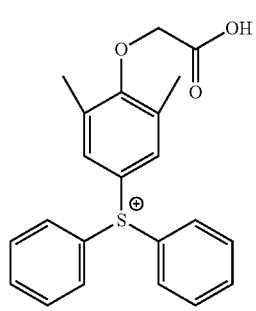
(ca-1-41c)
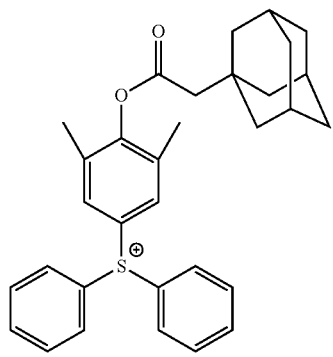
(ca-1-42c)
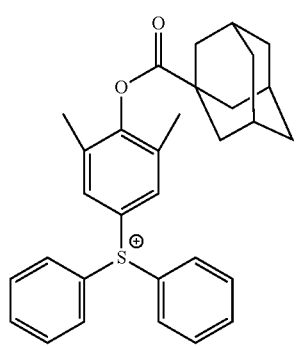
[Chem. 126]
(ca-1-43c)
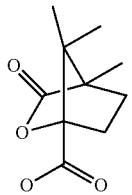
(ca-1-44c)
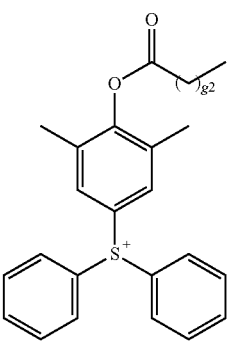
(ca-1-45c)
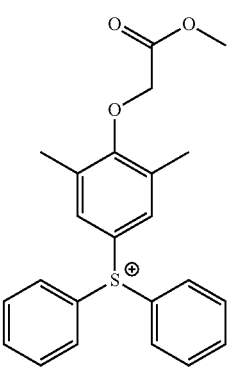
(ca-1-46c)
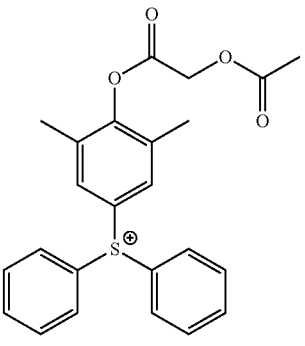

(ca-1-47c)
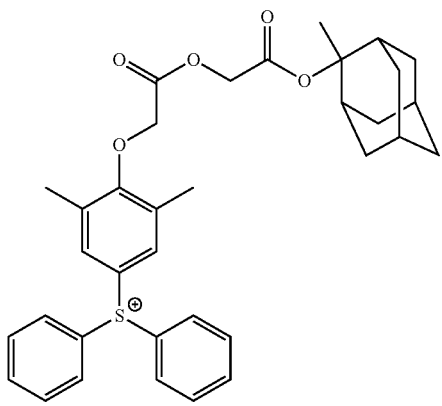
(ca-1-48c)
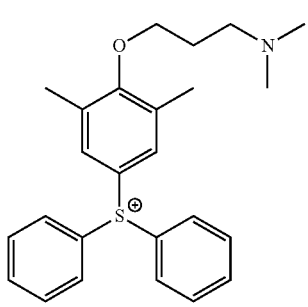
(ca-1-49c)
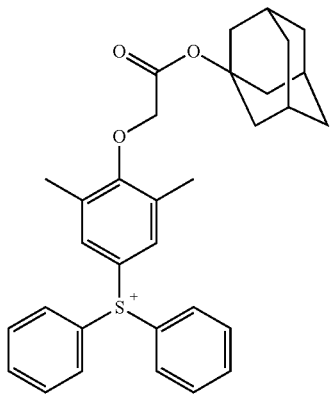
(ca-1-50c)
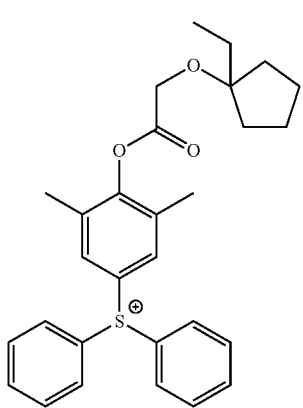
(ca-1-51c)
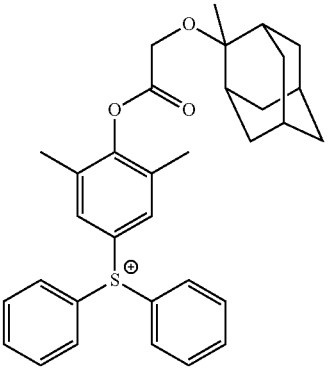
(ca-1-52c)
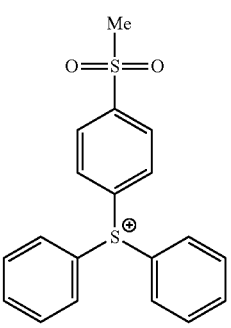
(ca-1-53c)
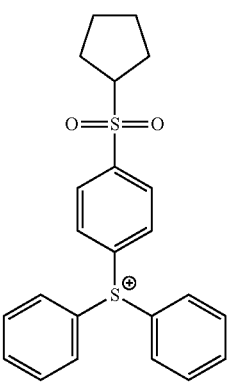
(ca-1-54c)
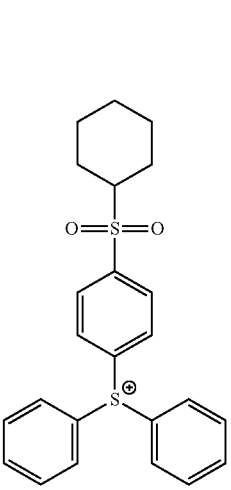
[In the formula, g2 represents a number of repetitions, and g2 is an integer of 0 to 20].

[Chem. 127]
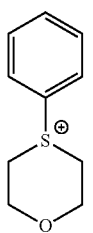
(ca-1-55c)
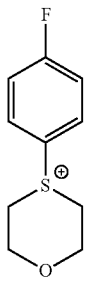
(ca-1-56c)
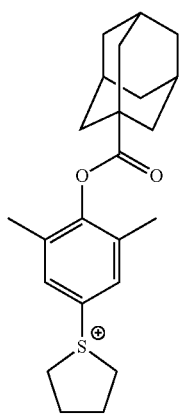
(ca-1-57c)
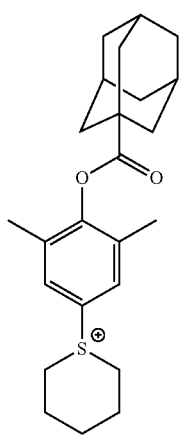
(ca-1-58c)
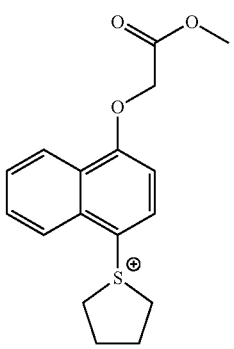
(ca-1-59c)
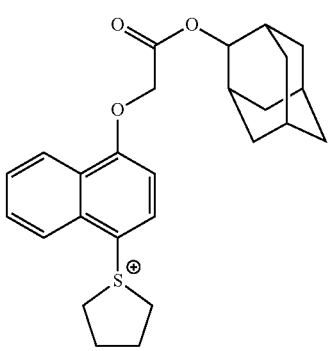
(ca-1-60c)
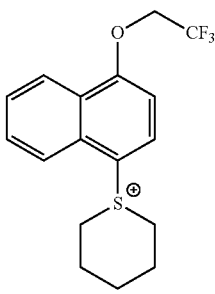
(ca-1-61c)
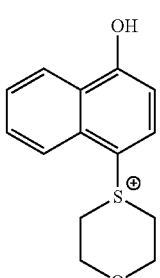
(ca-1-62c)
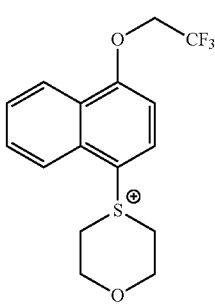
(ca-1-63c)

(ca-1-64c)
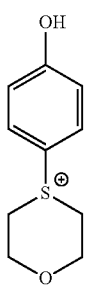
[Chem. 128]
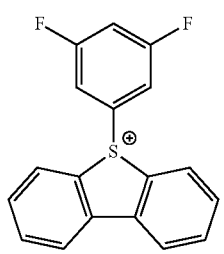
(ca-1-65c)
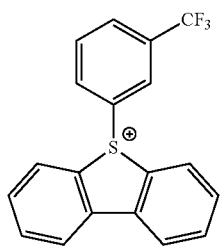
(ca-1-66c)
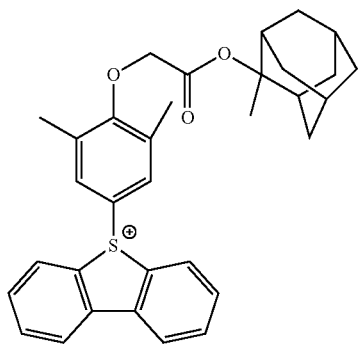
(ca-1-67c)
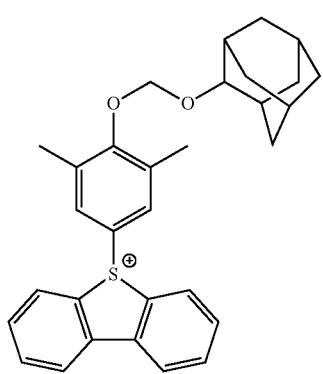
(ca-1-68c)
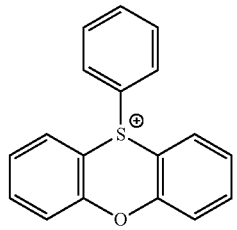
(ca-1-69c)
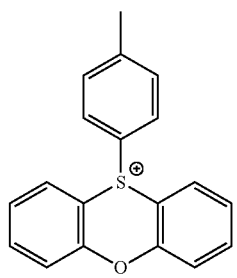
(ca-1-70c)
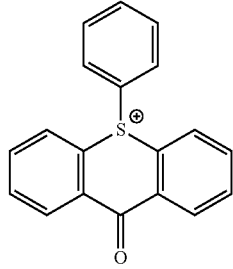
(ca-1-71c)
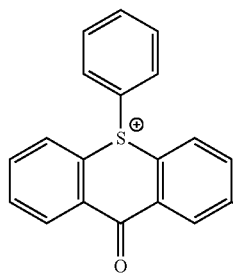
(ca-1-72c)
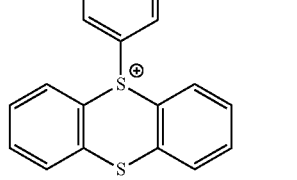
(ca-1-73c)
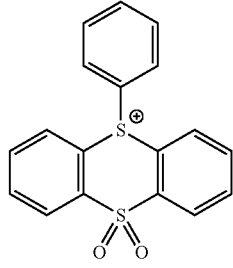
(ca-1-74c)

-continued (ca-1-75c)

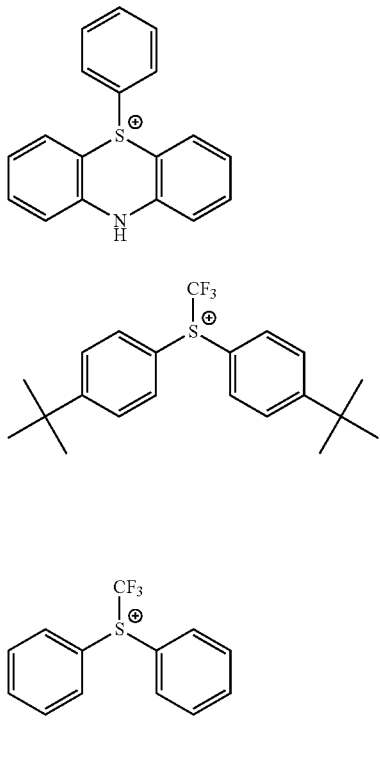

(ca-1-76c)

(ca-1-77c)

(ca-1-78c)

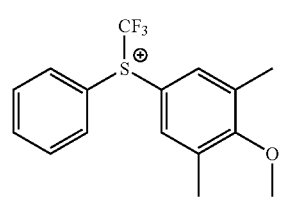

Specific examples of a suitable cation represented by the formula (ca0-2) include cations represented by the following formulae (ca-2-1c) to (ca-2-2c).

[Chem. 129]

(ca-2-1c)

(ca-2-2c)

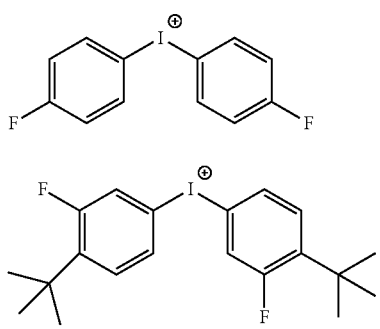

Specific examples of a suitable cation represented by the formula (ca0-3) include cations represented by the following formulae (ca-3-1c) to (ca-3-7c).

[Chem. 130]

(ca-3-1c)

(ca-3-2c)

(ca-3-3c)

(ca-3-4c)

(ca-3-5c)

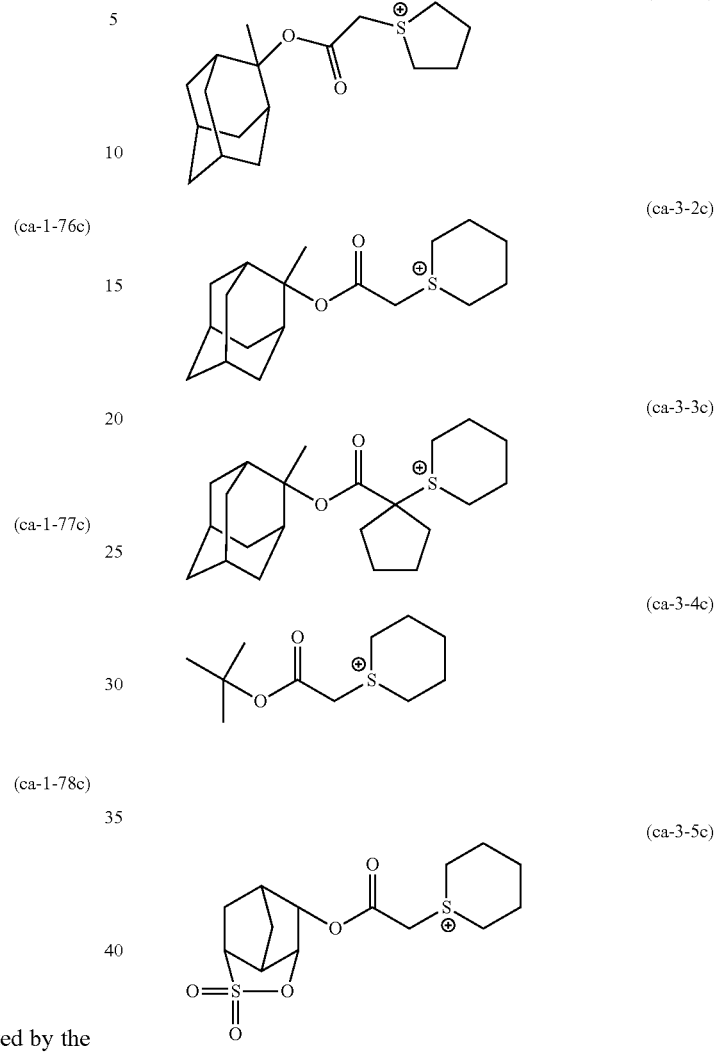

(ca-3-6c)

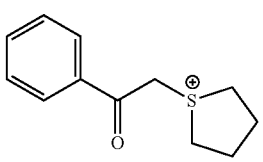

(ca-3-7c)

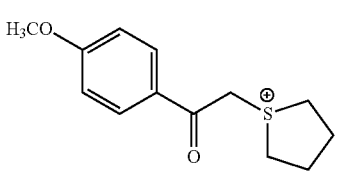

Specific examples of a suitable cation represented by the formula (ca0-4) include cations represented by the following formulae (ca-4-1c) to (ca-4-2c).

[Chem. 131]

(ca-4-1c)

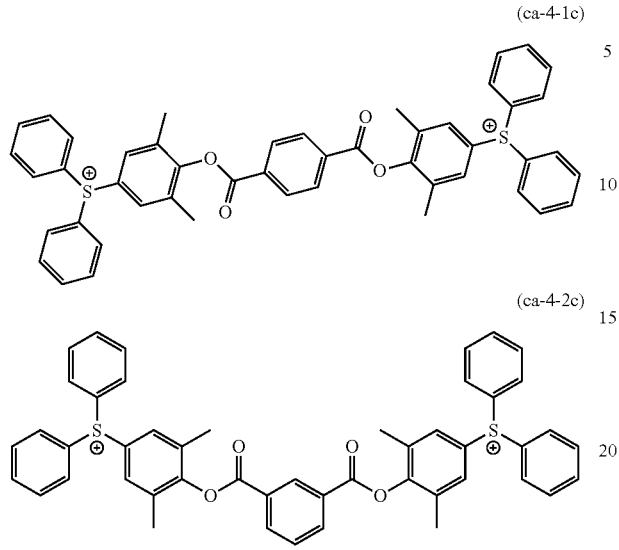

(ca-4-2c)

[Chem. 132]

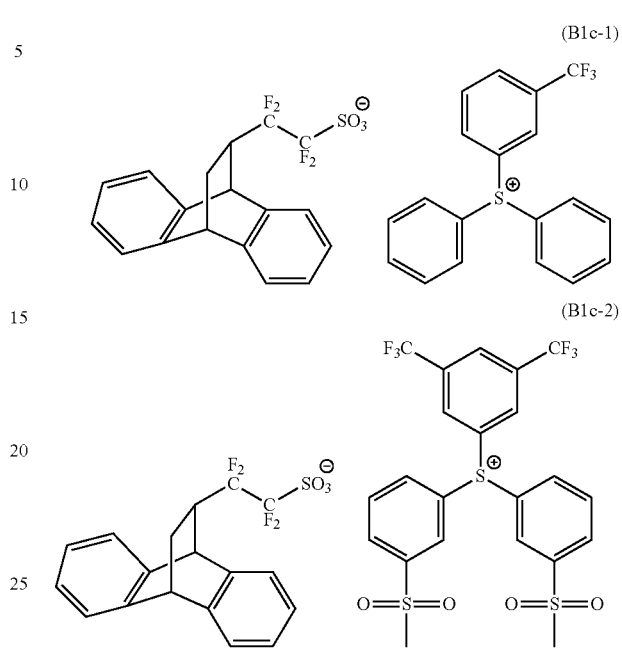

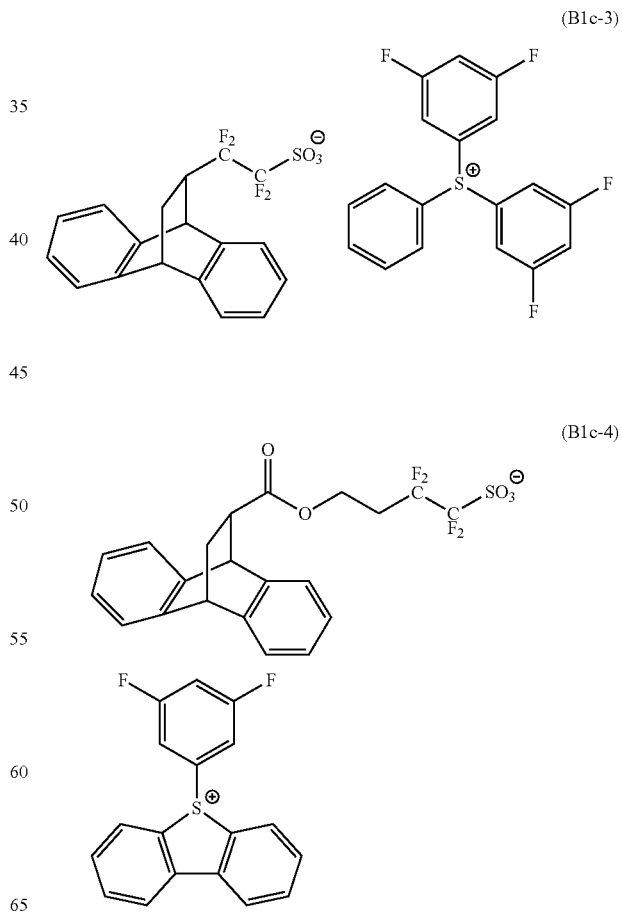

In addition, regarding an ammonium cation when the component (BD1-3) is used as the base component (D), cations (primary to quaternary ammonium cations) in which $NH_4^+$ or H bonded to a nitrogen atom thereof is substituted with a hydrocarbon group which may have a hetero atom and cyclic cations forming a ring together with a nitrogen atom thereof may be exemplified.

Among the above examples, regarding the cation moiety $((M_3^{m+})_{l/m})$, a cation represented by the general formula (ca0-1) is preferable, and cations represented by the formulae (ca-1-1c) to (ca-1-78c) are more preferable.

Among these, a cation when one or more of $R^{201}$ to $R^{203}$ in the general formula (ca0-1) are an aryl group having an electron-withdrawing group as a substituent is more preferable. In addition, a cation when one or more of $R^{201}$ to $R^{203}$ in the general formula (ca0-1) are an aryl group having an electron-withdrawing group as a substituent at the meta position is more preferable. Regarding the electron-withdrawing group, a halogen atom or a halogenated alkyl group is preferable, and a fluorine atom or a fluorinated alkyl group is more preferable. Specifically, cations represented by the above formulae (ca-1-1c) to (ca-1-17c), and (ca-1-18c) to (ca-1-20c) are preferably exemplified, and cations represented by the above formulae (ca-1-5c) to (ca-1-9c), (ca-1-12c) to (ca-1-14c), and (ca-1-18c) to (ca-1-19c) are more suitable.

Among the components (BD1-3) described above, regarding the acid-generator component (B) (hereinafter referred to as a "component (B1c)") that generates an acid acting on the component (A), various combinations of the above anions represented by the above formula (bd1-an1) to (bd1-an3) which are anions (more preferably, an anion represented by any of (bd1-an3-1) to (bd1-an3-15)) having an anion group represented by the general formula (bd1-r-an1) (more preferably, an anion group represented by any of the formulae (bd1-r-an11) to (bd1-r-an13)) and cations represented by formulae (ca-1c) to (ca-4c) (more preferably, cations represented by any of (ca-1-1c) to (ca-1-78c), (ca-2-1c) to (ca-2-2c), (ca-3-1c) to (ca-3-7c), and (ca-4-1c) to (ca-4-2c)) may be exemplified. Specific examples of the component (B1c) are shown below, but the component (B1c) is not limited thereto.

[Chem. 133]
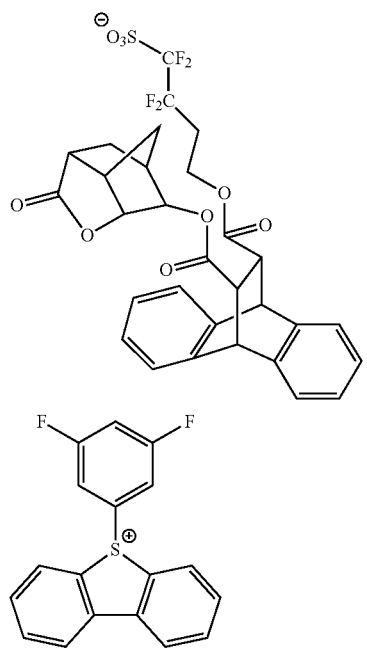
(B1c-5)
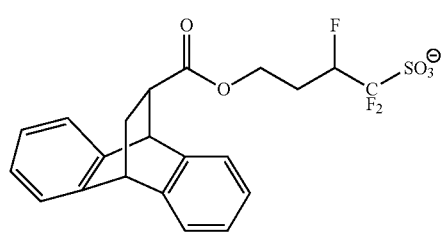
(B1c-6)
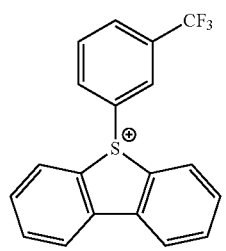
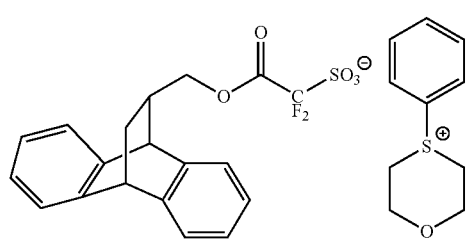
(B1c-7)
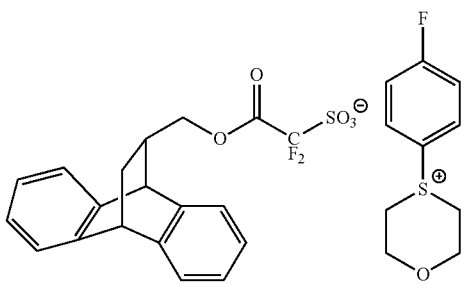
(B1c-8)
[Chem. 134]
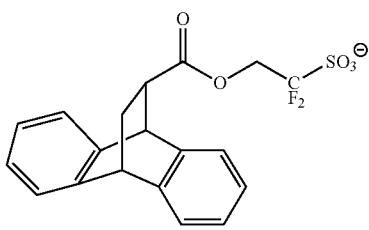
(B1c-9)
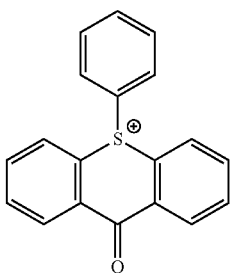
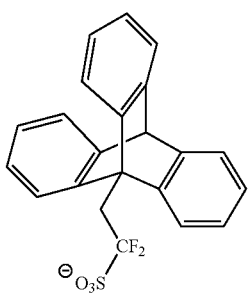
(B1c-10)
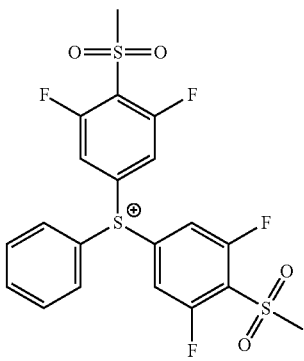

(B1c-11)
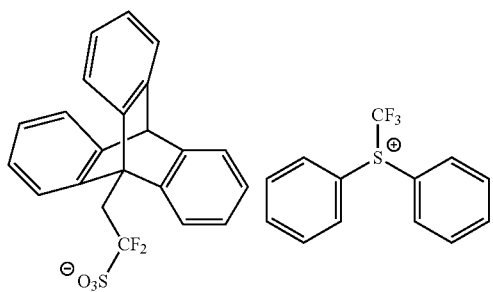
(B1c-12)
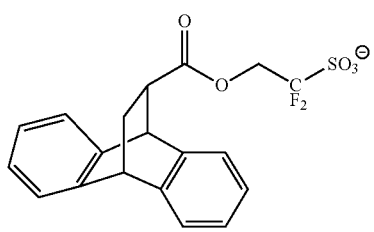
[Chem. 135]
(B1c-13)
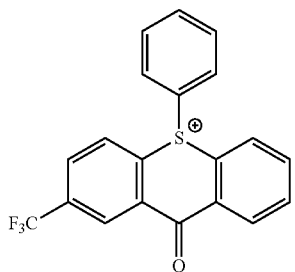
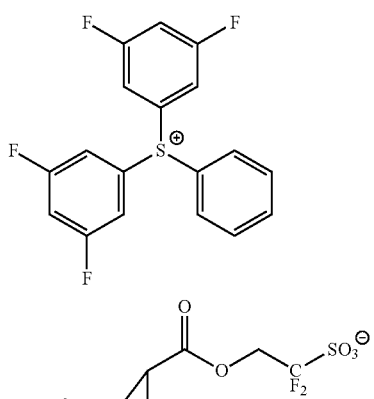
(B1c-14)
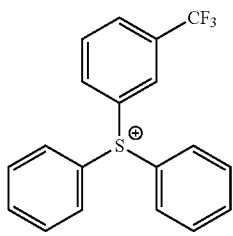
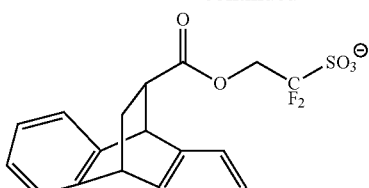
(B1c-15)
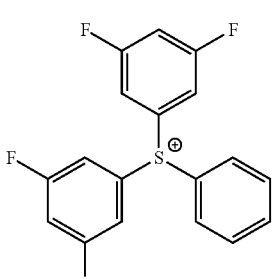
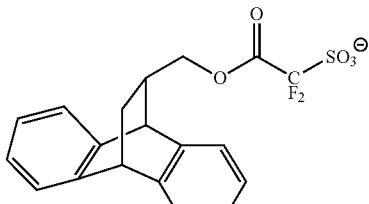
(B1c-16)
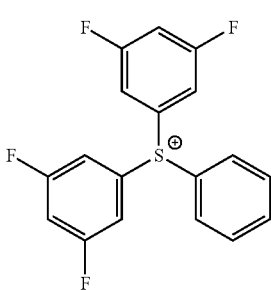
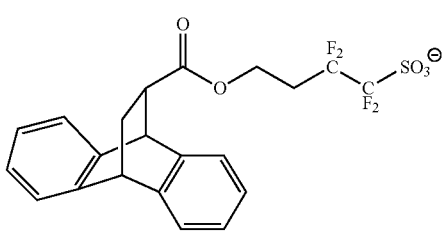
[Chem. 136]
(B1c-17)
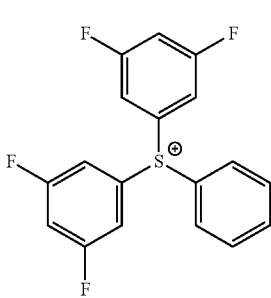

-continued
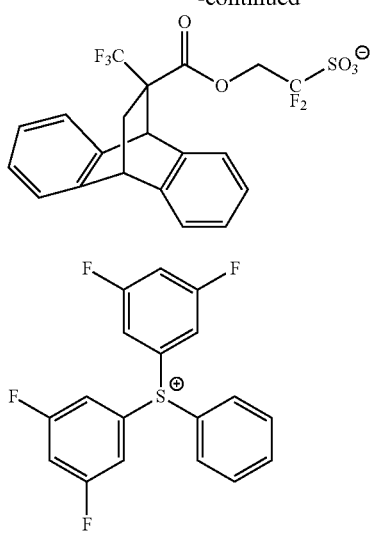
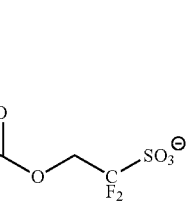 (B1c-18)
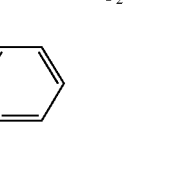
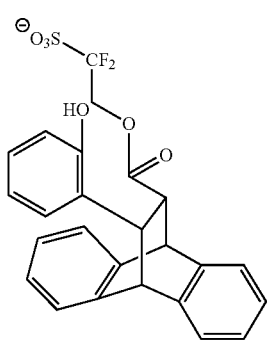
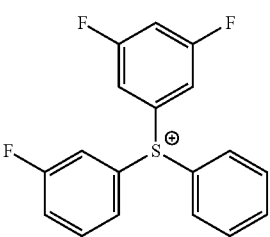 (B1c-20)
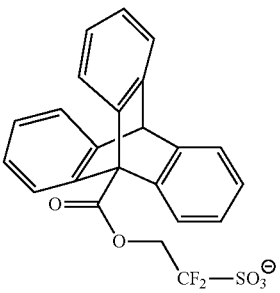
[Chem. 137]
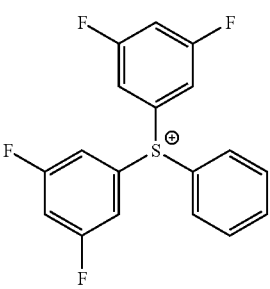 (B1c-21)
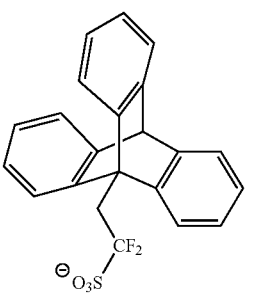 (B1c-19)
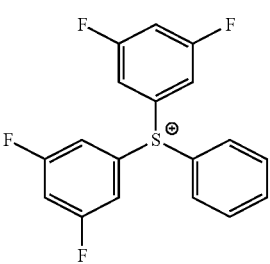 (B1c-22)

-continued

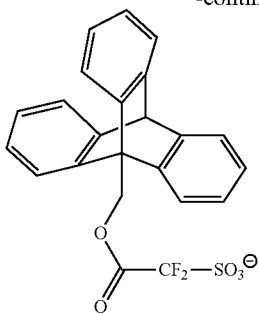

(B1c-23)

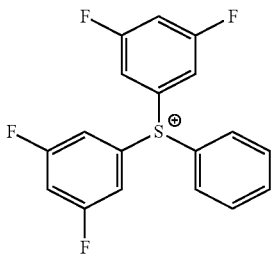

(B1c-24)

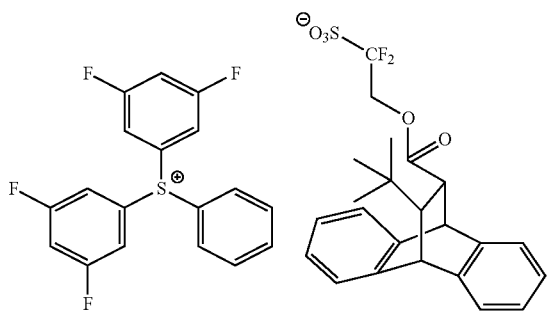

In the resist composition of the present embodiment, the component (B1c) may be used alone or two or more thereof may be used in combination.

In the resist composition of the present embodiment, an amount of the component (B1c) is preferably 5 to 65 parts by mass, more preferably 5 to 55 parts by mass, still more preferably 10 to 45 parts by mass, and particularly preferably 10 to 40 parts by mass with respect to 100 parts by mass of the component (A).

In the resist composition, within the entire acid-generator component (B) that generates an acid acting on the component (A), a proportion of the component (B c) is, for example, 50 mass % or more, preferably 70 mass % or more, and most preferably 95 mass % or more. Here, the proportion may be 100 mass %.

If an amount of the component (B1c) is equal to or more than a lower limit of the preferable range, in the resist pattern formation, lithography properties such as sensitivity, resolution performance, line-wise roughness (LWR) reduction, and the shape are further improved. On the other hand, if the amount thereof is equal to or less than an upper limit of the preferable range, when components in the resist composition are dissolved in an organic solvent, a homogeneous solution is easily obtained, and storage stability for the resist composition is further improved.

In addition, when the resist composition contains the component (B1c) and the component (D) (at least one of the components (D c), (D c), and (D3)), a ratio thereof (molar ratio) is, for example, (B1c):(D)=100:0 to 50:50, more preferably (B1c):(D)=99:1 to 51:49, and most preferably (B1c):(D)=90:10 to 60:40 because then favorable lithography properties and resist pattern shape are easily obtained.

In addition, among the components (BD1-3) described above, regarding the base component (D) that traps (controls acid diffusion) an acid generated from the component (B) upon exposure (hereinafter referred to as a "component (D1c)"), various combinations of the anions represented by any of the above formulae (bd1-an1) to (bd1-an3) which are anions (more preferably, anions represented by any of the formulae (bd1-an3-21) to (bd1-an3-24)) having an anion group represented by *—V'10-COO (V'$^{10}$ is a single bond or an alkylene group having 1 to 20 carbon atoms) or *—V'$^{11}$—SO$_3$ (V'$^{11}$ is a single bond or an alkylene group having 1 to 20 carbon atoms) and cations represented by any of the formulae (ca-1) to (ca-4) (more preferably, cations represented by any of formula (ca-1-1) to (ca-1-78), (ca-1-101) to (ca-1-169), (ca-2-1) to (ca-2-2), (ca-3-1) to (ca-3-7), and (ca-4-1) to (ca-4-2)) may be exemplified. Specific examples of the component (D c) are shown below, but the component (D c) is not limited thereto. Specific examples of a suitable compound are listed below.

[Chem. 138]

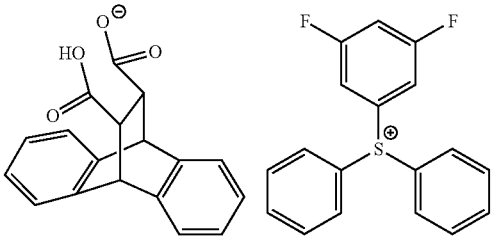

(D1c-1a)

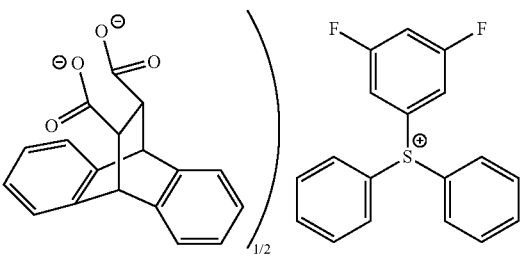

(D1c-1b)

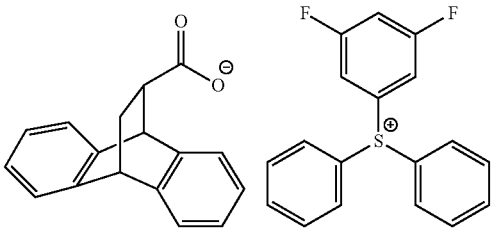

(D1c-2)

-continued (D1c-3)

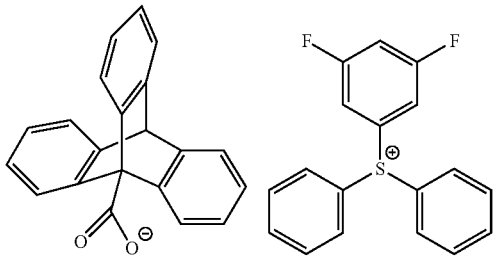

In the resist composition of the present embodiment, the component (D1c) may be used alone or two or more thereof may be used in combination.

In the resist composition of the present embodiment, an amount of the component (D1c) is preferably 1 to 35 parts by mass, more preferably 2 to 25 parts by mass, still more preferably 3 to 20 parts by mass, and particularly preferably 4 to 15 parts by mass with respect to 100 parts by mass of the component (A).

In the resist composition, within the entire base component (D) that traps (controls acid diffusion) an acid generated from the component (B) upon exposure, a proportion of the component (D1c) is, for example, 50 mass % or more, preferably 70 mass % or more, and most preferably 95 mass % or more. Here, the proportion may be 100 mass %. Here, a proportion of the component (D1c) within the entire component (D) when the resist composition contains the component (B1c) is not particularly limited, but it may be appropriately adjusted to be within a range of 0 mass % or more and 100 mass % or less.

If an amount of the component (D1c) is equal to or more than a lower limit of the preferable range, favorable lithography properties and resist pattern shape are easily obtained. On the other hand, when the amount thereof is equal to or less than an upper limit of the preferable range, a balance with other components can be achieved, and various lithography properties become favorable.

In addition, when the resist composition contains the component (D1c) and the component (B) (at least one of the components (B c) to (B2c)), a ratio thereof (molar ratio) is, for example, (B):(D1c)=100:0 to 50:50, more preferably (B):(D1c)=99:1 to 51:49, and most preferably (B):(D1c) =90:10 to 60:40 because the favorable lithography properties and resist pattern shape are easily obtained.

<Optional Components>

The resist composition of the present embodiment may further contain components (optional components) other than the component (A) and compound (BD1-3) described above.

Examples of such optional components include the component (B2c), component (D2c), component (D3), component (E), component (F), and component (S) described above.

Here, the component (B2c) is an acid-generator component other than the component (B1c) described above, and examples thereof include those in which a component corresponding to the component (B1c) is removed from those exemplified for the component (B1a) and component (B2a) described above.

In addition, the component (D2c) is a base component other than the component (D1c) described above, and is a photo-decomposable base which is decompose upon exposure and loses an ability to control acid diffusion. Specifically, those in which a component corresponding to the component (D1c) is removed from those exemplified for the component (D1a) and component (D2a) described above may be exemplified.

Regarding the component (D3), the component (E), the component (F), and the component (S), those the same as described in the resist composition of the first embodiment described above may be exemplified.

The resist composition of the present embodiment contains the component (A) and component (BD1-3) described above, and as necessary the above optional components.

For example, when the component (BD1-3) is used as the component (B 1), a resist composition containing the component (A), the component (B1), and the component (D2c) or the component (D3) is preferably exemplified. For example, when the component (BD1-3) is used as the component (D1c), a resist composition containing the component (A), the component (B2c), and the component (D1c) is preferably exemplified.

In addition, for example, when the component (BD1-3) is used as the component (B 1) and the component (D c), a resist composition containing the component (A), the component (B1), and the component (D1c) is preferably exemplified.

The resist composition of the present embodiment described above contains the compound (BD1-3) represented by the general formula (bd1-3). The component (BD1-3) has a relatively high hydrophobicity because it has a specific structure (bulky structure) in which the anion moiety is mainly composed of hydrocarbons.

Therefore, the compatibility between the compound (BD1-3) and the base component (A) is improved, and acid diffusivity in the resist film is appropriately controlled. In addition, in the component (BD1-3), since a cation moiety has an electron-withdrawing group, the reactivity is improved. It is speculated that, when the component (BD1-3) having such an anion moiety and cation moiety is contained, according to the resist composition of the embodiment, lithography properties (roughness reduction and the like) are further improved and the sensitivity is enhanced.

In addition, when the resist composition of the embodiment is used, since uniformity of the compound (BD1-3) in the resist film to be formed is improved, it is possible to easily form a resist pattern having a high resolution and a favorable shape with reduced roughness.

(Eighth Aspect: Method of Forming a Resist Pattern)

A method of forming a resist pattern according to an eighth aspect of the present invention is a method including a step of forming a resist film on a support using the resist composition according to the seventh aspect described above, a step of exposing the resist film, and a step of developing the exposed resist film to form a resist pattern.

Regarding one embodiment of the method of forming a resist pattern, the same method of forming a resist pattern according to the second embodiment described above except that the resist composition according to the seventh aspect is used may be exemplified.

In the method of forming a resist pattern of the present embodiment described above, since the resist composition according to the seventh aspect described above is used, when the resist pattern is formed, it is possible to form a resist pattern having high sensitivity and more favorable lithography properties (roughness reduction and the like).

(Ninth Aspect: Compound)

A compound according to a ninth aspect of the present invention is a compound having an anion moiety and a cation moiety represented by the following general formula (bd1-3).

[Chem. 139]

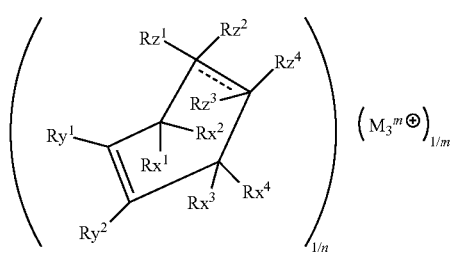

(bd1-3)

In the formula, $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

[Chem. 140]

- - - - - represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_3^{m+}$ represents an m-valent organic cation having an electron-withdrawing group.

The compound represented by the general formula (bd1-3) is the same compound as the component (BD1-3) described in the resist composition of the embodiment described above.

[Method of Producing Compound (BD1-3)]

Examples of a method of producing the component (BD1-3) include the same method as that of producing the component (BD1-1) described above. Specifically, a method in which an intermediate is obtained using a Diels-Alder reaction, a desired anion group is then introduced to obtain a precursor, a desired cation is introduced according to a salt exchange reaction, and thus a desired compound (B1c-0) is obtained may be exemplified.

[Chem. 141]

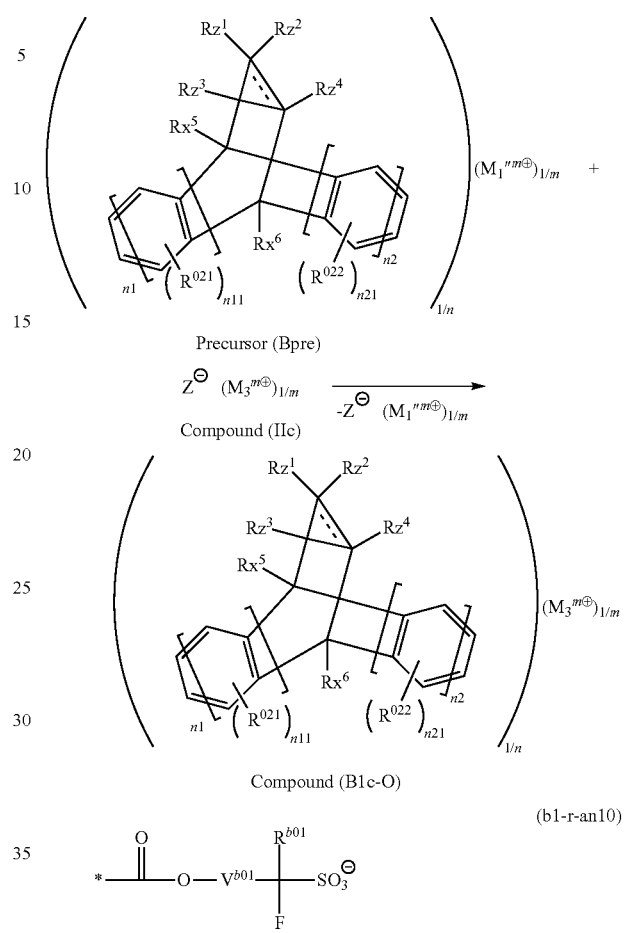

(Tenth Aspect: Acid Generator)

An acid generator according to a tenth aspect of the present invention includes the compound according to the ninth aspect described above.

The acid generator is useful as an acid-generator component for a chemically amplified resist composition. When such an acid-generator component is used for a chemically amplified resist composition, in the resist pattern formation, lithography properties such as roughness reduction are improved, a pattern shape is favorably maintained and the sensitivity is enhanced. When such an acid-generator component is used, in particular, high sensitivity with respect to an EB or EUV light source is easily obtained. In addition, according to a chemically amplified resist composition containing such an acid generator component, resolution performance is further improved.

EXAMPLES

As follows is a description of examples of the present invention, although the scope of the present invention is by no way limited by these examples. In the following examples, a compound represented by a chemical formula (1) is denoted as "compound (1)," and the same applies for compounds represented by other chemical formulae.

Compound Production 1a

Production Example 1a

Thianthrene-5-oxide (18.8 g, 81 mmol), and trimethylsilyl trifluoromethanesulfonate (36 g, 163 mmol) were dissolved in THF (47 g), and a phenylmagnesium bromide THF solution prepared by a conventional method using bromobenzene (12.7 g, 81 mmol), magnesium (2.0 g, 81 mmol), and THF (90 g) was added dropwise thereto so that the temperature in the system did not exceed −5° C. After dropwise addition was completed, the reaction continued at room temperature for 1 hour to complete the reaction. The reaction solution was put into ultra pure water (150 g) for 1 hour, and dichloromethane (170 g) was then added thereto, the mixture was stirred for 30 minutes and an aqueous layer was then removed. An organic layer was washed with ultra pure water (150 g) 3 times, the organic layer was then added dropwise to methyl tert-butyl ether (MTBE, 1700 g), and the precipitated solid was filtered off. The filtrate was dried under a reduced pressure to obtain an intermediate 1a (24.7 g, yield=68.9%).

[Chem. 142]

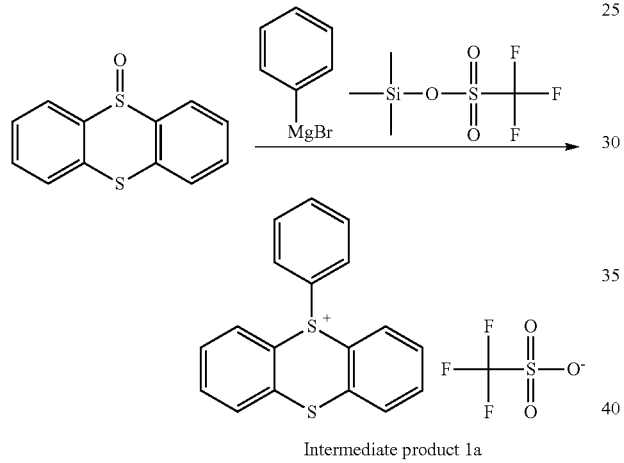

Production Example 2a

The intermediate 1a (6.6 g, 15 mmol) was dissolved in a solution in which ultra pure water (25 g) and methanol (75 g) were mixed, Oxone (registered trademark) (13.8 g, 22 mmol, molecular formula: $2KHSO_5 \cdot KHSO_4 \cdot K_2SO_4$, molecular weight: 614.76)) was added thereto, and the mixture was stirred at room temperature for 48 hours. The reaction solution was filtered, ultra pure water (50 g) and dichloromethane (200 g) were added thereto, and the mixture was stirred for 30 minutes, and an aqueous layer was then removed. Washing with a saturated sodium bisulfite aqueous solution (50 g) was performed, washing with ultra pure water (150 g) was then performed 3 times, an organic layer was then added dropwise to MTBE (500 g), and the precipitated solid was filtered off. The filtrate was dried under a reduced pressure to obtain a compound Aa (4.7 g, yield=65.4%).

[Chem. 143]

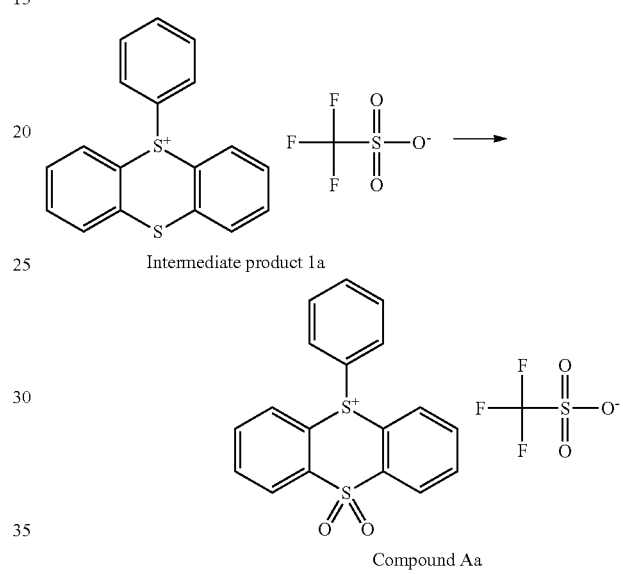

Production Example of Compound (B1-La)

A compound A (4.4 g, 9.3 mmol) and an anion precursor Bpre-aa (5.7 g, 9.3 mmol) were dissolved in dichloromethane (50 g), ultra pure water (50 g) was added thereto, and the mixture was reacted at room temperature for 30 minutes. After the reaction was completed, an aqueous phase was removed and an organic phase was then washed with ultra pure water (50 g) 4 times. The organic phase was concentrated and dried using a rotary evaporator to obtain a compound (B1a-1) (6.8 g, yield=93.4%).

[Chem. 144]

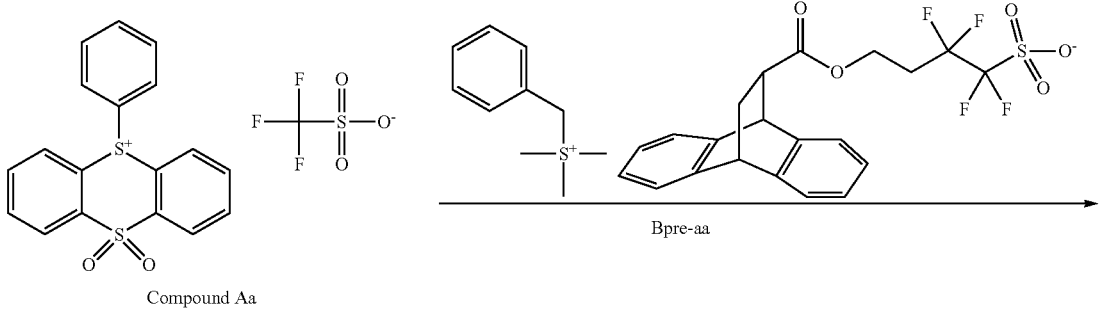

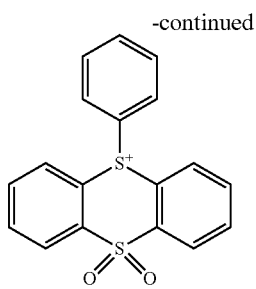

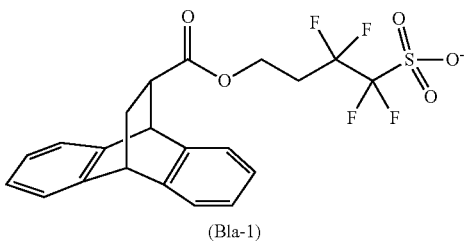

(Bla-1)

Production Example of Other Compounds

The following compound (B1a-2) to compound (B1a-13), compound (D1a-1), and compound (D1a-2) were obtained in the same manner as in the above "production example of compound (B1a-1)" except that combinations of the following compound Ba to compound Ja and the following compounds Bpre-ba to Bpre-ha were changed.

[Chem. 145]

Compound Aa

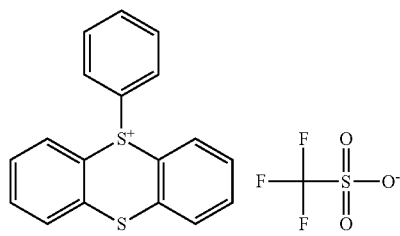

Compound Ba

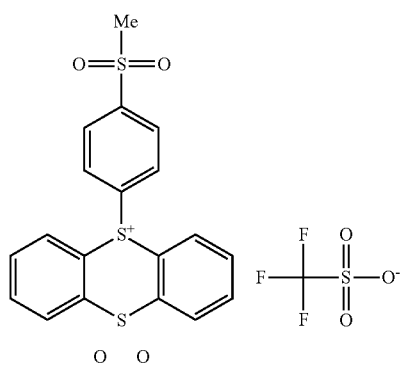

Compound Ca

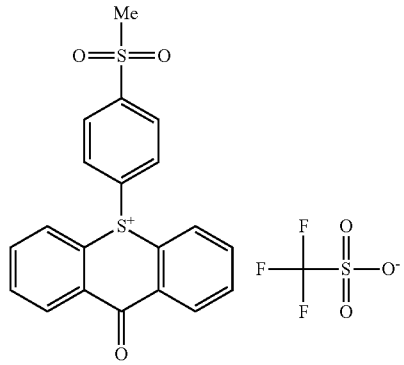

Compound Da

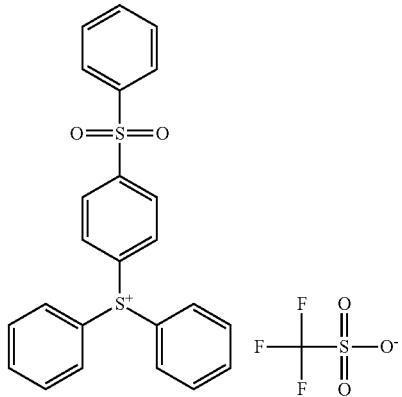

Compound Ea

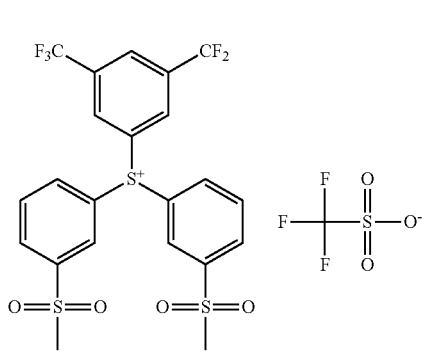

Compound Fa

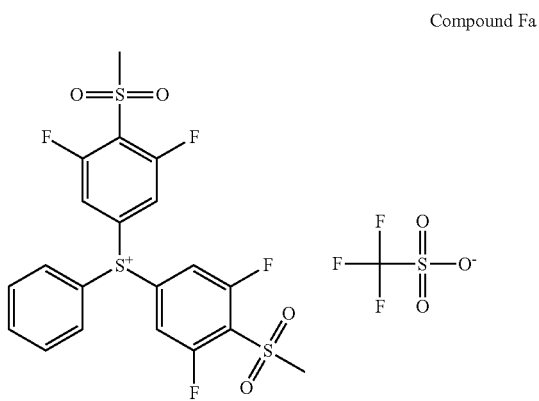

Compound Ga
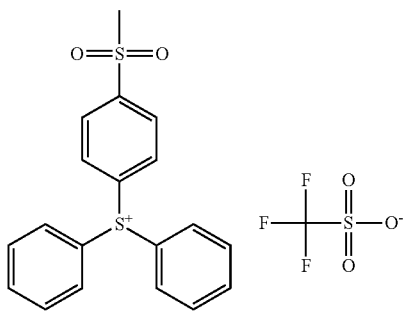
Compound Ha
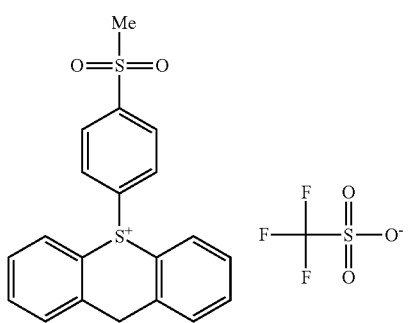
Compound Ia
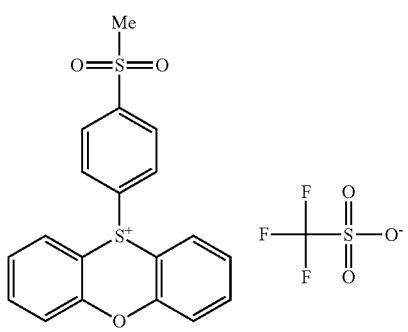
Compound Ja
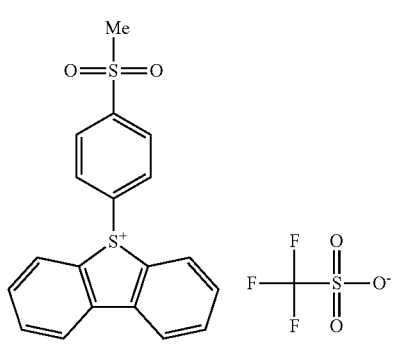
[Chem. 146]
Bpre-aa
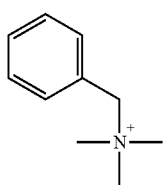
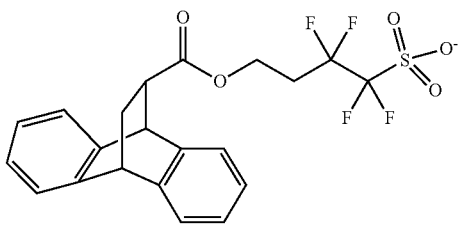
Bpre-ba
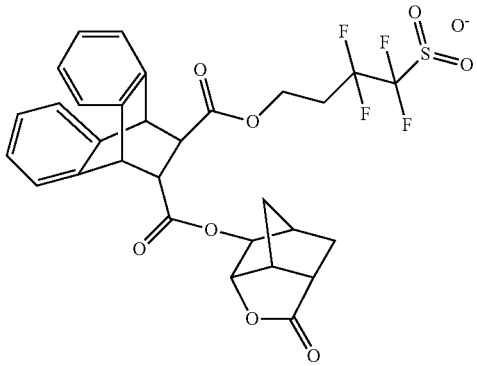
Bpre-ca
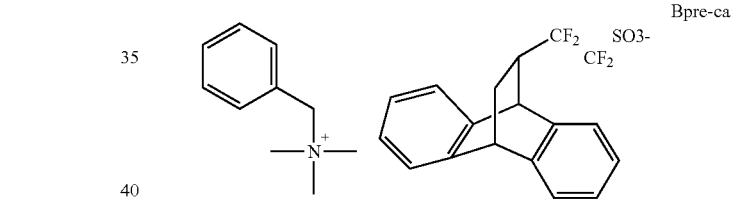
Bpre-da
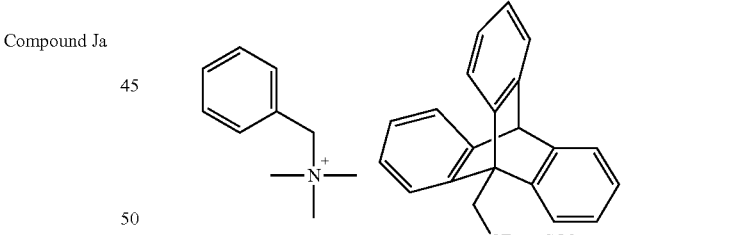
Bpre-ea
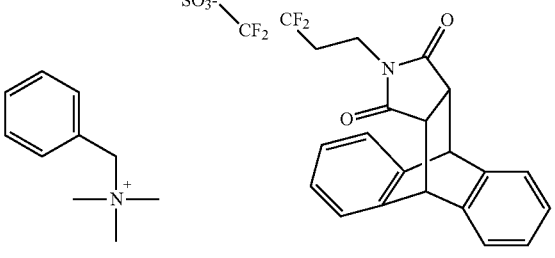

Bpre-fa
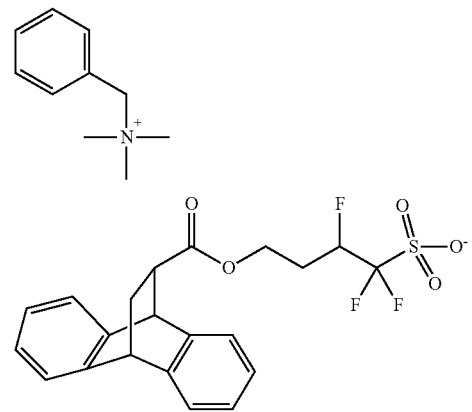
Bpre-ga
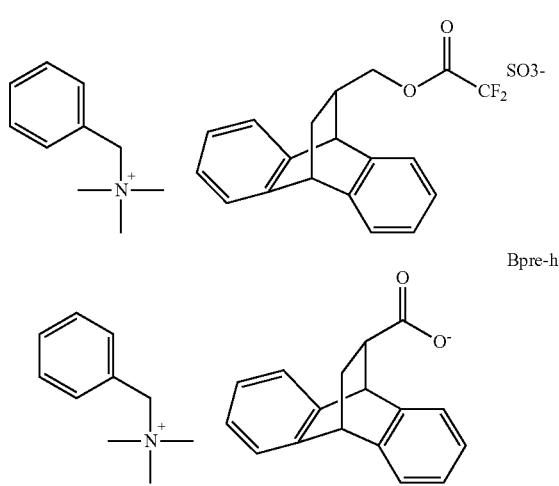
Bpre-ha
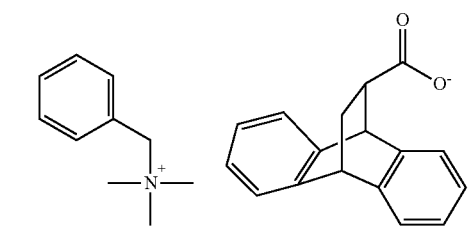
Each of the obtained compounds was analyzed by NMR, and the structure thereof was identified by the following analysis results.
[Chem. 147]
(B1a-1)
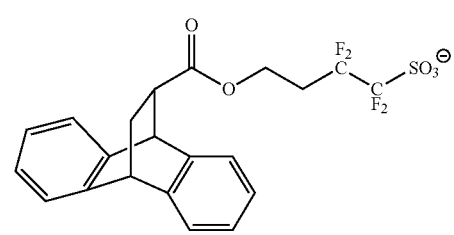
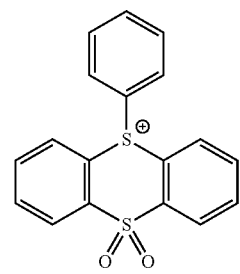
(B1a-2)
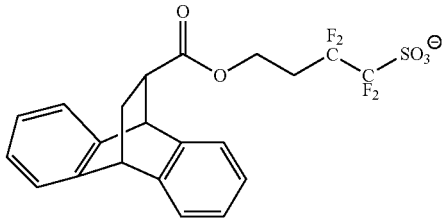
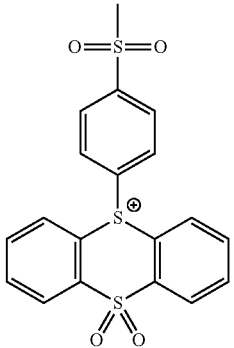
(B1a-3)
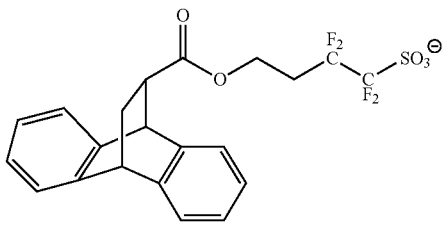
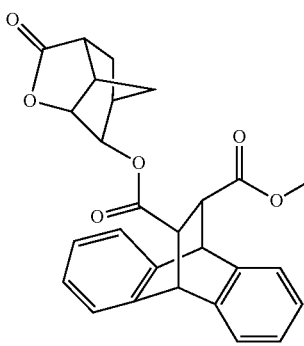
(B1a-4)

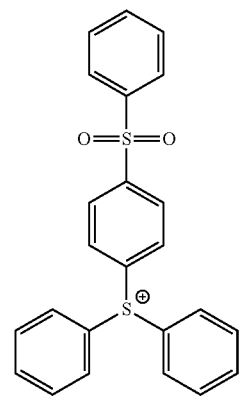
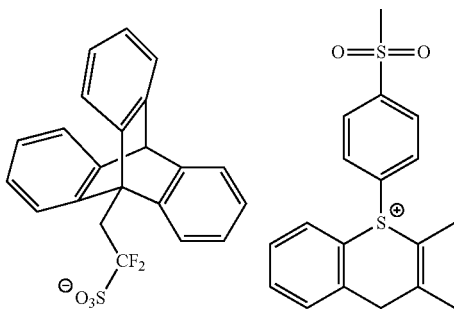
(B1a-5)
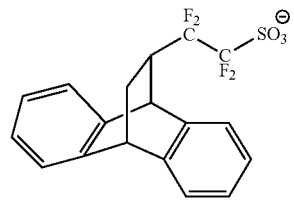
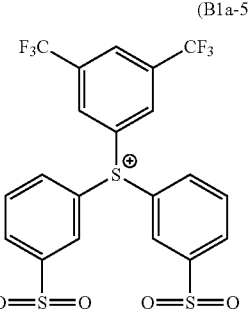
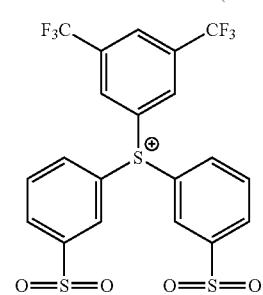
(B1a-6)
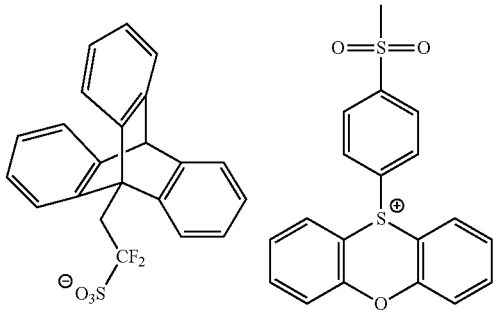
[Chem. 148]
(B1a-7)
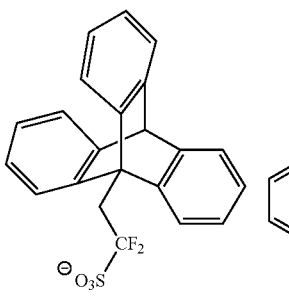
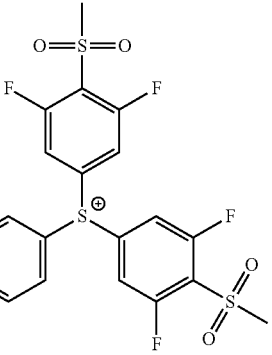
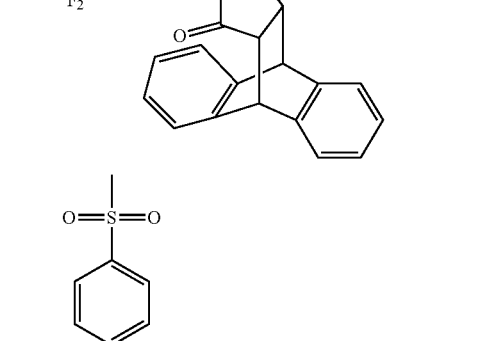
(B1a-8)
(B1a-9)
(B1a-10)
[Chem. 149]
(B1a-11)
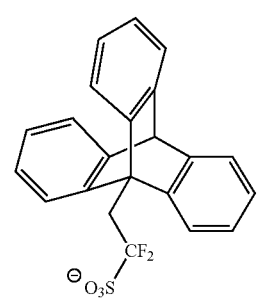
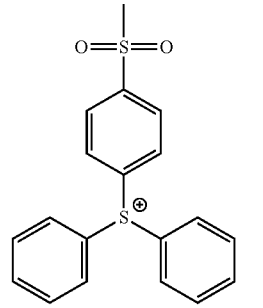
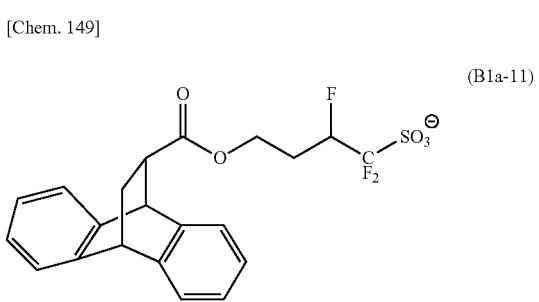
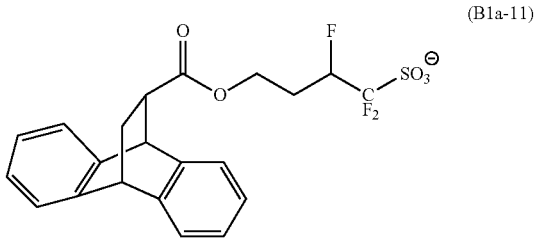

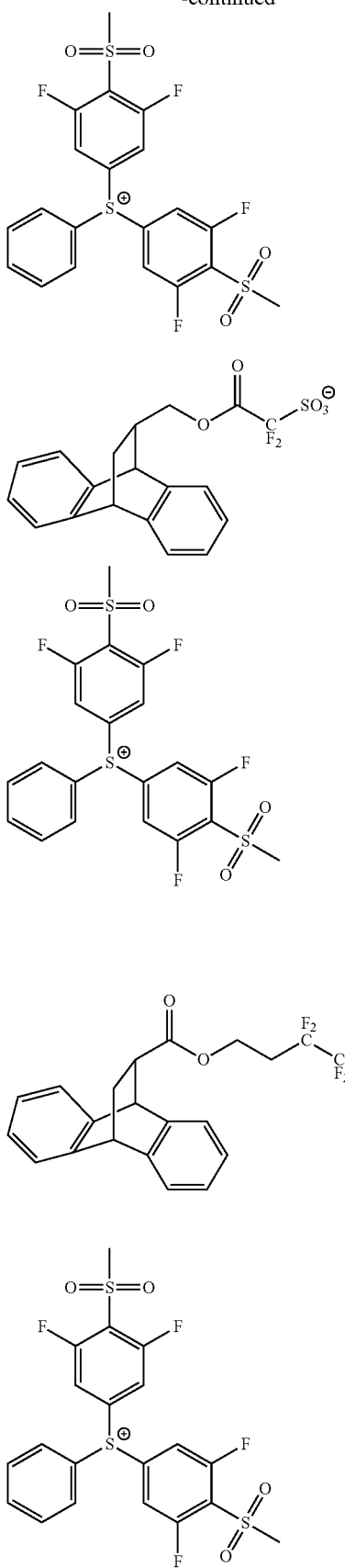

(B1a-12)

(B1a-13)

[Chem. 150]

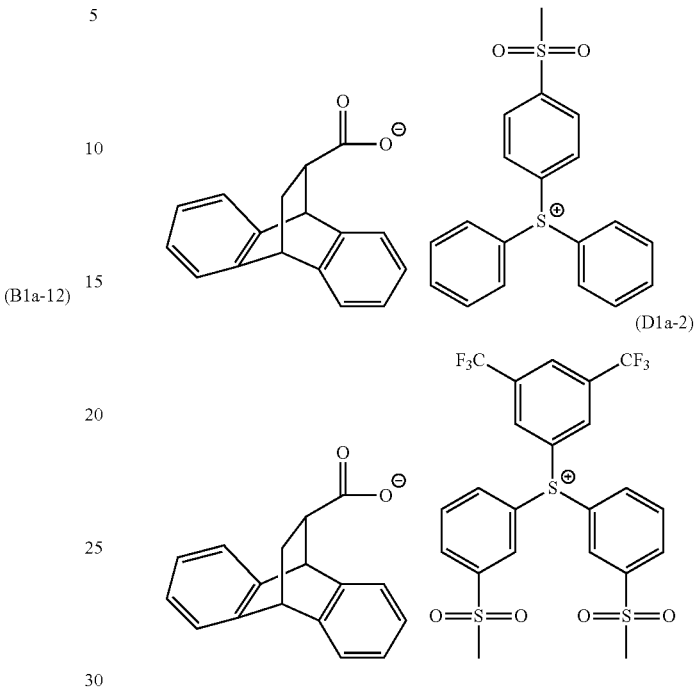

(D1a-1)

(D1a-2)

Compound (B1a-1): Combination of Compound Aa and Compound Bpre-Aa $^1$H-NMR (DMSO, 400 MHz): δ(ppm)=8.49 (d, ArH, 2H), 8.00-8.22 (m, ArH, 6H), 7.84-7.96 (m, ArH, 3H), 7.78 (d, ArH, 2H), 7.01-7.47 (m, ArH, 8H), 4.72 (s, CH, 1H), 4.43 (s, CH, 1H), 4.23, (t, CH2, 2H), 2.95-3.02 (m, CH, 1H), 2.63-2.73, (m, CF$_2$CH2, 2H), 1.86-2.07 (m, CH2, 2H)

$^{19}$F-NMR (DMSO, 376 MHz): δ(ppm)=−111.3, −117.4

Compound (B1a-2): Combination of Compound Ba and Compound Bpre-Aa $^1$H-NMR (DMSO, 400 MHz): δ(ppm)=8.62 (d, ArH, 2H), 8.05 (d, ArH, 2H), 7.82-7.98 (m, ArH, 4H), 7.50-7.66 (m, ArH, 2H), 7.01-7.47 (m, ArH, 10H), 4.72 (s, CH, 1H), 4.43 (s, CH, 1H), 4.23, (t, CH2, 2H), 3.51 (s, CH3, 3H), 2.95-3.02 (m, CH, 1H), 2.63-2.73, (m, CF$_2$CH2, 2H), 1.86-2.07 (m, CH2, 2H).

$^{19}$F-NMR (DMSO, 376 MHz): δ(ppm)=−111.3, −117.4

Compound (B1a-3): Combination of Compound Ca and Compound Bpre-Aa $^1$H-NMR (DMSO, 400 MHz): δ(ppm)=8.76 (s, ArH, 1H), 8.59-8.64 (m, ArH, 1H), 8.42 (t, ArH 2H), 8.03-8.19 (m, ArH, 5H), 7.81 (t, ArH, 2H), 7.69 (t, ArH, 1H), 7.01-7.47 (m, ArH, 8H), 4.72 (s, CH, 1H), 4.43 (s, CH, 1H), 4.23, (t, CH2, 2H), 3.51 (s, CH3, 3H), 2.95-3.02 (m, CH, 1H), 2.63-2.73, (m, CF$_2$CH2, 2H), 1.86-2.07 (m, CH2, 2H) $^{19}$F-NMR (DMSO, 376 MHz): δ(ppm)=−111.3, −117.4

Compound (B1a-4): Combination of Compound Da and Compound Bpre-Ba $^1$H-NMR (DMSO, 400 MHz): δ(ppm)=7.74-7.90 (m, 19H, ArH), 7.01-7.47 (m, ArH, 8H), 4.70 (d, OCH (lactone), 1H), 4.58 (t, COOCH (lactone), 1H), 4.50 (d, CH, 2H), 4.22, (t, COOCH2, 2H), 3.32 (m, CH (lactone), 1H), 3.20 (t, COCH, 2H), 2.63-2.73, (m, CF$_2$CH2, CH (lactone) 4H), 1.60-2.20 (m, CH2 (lactone), 4H)

$^{19}$F-NMR (DMSO, 376 MHz): δ (ppm)=−111.3, −117.6

Compound (B1a-5): Combination of Compound Ea and Compound Bpre-Ca $^1$H-NMR (DMSO, 400 MHz): δ (ppm)=8.60-8.80 (m, ArH, 5H), 8.41 (d, ArH, 2H), 8.28 (d, ArH, 2H), 8.06 (t, ArH, 2H), 7.00-7.48 (m, ArH, 8H), 4.70 (s, CH, 1H), 4.40 (s, CH, 1H), 3.52 (s, CH3, 6H), 3.15-3.22 (m, CF$_2$CH, 1H), 1.95-2.15 (m, CH2, 2H)$^{19}$F-NMR (DMSO, 376 MHz): δ(ppm)=−61.2, −111.3, −117.4

Compound (B1a-6): Combination of Compound Fa and Compound Bpre-Da $^1$H-NMR (DMSO, 400 MHz): δ (ppm)=7.98-8.07 (m, ArH, 6H), 7.94 (t, ArH, 1H), 7.83 (t, ArH, 2H), 7.68-7.82 (m, ArH, 6H), 6.60-6.80 (m, ArH, 6H), 5.54 (s, CH, 1H), 3.52 (s, CH3, 6H), 2.42-2.47 (t, CF$_2$CH2, 2H)

$^{19}$F-NMR (DMSO, 376 MHz): δ(ppm)=−102.3, −103.9, −105.6

Compound (B1a-7): Combination of Compound Ga and Compound Bpre-Da $^1$H-NMR (DMSO, 400 MHz): δ(ppm)=7.74-7.90 (m, ArH, 14H), 7.68-7.82 (m, ArH, 6H), 6.60-6.80 (m, ArH, 6H), 5.54 (s, CH, 1H), 3.51 (s, CH3, 3H), 2.42-2.47 (t, CF$_2$CH2, 2H)

$^{19}$F-NMR (DMSO, 376 MHz): δ(ppm)=−103.9, −105.6

Compound (B1a-8): Combination of Compound Ha and Compound Bpre-Da $^1$H-NMR (DMSO, 400 MHz): δ(ppm)=8.47 (d, ArH, 2H), 7.82-7.90 (m, ArH, 4H), 7.70-7.80 (m, ArH, 2H), 7.45-7.69 (m, ArH, 10H), 6.60-6.80 (m, ArH, 6H), 5.54 (s, CH, 1H), 4.58 (d, CH2, 1H), 4.01 (d, CH2, 1H), 3.51 (s, CH3, 3H), 2.42-2.47 (t, CF$_2$CH2, 2H)

$^{19}$F-NMR (DMSO, 376 MHz): δ(ppm)=−103.9, −105.6

Compound (B1a-9): Combination of Compound Ia and Compound Bpre-Da $^1$H-NMR (DMSO, 400 MHz): δ(ppm)=8.62 (d, ArH, 2H), 8.05 (d, ArH, 2H), 7.82-7.98 (m, ArH, 10H), 7.23-7.66 (m, ArH, 4H), 6.60-6.80 (m, ArH, 6H), 5.54 (s, CH, 1H), 3.51 (s, CH3, 3H), 2.42-2.47 (t, CF$_2$CH2, 2H)

$^{19}$F-NMR (DMSO, 376 MHz): δ(ppm)=−103.9, −105.6

Compound (B1a-10): Combination of Compound Ja and Compound Bpre-Ea $^1$H-NMR (DMSO, 400 MHz): δ(ppm)=8.50 (d, ArH, 2H), 8.37 (d, ArH, 2H), 7.93 (t, ArH 2H), 7.55-7.75 (m, ArH 6H), 7.01-7.47 (m, ArH, 8H), 4.62 (d, CH, 2H), 3.56 (t, NCH2, 2H), 3.51 (s, CH3, 3H), 3.14 (t, COCH, 2H), 2.63-2.73 (m, CF$_2$CH2, 2H)

$^{19}$F-NMR (DMSO, 376 MHz): δ (ppm)=−111.3, −117.6

Compound (B1a-11): Combination of Compound Fa and Compound Bpre-Fa $^1$H-NMR (DMSO, 400 MHz): δ (ppm)=7.98-8.07 (m, ArH, 6H), 7.94 (t, ArH, 1H), 7.83 (t, ArH, 2H), 7.01-7.47 (m, ArH, 8H), 5.08 (m, CFCH, 1H), 4.71 (s, CH, 1H), 4.42 (s, CH, 1H), 4.23 (m, CH2, 2H), 3.52 (s, CH3, 6H), 2.90 (m, CH, 1H), 2.45 (m, CFCH, 1H), 1.82-2.07 (m, CH2, CFCH, 3H)

$^{19}$F-NMR (DMSO, 376 MHz): δ (ppm)=−102.3, −112.5, −121.2, −203.2

Compound (B1a-12): Combination of Compound Fa and Compound Bpre-Ga $^1$H-NMR (DMSO, 400 MHz): δ(ppm)=7.98-8.07 (m, ArH, 6H), 7.94 (t, ArH, 1H), 7.83 (t, ArH, 2H), 7.01-7.45 (m, ArH, 8H), 4.71 (s, CH, 1H), 4.44 (S, CH, 1H), 4.31 (s, CH2, 2H), 3.52 (s, CH3, 6H), 2.93-3.00 (m, CH, 1H), 1.87-2.07 (m, CH2, 1H), 0.98-1.03 (m, CH, 1H)

$^{19}$F-NMR (DMSO, 376 MHz): δ(ppm)=−102.3, −107.9

Compound (B1a-13): Combination of Compound Fa and Compound Bpre-Aa $^1$H-NMR (DMSO, 400 MHz): δ(ppm)=7.98-8.07 (m, ArH, 6H), 7.94 (t, ArH, 1H), 7.83 (t, ArH, 2H), 7.01-7.47 (m, ArH, 8H), 4.72 (s, CH, 1H), 4.43 (s, CH, 1H), 4.23, (t, CH2, 2H), 3.52 (s, CH3, 6H), 2.95-3.02 (m, CH, 1H), 2.63-2.73, (m, CF$_2$CH2, 2H), 1.86-2.07 (m, CH2, 2H)

$^{19}$F-NMR (DMSO, 376 MHz): δ(ppm)=−102.3, −111.3, −117.4

Compound (D1a-1): Combination of Compound Ga and Compound Bpre-Ha $^1$H-NMR (DMSO, 400 MHz): δ(ppm)=7.74-7.90 (m, 14H, ArH), 7.00-7.48 (m, ArH, 8H), 4.68 (s, CH, 1H), 4.41 (s, CH, 1H), 3.51 (s, CH3, 3H), 2.95-3.02 (m, CH, 1H), 1.85-2.04 (m, CH2, 2H)

Compound (D1a-2): Combination of Compound Ea and Compound Bpre-Ha $^1$H-NMR (DMSO, 400 MHz): δ(ppm)=8.60-8.80 (m, ArH, 5H), 8.41 (d, ArH, 2H), 8.28 (d, ArH, 2H), 8.06 (t, ArH, 2H), 7.00-7.48 (m, ArH, 8H), 4.68 (s, CH, 1H), 4.41 (s, CH, 1H), 3.52 (s, CH3, 6H), 2.95-3.02 (m, CH, 1H), 1.85-2.04 (m, CH2, 2H)$^{19}$F-NMR (DMSO, 376 MHz): δ(ppm)=−61.2

Resist Composition Preparation 1a

Examples 1a to 16a, Comparative Examples 1a to 10a, and Reference Example 1a

Components shown in Tables 1 and 2 were mixed and dissolved to prepare resist compositions of respective examples.

TABLE 1

| | Component (A) | Component (B) | Component (D) | Component (S) |
| --- | --- | --- | --- | --- |
| Comparative Example 1a | (A)-1a [100] | (B2a)-1 [12.8] | (D2a)-1 [3.8] | (S)-1a [6400] |
| Comparative Example 2a | (A)-1a [100] | (B2a)-2 [18.5] | (D2a)-1 [3.8] | (S)-1a [6400] |
| Example 1a | (A)-1a [100] | (B1a)-1 [22.3] | (D2a)-1 [3.8] | (S)-1a [6400] |
| Example 2a | (A)-1a [100] | (B1a)-2 [24.5] | (D2a)-1 [3.8] | (S)-1a [6400] |
| Example 3a | (A)-1a [100] | (B1a)-3 [23.5] | (D2a)-1 [3.8] | (S)-1a [6400] |
| Comparative Example 3a | (A)-1a [100] | (B2a)-3 [25.6] | (D2a)-1 [3.8] | (S)-1a [6400] |
| Example 4a | (A)-1a [100] | (B1a)-4 [30.1] | (D2a)-1 [3.81] | (S)-1a [64001] |
| Reference Example 1a | (A)-1a [100] | (B2a)-4 [22.3] | (D2a)-1 [3.8] | (S)-1a [6400] |
| Example 5a | (A)-1a [100] | (B1a)-5 [26.8] | (D2a)-1 [3.8] | (S)-1a [6400] |
| Comparative Example 4a | (A)-1a [100] | (B2a)-5 [18.8] | (D2a)-1 [3.8] | (S)-1a [6400] |
| Example 6a | (A)-1a [100] | (B1a)-6 [25.3] | (D2a)-1 [3.8] | (S)-1a [6400] |
| Example 7a | (A)-1a [100] | (B1a)-7 [21.0] | (D2a)-1 [3.8] | (S)-1a [6400] |
| Example 8a | (A)-1a [100] | (B1a)-8 [21.4] | (D2a)-1 [3.8] | (S)-1a [6400] |
| Example 9a | (A)-1a [100] | (B1a)-9 [21.4] | (D2a)-1 [3.8] | (S)-1a [6400] |

TABLE 2

| | Component (A) | | Component (B) | Component (D) | Component (S) |
|---|---|---|---|---|---|
| Comparative Example 5a | (A)-1a [100] | — | (B2a)-6 [21.2] | (D2a)-1 [3.8] | (S)-1a [6400] |
| Example 10a | (A)-1a [100] | — | (B1a)-10 [23.4] | (D2a)-1 [3.8] | (S)-1a [6400] |
| Comparative Example 6a | (A)-2a [50] | (A)-3a [50] | (B2a)-7 [20.0] | (D2a)-1 [3.8] | (S)-1a [6400] |
| Comparative Example 7a | (A)-2a [50] | (A)-4a [50] | (B2a)-8 [18.7] | (D2a)-1 [3.8] | (S)-1a [6400] |
| Comparative Example 8a | (A)-3a [100] | — | (B2a)-9 [18.5] | (D2a)-1 [3.8] | (S)-1a [6400] |
| Example 11a | (A)-2a [50] | (A)-3a [50] | (B1a)-11 [26.5] | (D2a)-1 [3.8] | (S)-1a [6400] |
| Example 12a | (A)-2a [50] | (A)-4a [50] | (B1a)-12 [25.2] | (D2a)-1 [3.8] | (S)-1a [6400] |
| Example 13a | (A)-3a [100] | — | (B1a)-13 [25.0] | (D2a)-1 [3.8] | (S)-1a [6400] |
| Comparative Example 9a | (A)-1a [100] | — | (B2a)-10 [16.7] | (D2a)-2 [4.9] | (S)-1a [6400] |
| Example 14a | (A)-1a [100] | — | (B2a)-10 [16.7] | (D1a)-1 [5.6] | (S)-1a [6400] |
| Example 15a | (A)-1a [100] | — | (B2a)-10 [16.7] | (D1a)-2 [7.6] | (S)-1a [6400] |
| Comparative Example 10a | (A)-2a [50] | (A)-3a [50] | (B2a)-10 [16.7] | (D2a)-3 [4.6] | (S)-1a [6400] |
| Example 16a | (A)-2a [50] | (A)-3a [50] | (B2a)-10 [16.7] | (D1a)-1 [5.6] | (S)-1a [6400] |

In Tables 1 and 2, the reference characters indicate the following. The values in brackets [ ] indicate the amount (in terms of parts by mass) of the component added.

(A)-1a: A high-molecular-weight compound represented by the following chemical formula (A1)-1a. The high-molecular-weight compound (A)-1a was obtained by performing radical polymerization using monomers deriving structural units constituting the high-molecular-weight compound in a predetermined molar ratio. Regarding the high-molecular-weight compound (A)-1a, a weight average molecular weight (Mw) in terms of polystyrene standards obtained through GPC measurement was 7,000, and a molecular weight dispersity (Mw/Mn) was 1.72. The composition of the copolymer (ratio (molar ratio) of the respective structural units within the structural formula) as determined by $^{13}$C-NMR was l/m/n=30/60/10.

(A)-2a: A high-molecular-weight compound represented by the following chemical formula (A1)-2a. The high-molecular-weight compound (A)-2a was obtained by performing radical polymerization using monomers deriving structural units constituting the high-molecular-weight compound in a predetermined molar ratio. Regarding the high-molecular-weight compound (A)-2a, a weight average molecular weight (Mw) in terms of polystyrene standards obtained through GPC measurement was 6,800, and a molecular weight dispersity (Mw/Mn) was 1.65. The composition of the copolymer (ratio (molar ratio) of the respective structural units within the structural formula) as determined by $^{13}$C-NMR was l/m/n=30/60/10.

(A)-3a: A high-molecular-weight compound represented by the following chemical formula (A1)-3a. The high-molecular-weight compound (A)-3a was obtained by performing radical polymerization using monomers deriving structural units constituting the high-molecular-weight compound in a predetermined molar ratio. Regarding the high-molecular-weight compound (A)-3a, a weight average molecular weight (Mw) in terms of polystyrene standards obtained through GPC measurement was 7,100, and a molecular weight dispersity (Mw/Mn) was 1.69. The composition of the copolymer (ratio (molar ratio) of the respective structural units within the structural formula) as determined by $^{13}$C-NMR was l/m=50/50.

(A)-4a: A high-molecular-weight compound represented by the following chemical formula (A1)-4a. The high-molecular-weight compound (A)-4a was obtained by performing radical polymerization using monomers deriving structural units constituting the high-molecular-weight compound in a predetermined molar ratio. Regarding the high-molecular-weight compound (A)-4a, a weight average molecular weight (Mw) in terms of polystyrene standards obtained through GPC measurement was 7,200, and a molecular weight dispersity (Mw/Mn) was 1.71. The composition of the copolymer (ratio (molar ratio) of the respective structural units within the structural formula) as determined by $^{13}$C-NMR was l/m=50/50.

[Chem. 151]

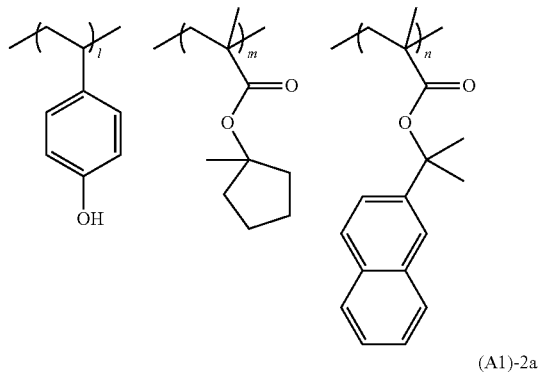

(A1)-1a

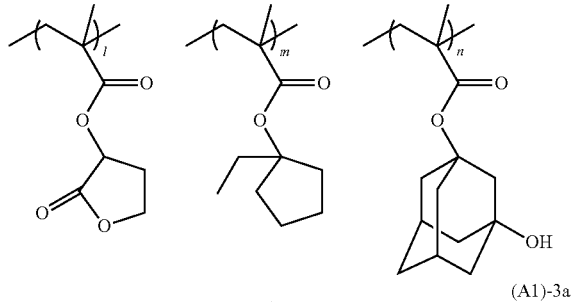

(A1)-2a

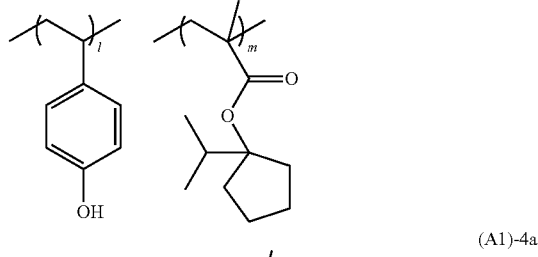

(A1)-3a

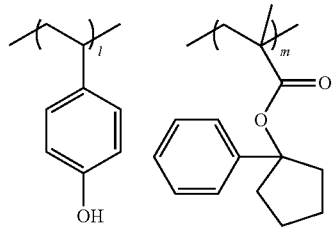

(A1)-4a (B1a)-1 to (B1a)-13: respective acid generators including the above compound (B1a-1) to compound (B1a-13)

(B2a)-1: respective acid generator including the following compound (B2a-1).

(B2a)-2: acid generator including the following compound (B2a-2).

(B2a)-3: acid generator including the following compound (B2a-3).

(B2a)-4: acid generator including the following compound (B2a-4).

(B2a)-5: acid generator including the following compound (B2a-5).

(B2a)-6: acid generator including the following compound (B2a-6).

(B2a)-7: acid generator including the following compound (B2a-7).

(B2a)-8: acid generator including the following compound (B2a-8).

(B2a)-9: acid generator including the following compound (B2a-9).

(B2a)-10: acid generator including the following compound (B2a-10).

[Chem. 152]

(B2a-1)
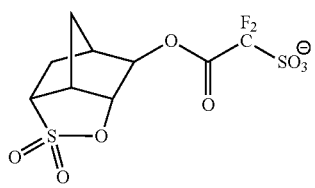
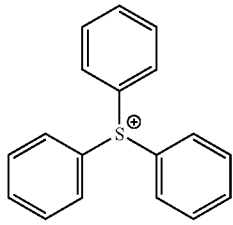

(B2a-2)
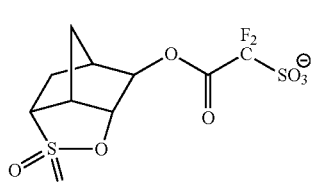
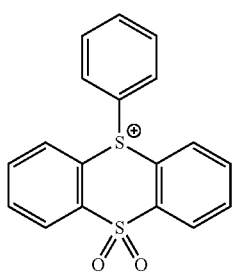

(B2a-3)
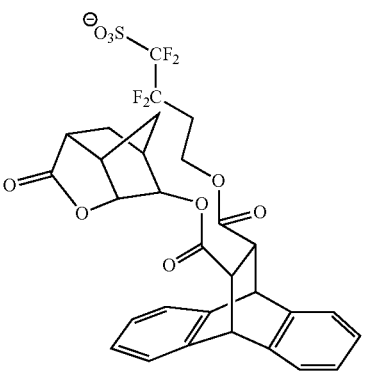
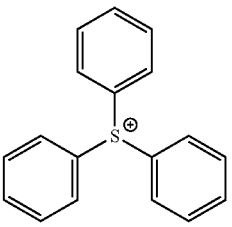

(B2a-4)
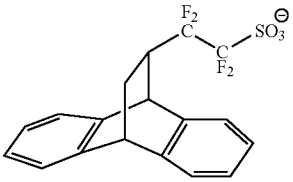
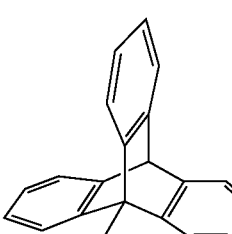

(B2a-5)
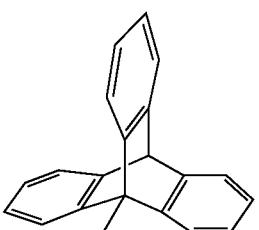
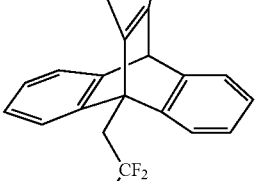

(B2a-6)
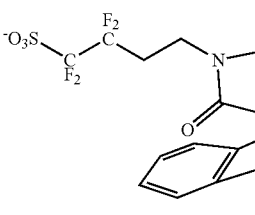

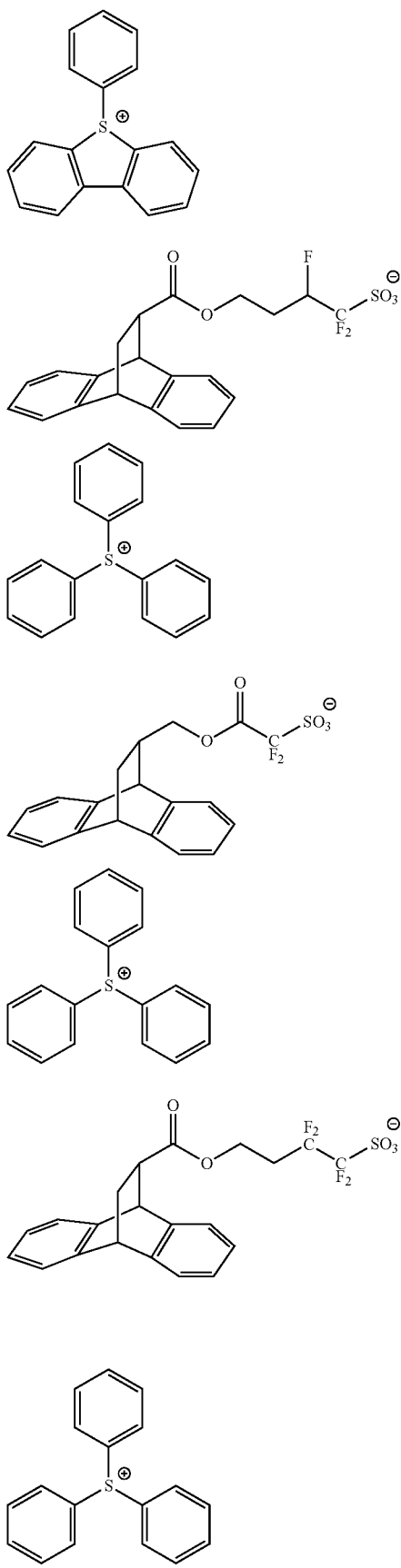

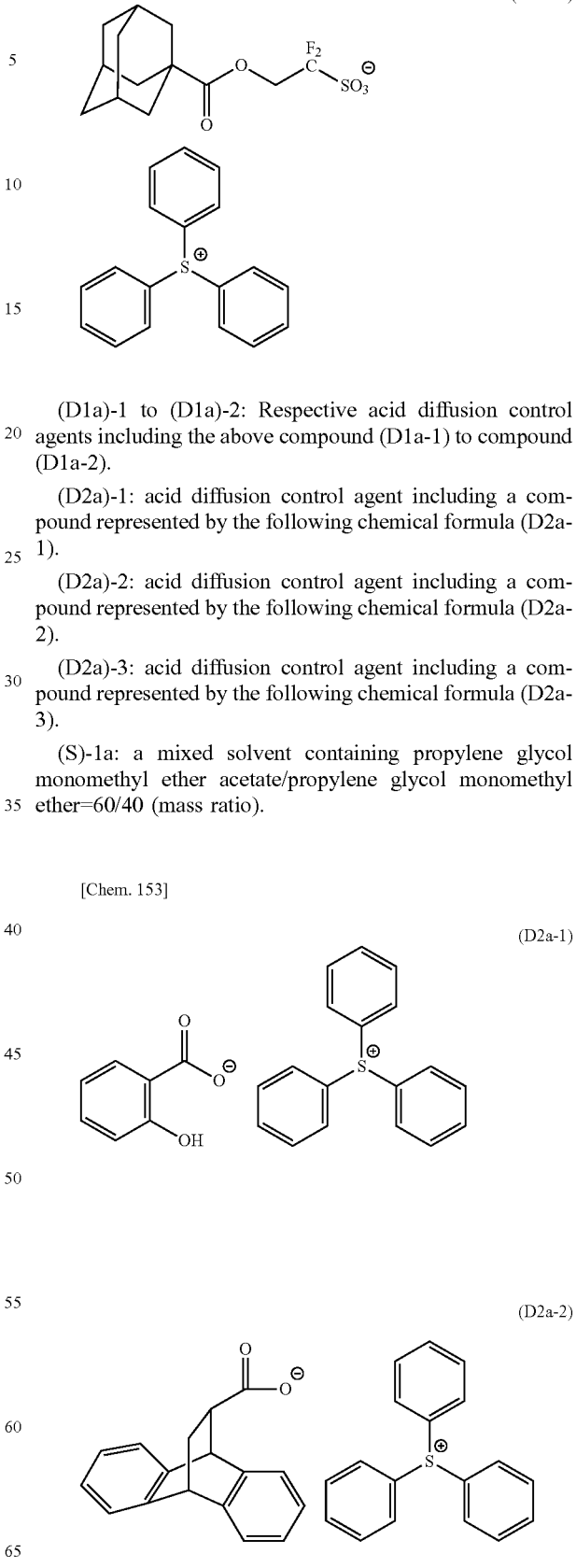

(D1a)-1 to (D1a)-2: Respective acid diffusion control agents including the above compound (D1a-1) to compound (D1a-2).

(D2a)-1: acid diffusion control agent including a compound represented by the following chemical formula (D2a-1).

(D2a)-2: acid diffusion control agent including a compound represented by the following chemical formula (D2a-2).

(D2a)-3: acid diffusion control agent including a compound represented by the following chemical formula (D2a-3).

(S)-1a: a mixed solvent containing propylene glycol monomethyl ether acetate/propylene glycol monomethyl ether=60/40 (mass ratio).

[Chem. 153]

-continued

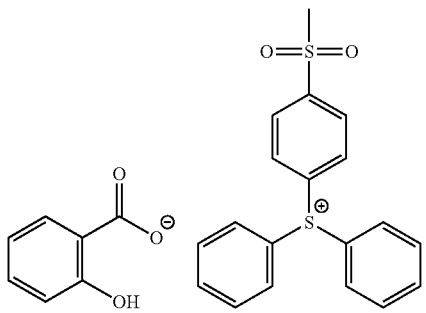

(D2a-3)

<Resist Pattern Formation 1a>

Each of the resist compositions of examples and comparative examples was applied to an 8-inch silicon substrate which had been treated with hexamethyldisilazane (HMDS) using a spinner, and was then prebaked (PAB) on a hot plate at 110° C. for 60 seconds and dried, thereby forming a resist film having a film thickness of 50 nm.

Next, drawing (exposure) was performed on the resist film using an electron beam lithography system JEOL-JBX-9300FS (commercially available from JEOL. Ltd.) at an acceleration voltage of 100 kV to obtain a 1:1 line and space pattern (hereinafter referred to as an "LS pattern") with a target size of a line width of 50 nm. Then, a post exposure bake (PEB) treatment was conducted at 100° C. for 60 seconds.

Thereafter, alkali developing was conducted for 60 seconds at 23° C. in a 2.38% by weight aqueous solution of tetramethylammonium hydroxide (TMAH) (product name: NMD-3; manufactured by Tokyo Ohka Kogyo Co., Ltd.).

Then, water rinsing was conducted for 15 seconds using pure water.

As a result, a 1:1 LS pattern with a line width of 50 nm was formed.

[Evaluation of Optimum Exposure Dose (Eop)]

An optimal exposure amount Eop ($\mu C/cm^2$) at which an LS pattern with a target size was formed according to the above "resist pattern formation method 1a" was obtained. This is shown as "Eop ($\mu C/cm^2$)" in Tables 3 and 4.

[Evaluation for Defects]

Resist compositions of respective examples were applied to 8-inch silicon substrates at 1,500 rpm using a spinner, and a pre-bake (PAB) treatment was performed on a hot plate at a temperature of 110° C. for 60 seconds, and drying was performed, and thereby resist films with a film thickness of 50 nm were formed.

Regarding the formed resist films, a number of defects in total (total number of defects) in the wafer was measured using a surface defect observation device (commercially available from KLA-TENCOR, product name: Surfscan SP2).

In evaluation for defects, when the number of defects in the resist film formed using the resist composition of Comparative Example 1 was 1.0, a result of evaluation thereof as "Defect" is shown in Tables 3 and 4 according to the following evaluation criteria.

Evaluation Criteria

A: 0.5 or less
B: more than 0.5 to 1.0 or less
C: more than 1.0

[Evaluation of Line Width Roughness (LWR)]

$3\sigma$ which is a scale showing LWR was obtained from the LS pattern formed in the above "resist pattern formation 1a." This is shown as "LWR (nm)" in Tables 3 and 4. "$3\sigma$" indicates a value of 3 times ($3\sigma$) the standard deviation ($\sigma$) as "LWR" (unit: nm) obtained from measurement results when the line positions at 400 points in the lengthwise direction of the line were measured using a scanning electron microscope (an acceleration voltage of 800 V, product name: S-9380, commercially available from Hitachi High-Technologies Corporation).

The smaller this $3\sigma$ value is, the lower the level of roughness on the side walls of the line, indicating that an LS pattern with a uniform width was obtained.

[Evaluation of Critical Resolution]

When an LS pattern was formed by gradually reducing an exposure amount from a critical resolution at the above Eop, specifically, the optimal exposure amount Eop, a minimum space width of a resolved pattern was obtained using a scanning electron microscope S-9380 (commercially available from Hitachi High-Technologies Corporation). The results are shown as "critical resolution (nm)" in Tables 3 and 4.

TABLE 3

| | Eop ($\mu C/cm^2$) | Defect | LWR (nm) | Critical resolution (nm) |
| --- | --- | --- | --- | --- |
| Comparative Example 1a | 125 | Reference | 6.0 | 42.0 |
| Comparative Example 2a | 110 | C | 6.3 | 42.0 |
| Example 1a | 100 | A | 5.5 | 30.0 |
| Example 2a | 90 | A | 5.3 | 29.0 |
| Example 3a | 95 | A | 5.4 | 29.5 |
| Comparative Example 3a | 115 | A | 5.3 | 37.0 |
| Example 4a | 95 | A | 5.3 | 29.0 |
| Reference Example 1a | 100 | A | 6.2 | 43.0 |
| Example 5a | 80 | A | 5.3 | 25.0 |
| Comparative Example 4a | 110 | A | 5.4 | 36.5 |
| Example 6a | 75 | A | 5.4 | 24.0 |
| Example 7a | 95 | A | 5.0 | 28.0 |
| Example 8a | 100 | A | 5.4 | 29.0 |
| Example 9a | 85 | A | 5.3 | 27.0 |

TABLE 4

| | Eop ($\mu C/cm^2$) | Defect | LWR (nm) | Critical resolution (nm) |
| --- | --- | --- | --- | --- |
| Comparative Example 5a | 110 | A | 5.6 | 38.0 |
| Example 10a | 100 | A | 5.0 | 30.0 |
| Comparative Example 6a | 120 | A | 5.5 | 36.0 |
| Comparative Example 7a | 105 | A | 5.4 | 35.0 |
| Comparative Example 8a | 100 | A | 5.3 | 37.0 |
| Example 11a | 80 | A | 5.3 | 26.0 |
| Example 12a | 75 | A | 5.2 | 25.0 |
| Example 13a | 70 | A | 4.9 | 27.0 |
| Comparative Example 9a | 125 | A | 6.0 | 37.0 |
| Example 14a | 115 | A | 5.6 | 28.0 |
| Example 15a | 110 | A | 5.5 | 28.5 |
| Comparative Example 10a | 115 | C | 6.0 | 36.5 |
| Example 16a | 105 | A | 5.5 | 29.0 |

Based on the results shown in Tables 3 and 4, it was confirmed that, according to the resist compositions of the examples, high sensitivity was achieved in the formation of the resist pattern, the roughness and the number of defects were reduced, and a resist pattern with an improved resolution and a favorable shape was formed.

Compound Production 1b

Production Example 1b

Anthracene (5.0 g, 28 mmol), methyl acrylate (3.6 g, 42 mmol), aluminum chloride (0.37 g, 2.8 mmol) and toluene (50 g) were added to a 100 mL three-necked flask, and a reaction was conducted at 80° C. for 4 hours while stirring. After cooling, ultra pure water (50 g) and MTBE (74 g) were added. After stirring for 30 minutes, the aqueous phase was removed. The organic phase was washed with ultra pure water (50 g) 3 times, and the organic phase was concentrated using a rotary evaporator. The concentrate was recrystallized with 2-isopropanol to obtain an intermediate 1b (5.9 g, yield=79.6%).

Sodium hydroxide (3.8 g, 95 mmol) and ultra pure water (38 g) were put into a 100 mL 3-necked flask, the mixture was stirred and dissolved, and the intermediate 1b (5.0 g, 19 mmol) was then dispersed, and reacted at 90° C. for 4 hours. After cooling to room temperature, hydrochloric acid was added until the solution was neutralized. Then, MTBE (50 g) was added, and stirred for 30 minutes, followed by removing the aqueous phase. An organic layer was washed with ultra pure water (50 g) 3 times, and the organic layer was concentrated using a rotary evaporator to obtain an intermediate 2b (4.6 g, yield=97.2%).

[Chem. 154]

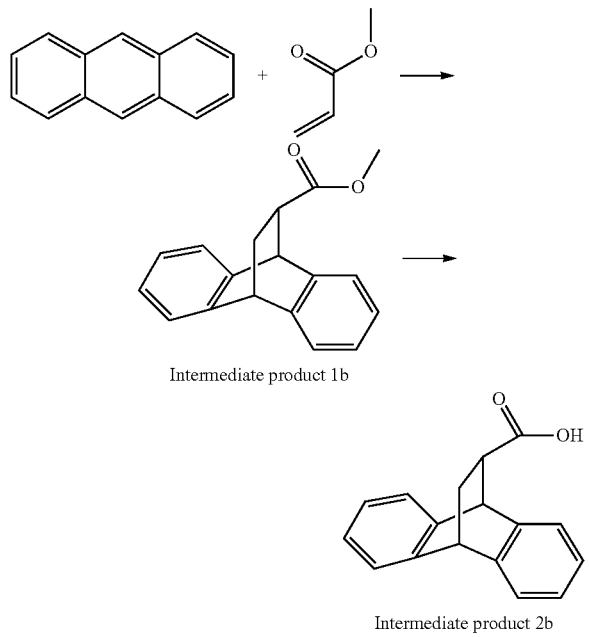

Intermediate product 1b

Intermediate product 2b

The intermediate 2b (4.0 g, 16 mmol), the compound (I-1b) (5.7 g, 16 mmol), and dichloromethane (87 g) were put into a 100 mL 3-necked flask, and the mixture was stirred and dissolved at room temperature.

Then, diisopropylcarbodiimide (2.2 g, 18 mmol) and dimethylaminopyridine (0.098 g, 0.8 mmol) were added, and reacted at room temperature for 5 hours. The reaction liquid was subjected to filtration, and the filtrate was concentrated using a rotary evaporator. The concentrate was dissolved in acetonitrile (17 g) and then added dropwise to MTBE (170 g), and the precipitated solid was filtered off. The filtrate was dissolved again in acetonitrile (17 g) and added dropwise to MTBE (170 g), and the precipitated solid was filtered off. This operation was repeated twice, and the filtrate was then dried under a reduced pressure to obtain a precursor (Bpre-1b) (7.6 g, yield=78.2%).

[Chem. 155]

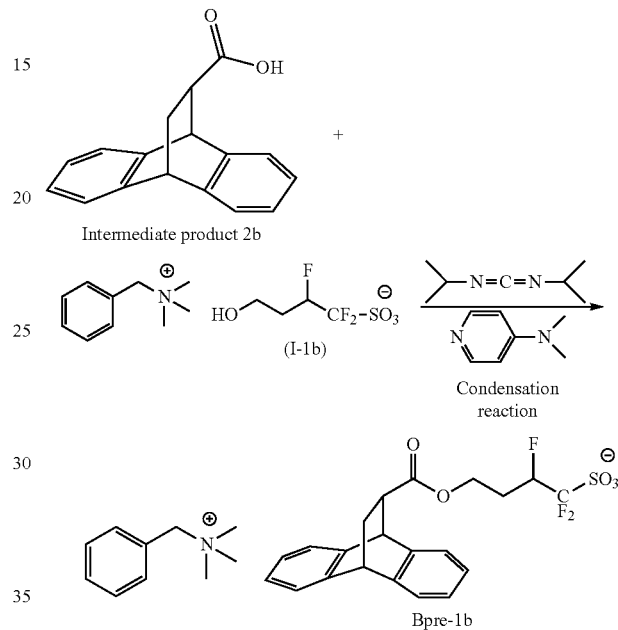

Production Example 2b

The intermediate 2b (4.8 g, 19 mmol) and tetrahydrofuran (THF) (50 g) were put into a 100 mL 3-necked flask, and the mixture was stirred and dissolved at room temperature. Then, LiAlH$_4$ (0.86 g, 23 mmol) was added, and reacted at room temperature for 3 hours. Subsequently, ultra pure water (50 g) and MTBE (50 g) were added. After stirring for 30 minutes, the aqueous phase was removed. Then, an organic layer was washed with ultra pure water (50 g) three times, and the organic layer was concentrated using a rotary evaporator to obtain an intermediate 3b (4.1 g, yield=91.0%).

The intermediate 3b (4.0 g, 19 mmol), the compound (I-2b) (3.6 g, 18 mmol), p-toluenesulfonic acid monohydrate (0.18 g, 0.9 mmol), and toluene (40 g) were put into a 100 mL 3-necked flask, and the mixture was refluxed at 110° C. for 24 hours. After cooling, the resultant was subjected to filtration. Acetonitrile (160 g) was added to the residue, followed by stirring at room temperature for 30 minutes, and filtration.

The filtrate was concentrated, and methyl ethyl ketone (78 g) was added to the residue, followed by stirring. Then, the resultant was filtered off, and the filtrate was dried to obtain a precursor (Bpre-2b) (4.9 g, yield=62.4%).

[Chem. 156]

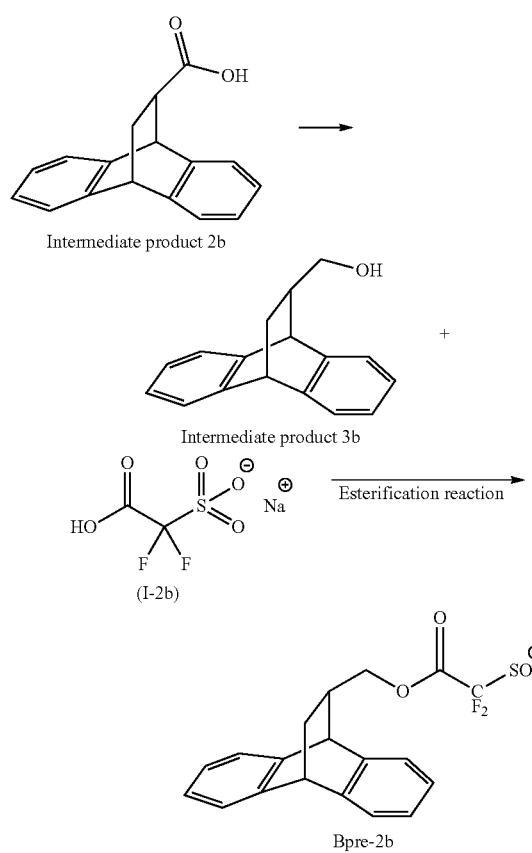

Production Example 3b

A precursor (Bpre-3b) (7.6 g, yield=78.2%) was obtained in the same manner as in the production example of the precursor (Bpre-1b) except that the compound (I-3b) (5.7 g, 16 mmol) was used in place of the compound (I-1b) (5.7 g, 16 mmol).

[Chem. 157]

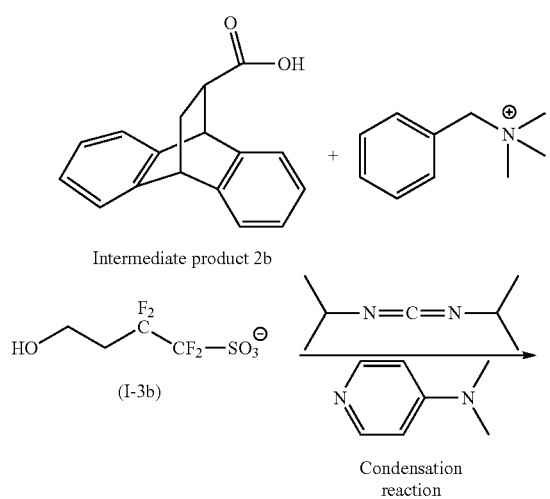

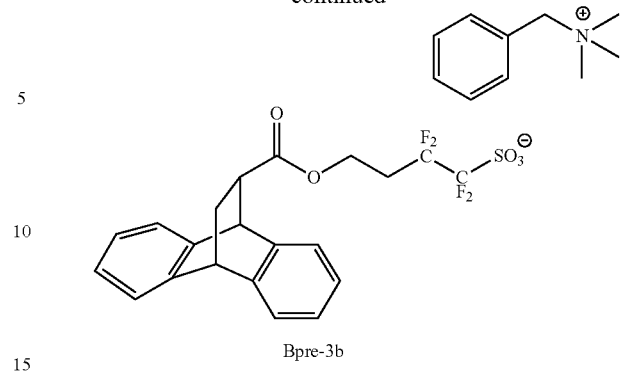

Production Example 4b

A precursor (Bpre-4b) (5.8 g, yield=66.8%) was obtained in the same manner as in the production example of the precursor (Bpre-1b) except that the compound (I-4b) (5.0 g, 16 mmol) was used in place of the compound (I-1b) (5.7 g, 16 mmol).

[Chem. 158]

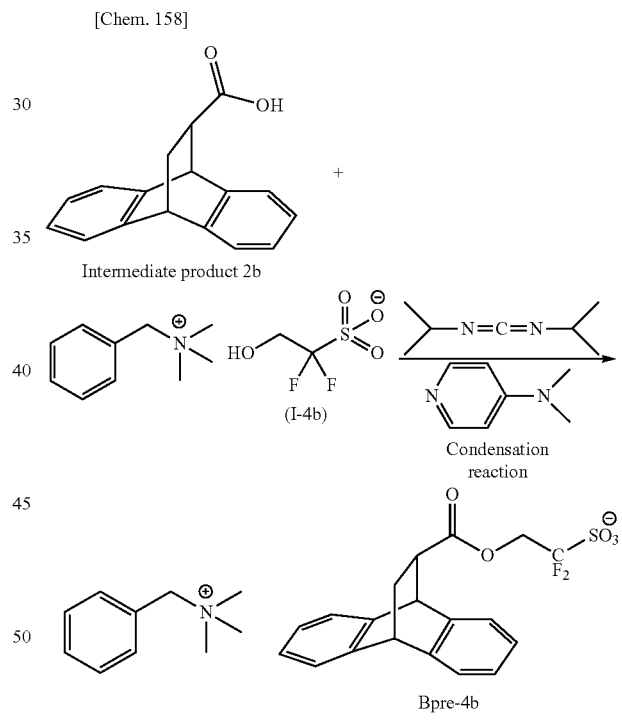

Production Example 5b

4-Bromo-3,3,4,4-tetrafluoro-1-butene (8.7 g, 42 mmol), anthracene (5.0 g, 28 mmol), and toluene (100 g) were put into a 300 mL pressure resistant reaction container and reacted at 150° C. for 24 hours. Subsequently, after cooling to room temperature, the resultant was concentrated using a rotary evaporator. Methanol (50 g) was added to the concentrate, followed by stirring. The precipitated solid was subjected to filtration. Then, the filtrate was dried under a reduced pressure to obtain an intermediate 4b (6.0 g, yield=55.6%).

[Chem. 159]

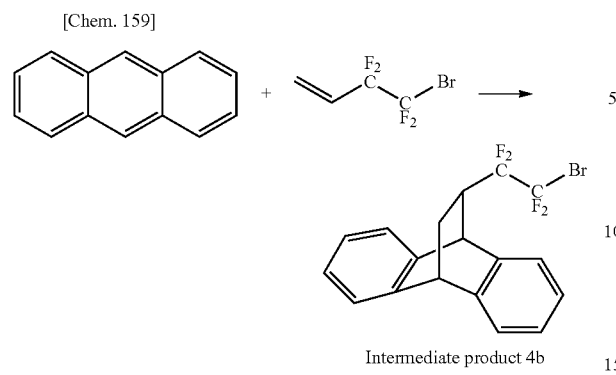

Intermediate product 4b

The intermediate 4b (5.8 g, 15 mmol), benzyltrimethylammonium chloride (2.9 g, 16 mmol), sodium dithionite (6.7, 38 mmol), sodium bicarbonate (3.8 g, 45 mmol), acetonitrile (16 g), and $H_2O$ (16 g) were put into a 200 mL 3-necked flask, and the mixture was stirred and reacted at 65° C. for 4 hours. Subsequently, after cooling to room temperature, the reaction liquid was subjected to filtration. $H_2O$ (16 g) and dichloromethane (25 g) were added to the filtrate, followed by stirring for 30 minutes and removing the aqueous phase. Thereafter, the resultant was washed with ultra pure water (160 g) twice, and the organic phase was concentrated using a rotary evaporator. The concentrate was added to and dissolved in acetonitrile (77 g). 30% hydrogen peroxide solution (2.7 g, 24 mmol) was added, and a reaction was conducted at 45° C. for 7 hours. After cooling to room temperature, dichloromethane (78 g) and a saturated aqueous solution of sodium sulfite (78 g) was added, followed by stirring for 30 minutes in ultra pure water, and removing the aqueous phase. Washing with ultra pure water (78 g) was performed twice, methyl tert-butyl ether (MTBE) (156 g) was then added thereto, and the mixture was stirred for 30 minutes. The precipitate was filtered off and dried under a reduced pressure to obtain a precursor (Bpre-5b) (5.8 g, yield=66.8%).

[Chem. 160]

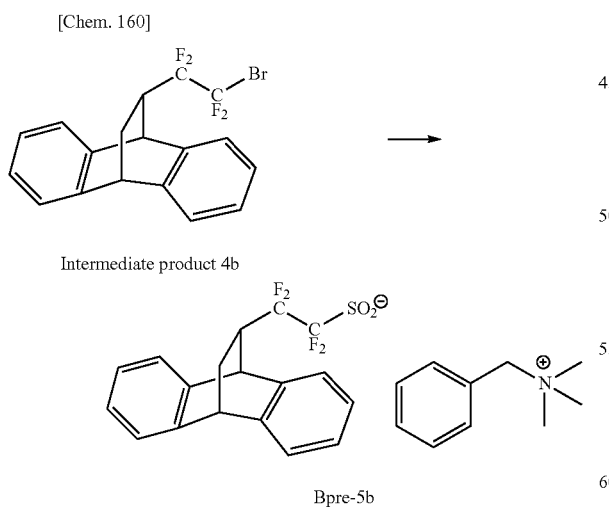

Production Example 6b

An intermediate 5b (6.4 g, yield=82.3%) was obtained in the same manner as in the production example of the intermediate 1b except that anhydrous maleic acid (4.0 g, 42 mmol) was used in place of methyl acrylate (3.6 g, 42 mmol).

[Chem. 161]

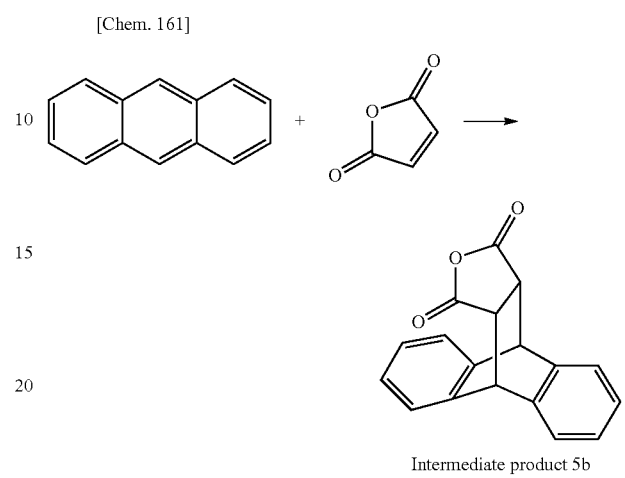

Intermediate product 5b

The intermediate 5b (6.0 g, 22 mmol), 5-hydroxynorbomane 2,6-lactone (4.0 g, 26 mmol), and dichloromethane (120 g) were put into a 100 mL 3-necked flask, and the mixture was stirred and dissolved at room temperature. Next, dimethylaminopyridine (0.13 g, 1 mmol) and trimethylamine (5.5 g, 54 mmol) were put thereinto, and the mixture was reacted at room temperature for 24 hours. Ultra pure water (120 g) was put thereinto, the mixture was stirred, hydrochloric acid was then added so that the aqueous layer became acidic for neutralization, and additionally the mixture was stirred for 30 minutes, and an aqueous layer was then removed. An organic layer was washed with ultra pure water (120 g) 3 times, and the organic layer was concentrated using a rotary evaporator to obtain an intermediate 6b (7.2 g, yield=77.1%).

[Chem. 162]

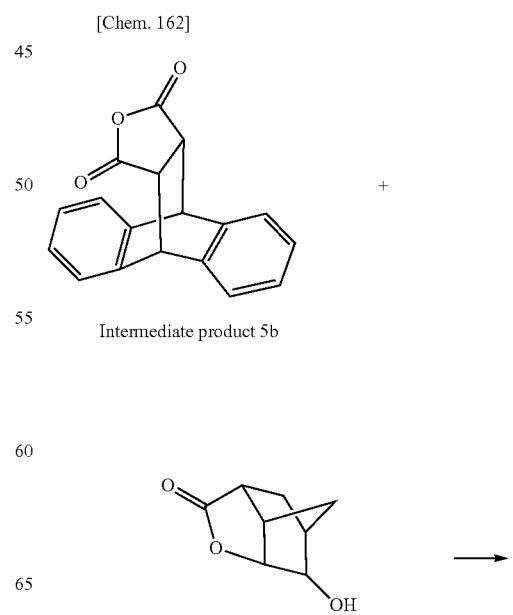

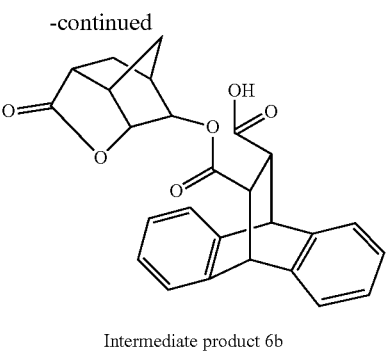

Intermediate product 6b

A precursor (Bpre-6b) (6.6 g, yield=53.1%) was obtained in the same manner as in the production example of the precursor (Bpre-3b) except that the intermediate 6b (6.8 g, 16 mmol) was used in place of the intermediate 3b (4.0 g, 16 mmol).

[Chem. 163]

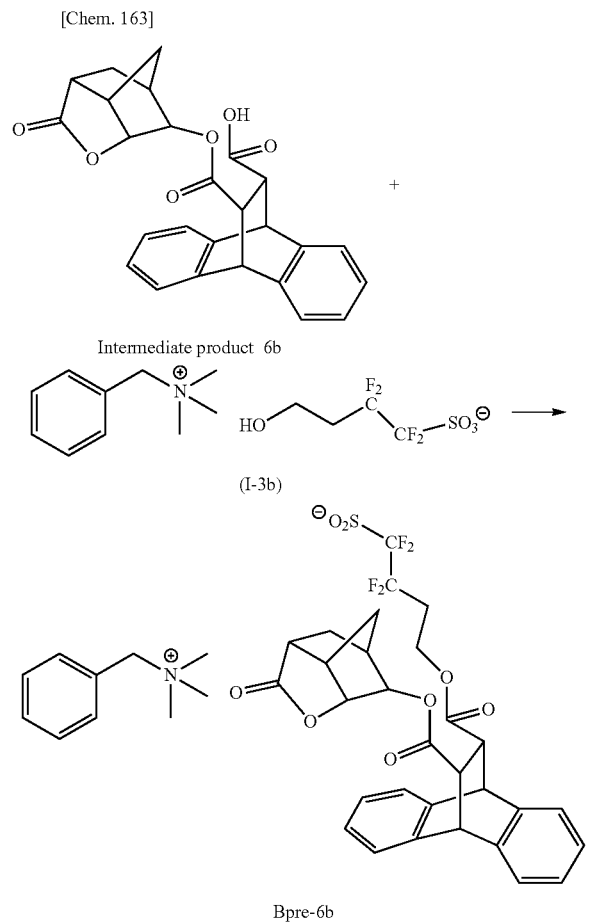

Bpre-6b

Production Example 7b

A Grignard reagent was prepared by a conventional method using 9-bromotriptycene (20.0 g, 60 mmol), magnesium (1.6 g, 66 mmol) and TH. (400 g). To the Grignard reagent was introduced carbon dioxide at 25 to 35° C., and a reaction was conducted at room temperature for 2 hours. Ultra pure water (400 g) was added to the reaction liquid, followed by stirring for 1 hour. Then, hydrochloric acid was added until the solution was neutralized, and the precipitate was subjected to filtration. The filtrate was washed with ultra pure water (100 g) twice, and washed with methanol (50 g) twice. The filtrate was dried under a reduced pressure to obtain an intermediate 7b. The intermediate 7b (5.0 g, 17 mmol), sodium hydroxide (0.74 g, 18 mmol), and benzyltrimethylammonium chloride (3.1 g, 17 mmol) were dissolved in ultra pure water (100 g). Then, dichloromethane (50 g) was added thereto and the mixture was stirred for 30 minutes, and an aqueous layer was then removed. An organic layer was washed with ultra pure water (50 g) 3 times, and the organic layer was concentrated using a rotary evaporator to obtain a precursor (Bpre-7b) (2.6 g, yield=34.0%).

[Chem. 164]

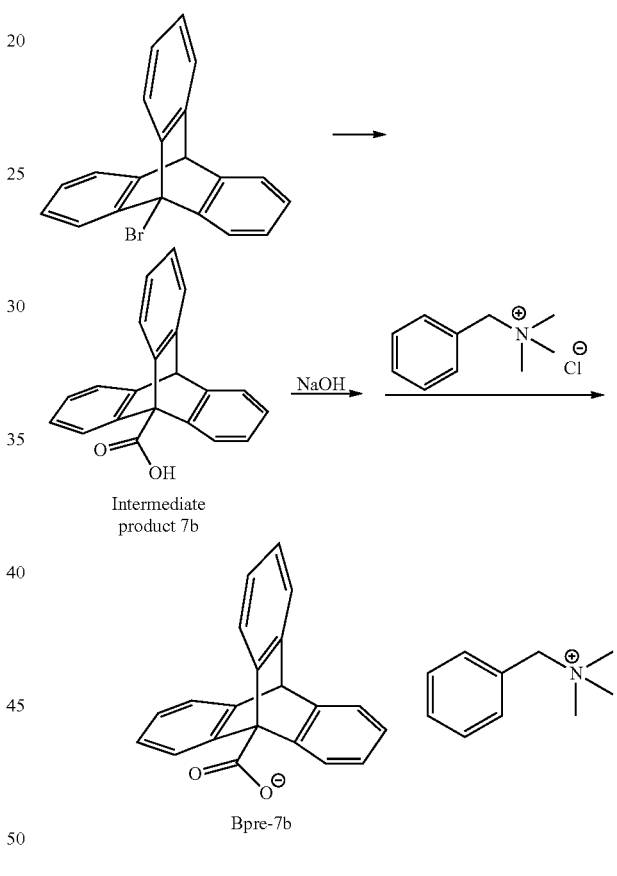

Bpre-7b

Production Example 8b

Sodium hydroxide (3.6 g, 90 mmol) and ultra pure water (36 g) were put into a 100 mL 3-necked flask, the mixture was stirred and dissolved, and the intermediate 5b (5.0 g, 18 mmol) was then dispersed and reacted at 90° C. for 4 hours. After cooling to room temperature, 20% hydrochloric acid (13.2 g, 72.4 mmol) and benzyltrimethylammonium chloride (5.0 g, 27 mmol) were added thereto, and MTBE (50 g) was then added thereto, the mixture was stirred for 30 minutes, and an aqueous layer was then removed. An organic layer was washed with ultra pure water (50 g) 3 times, and the organic layer was concentrated using a rotary evaporator to obtain a precursor (Bpre-8b) (5.7 g, yield=71.0%).

[Chem. 165]

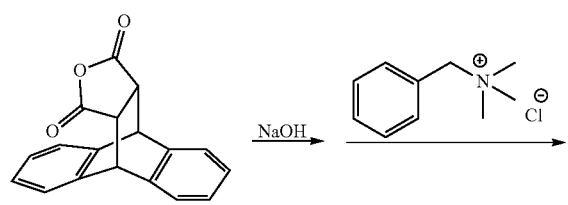

Production Example 9b

Sodium hydroxide (3.6 g, 90 mmol) and ultra pure water (36 g) were put into a 100 mL 3-necked flask, the mixture was stirred and dissolved, and the intermediate 1b (4.8 g, 18 mmol) was then dispersed and reacted at 90° C. for 4 hours. After cooling to room temperature, 20% hydrochloric acid (13.2 g, 72.4 mmol) and benzyltrimethylammonium chloride (5.0 g, 27 mmol) were added thereto, and MTBE (50 g) was then added thereto, the mixture was stirred for 30 minutes, and an aqueous layer was then removed. An organic layer was washed with ultra pure water (50 g) 3 times and the organic layer was concentrated using a rotary evaporator to obtain a precursor (Bpre-9b) (4.5 g, yield=62.3%).

[Chem. 166]

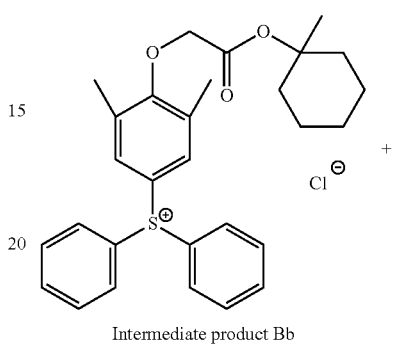

Production Example of Compound (B1-6b)

The precursor (Bpre-5b) (5.3 g, 10 mmol) and the compound Bb for salt exchange (5.0 g, 10 mmol) were dissolved in diethyl ketone (170 g), ultra pure water (85 g) was added thereto, and the mixture was reacted at room temperature for 30 minutes. After the reaction was completed, an aqueous phase was removed, an organic phase was then washed with ultra pure water (85 g) 6 times, and the organic phase was concentrated and dried using a rotary evaporator to obtain a compound (B1b-6) (5.0 g, yield=60.2%).

[Chem. 167]

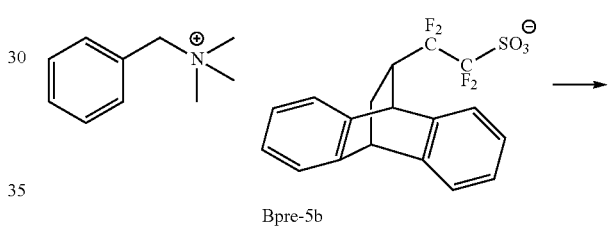

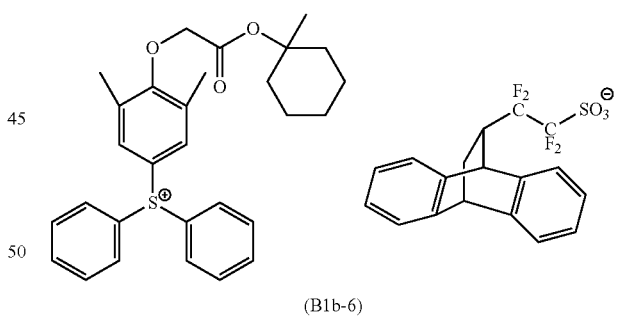

Production Example of Other Compounds

The following compound (B1b-1) to compound (B1b-9), compound (B2b-2) to compound (B2b-4), compound (B2b-8) to compound (B2b-10), compound (D1b-1) to compound (D1b-3), and compound (D2b-2) to compound (D2b-4) were obtained in the same manner as in the above "production example of the compound (B1b-6)" except that combinations of the above precursor (Bpre-1b) to precursor (Bpre-9b), and the following compound Ab for salt exchange to compound Db for salt exchange were changed.

[Chem. 168]
Compound Ab
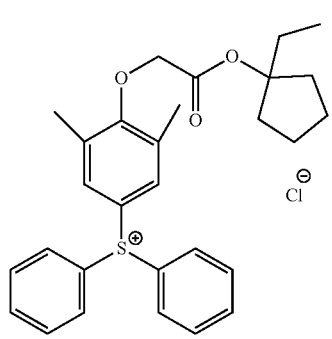
Compound Bb
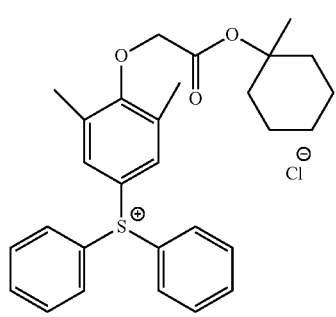
Compound Cb
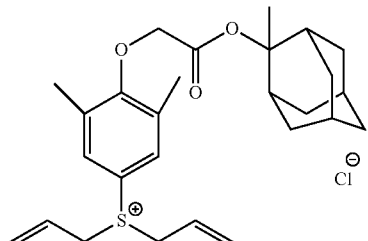
Compound Db
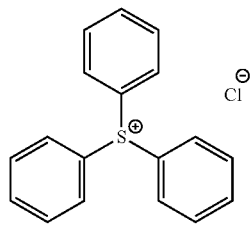
[Chem. 169]
(B1b-1)
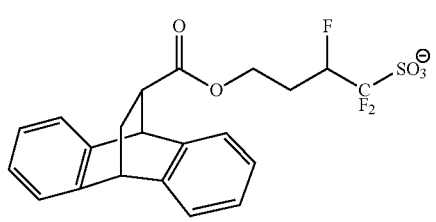
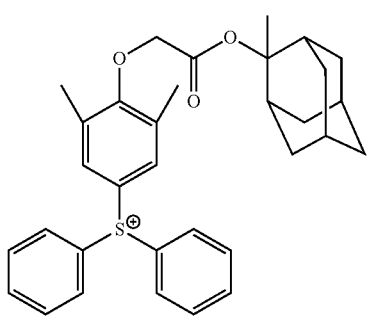
(B1b-2)
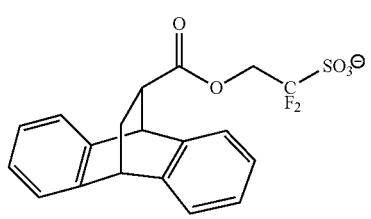
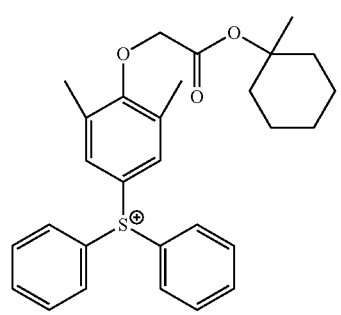
Each of the obtained compounds was analyzed by NMR, and the structure thereof was identified by the following analysis results.

-continued
(B1b-3)
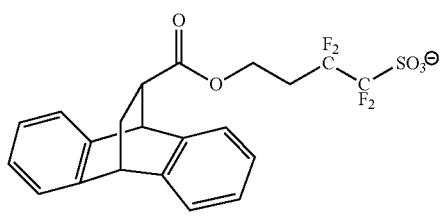
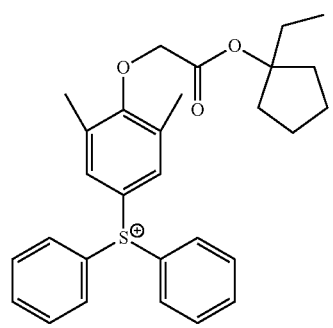
(B1b-4)
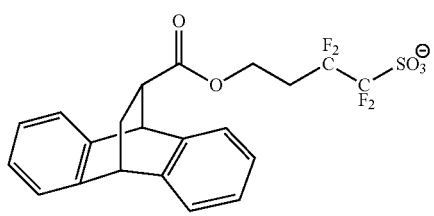
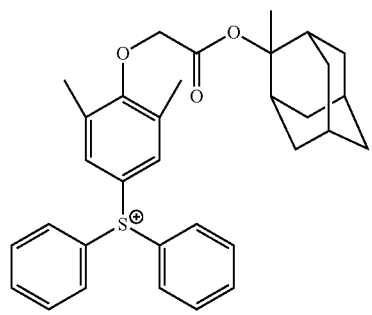
(B1b-5)
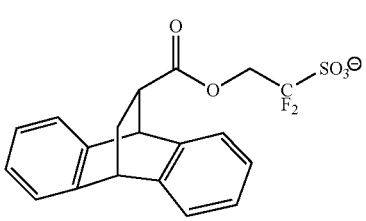
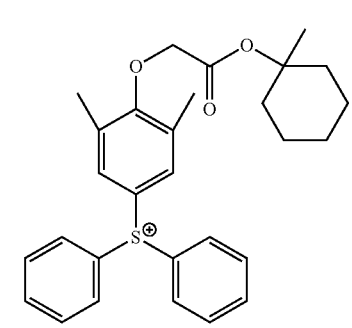
(B1b-6)
(B1b-7)
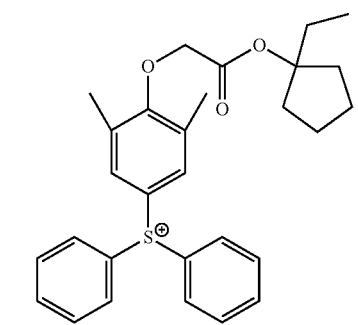

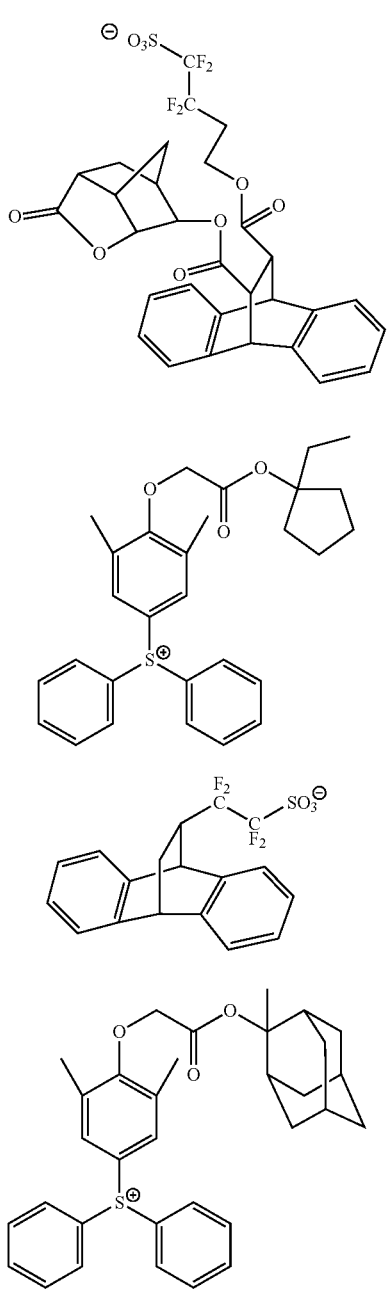

(B1b-8)

(B1b-9)

Compound (B b-1): Combination of the Precursor (Bpre-1b) and the Compound Cb for Salt Exchange $^1$H-NMR (DMSO, 400 MHz): δ(ppm)=7.75-7.86 (m, 10H, ArH), 7.61 (s, 2H, ArH), 7.01-7.47 (m, ArH, 8H), 5.08 (m, CFCH, 1H), 4.71 (s, CH, 1H), 4.62 (s, 2H, CH2), 4.42 (s, CH, 1H), 4.23 (m, CH2, 2H), 2.90 (m, CH, 1H), 2.45 (m, CFCH, 1H), 2.31 (s, 6H, CH3), 1.49-2.07 (m, 20H, adamantyl, CH2, CFCH)

$^{19}$F-NMR (DMSO, 376 MHz): δ(ppm)=−112.5, −121.2, −203.2

Compound (B1b-2): Combination of the Precursor (Bpre-2b) and the Compound Bb for Salt Exchange $^1$H-NMR (DMSO, 400 MHz): δ(ppm)=7.76-7.82 (m, 10H, ArH), 7.59 (s, 2H, ArH), 7.01-7.45 (m, ArH, 8H), 4.71 (s, CH, 1H), 4.55 (s, 2H, CH2), 2.29 (m, 6H, CH3), 4.44 (S, CH, 1H), 4.31 (S, CH2, 2H), 2.93-3.00 (m, CH, 1H), 2.22-2.28 (m, 2H, CH2, cyclohexyl), 1.87-2.07 (m, CH2, 2H), 1.78-1.84 (m, 2H, cyclohexyl), 1.62-1.68 (s, 3H, CH3), 1.12-1.54 (m, 6H, cyclohexyl), 0.98-1.03 (m, CH, 1H)

$^{19}$F-NMR (DMSO, 376 MHz): δ(ppm)=−107.9

Compound (B1b-3): Combination of the Precursor (Bpre-3b) and the Compound Ab for Salt Exchange $^1$H-NMR (DMSO, 400 MHz): δ(ppm)=7.76-7.82 (m, 10H, ArH), 7.59 (s, 2H, ArH), 7.01-7.47 (m, ArH, 8H), 4.72 (s, CH, 1H), 4.55 (s, 2H, CH2), 4.43 (S, CH, 1H), 4.23, (t, CH2, 2H), 2.95-3.02 (m, CH, 1H), 2.63-2.73, (m, CF$_2$CH2, 2H), 2.29 (m, 6H, CH3), 1.86-2.07 (m, 6H, CH2, CH2, cyclopentyl), 1.48-1.75 (m, 6H, cyclopentyl), 0.77-0.81 (t, 3H, CH3)

$^{19}$F-NMR (DMSO, 376 MHz): δ(ppm)=−111.3, −117.4

Compound (B 1b-4): combination of the precursor (Bpre-3b) and the compound Cb for salt exchange $^1$H-NMR (DMSO, 400 MHz): δ(ppm)=7.75-7.86 (m, 10H, ArH), 7.61 (s, 2H, ArH), 7.01-7.47 (m, ArH, 8H), 4.72 (s, CH, 1H), 4.62 (s, 2H, CH2), 4.43 (S, CH, 1H), 4.23, (t, CH2, 2H), 2.95-3.02 (m, CH, 1H), 2.63-2.73, (m, CF$_2$CH2, 2H), 2.31 (s, 6H, CH3), 1.49-2.07 (m, 19H, adamantyl, CH2)

$^{19}$F-NMR (DMSO, 376 MHz): δ(ppm)=−111.3, −117.4

Compound (B1b-5): Combination of the Precursor (Bpre-4b) and the Compound Bb for Salt Exchange $^1$H-NMR (DMSO, 400 MHz): δ(ppm)=7.76-7.82 (m, 10H, ArH), 7.59 (s, 2H, ArH), 7.00-7.48 (m, ArH, 8H), 4.70 (s, CH, 1H), 4.31-4.58 (m, CH, CH2, CF$_2$CH2, 5H), 2.95-3.02 (m, CH, 1H), 2.29 (m, 6H, CH3), 2.22-2.28 (m, 2H, CH2, cyclohexyl), 1.78-2.05 (m, 4H, cyclohexyl, CH2), 1.62-1.68 (s, 3H, CH3), 1.12-1.54 (m, 6H, cyclohexyl)

$^{19}$F-NMR (DMSO, 376 MHz): δ(ppm)=−111.4

Compound (B 1b-6): Combination of the Precursor (Bpre-5b) and the Compound Bb for Salt Exchange $^1$H-NMR (DMSO, 400 MHz): δ(ppm)=7.76-7.82 (m, 10H, ArH), 7.59 (s, 2H, ArH), 7.00-7.48 (m, ArH, 8H), 4.70 (s, CH, 1H), 4.55 (s, 2H, CH2), 4.40 (s, CH, 1H), 3.15-3.22 (m, CF$_2$CH, 1H), 2.29 (m, 6H, CH3), 2.22-2.28 (m, 2H, CH2, cyclohexyl), 1.95-2.15 (m, CH2, 2H), 1.78-1.84 (m, 2H, cyclohexyl), 1.62-1.68 (s, 3H, CH3), 1.12-1.54 (m, 6H, cyclohexyl)

$^{19}$F-NMR (DMSO, 376 MHz): δ(ppm)=−111.3, −117.4

Compound (B 1b-7): Combination of the Precursor (Bpre-5b) and the Compound Ab for Salt Exchange $^1$H-NMR (DMSO, 400 MHz): δ(ppm)==7.76-7.82 (m, 10H, ArH), 7.59 (s, 2H, ArH), 7.00-7.48 (m, ArH, 8H), 4.70 (s, CH, 1H), 4.55 (s, 2H, CH2), 4.40 (s, CH, 1H), 3.15-3.22 (m, CF$_2$CH, 1H), 2.29 (m, 6H, CH3), 1.95-2.15 (m, CH2, 2H), 1.90-1.93 (m, 4H, CH2, cyclopentyl), 1.48-1.75 (m, 6H, cyclopentyl), 0.77-0.81 (t, 3H, CH3)

$^{19}$F-NMR (DMSO, 376 MHz): δ(ppm)=−111.3, −117.4

Compound (B1b-8): Combination of the Precursor (Bpre-6b) and the Compound Ab for Salt Exchange $^1$H-NMR (DMSO, 400 MHz): δ(ppm)=7.76-7.82 (m, 10H, ArH), 7.59 (s, 2H, ArH), 7.01-7.47 (m, ArH, 8H), 4.70 (d, OCH (lactone), 1H), 4.58 (t, COOCH (lactone), 1H), 4.55 (s, 2H, CH2), 4.50 (d, CH, 2H), 4.22, (t, COOCH2, 2H), 3.32 (m, CH (lactone), 1H), 3.20 (t, COCH, 2H), 2.63-2.73, (m, CF$_2$CH2, CH (lactone) 4H), 2.29 (m, 6H, CH3), 1.90-1.93 (m, 4H, CH2, cyclopentyl), 1.48-2.20 (m, 10H, cyclopentyl, lactone), 0.77-0.81 (t, 3H, CH3)

$^{19}$F-NMR (DMSO, 376 MHz): δ (ppm)=−111.3, −117.4

Compound (B 1b-9): Combination of the Precursor (Bpre-5b) and the Cb for Salt Exchange $^1$H-NMR (DMSO, 400 MHz): δ(ppm)=7.75-7.86 (m, 10H, ArH), 7.61 (s, 2H, ArH), 7.00-7.48 (m, ArH, 8H), 4.70

(s, CH, 1H), 4.62 (s, 2H, CH2), 4.40 (s, CH, 1H), 3.15-3.22 (m, CF₂CH, 1H), 2.31 (s, 6H, CH3), 1.49-2.15 (m, 19H, adamantyl, CH2)
¹⁹F-NMR (DMSO, 376 MHz): δ (ppm)=−111.3, −117.4
[Chem. 170]
(B2b-2)
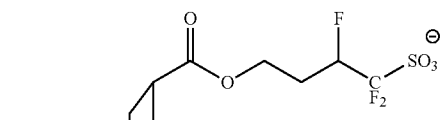
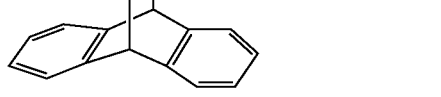
(B2b-3)
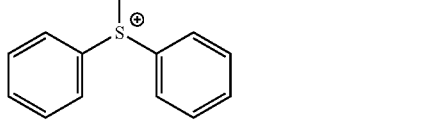
(B2b-4)
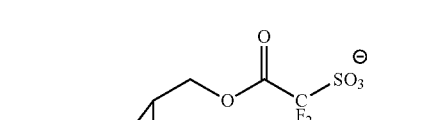
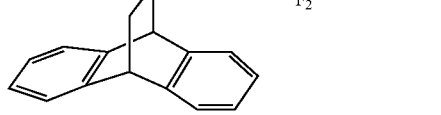
(B2b-8)
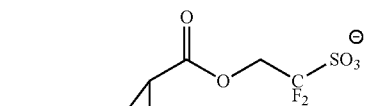
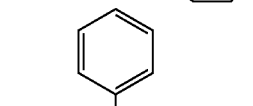
(B2b-9)
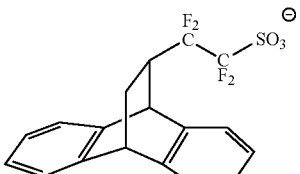
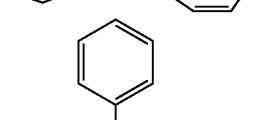
(B2b-10)
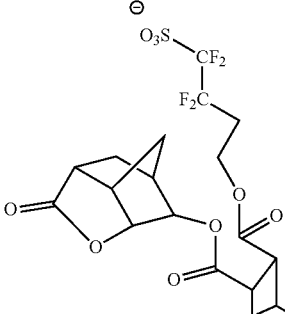
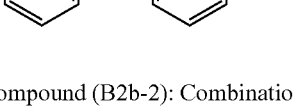
Compound (B2b-2): Combination of the Precursor (Bpre-1b) and the Compound Db for Salt Exchange
¹H-NMR (DMSO, 400 MHz): δ(ppm)=7.74-7.90 (m, 15H, ArH), 7.01-7.47 (m, ArH, 8H), 5.08 (m, CFCH, 1H), 4.71 (s, CH, 1H), 4.42 (s, CH, 1H), 4.23 (m, CH2, 2H), 2.90 (m, CH, 1H), 2.45 (m, CFCH, 1H), 1.82-2.07 (m, CH2, CFCH, 3H)

$^{19}$F-NMR (DMSO, 376 MHz): δ(ppm)=−112.5, −121.2, −203.2

Compound (B2b-3): Combination of the Precursor (Bpre-2b) and the Compound Db for Salt Exchange $^{1}$H-NMR (DMSO, 400 MHz): δ(ppm)=7.74-7.90 (m, 15H, ArH), 7.01-7.45 (m, ArH, 8H), 4.71 (s, CH, 1H), 4.44 (S, CH, 1H), 4.31 (S, CH2, 2H), 2.93-3.00 (m, CH, 1H), 1.87-2.07 (m, CH2, 1H), 0.98-1.03 (m, CH2, 1H)

$^{19}$F-NMR (DMSO, 376 MHz): δ(ppm)=−107.9

Compound (B2b-4): Combination of the Precursor (Bpre-3b) and the Compound Db for Salt Exchange $^{1}$H-NMR (DMSO, 400 MHz): δ(ppm)=7.74-7.90 (m, 15H, ArH), 7.01-7.47 (m, ArH, 8H), 4.72 (s, CH, 1H), 4.43 (S, CH, 1H), 4.23, (t, CH2, 2H), 2.95-3.02 (m, CH, 1H), 2.63-2.73, (m, CF$_2$CH2, 2H), 1.86-2.07 (m, CH2, 2H)

$^{19}$F-NMR (DMSO, 376 MHz): δ(ppm)=−111.3, −117.4

Compound (B2b-8): Combination of the Precursor (Bpre-4b) and the Compound Db for Salt Exchange $^{1}$H-NMR (DMSO, 400 MHz): δ(ppm)=7.74-7.90 (m, 15H, ArH), 7.00-7.48 (m, ArH, 8H), 4.70 (s, CH, 1H), 4.31-4.58 (m, CH, CF$_2$CH2, 3H), 2.95-3.02 (m, CH, 1H), 1.85-2.05 (m, CH2, 2H)

$^{19}$F-NMR (DMSO, 376 MHz): δ(ppm)=−111.4

Compound (B2b-9): Combination of the Precursor (Bpre-5b) and the Compound Db for Salt Exchange $^{1}$H-NMR (DMSO, 400 MHz): δ(ppm)=7.74-7.90 (m, 15H, ArH), 7.00-7.48 (m, ArH, 8H), 4.70 (s, CH, 1H), 4.40 (s, CH, 1H), 3.15-3.22 (m, CF$_2$CH, 1H), 1.95-2.15 (m, CH2, 2H)

$^{19}$F-NMR (DMSO, 376 MHz): δ(ppm)=−111.3, −117.4

Compound (B2b-10): Combination of the Precursor (Bpre-6b) and the Compound Db for Salt Exchange $^{1}$H-NMR (DMSO, 400 MHz): δ(ppm)=7.74-7.90 (m, 15H, ArH), 7.01-7.47 (m, ArH, 8H), 4.70 (d, OCH (lactone), 1H), 4.58 (t, COOCH (lactone), 1H), 4.50 (d, CH, 2H), 4.22, (t, COOCH2, 2H), 3.32 (m, CH (lactone), 1H), 3.20 (t, COCH, 2H), 2.63-2.73, (m, CF$_2$CH2, CH (lactone) 4H), 1.60-2.20 (m, CH2 (lactone), 4H)$^{19}$F-NMR (DMSO, 376 MHz): δ (ppm)=−111.3, −117.4

[Chem. 171]

(D1b-1)

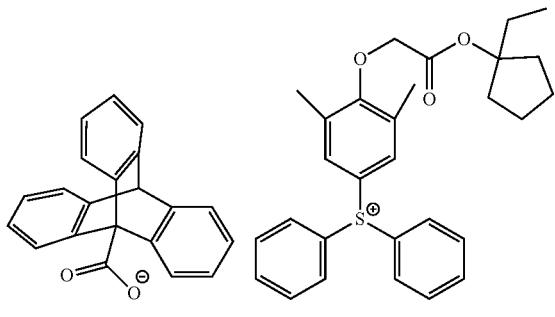

(D1b-2)

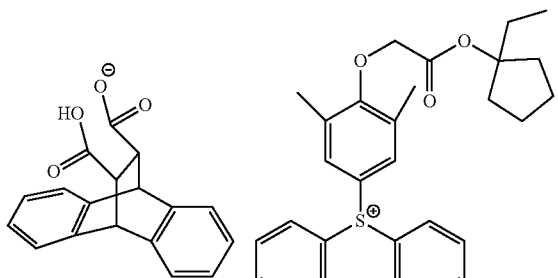

(D1-b3)

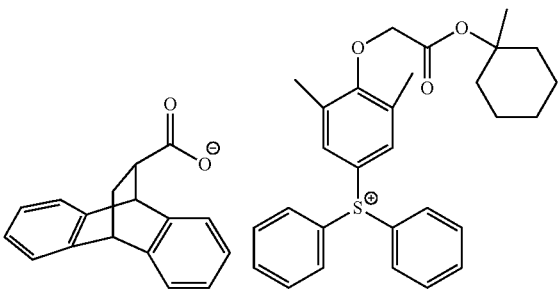

Compound (D1b-1): Combination of the Precursor (Bpre-7b) and the Compound Ab for Salt Exchange $^{1}$H-NMR (DMSO, 400 MHz): δ (ppm)=7.76-7.82 (m, 10H, ArH), 7.68-7.82 (m, Ph, 6H), 7.59 (s, 2H, ArH), 6.60-6.80 (m, Ph, 6H), 5.47 (s, CH, 1H), 4.55 (s, 2H, CH2), 2.29 (m, 6H, CH3), 1.90-1.93 (m, 4H, CH2, cyclopentyl), 1.48-1.75 (m, 6H, cyclopentyl), 0.77-0.81 (t, 3H, CH3)

Compound (D1b-2): Combination of the Precursor (Bpre-8b) and the Compound Ab for Salt Exchange $^{1}$H-NMR (DMSO, 400 MHz): δ(ppm)=7.76-8.00 (m, 21H, ArH), 7.59 (s, 2H, ArH), 7.00-7.48 (m, ArH, 8H), 4.85 (s, ArCH, 2H), 4.55 (s, 2H, CH2), 3.16 (s, CH, 2H), 2.29 (m, 6H, CH3), 1.90-1.93 (m, 4H, CH2, cyclopentyl), 1.48-1.75 (m, 6H, cyclopentyl), 0.77-0.81 (t, 3H, CH3)

Compound (D1b-3): Combination of the Precursor (Bpre-9b) and the Compound Bb for Salt Exchange $^{1}$H-NMR (DMSO, 400 MHz): δ(ppm)=7.76-7.82 (m, 10H, ArH), 7.59 (s, 2H, ArH), 7.00-7.48 (m, Ph, 8H), 4.68 (s, CH, 1H), 4.55 (s, 2H, CH2), 4.41 (s, CH, 1H), 2.95-3.02 (m, CH, 1H), 2.29 (m, 6H, CH3), 2.22-2.28 (m, 2H, CH2, cyclohexyl), 1.90-2.04 (m, CH2, 2H), 1.78-1.84 (m, 2H, cyclohexyl), 1.62-1.68 (s, 3H, CH3), 1.12-1.54 (m, 6H, cyclohexyl)

[Chem. 172]

(D2b-2)

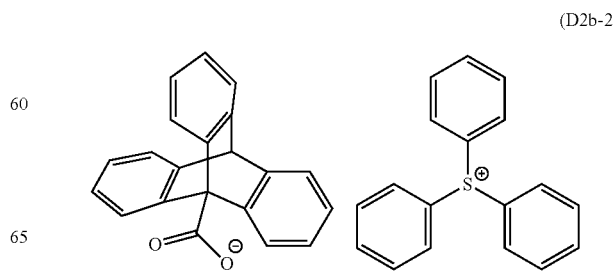

-continued

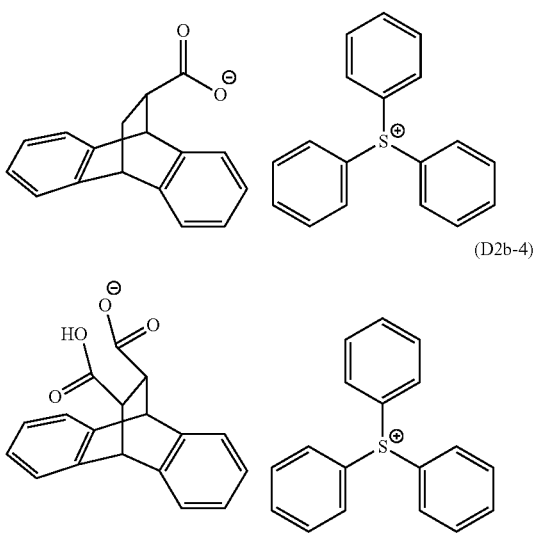

Compound (D2b-2): Combination of the Precursor (Bpre-7b) and the Compound Db for Salt Exchange
¹H-NMR (DMSO, 400 MHz): δ(ppm)=7.74-7.90 (m, 15H, ArH),
7.68-7.82 (m, Ph, 6H), 6.60-6.80 (m, Ph, 6H), 5.47 (s, CH, 1H), Compound (D2b-3): Combination of the Precursor (Bpre-9b) and the Compound Db for Salt Exchange
¹H-NMR (DMSO, 400 MHz): δ(ppm)=7.74-7.90 (m, 15H, ArH), 7.00-7.48 (m, Ph, 8H), 4.68 (s, CH, 1H), 4.41 (s, CH, 1H), 2.95-3.02 (m, CH, 1H), 1.86-2.04 (m, CH2, 2H)

Compound (D2b-4): Combination of the Precursor (Bpre-8b) and the Compound Db for Salt Exchange
¹H-NMR (DMSO, 400 MHz): δ(ppm)=7.74-7.90 (m, 15H, ArH), 7.00-7.48 (m, ArH, 8H), 4.85 (s, ArCH, 2H), 3.16 (s, CH, 2H)

Resist Composition Preparation 1b

Examples 1b to 13b, and Comparative Examples 1b to 15b

Components shown in Tables 5 to 7 were mixed and dissolved to prepare resist compositions in respective examples.

TABLE 5

|  | | Compound (B) | | Compound (D) | Compound (S) |
|---|---|---|---|---|---|
|  | Compound (A) | Compound (B1b) | Compound (B2) | Compound (D) | Compound (S) |
| Comparative Example 1b | (A)-1b [100] | — | (B2b)-1 [21.3] | (D2b)-1 [3.8] | (S)-1b [6400] |
| Comparative Example 2b | (A)-1b [100] | — | (B2b)-2 [20.0] | (D2b)-1 [3.8] | (S)-1b [6400] |
| Comparative Example 3b | (A)-1b [100] | — | (B2b)-3 [18.7] | (D2b)-1 [3.8] | (S)-1b [6400] |
| Comparative Example 4b | (A)-1b [100] | — | (B2b)-4 [20.5] | (D2b)-1 [3.8] | (S)-1b [6400] |
| Comparative Example 5b | (A)-1b [100] | — | (B2b)-5 [24.5] | (D2b)-1 [3.8] | (S)-1b [6400] |
| Comparative Example 6b | (A)-1b [100] | — | (B2b)-6 [23.4] | (D2b)-1 [3.8] | (S)-1b [6400] |
| Comparative Example 7b | (A)-1b [100] | — | (B2b)-7 [23.0] | (D2b)-1 [3.8] | (S)-1b [6400] |
| Example 1b | (A)-1b [100] | (B1b)-1 [27.1] | — | (D2b)-1 [3.8] | (S)-1b [6400] |
| Example 2b | (A)-1b [100] | (B1b)-2 [24.7] | — | (D2b)-1 [3.8] | (S)-1b [6400] |
| Example 3b | (A)-1b [100] | (B1b)-3 [26.2] | — | (D2b)-1 [3.8] | (S)-1b [6400] |

TABLE 6

|  |  | Compound (B) | | Compound (D) | | |
|---|---|---|---|---|---|---|
|  | Compound (A) | Compound (B1b) | Compound (B2b) | Compound (D1b) | Compound (D2b) | Compound (S) |
| Comparative Example 8b | (A)-2b [100] | — | (B2b)-4 [20.5] | — | (D2b)-2 [5.3] | (S)-1b [6400] |
| Comparative Example 9b | (A)-2b [100] | — | (B2b)-8 [18.7] | — | (D2b)-3 [4.8] | (S)-1b [6400] |
| Comparative Example 10b | (A)-2b [100] | — | (B2b)-9 [18.5] | — | (D2b)-4 [5.3] | (S)-1b [6400] |
| Comparative Example 11b | (A)-2b [100] | — | (B2b)-10 [25.6] | — | (D2b)-4 [5.3] | (S)-1b [6400] |
| Comparative Example 12b | (A)-2b [100] | — | (B2b)-4 [20.5] | — | (D2b)-5 [6.2] | (S)-1b [6400] |

TABLE 6-continued

|  | Compound (A) | Compound (B) | | Compound (D) | | Compound (S) |
|---|---|---|---|---|---|---|
|  |  | Compound (B1b) | Compound (B2b) | Compound (D1b) | Compound (D2b) |  |
| Example 4b | (A)-2b [100] | (B1b)-4 [27.6] | — | — | (D2b)-2 [5.3] | (S)-1b [6400] |
| Example 5b | (A)-2b [100] | (B1b)-5 [24.7] | — | — | (D2b)-3 [4.8] | (S)-1b [6400] |
| Example 6b | (A)-2b [100] | (B1b)-6 [24.5] | — | — | (D2b)-4 [5.3] | (S)-1b [6400] |
| Example 7b | (A)-2b [100] | (B1b)-7 [24.1] | — | (D1b)-1 [7.2] | — | (S)-1b [6400] |
| Example 8b | (A)-2b [100] | (B1b)-8 [31.3] | — | (D1b)-2 [7.2] | — | (S)-1b [6400] |

TABLE 7

|  | Component (A) | Component (B) | | Component (D) | | Component (S) |
|---|---|---|---|---|---|---|
|  |  | Component (B1b) | Component (B2b) | Component (D1b) | Component (D2b) |  |
| Comparative Example 13b | (A)-3b [100] | — | (B2b)-9 [20.5] | — | (D2b)-1 [3.8] | (S)-1b [6400] |
| Example 9b | (A)-3b [100] | (B1b)-6 [24.5] | — | — | (D2b)-1 [3.8] | (S)-1b [6400] |
| Example 10b | (A)-3b [100] | (B1b)-6 [24.5] | — | — | (D2b)-3 [4.8] | (S)-1b [6400] |
| Example 11b | (A)-3b [100] | (B1b)-6 [24.5] | — | (D1b)-3 [6.7] | — | (S)-1b [6400] |
| Comparative Example 14b | (A)-4b [100] | — | (B2b)-4 [20.5] | — | (D2b)-1 [3.8] | (S)-1b [6400] |
| Example 12b | (A)-4b [100] | (B1b)-4 [27.6] | — | — | (D2b)-1 [3.8] | (S)-1b [6400] |
| Comparative Example 15b | (A)-5b [100] | — | (B2b)-9 [18.5] | — | (D2b)-1 [3.8] | (S)-1b [6400] |
| Example 13b | (A)-5b [100] | (B1b)-9 [25.6] | — | — | (D2b)-1 [3.8] | (S)-1b [6400] |

In Tables 5 to 7, respective abbreviations have the following meanings. The values in brackets [ ] indicate the amount (in terms of parts by mass) of the component added.

(A)-1b: A high-molecular-weight compound represented by the following chemical formula (A1)-1b. The high-molecular-weight compound (A1)-1b was obtained by performing radical polymerization using monomers deriving structural units constituting the high-molecular-weight compound in a predetermined molar ratio. Regarding the high-molecular-weight compound (A1)-1b, a weight average molecular weight (Mw) in terms of polystyrene standards obtained through GPC measurement was 6,900, and a molecular weight dispersity (Mw/Mn) was 1.72. The composition of the copolymer (ratio (molar ratio) of the respective structural units within the structural formula) as determined by $^{13}$C-NMR was l/m/n=30/60/10.

(A)-2b: A high-molecular-weight compound represented by the following chemical formula (A1)-2b. The high-molecular-weight compound (A1)-2b was obtained by performing radical polymerization using monomers deriving structural units constituting the high-molecular-weight compound in a predetermined molar ratio. Regarding the high-molecular-weight compound (A1)-2b, a weight average molecular weight (Mw) in terms of polystyrene standards obtained through GPC measurement was 7,000, and a molecular weight dispersity (Mw/Mn) was 1.76. The composition of the copolymer (ratio (molar ratio) of the respective structural units within the structural formula) as determined by $^{13}$C-NMR was l/m=50/50.

(A)-3b: A high-molecular-weight compound represented by the following chemical formula (A1)-3b. The high-molecular-weight compound (A1)-3b was obtained by performing radical polymerization using monomers deriving structural units constituting the high-molecular-weight compound in a predetermined molar ratio. Regarding the high-molecular-weight compound (A1)-3b, a weight average molecular weight (Mw) in terms of polystyrene standards obtained through GPC measurement was 7,200, and a molecular weight dispersity (Mw/Mn) was 1.69. The composition of the copolymer (ratio (molar ratio) of the respective structural units within the structural formula) as determined by $^{13}$C-NMR was l/m=50/50.

[Chem. 173]

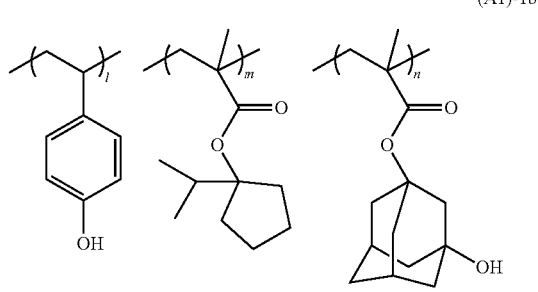

(A1)-1b (A1)-2b

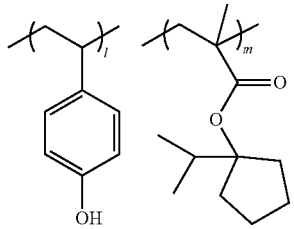

(A1)-3b

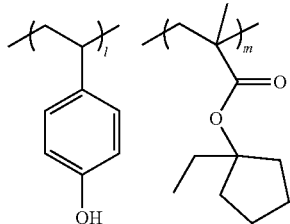

(A)-4b: A high-molecular-weight compound represented by the following chemical formula (A1)-4b. The high-molecular-weight compound (A1)-4b was obtained by performing radical polymerization using monomers deriving structural units constituting the high-molecular-weight compound in a predetermined molar ratio. Regarding the high-molecular-weight compound (A1)-4b, a weight average molecular weight (Mw) in terms of polystyrene standards obtained through GPC measurement was 7,300, and a molecular weight dispersity (Mw/Mn) was 1.65. A copolymer composition ratio (ratio (molar ratio) of structural units in the structural formula) obtained through $^{13}$C-NMR was l/m/n/o=15/30/50/5.

(A)-5b: A high-molecular-weight compound represented by the following chemical formula (A1)-5b. The high-molecular-weight compound (A1)-5b was obtained by performing radical polymerization using monomers deriving structural units constituting the high-molecular-weight compound in a predetermined molar ratio. Regarding the high-molecular-weight compound (A1)-5b, a weight average molecular weight (Mw) in terms of polystyrene standards obtained through GPC measurement was 6,900, and a molecular weight dispersity (Mw/Mn) was 1.76. A copolymer composition ratio (ratio (molar ratio) of structural units in the structural formula) obtained through $^{13}$C-NMR was l/m/n/o=15/30/50/5.

[Chem. 174]

(A1)-4b

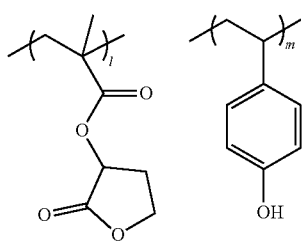

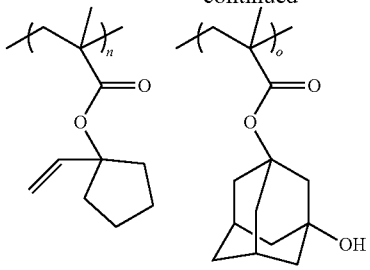

(A1)-5b

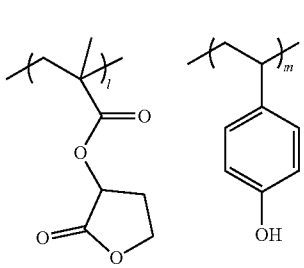

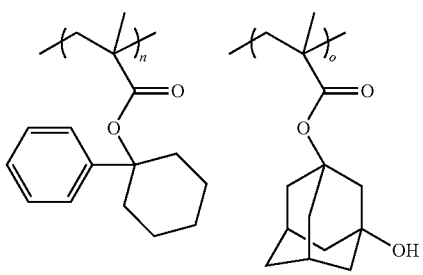

(B1b)-1 to (B1b)-9: Respective acid generators including the above compound (B1b-1) to compound (B1b-9).

(B2b)-1: acid generator including the following compound (B2b-1).

(B2b)-2: acid generator including the following compound (B2b-2).

(B2b)-3: acid generator including the following compound (B2b-3).

(B2b)-4: acid generator including the following compound (B2b-4).

(B2b)-5: acid generator including the following compound (B2b-5).

(B2b)-6: acid generator including the following compound (B2b-6).

(B2b)-7: acid generator including the following compound (B2b-7).

(B2b)-8: acid generator including the following compound (B2b-8).

(B2b)-9: acid generator including the following compound (B2b-9).

(B2b)-10: acid generator including the following compound (B2b-10).

[Chem. 175]
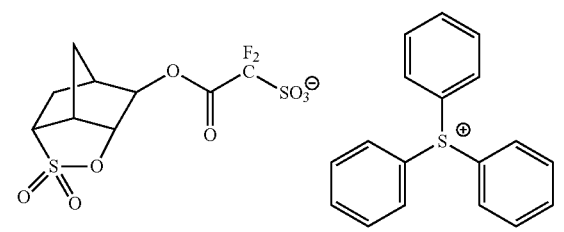 (B2b-1) 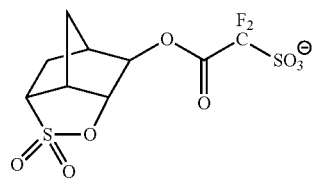
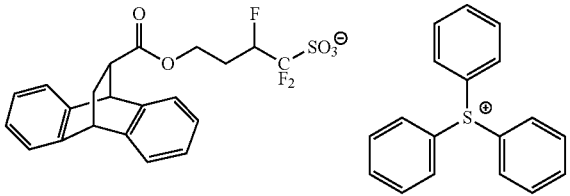 (B2b-2) 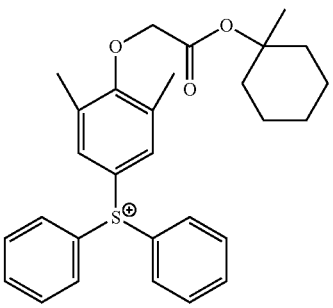
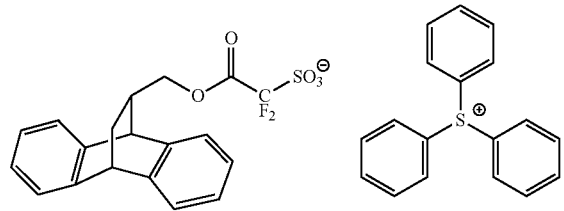 (B2-b3) 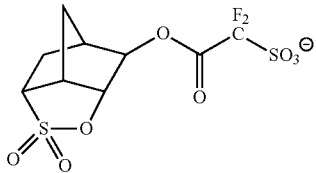
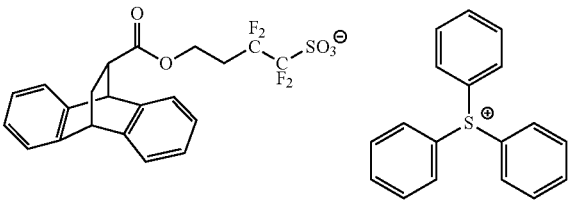 (B2-b-4) 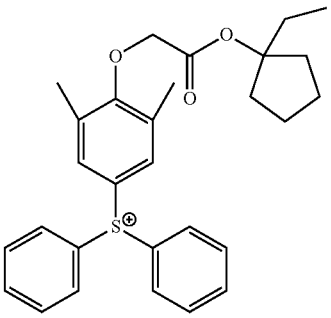
(B2b-5)
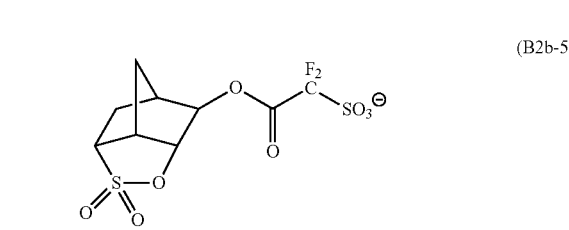
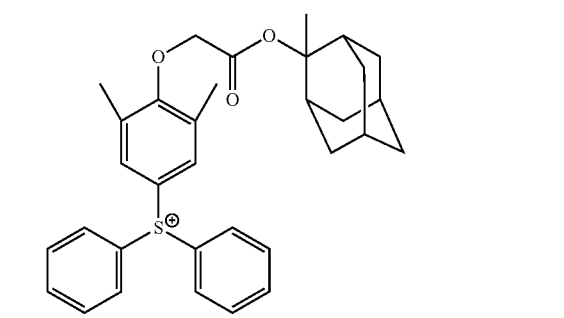
-continued
(B2b-6)
(B2b-7)
[Chem. 176]
(B2b-8)
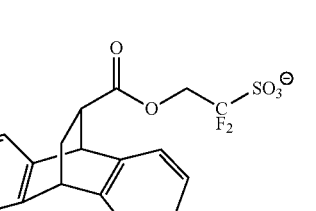
(B2b-9)
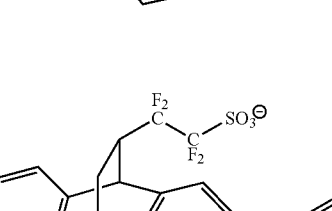
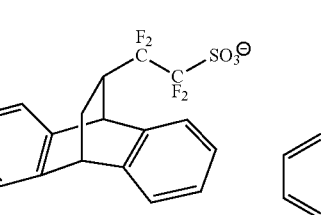

-continued (B2b-10)

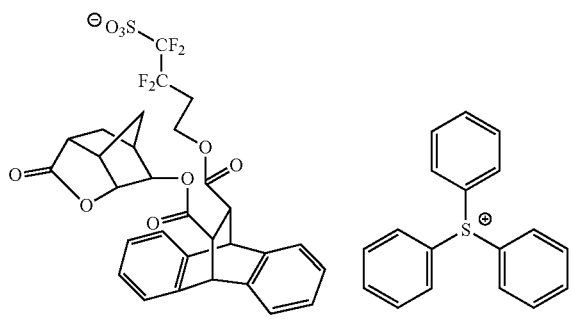

(D1b)-1 to (D1b)-3: Respective acid diffusion control agents including the above compound (D1b-1) to compound (D1b-3).

(D2b)-2 to (D2b)-4: Respective acid diffusion control agents including the above compound (D2b-2) to compound (D2b-4).

(D2b)-1: acid diffusion control agent including a compound represented by the following chemical formula (D2b-1).

(D2b)-5: acid diffusion control agent including a compound represented by the following chemical formula (D2b-5).

(S)-1b: solvent in which propylene glycol monomethyl ether acetate/propylene glycol monomethyl ether=60/40 (mass ratio) were mixed.

[Chem. 177]

(D2b-1)

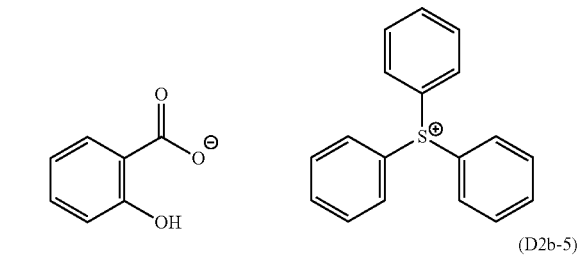

(D2b-5)

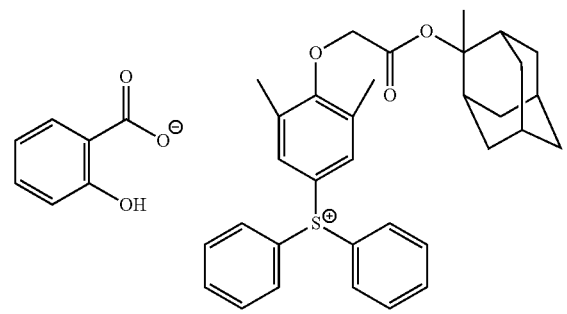

<Resist Pattern Formation 1b>

Each of the resist compositions of examples and comparative examples was applied to an 8-inch silicon substrate which had been treated with hexamethyldisilazane (HMDS) using a spinner, and was then prebaked (PAB) on a hot plate at 110° C. for 60 seconds and dried, thereby forming a resist film having a film thickness of 50 nm.

Next, drawing (exposure) was performed on the resist film using an electron beam lithography system JEOL-JBX-9300FS (commercially available from JEOL. Ltd.) at an acceleration voltage of 100 kV to obtain a 1:1 line and space pattern (hereinafter referred to as an "LS pattern") with a target size of a line width of 50 nm. Then, a post exposure bake (PEB) treatment was conducted at 110° C. for 60 seconds.

Thereafter, alkali developing was conducted for 60 seconds at 23° C. in a 2.38% by weight aqueous solution of tetramethylammonium hydroxide (TMAH) (product name: NMD-3; manufactured by Tokyo Ohka Kogyo Co., Ltd.).

Then, water rinsing was conducted for 15 seconds using pure water.

As a result, a 1:1 LS pattern with a line width of 50 nm was formed.

[Evaluation of Optimum Exposure Dose (Eop)]

An optimal exposure amount Eop ($\mu C/cm^2$) at which an LS pattern with a target size was formed according to the above "resist pattern formation method 1b" was obtained. This is shown as "Eop ($\mu C/cm^2$)" in Tables 8 to 10.

[Evaluation of Line Width Roughness (LWR)]

$3\sigma$ which is a scale showing LWR was obtained from the LS pattern formed in the above "resist pattern formation 1b." This is shown as "LWR (nm)" in Tables 8 to 10.

"$3\sigma$" indicates a value of 3 times the standard deviation (σ) (i.e., $3\sigma$) (unit: nm) determined by measuring the line positions at 400 points in the lengthwise direction of the line using a scanning electron microscope (product name: S-9380, manufactured by Hitachi High-Technologies Corporation; acceleration voltage: 800 V).

The smaller this $3\sigma$ value is, the lower the level of roughness on the side walls of the line, indicating that an LS pattern with a uniform width was obtained.

[Evaluation of Resolution]

The critical resolution (nm) with the above Eop was determined using a scanning electron microscope (product name: S-9380, manufactured by Hitachi High-Technologies Corporation). Specifically, the exposure dose was gradually increased from the optimum exposure dose Eop, and the minimum size of the pattern which resolves without collapse (fall) was determined. This is shown as "resolution (nm)" in Tables 8 to 10.

TABLE 8

| | PAB (° C.) | PEB (° C.) | Eop [$\mu C/cm^2$] | LWR [nm] | Resolution [nm] |
|---|---|---|---|---|---|
| Comparative Example 1b | 110 | 110 | 115 | 6.3 | 42.0 |
| Comparative Example 2b | 110 | 110 | 105 | 5.2 | 36.0 |
| Comparative Example 3b | 110 | 110 | 100 | 5.0 | 36.0 |
| Comparative Example 4b | 110 | 110 | 100 | 5.1 | 37.0 |
| Comparative Example 5b | 110 | 110 | 125 | 5.8 | 40.0 |
| Comparative Example 6b | 110 | 110 | 120 | 5.9 | 41.0 |
| Comparative Example 7b | 110 | 110 | 120 | 6.0 | 40.0 |
| Example 1b | 110 | 110 | 115 | 4.6 | 28.0 |
| Example 2b | 110 | 110 | 110 | 4.5 | 28.0 |
| Example 3b | 110 | 110 | 105 | 4.6 | 26.0 |

TABLE 9

| | PAB (° C.) | PEB (° C.) | Eop [$\mu C/cm^2$] | LWR [nm] | Resolution [nm] |
|---|---|---|---|---|---|
| Comparative Example 8b | 110 | 110 | 95 | 4.7 | 36.0 |
| Comparative Example 9b | 110 | 110 | 100 | 4.8 | 36.0 |
| Comparative Example 10b | 110 | 110 | 95 | 5.0 | 37.0 |
| Comparative Example 11b | 110 | 110 | 95 | 5.2 | 38.0 |

TABLE 9-continued

|  | PAB (° C.) | PEB (° C.) | Eop [μC/cm²] | LWR [nm] | Resolution [nm] |
|---|---|---|---|---|---|
| Comparative Example 12b | 110 | 110 | 100 | 4.9 | 36.0 |
| Example 4b | 110 | 110 | 95 | 4.7 | 26.0 |
| Example 5b | 110 | 110 | 105 | 4.6 | 25.0 |
| Example 6b | 110 | 110 | 95 | 4.7 | 23.0 |
| Example 7b | 110 | 110 | 95 | 4.2 | 22.0 |
| Example 8b | 110 | 110 | 100 | 4.5 | 24.0 |

TABLE 10

|  | PAB (° C.) | PEB (° C.) | Eop [μC/cm²] | LWR [nm] | Resolution [nm] |
|---|---|---|---|---|---|
| Comparative Example 13b | 110 | 110 | 100 | 5.0 | 39.0 |
| Example 9b | 110 | 110 | 100 | 4.8 | 32.0 |
| Example 10b | 110 | 110 | 95 | 4.6 | 30.0 |
| Example 11b | 110 | 110 | 100 | 4.4 | 26.0 |
| Comparative Example 14b | 110 | 110 | 115 | 5.0 | 32.0 |
| Example 12b | 110 | 110 | 115 | 4.2 | 24.0 |
| Comparative Example 15b | 110 | 110 | 110 | 5.2 | 32.0 |
| Example 13b | 110 | 110 | 105 | 4.4 | 26.0 |

Based on the results shown in Tables 8 to 10, it was confirmed that, according to the resist compositions of the examples, high sensitivity and high resolution were obtained in the formation of the resist pattern, and a resist pattern having a favorable shape with reduced roughness was able to be formed.

Compound Production 1c

Production Example 1c

4-Bromo-3,3,4,4-tetrafluoro-1-butene (8.7 g, 42 mmol), anthracene (5.0 g, 28 mmol), and toluene (100 g) were put into a 300 mL pressure resistant reaction container, and the mixture was reacted at 150° C. for 24 hours. Subsequently, after cooling to room temperature, the resultant was concentrated using a rotary evaporator. Methanol (50 g) was added to the concentrate, followed by stirring. The precipitated solid was subjected to filtration. Then, the filtrate was dried under a reduced pressure to obtain an intermediate 1c (6.0 g, yield=55.6%).

[Chem. 178]

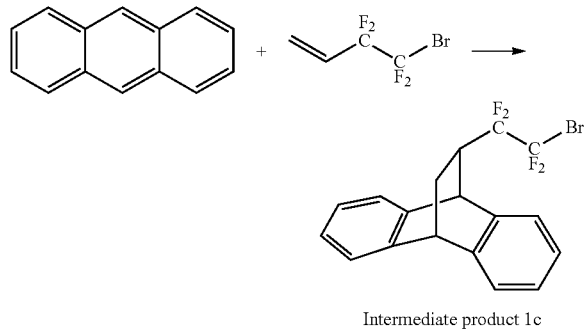

Intermediate product 1c

The intermediate 1c (5.8 g, 15 mmol), benzyltrimethylammonium chloride (2.9 g, 16 mmol), sodium dithionite (6.7, 38 mmol), sodium bicarbonate (3.8 g, 45 mmol), acetonitrile (16 g), and H₂O (16 g) were put into a 200 mL 3-necked flask, and the mixture was stirred and reacted at 65° C. for 4 hours. Subsequently, after cooling to room temperature, the reaction liquid was subjected to filtration. H₂O (16 g) and dichloromethane (25 g) were added to the filtrate, followed by stirring for 30 minutes and removing the aqueous phase. Thereafter, the resultant was washed with ultra pure water (160 g) twice, and the organic phase was concentrated using a rotary evaporator. The concentrate was added to and dissolved in acetonitrile (77 g). 30% hydrogen peroxide solution (2.7 g, 24 mmol) was added, and a reaction was conducted at 45° C. for 7 hours. After cooling to room temperature, dichloromethane (78 g) and a saturated aqueous solution of sodium sulfite (78 g) was added, followed by stirring for 30 minutes in ultra pure water, and removing the aqueous phase. Washing with ultra pure water (78 g) was performed twice, methyl tert-butyl ether (MTBE) (156 g) was then added thereto, and the mixture was stirred for 30 minutes. The precipitate was filtered off and dried under a reduced pressure to obtain a precursor (Bpre-1c) (5.8 g, yield=66.8%).

[Chem. 179]

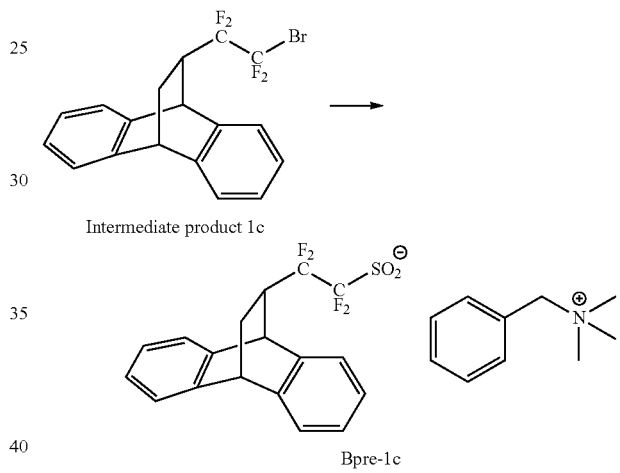

Production Example 2c

Anthracene (5.0 g, 28 mmol), methyl acrylate (3.6 g, 42 mmol), aluminum chloride (0.37 g, 2.8 mmol) and toluene (50 g) were added to a 100 mL three-necked flask, and a reaction was conducted at 80° C. for 4 hours while stirring. After cooling, ultra pure water (50 g) and MTBE (74 g) were added. After stirring for 30 minutes, the aqueous phase was removed. The organic phase was washed with ultra pure water (50 g) 3 times, and the organic phase was concentrated using a rotary evaporator. The concentrate was recrystallized with 2-isopropanol to obtain an intermediate 2c (5.9 g, yield=79.6%).

Sodium hydroxide (3.8 g, 95 mmol) and ultra pure water (38 g) were put into a 100 mL 3-necked flask, the mixture was stirred and dissolved, and the intermediate 2c (5.0 g, 19 mmol) was dispersed, and reacted at 90° C. for 4 hours. After cooling to room temperature, hydrochloric acid was added until the solution was neutralized. Then, MTBE (50 g) was added, and stirred for 30 minutes, followed by removing the aqueous phase. An organic layer was washed with ultra pure water (50 g) 3 times, and the organic layer was concentrated using a rotary evaporator to obtain an intermediate 3c (4.6 g, yield=97.2%).

[Chem. 180]

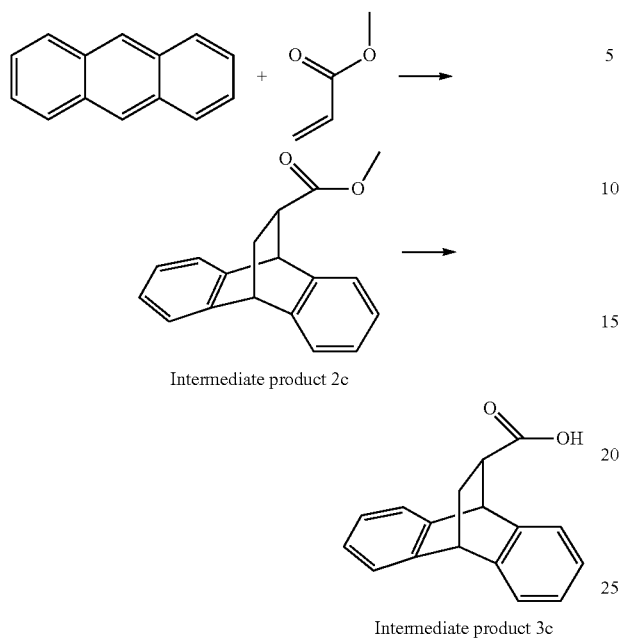

Intermediate product 2c

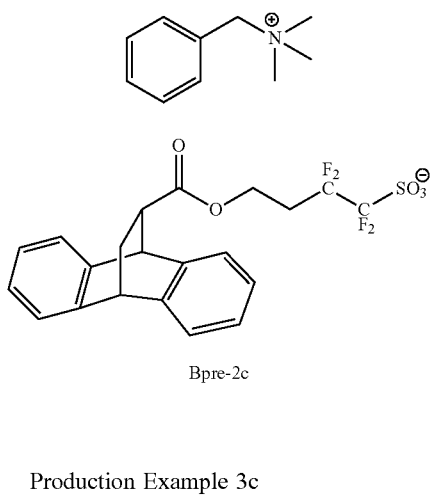

Bpre-2c

Production Example 3c

An intermediate 4c (6.4 g, yield=82.3%) was obtained in the same manner as in the production example of the intermediate 2c except that anhydrous maleic acid (4.0 g, 42 mmol) was used in place of methyl acrylate (3.6 g, 42 mmol).

The intermediate 3c (4.0 g, 16 mmol), the compound (I-1c) (6.0 g, 16 mmol), and dichloromethane (87 g) were put into a 100 mL 3-necked flask, and the mixture was stirred and dissolved at room temperature.

Then, diisopropylcarbodiimide (2.2 g, 18 mmol) and dimethylaminopyridine (0.098 g, 0.8 mmol) were added, and reacted at room temperature for 5 hours. The reaction liquid was subjected to filtration, and the filtrate was concentrated using a rotary evaporator. The concentrate was dissolved in acetonitrile (17 g) and then added dropwise to MTBE (170 g), and the precipitated solid was filtered off. The filtrate was dissolved again in acetonitrile (17 g), and added dropwise to MTBE (170 g), and the precipitated solid was filtered off. This operation was repeated twice, and the filtrate was then dried under a reduced pressure to obtain a precursor (Bpre-2c) (7.6 g, yield=78.2%).

[Chem. 182]

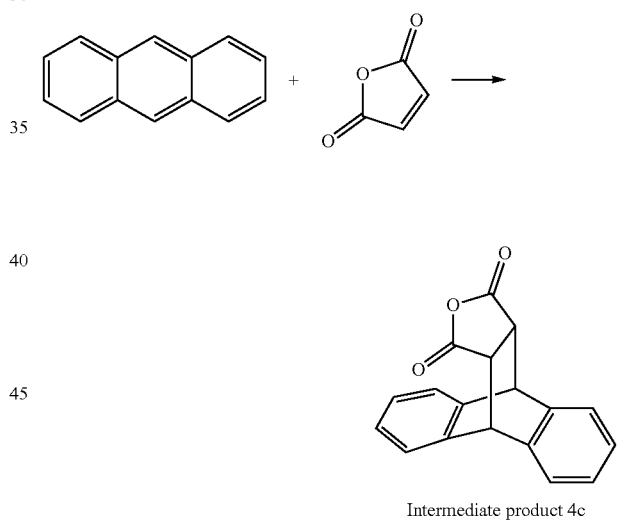

Intermediate product 4c

[Chem. 181]

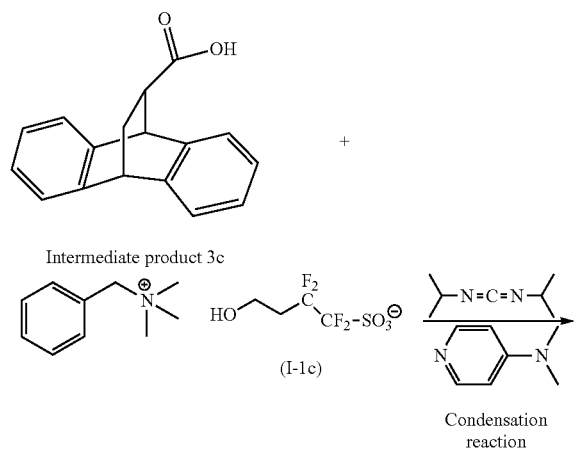

The intermediate 4c (6.0 g, 22 mmol), 5-hydroxynorbomane 2,6-lactone (4.0 g, 26 mmol), and dichloromethane (120 g) were put into a 100 mL 3-necked flask, and the mixture was stirred and dissolved at room temperature. Next, dimethylaminopyridine (0.13 g, 1 mmol) and trimethylamine (5.5 g, 54 mmol) were put thereinto and reacted at room temperature for 24 hours. Ultra pure water (120 g) was put thereinto, the mixture was stirred, and hydrochloric acid was then added so that the aqueous layer became acidic for neutralization, and additionally the mixture was stirred for 30 minutes, and an aqueous layer was then removed. An organic layer was washed with ultra pure water (120 g) 3 times, and the organic layer was concentrated using a rotary evaporator to obtain an intermediate 5c (7.2 g, yield=77.1%).

[Chem. 183]

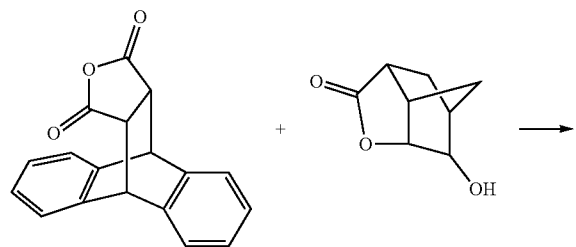

Intermediate product 4c

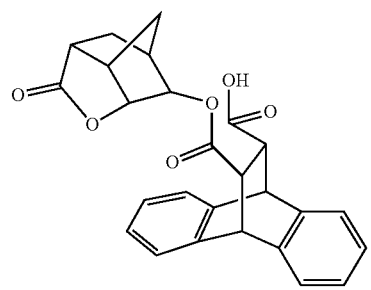

Intermediate product 5c

A precursor (Bpre-3c) (6.6 g, yield=53.1%) was obtained in the same manner as in the production example of the precursor (Bpre-2) except that the intermediate 5c (6.8 g, 16 mmol) was used in place of the intermediate 3c (4.0 g, 16 mmol).

[Chem. 184]

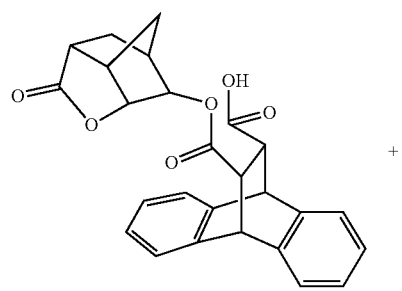

Intermediate product 5c

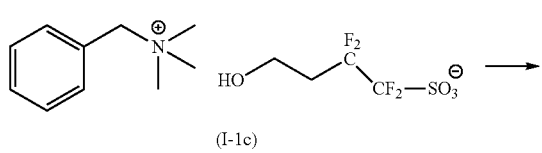

(I-1c)

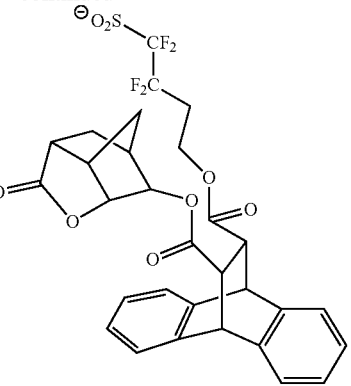

Bpre-3c

Production Example 4

A precursor (Bpre-4c) (6.2 g, yield=65.4%) was obtained in the same manner as in the production example of the precursor (Bpre-2c) except that the compound (I-2c) (5.7 g, 16 mmol) was used in place of the compound (I-1c) (6.0 g, 16 mmol).

[Chem. 185]

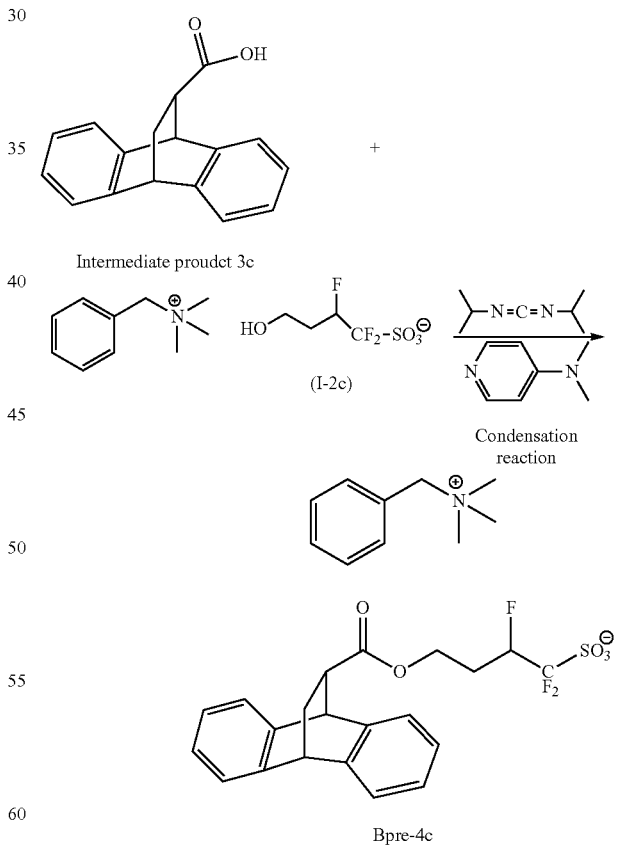

Production Example 5c

The intermediate 3c (4.8 g, 19 mmol) and tetrahydrofuran (THF) (50 g) were put into a 100 mL 3-necked flask, and the mixture was stirred and dissolved at room temperature. Then, LiAlH₄ (0.86 g, 23 mmol) was added, and reacted at room temperature for 3 hours. Subsequently, ultra pure water (50 g) and MTBE (50 g) were added. After stirring for 30 minutes, the aqueous phase was removed. Then, an organic layer was washed with ultra pure water (50 g) 3 times, and the organic layer was concentrated using a rotary evaporator to obtain an intermediate 6c (4.1 g, yield=91.0%).

The intermediate 6c (4.0 g, 19 mmol), the compound (I-3c) (3.6 g, 18 mmol), p-toluenesulfonic acid monohydrate (0.18 g, 0.9 mmol) and toluene (40 g) were put into a 100 mL 3-necked flask and the mixture was refluxed at 110° C. for 24 hours. After cooling, the resultant was subjected to filtration. Acetonitrile (160 g) was added to the residue, followed by stirring at room temperature for 30 minutes, and filtration.

The filtrate was concentrated, and methyl ethyl ketone (78 g) was added to the residue, followed by stirring. Then, the resultant was filtered off, and the filtrate was dried to obtain a precursor (Bpre-5c) (4.9 g, yield=62.4%).

[Chem. 186]

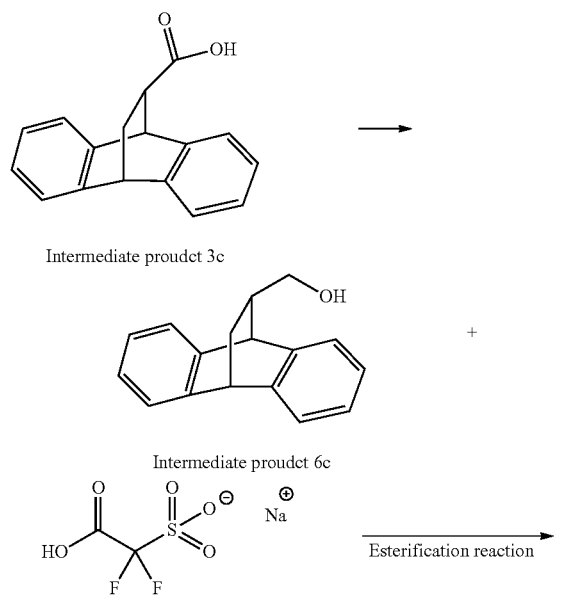

Subsequently, pyridine (3.0 g, 39 mmol) was added over 30 minutes, and a reaction was conducted at room temperature for 6 hours. The reaction liquid was washed with ultra pure water (100 g) 4 times. Then, MTBE (150 g) was added to the organic phase, followed by stirring for 30 minutes. The precipitate was filtered off and dried under a reduced pressure to obtain an intermediate 7c (5.8 g, yield=66.8%).

[Chem. 187]

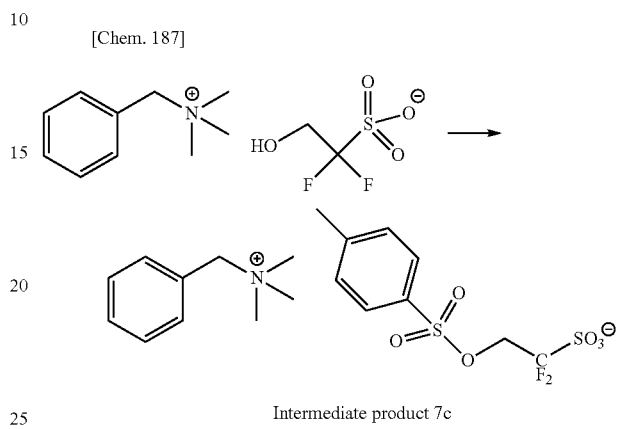

Intermediate product 7c

Production Example 6c

9-Bromotriptycene (10.0 g, 30 mmol) and THF (100 g) were added to a 200 mL three-necked flask, followed by stirring to dissolve the contents. After cooling to −78° C., 1.6 M n-butyllithium in hexane solution (20.6 ml, 33 mmol) was added, followed by stirring at −78° C. for 1 hour. Next, the intermediate 7c (12.6 g, 27 mmol) dissolved in THF (126 g) was put thereinto and reacted at −50° C. for 3 hours. The reaction liquid was added to ultra pure water (250 g) over 1 hour. Then, dichloromethane (160 g) was added, followed by stirring for 30 minutes and removing the aqueous phase. The organic phase was washed with ultra pure water (150 g) 3 times. Then, the organic phase was dropwise added to MTBE (160 g), and the precipitated solid was subjected to filtration. The residue was dissolved in acetonitrile (70 g), and the resultant was dropwise added to MTBE (140 g). The precipitated solid was subjected to filtration. This operation was repeated twice, and the filtrate was dried under a reduced pressure to obtain a precursor (Bpre-6c) (6.0 g, yield=36.7%).

[Chem. 188]

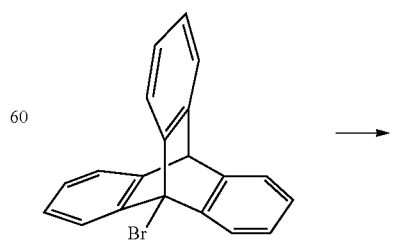

Production Example 6c

The compound (I-4c) (10.0 g, 32 mmol), para-toluene sulfonyl chloride (6.7 g, 35 mmol), and dichloromethane (100 g) were put into a 100 mL 3-necked flask, and the mixture was stirred and dispersed at room temperature.

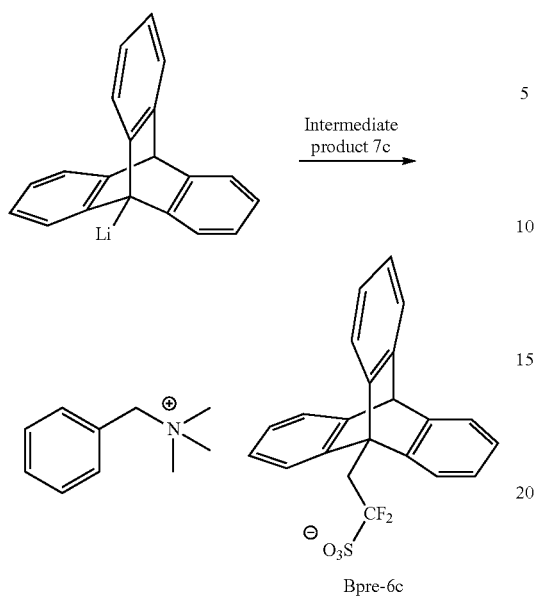

Bpre-6c

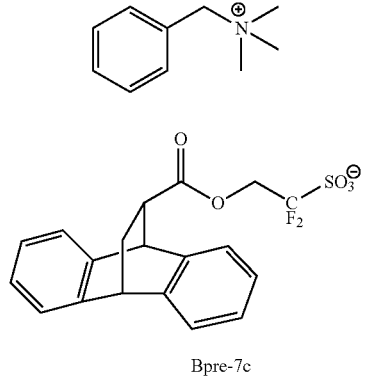

Bpre-7c

Production Example 7c

The intermediate 3c (4.0 g, 16 mmol), the compound (I-5c) (5.0 g, 16 mmol), and dichloromethane (87 g) were put into a 100 mL 3-necked flask, and the mixture was stirred and dissolved at room temperature. Then, diisopropylcarbodiimide (2.2 g, 18 mmol) and dimethylaminopyridine (0.098 g, 0.8 mmol) were added, and reacted at room temperature for 5 hours. The reaction liquid was subjected to filtration, and the filtrate was concentrated using a rotary evaporator. The concentrate was dissolved in acetonitrile (17 g), and then added dropwise to MTBE (170 g), and the precipitated solid was filtered off. The filtrate was dissolved again in acetonitrile (17 g), and added dropwise to MTBE (170 g), and the precipitated solid was filtered off. This operation was repeated twice, and then the filtrate was dried under a reduced pressure to obtain a precursor (Bpre-7c) (5.8 g, yield=66.8%).

[Chem. 189]

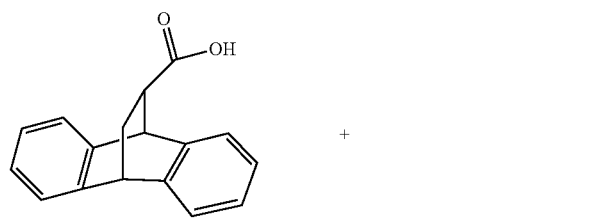

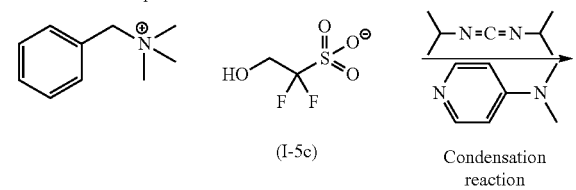

Production Example 8c

Sodium hydroxide (3.6 g, 90 mmol) and ultra pure water (36 g) were put into a 100 mL 3-necked flask, the mixture was stirred and dissolved, and the intermediate 4c (5.0 g, 18 mmol) was then dispersed and reacted at 90° C. for 4 hours. After cooling to room temperature, 20% hydrochloric acid (13.2 g, 72.4 mmol) and benzyltrimethylammonium chloride (5.0 g, 27 mmol) were added thereto, MTBE (50 g) was then added thereto, and the mixture was stirred for 30 minutes, and an aqueous layer was then removed. An organic layer was washed with ultra pure water (50 g) 3 times, and the organic layer was concentrated using a rotary evaporator to obtain a precursor (Bpre-8c) (5.7 g, yield=71.0%).

[Chem. 190]

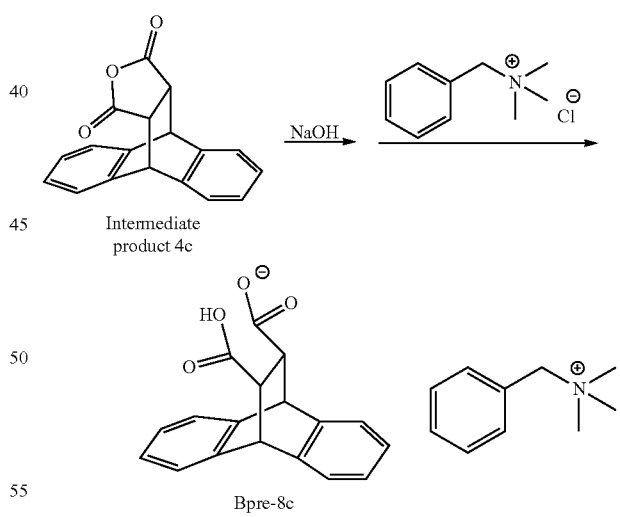

Bpre-8c

Production Example of Compound (B1-3c)

The precursor (Bpre-1c) (5.0 g, 9.3 mmol), and the compound Cc for salt exchange (3.5 g, 9.3 mmol) were dissolved in dichloromethane (50 g), ultra pure water (50 g) was added thereto, and the mixture was reacted at room temperature for 30 minutes. After the reaction was completed, an aqueous phase was removed, and an organic phase was then washed with ultra pure water (50 g) 4 times. The organic phase was concentrated and dried using a rotary evaporator to obtain a compound (B1-3c) (6.0 g, yield=88.9%).

[Chem. 191]

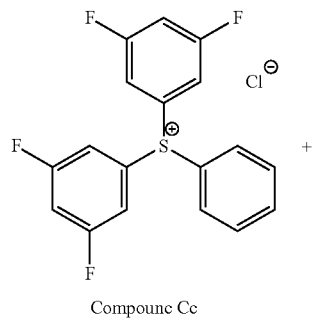

Compound Cc

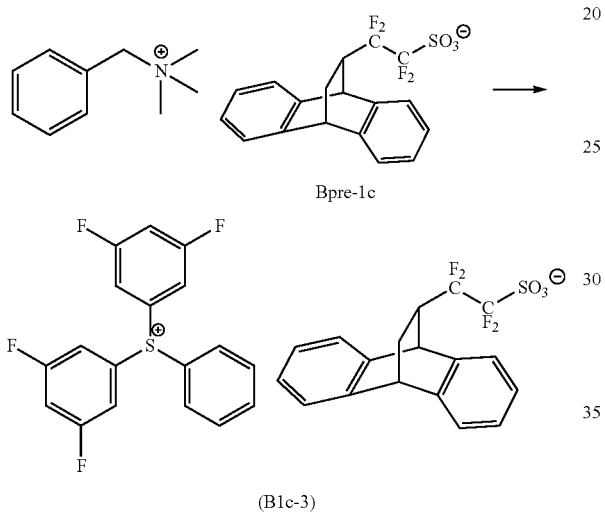

(B1c-3)

Production Examples of Other Compounds

The following compound (B1-1c) to compound (B1c-12), compound (B2c-1), compound (B2c-4) to compound (B2c-7), compound (D2c-4), and compound (D1c-1) were obtained in the same manner as in the "production example of the compound (B1-3c)" except that combinations of the above precursor (Bpre-1c) to precursor (Bpre-8c), and the following compound Ac for salt exchange to compound Pc for salt exchange were changed.

[Chem. 192]

Compound Ac

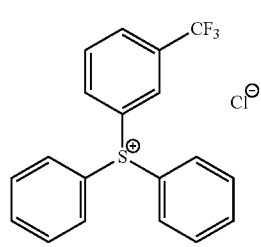

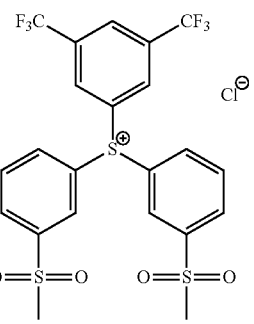

Compound Bc

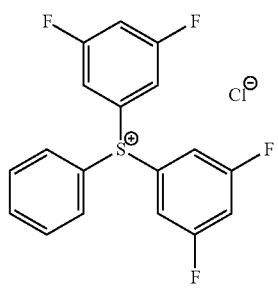

Compound Cc

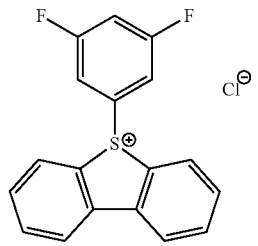

Compound Dc

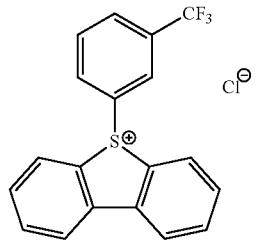

Compound Ec

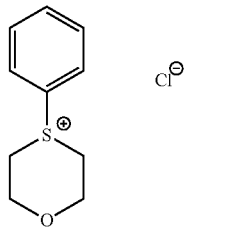

Compound Fc

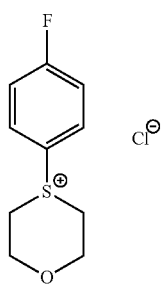

Compound Gc

-continued
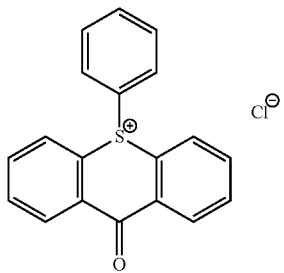
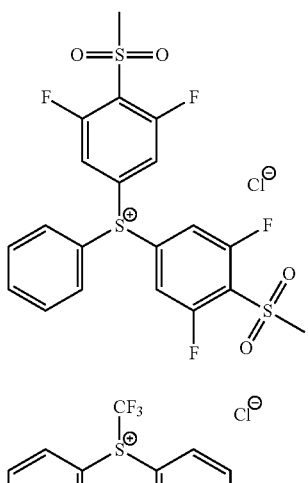
[Chem. 193]
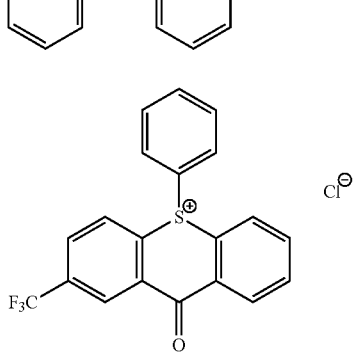
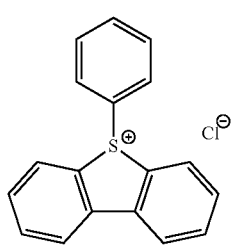
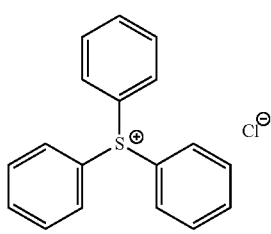
-continued
Compound Hc
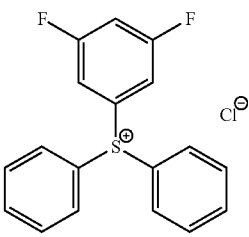
[Chem. 194]
Compound Ic
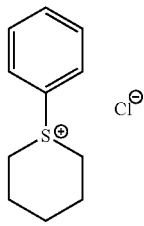
Compound Jc
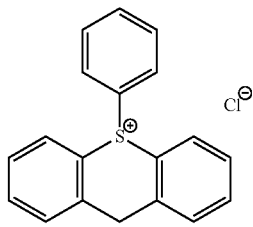
Compound Kc
Each of the obtained compounds was analyzed by NMR, and the structure thereof was identified by the following analysis results.
[Chem. 195]
Compound Lc
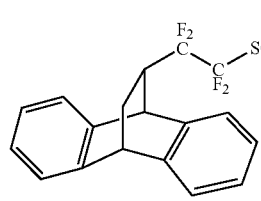
(B1c-1)
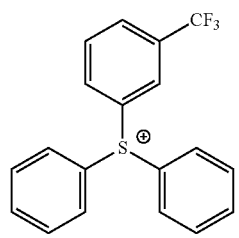
Compound Mc
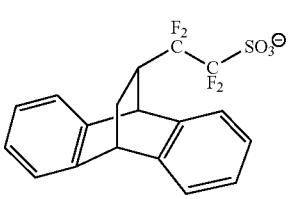
(B1c-2)
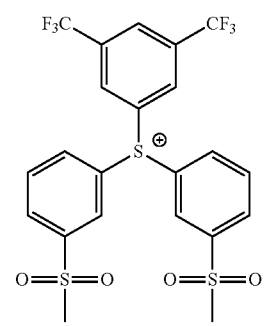

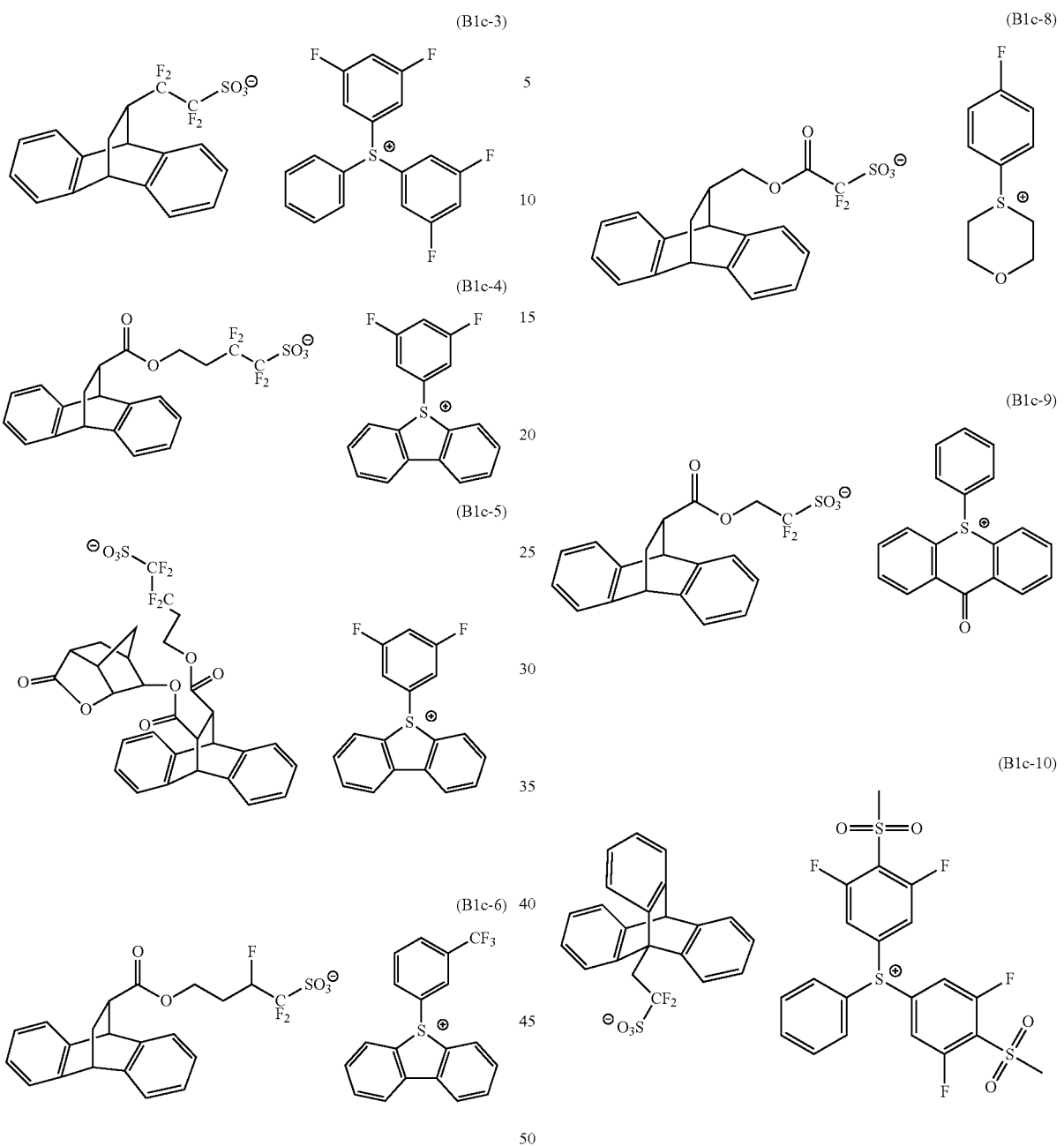

-continued (B1c-12)

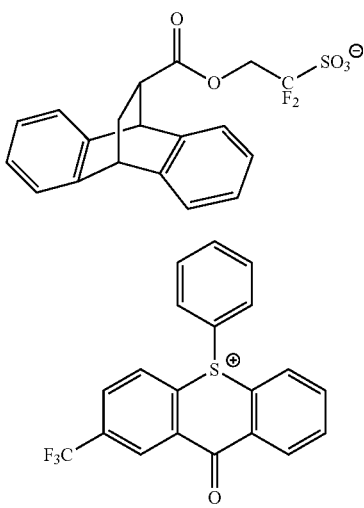

Compound (B1c-1): Combination of the Precursor (Bpre-1c) and the Compound Ac for Salt Exchange $^1$H-NMR (DMSO, 400 MHz): δ(ppm)=8.44 (s, Ph, 1H), 8.26 (d, Ph, 1H), 7.78-8.03 (m, Ph, 12H), 7.00-7.48 (m, ArH, 8H), 4.70 (s, CH, 1H), 4.40 (s, CH, 1H), 3.15-3.22 (m, CF$_2$CH, 1H), 1.95-2.15 (m, CH2, 2H)

$^{19}$F-NMR (DMSO, 376 MHz): δ(ppm)=−62.9, −111.3, −117.4

Compound (B1c-2): Combination of the Precursor (Bpre-1c) and the Compound Bc for Salt Exchange $^1$H-NMR (DMSO, 400 MHz): δ(ppm)=8.60-8.80 (m, ArH, 5H), 8.41 (d, ArH, 2H), 8.28 (d, ArH, 2H), 8.06 (t, ArH, 2H), 7.00-7.48 (m, ArH, 8H), 4.70 (s, CH, 1H), 4.40 (s, CH, 1H), 3.32 (s, CH3, 6H), 3.15-3.22 (m, CF$_2$CH, 1H), 1.95-2.15 (m, CH2, 2H)

$^{19}$F-NMR (DMSO, 376 MHz): δ(ppm)=−61.2, −111.3, −117.4

Compound (B1c-3): Combination of the Precursor (Bpre-1c) and the Compound Cc for Salt Exchange $^1$H-NMR (DMSO, 400 MHz): δ(ppm)=7.77-7.98 (m, ArH, 11H), 7.00-7.48 (m, ArH, 8H), 4.70 (s, CH, 1H), 4.40 (s, CH, 1H), 3.15-3.22 (m, CF$_2$CH, 1H), 1.95-2.15 (m, CH2, 2H)

$^{19}$F-NMR (DMSO, 376 MHz): δ (ppm)=−103.9, −111.3, −117.4

Compound (B1c-4): Combination of the Precursor (Bpre-2c) and the Compound Dc for Salt Exchange $^1$H-NMR (DMSO, 400 MHz): δ (ppm)=8.49 (dd, ArH, 4H), 7.99 (t, ArH, 2H), 7.66-7.87 (m, ArH, 3H), 7.42-7.58 (m, ArH, 2H), 7.01-7.47 (m, ArH, 8H), 4.72 (s, CH, 1H), 4.43 (s, CH, 1H), 4.23, (t, CH2, 2H), 2.95-3.02 (m, CH, 1H), 2.63-2.73, (m, CF$_2$CH2, 2H), 1.86-2.07 (m, CH2, 2H)

$^{19}$F-NMR (DMSO, 376 MHz): δ (ppm)=−104.1, −111.3, −117.4

Compound (B1c-5): Combination of the Precursor (Bpre-3c) and the Compound Dc for Salt Exchange $^1$H-NMR (DMSO, 400 MHz): δ (ppm)=8.49 (dd, ArH, 4H), 7.99 (t, ArH, 2H), 7.66-7.87 (m, ArH, 3H), 7.42-7.58 (m, ArH, 2H), 7.01-7.47 (m, ArH, 8H), 4.70 (d, OCH (lactone), 1H), 4.58 (t, COOCH (lactone), 1H), 4.50 (d, CH, 2H), 4.22, (t, COOCH2, 2H), 3.32 (m, CH (lactone), 1H), 3.20 (t, COCH, 2H), 2.63-2.73, (m, CF$_2$CH2, CH (lactone) 4H), 1.60-2.20 (m, CH2 (lactone), 4H)

$^{19}$F-NMR (DMSO, 376 MHz): δ (ppm)=−104.1, −111.3, −117.4

Compound (B1c-6): Combination of the Precursor (Bpre-4c) and the Compound Ec for Salt Exchange $^1$H-NMR (DMSO, 400 MHz): δ(ppm)=8.60 (s, ArH, 1H), 8.55 (d, ArH, 2H), 8.41 (d, ArH, 2H), 8.08 (d, ArH, 1H), 7.98 (t, ArH, 2H), 7.78 (t, ArH, 2H), 7.70 (t, ArH, 1H), 7.34 (d, ArH, 1H), 7.01-7.47 (m, ArH, 8H), 5.08 (m, CFCH, 1H), 4.71 (s, CH, 1H), 4.42 (s, CH, 1H), 4.23 (m, CH2, 2H), 2.90 (m, CH, 1H), 2.45 (m, CFCH, 1H), 1.82-2.07 (m, CH2, CFCH, 3H)

$^{19}$F-NMR (DMSO, 376 MHz): δ (ppm)=−61.4, −112.5, −121.2

Compound (B1c-7): Combination of the Precursor (Bpre-5c) and the Compound Fc for Salt Exchange $^1$H-NMR (DMSO, 400 MHz): δ(ppm)=8.02-8.05 (m, ArH, 2H), 7.61-7.73 (m, ArH, 3H), 7.01-7.45 (m, ArH, 8H), 4.71 (s, CH, 1H), 4.44 (S, CH, 1H), 4.31 (s, CH2, 2H), 3.86-3.96 (m, SCH2, 4H), 3.75 (t, OCH2, 4H), 2.93-3.00 (m, CH, 1H), 1.87-2.07 (m, CH2, 1H), 0.98-1.03 (m, CH, 1H)

$^{19}$F-NMR (DMSO, 376 MHz): δ(ppm)=−107.9

Compound (B1c-8): Combination of the Precursor (Bpre-5c) and the Compound Gc for Salt Exchange $^1$H-NMR (DMSO, 400 MHz): δ(ppm)=8.15 (d, ArH, 2H), 7.84 (d, ArH, 2H), 7.01-7.45 (m, ArH, 8H), 4.71 (s, CH, 1H), 4.44 (s, CH, 1H), 4.31 (s, CH2, 2H), 3.86-3.96 (m, SCH2, 4H), 3.75 (t, OCH2, 4H), 2.93-3.00 (m, CH, 1H), 1.87-2.07 (m, CH2, 1H), 0.98-1.03 (m, CH, 1H)

$^{19}$F-NMR (DMSO, 376 MHz): δ (ppm)=−104.0, −107.9

Compound (B1c-9): Combination of the Precursor (Bpre-7c) and the Compound Hc for Salt Exchange $^1$H-NMR (DMSO, 400 MHz): δ (ppm)=8.58 (d, ArH, 2H), 8.17 (d, ArH, 2H), 7.95-8.11 (m, ArH, 6H), 7.76 (t, ArH, 1H), 7.65 (t, ArH, 2H), 7.00-7.48 (m, ArH, 8H), 4.70 (s, CH, 1H), 4.31-4.58 (m, CH, CF$_2$CH2, 3H), 2.95-3.02 (m, CH, 1H), 1.85-2.05 (m, CH2, 2H)

$^{19}$F-NMR (DMSO, 376 MHz): δ (ppm)=−111.4

Compound (B c-10): Combination of the Precursor (Bpre-6c) and the Compound Ic for Salt Exchange $^1$H-NMR (DMSO, 400 MHz): δ (ppm)=7.98-8.07 (m, ArH, 6H), 7.94 (t, ArH, 1H), 7.83 (t, ArH, 2H), 7.68-7.82 (m, ArH, 6H), 6.60-6.80 (m, ArH, 6H), 5.54 (s, CH, 1H), 2.42-2.47 (t, CF$_2$CH2,2H)

$^{19}$F-NMR (DMSO, 376 MHz): δ (ppm)=−102.3, −105.6

Compound (B1c-11): Combination of the Precursor (Bpre-6c) and the Compound Jc for Salt Exchange $^1$H-NMR (DMSO, 400 MHz): δ(ppm)=8.29 (d, ArH, 4H), 7.93-8.09 (m, ArH, 6H), 7.68-7.82 (m, ArH, 6H), 6.60-6.80 (m, ArH, 6H), 5.54 (s, CH, 1H), 2.42-2.47 (t, CF$_2$CH2,2H)

$^{19}$F-NMR (DMSO, 376 MHz): δ(ppm)=−47.9, −105.6

Compound (B1c-12): Combination of the Precursor (Bpre-7c) and the Compound Kc for Salt Exchange $^1$H-NMR (DMSO, 400 MHz): δ(ppm)=8.76 (s, ArH, 1H), 8.59-8.64 (n, ArH, 1H), 8.42 (t, ArH, 2H), 8.03-8.19 (m, ArH, 5H), 7.81 (t, ArH, 1H), 7.69 (t, ArH, 2H), 7.00-7.48 (m, ArH, 8H), 4.70 (s, CH, 1H), 4.31-4.58 (m, CH, CF$_2$CH2, 3H), 2.95-3.02 (m, CH, 1H), 1.85-2.05 (m, CH2, 2H)

$^{19}$F-NMR (DMSO, 376 MHz): δ (ppm)=−62.1, −111.4

[Chem. 197]

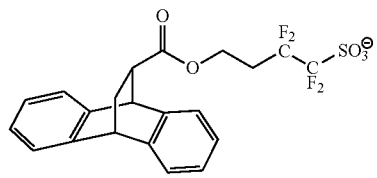
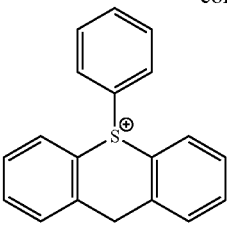

(B2c-1)

(B2c-4)

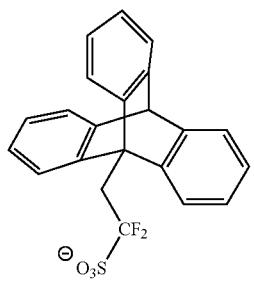
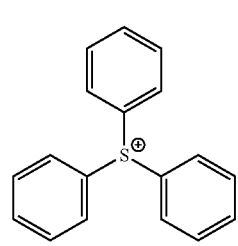

Compound (B2c-1): Combination of the Precursor (Bpre-2c) and the Compound Lc for Salt Exchange $^{1}$H-NMR (DMSO, 400 MHz): δ (ppm)=8.50 (d, ArH, 2H), 8.37 (d, ArH, 2H), 7.93 (t, ArH, 2H), 7.55-7.75 (m, ArH, 7H), 7.01-7.47 (m, ArH, 8H), 4.72 (s, CH, 1H), 4.43 (s, CH, 1H), 4.23, (t, CH2, 2H), 2.95-3.02 (m, CH, 1H), 2.63-2.73, (m, CF$_2$CH2, 2H), 1.86-2.07 (m, CH2, 2H)

$^{19}$F-NMR (DMSO, 376 MHz): δ (ppm)=−111.3, −117.4

Compound (B2c-4): Combination of the Precursor (Bpre-6c) and the Compound Mc for Salt Exchange $^{1}$H-NMR (DMSO, 400 MHz): δ(ppm)=7.74-7.90 (m, 15H, ArH), 7.68-7.82 (m, ArH, 6H), 6.60-6.80 (m, ArH, 6H), 5.54 (s, CH, 1H), 2.42-2.47 (t, CF$_2$CH2,2H)

$^{19}$F-NMR (DMSO, 376 MHz): δ (ppm)=−105.6

[Chem. 198]

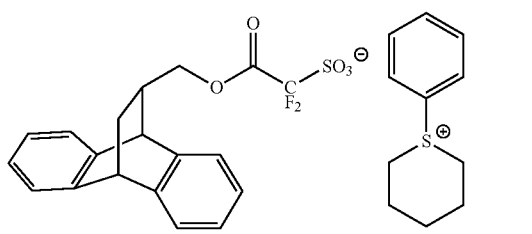

(B2c-5)

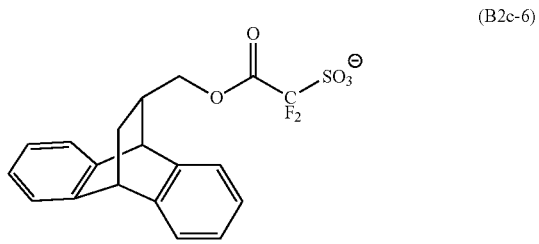

(B2c-6)

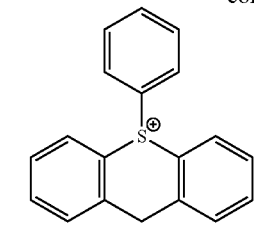

Compound (B2c-5): Combination of the Precursor (Bpre-5c) and the Compound Oc for Salt Exchange $^{1}$H-NMR (DMSO, 400 MHz): δ(ppm)=8.07 (d, ArH, 2H), 7.59-7.75 (m, ArH, 3H), 7.01-7.45 (m, ArH, 8H), 4.71 (s, CH, 1H), 4.44 (s, CH, 1H), 4.31 (s, CH2, 2H), 3.94 (t, SCH2, 2H), 3.71 (d, SCH2, 2H), 2.93-3.00 (m, CH, 1H), 2.34-2.42 (m, CH2, 2H), 1.80-2.08 (m, CH2, 5H), 0.98-1.03 (m, CH, 1H)

$^{19}$F-NMR (DMSO, 376 MHz): δ(ppm)=−107.9

Compound (B2c-6): Combination of the Precursor (Bpre-5c) and the Compound Pc for Salt Exchange $^{1}$H-NMR (DMSO, 400 MHz): δ(ppm)=8.47 (d, ArH, 2H), 7.82-7.90 (m, ArH, 4H), 7.70-7.80 (m, ArH, 2H), 7.58-7.69 (m, ArH, 3H), 7.00-7.51 (m, ArH, 10H), 4.70 (s, CH, 1H), 4.31-4.58 (m, CH, CF$_2$CH2, ArCH2, 4H), 4.01 (d, ArCH2, 1H), 2.95-3.02 (m, CH, 1H), 1.85-2.05 (m, CH2, 2H)

$^{19}$F-NMR (DMSO, 376 MHz): δ (ppm)=−111.4

[Chem. 199]

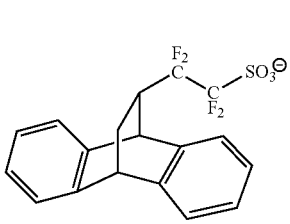
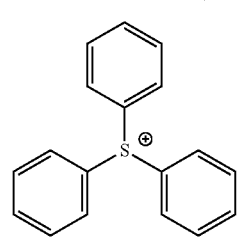

(B2c-7)

Compound (B2c-7): Combination of the Precursor (Bpre-1c) and the Compound Mc for Salt Exchange $^{1}$H-NMR (DMSO, 400 MHz): δ (ppm)=7.74-7.90 (m, 15H, ArH), 7.00-7.48 (m, ArH, 8H), 4.70 (s, CH, 1H), 4.40 (s, CH, 1H), 3.15-3.22 (m, CF$_2$CH, 1H), 1.95-2.15 (m, CH2, 2H)

$^{19}$F-NMR (DMSO, 376 MHz): δ (ppm)=−111.3, −117.4

[Chem. 200]

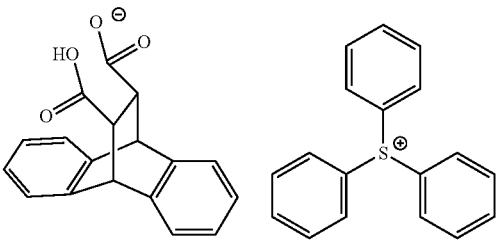

(D2c-4)

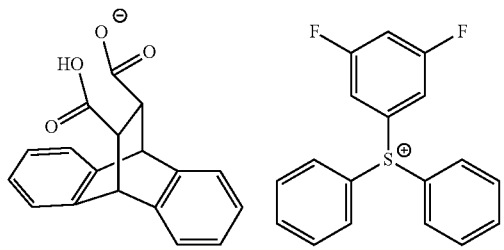

(D1c-1)

Compound (D2c-4): Combination of the Precursor (Bpre-8c) and the Compound Mc for Salt Exchange
$^1$H-NMR (DMSO, 400 MHz): δ (ppm)=7.74-7.90 (m, 15H, ArH), 7.00-7.48 (m, ArH, 8H), 4.85 (s, ArCH, 2H), 3.16 (s, CH, 2H)

Compound (D1c-1): Combination of the Precursor (Bpre-8c) and the Compound Nc for Salt Exchange
$^1$H-NMR (DMSO, 400 MHz): δ (ppm)=7.77-7.98 (m, ArH, 11H), 7.00-7.48 (m, ArH, 8H), 4.85 (s, ArCH, 2H), 3.16 (s, CH, 2H)
$^{19}$F-NMR (DMSO, 376 MHz): δ (ppm)=−103.9

Resist Composition Preparation 1c

Examples 1c to 14c, and Comparative Examples 1c to 8c

Components shown in Tables 11 to 13 were mixed and dissolved to prepare resist compositions of respective examples.

TABLE 11

| | | Compound (B) | | | |
|---|---|---|---|---|---|
| | Compound (A) | Compound (B1c) | Compound (B2c) | Compound (D) | Compound (S) |
| Comparative Example 1c | (A)-1c [100] | — | (B2c)-7 [18.5] | (D2c)-1 [3-8] | (S)-1c [6400] |
| Example 1c | (A)-1c [100] | (B1c)-1 [20.4] | — | (D2c)-1 [3.8] | (S)-1c [6400] |
| Example 2c | (A)-1c [100] | (B1c)-2 [26.8] | — | (D2c)-1 [3.8] | (S)-1c [6400] |
| Example 3c | (A)-1c [100] | (B1c)-3 [20.5] | — | (D2c)-1 [3.8] | (S)-1c [6400] |
| Comparative Example 2c | (A)-2c [100] | — | (B2c)-1 [20.5] | (D2c)-1 [3.8] | (S)-1c [6400] |
| Comparative Example 3c | (A)-2c [100] | — | (B2c)-2 [17.7] | (D2c)-1 [3.8] | (S)-1c [6400] |
| Example 4c | (A)-2c [100] | (B1c)-4 [21.5] | — | (D2c)-1 [3.8] | (S)-1c [6400] |
| Example 5c | (A)-2c [100] | (B1c)-5 [26.6] | — | (D2c)-1 [3.8] | (S)-1c [6400] |
| Example 6c | (A)-2c [100] | (B1c)-6 [21.9] | — | (D2c)-1 [3.8] | (S)-1c [6400] |
| Comparative Example 4c | (A)-3c [100] | — | (B2c)-5 [16.3] | (D2c)-2 [4.5] | (S)-1c [6400] |
| Example 7c | (A)-3c [100] | (B1c)-7 [16.4] | — | (D2c)-2 [4.5] | (S)-1c [6400] |
| Example 8c | (A)-3c [100] | (B1c)-8 [16.9] | — | (D2c)-2 [4.5] | (S)-1c [6400] |

TABLE 12

| | | Compound (B) | | Compound (D) | | |
|---|---|---|---|---|---|---|
| | Compound (A) | Compound (B1c) | Compound (B2c) | Compound (D1c) | Compound (D2c) | Compound (S) |
| Comparative Example 5c | (A)-4c [100] | — | (B2c)-3 [17.4] | — | (D2c)-3 [4.1] | (S)-1c [6400] |
| Comparative Example 6c | (A)-4c [100] | — | (B2c)-3 [17.4] | — | (D2c)-4 [5.3] | (S)-1c [6400] |
| Example 9c | (A)-4c [100] | — | (B2c)-3 [17.4] | (D1c)-1 [5.5] | — | (S)-1c [6400] |
| Example 10c | (A)-4c [100] | (B1c)-1 [20.4] | — | (D1c)-1 [5.5] | — | (S)-1c [6400] |

TABLE 13

| | Compound (A) | Compound (B) | | Compound (D) | Compound (S) |
|---|---|---|---|---|---|
| | | Compound (B1c) | Compound (B2c) | | |
| Comparative Example 7c | (A)-5c [100] | — | (B2c)-4 [18.8] | (D2c)-1 [3-8] | (S)-1c [6400] |
| Comparative Example 8c | (A)-5c [100] | — | (B2c)-6 [19.0] | (D2c)-1 [3.8] | (S)-1c [6400] |
| Example 11c | (A)-5c [100] | (B1c)-9 [21.0] | — | (D2c)-1 [3.8] | (S)-1c [6400] |
| Example 12c | (A)-5c [100] | (B1c)-10 [25.3] | — | (D2c)-1 [3.8] | (S)-1c [6400] |
| Example 13c | (A)-5c [100] | (B1c)-11 [18.6] | — | (D2c)-1 [3.8] | (S)-1c [6400] |
| Example 14c | (A)-5c [100] | (B1c)-12 [21.4] | — | (D2c)-1 [3.8] | (S)-1c [6400] |

In Tables 11 to 13, respective abbreviations have the following meanings. The values in brackets [ ] indicate the amount (in terms of parts by mass) of the component added.

(A)-1c: A high-molecular-weight compound represented by the following chemical formula (A1)-1c. The high-molecular-weight compound (A1)-1c was obtained by performing radical polymerization using monomers deriving structural units constituting the high-molecular-weight compound in a predetermined molar ratio. Regarding the high-molecular-weight compound (A1)-1c, a weight average molecular weight (Mw) in terms of polystyrene standards obtained through GPC measurement was 7,700, and a molecular weight dispersity (Mw/Mn) was 1.72. The composition of the copolymer (ratio (molar ratio) of the respective structural units within the structural formula) as determined by $^{13}$C-NMR was l/m/n=30/60/10.

(A)-2c: A high-molecular-weight compound represented by the following chemical formula (A1)-2c. The high-molecular-weight compound (A1)-2c was obtained by performing radical polymerization using monomers deriving structural units constituting the high-molecular-weight compound in a predetermined molar ratio. Regarding the high-molecular-weight compound (A1)-2c, a weight average molecular weight (Mw) in terms of polystyrene standards obtained through GPC measurement was 6,400, and a molecular weight dispersity (Mw/Mn) was 1.66. A copolymer composition ratio (ratio (molar ratio) of structural units in the structural formula) obtained through $^{13}$C-NMR was l/m=60/40.

(A)-3c: A high-molecular-weight compound represented by the following chemical formula (A1)-3c. The high-molecular-weight compound (A1)-3c was obtained by performing radical polymerization using monomers deriving structural units constituting the high-molecular-weight compound in a predetermined molar ratio. Regarding the high-molecular-weight compound (A1)-3c, a weight average molecular weight (Mw) in terms of polystyrene standards obtained through GPC measurement was 6,900, and a molecular weight dispersity (Mw/Mn) was 1.72. The composition of the copolymer (ratio (molar ratio) of the respective structural units within the structural formula) as determined by $^{13}$C-NMR was l/m/n=30/60/10.

[Chem. 201]

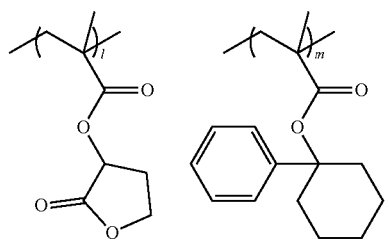

(A1)-1c

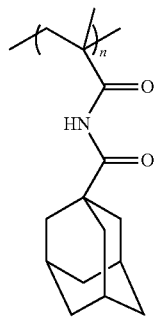

(A1)-2c

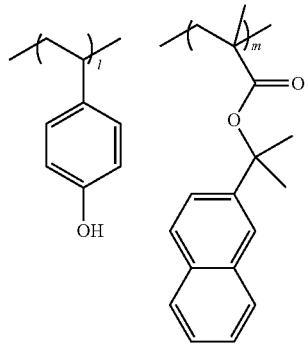

-continued (A1)-3c

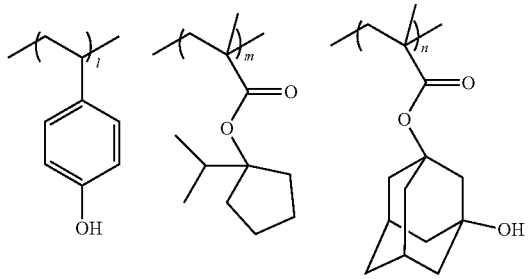

(A)-4c: A high-molecular-weight compound represented by the following chemical formula (A1)-4c. The high-molecular-weight compound (A1)-4c was obtained by performing radical polymerization using monomers deriving structural units constituting the high-molecular-weight compound in a predetermined molar ratio. Regarding the high-molecular-weight compound (A1)-4c, a weight average molecular weight (Mw) in terms of polystyrene standards obtained through GPC measurement was 7,200, and a molecular weight dispersity (Mw/Mn) was 1.69. The composition of the copolymer (ratio (molar ratio) of the respective structural units within the structural formula) as determined by $^{13}$C-NMR was l/m=50/50.

(A)-5c: A high-molecular-weight compound represented by the following chemical formula (A1)-5c. The high-molecular-weight compound (A1)-5c was obtained by performing radical polymerization using monomers deriving structural units constituting the high-molecular-weight compound in a predetermined molar ratio. Regarding the high-molecular-weight compound (A1)-5c, a weight average molecular weight (Mw) in terms of polystyrene standards obtained through GPC measurement was 7,300, and a molecular weight dispersity (Mw/Mn) was 1.75. A copolymer composition ratio (ratio (molar ratio) of structural units in the structural formula) obtained through $^{13}$C-NMR was l/m=30/70.

[Chem. 202]

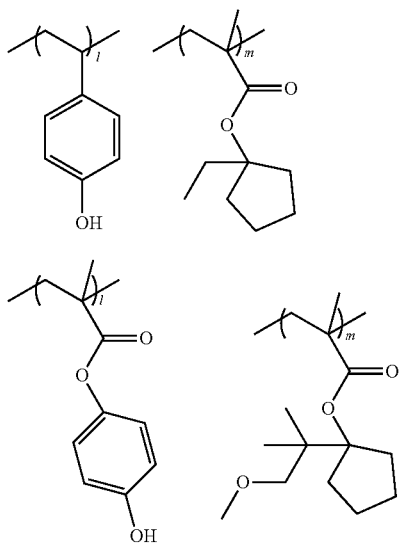

(A1)-4c (A1)-5c (B1c)-1 to (B1c)-12: respective acid generators including the above compound (B1c-1) to compound (B1c-12)

(B2c)-1: acid generator including the following compound (B2c-1).

(B2c)-2: acid generator including the following compound (B2c-2).

(B2c)-3: acid generator including the following compound (B2c-3).

(B2c)-4: acid generator including the following compound (B2c-4).

(B2c)-5: acid generator including the following compound (B2c-5).

(B2c)-6: acid generator including the following compound (B2c-6).

(B2c)-7: acid generator including the following compound (B2c-7).

[Chem. 203]

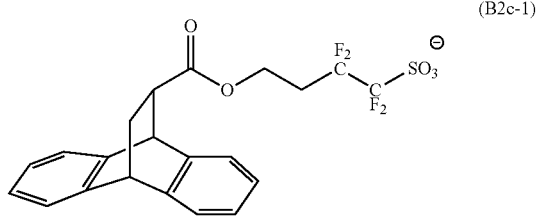

(B2c-1)

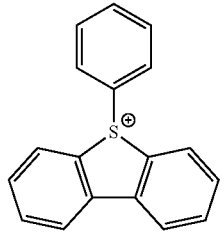

(B2c-2)

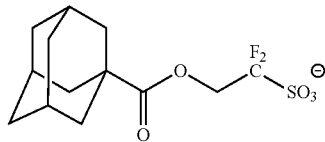

(B2c-3)

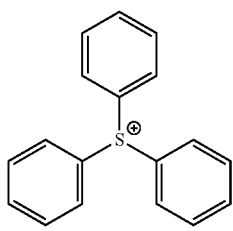

(B2c-4)

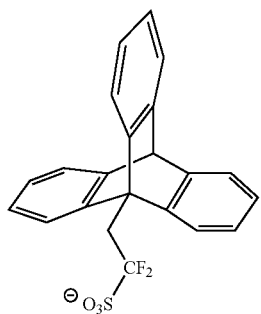

(B2c-5)

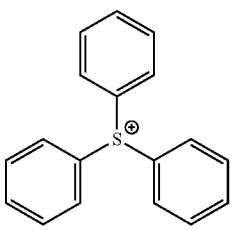

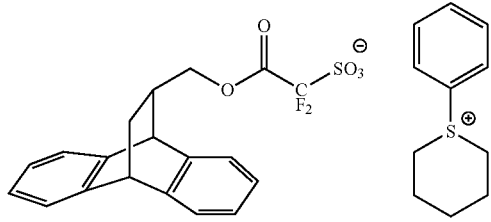

(B2c-6)

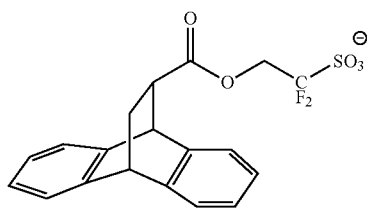

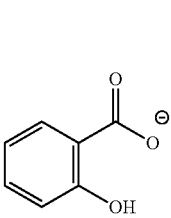

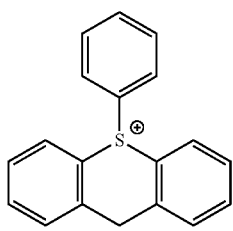

(B2c-7)

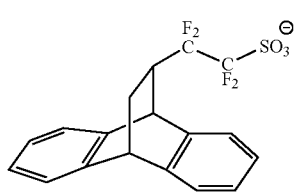

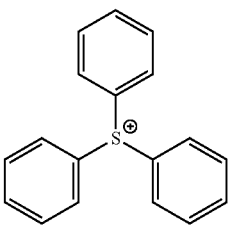

(D2c)-1: acid diffusion control agent including a compound represented by the following chemical formula (D2c-1).

(D2c)-2: acid diffusion control agent including a compound represented by the following chemical formula (D2c-2).

(D2c)-3: acid diffusion control agent including a compound represented by the following chemical formula (D2c-3).

(D2c)-4: acid diffusion control agent including a compound represented by the following chemical formula (D2c-4).

(D1c)-1: acid diffusion control agent including a compound represented by the following chemical formula (D1c-1).

(S)-1c: a solvent in which propylene glycol monomethyl ether acetate/propylene glycol monomethyl ether=60/40 (mass ratio) were mixed.

[Chem. 204]

(D2c-1)

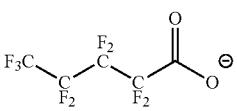 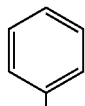

(D2c-2)

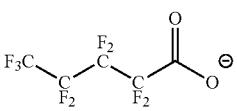 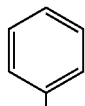

(D2c-3)

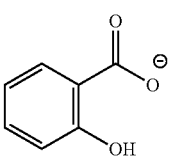 

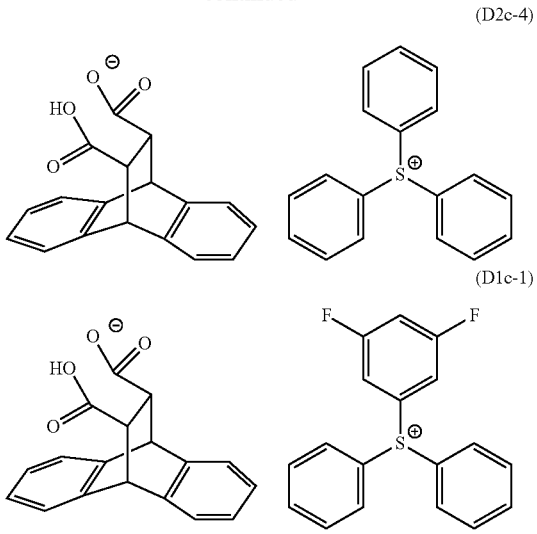

<Resist Pattern Formation 1c>

Each of the resist compositions of examples and comparative examples was applied to an 8-inch silicon substrate which had been treated with hexamethyldisilazane (HMDS) using a spinner, and was then prebaked (PAB) on a hot plate at 110° C. for 60 seconds and dried, thereby forming a resist film having a film thickness of 50 nm.

Next, drawing (exposure) was performed on the resist film using an electron beam lithography system JEOL-JBX-9300FS (commercially available from JEOL. Ltd.) at an acceleration voltage of 100 kV to obtain a 1:1 line and space pattern (hereinafter referred to as an "LS pattern") with a target size of a line width of 50 nm. Then, a post exposure bake (PEB) treatment was conducted at 100° C. for 60 seconds.

Thereafter, alkali developing was conducted for 60 seconds at 23° C. in a 2.38% by weight aqueous solution of tetramethylammonium hydroxide (TMAH) (product name: NMD-3; manufactured by Tokyo Ohka Kogyo Co., Ltd.).

Then, water rinsing was conducted for 15 seconds using pure water.

As a result, a 1:1 LS pattern with a line width of 50 nm was formed.

[Evaluation of Optimum Exposure Dose (Eop)]

An optimal exposure amount Eop ($\mu C/cm^2$) at which an LS pattern with a target size was formed according to the above "resist pattern formation method 1c" was obtained. This is shown as "Eop ($\mu C/cm^2$)" in Tables 14 to 16.

[Evaluation of Line Width Roughness (LWR)]

3σ which is a scale showing LWR was obtained from the LS pattern formed in the above "resist pattern formation 1c." This is shown as "LWR (nm)" in Tables 14 to 16.

"3σ" indicates a value of 3 times the standard deviation (σ) (i.e., 3σ) (unit: nm) determined by measuring the line positions at 400 points in the lengthwise direction of the line using a scanning electron microscope (product name: S-9380, manufactured by Hitachi High-Technologies Corporation; acceleration voltage: 800 V).

The smaller this 3σ value is, the lower the level of roughness on the side walls of the line, indicating that an LS pattern with a uniform width was obtained.

TABLE 14

| | PAB (° C.) | PEB (° C.) | Eop ($\mu C/cm^2$) | LWR (nm) |
|---|---|---|---|---|
| Comparative Example 1c | 110 | 100 | 145 | 5.6 |
| Example 1c | 110 | 100 | 125 | 4.9 |
| Example 2c | 110 | 100 | 105 | 5.4 |
| Example 3c | 110 | 100 | 110 | 5.1 |
| Comparative Example 2c | 110 | 100 | 95 | 5.5 |
| Comparative Example 3c | 110 | 100 | 80 | 6.4 |
| Example 4c | 110 | 100 | 85 | 5.0 |
| Example 5c | 110 | 100 | 90 | 5.3 |
| Example 6c | 110 | 100 | 85 | 4.8 |
| Comparative Example 4c | 110 | 100 | 130 | 5.8 |
| Example 7c | 110 | 100 | 120 | 5.8 |
| Example 8c | 110 | 100 | 100 | 5.3 |

TABLE 15

| | PAB (° C.) | PEB (° C.) | Eop ($\mu C/cm^2$) | LWR (nm) |
|---|---|---|---|---|
| Comparative Example 5c | 110 | 100 | 110 | 6.3 |
| Comparative Example 6c | 110 | 100 | 120 | 5.9 |
| Example 9c | 110 | 100 | 105 | 5.6 |
| Example 10c | 110 | 100 | 80 | 4.6 |

TABLE 16

| | PAB (° C.) | PEB (° C.) | Eop ($\mu C/cm^2$) | LWR (nm) |
|---|---|---|---|---|
| Comparative Example 7c | 110 | 100 | 105 | 5.4 |
| Comparative Example 8c | 110 | 100 | 115 | 5.8 |
| Example 11c | 110 | 100 | 95 | 5.7 |
| Example 12c | 110 | 100 | 75 | 5.3 |
| Example 13c | 110 | 100 | 70 | 5.4 |
| Example 14c | 110 | 100 | 75 | 5.1 |

Based on the results shown in Tables 14 to 16, it was confirmed that, according to the resist compositions of the examples, in the formation of the resist pattern, high sensitivity was achieved, and a resist pattern having a favorable shape with reduced roughness was formed.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates an acid upon exposure and exhibits a changed solubility in a developing solution under the action of acid, the resist composition comprising:

a base component (A) that exhibits a changed solubility in a developing solution under the action of acid; and a compound (BD1-1) having an anion moiety and a cation moiety and which is represented by the following general formula (bd1-1):

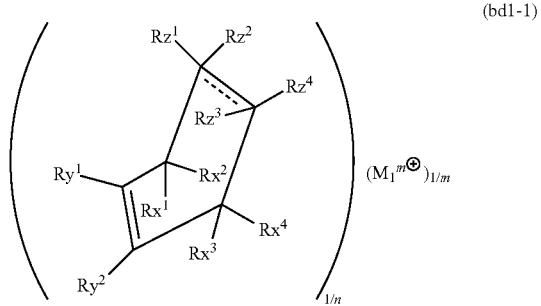

(bd1-1)

wherein $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

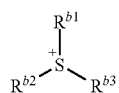

represents a double bond or a single bond; $Rz^1$ to $Rz^4$ each independently represent, where valence allows, a hydrogen atom or a hydrocarbon group which may have a substituent, provided that two or more of $Rz^1$ to $Rz^4$ are mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_1^{m+}$ is a cation represented by general formula (ca-0) shown below:

(ca-0)

$$\underset{R^{b2}}{\overset{R^{b1}}{\underset{|}{\overset{|}{S^+}}}}R^{b3}$$

wherein $R^{b1}$ represents an aryl group which may have a substituent; $R^{b2}$ and $R^{b3}$ each independently represent an aryl group which may have a substituent or an alkyl group which may have a substituent; $R^{b2}$ and $R^{b3}$ may be mutually bonded to form a ring with the sulfur atom; provided that at least one of $R^{b1}$ to $R^{b3}$ has a substituent containing a sulfonyl group.

2. The resist composition according to claim 1, wherein at least one of $Rx^1$ to $Rx^2$ and at least one of $Rx^3$ to $Rx^4$ are mutually bonded to form a ring structure.

3. The resist composition according to claim 1, wherein the anion moiety in the compound (BD1-1) is an anion represented by the following general formula (bd1-an1):

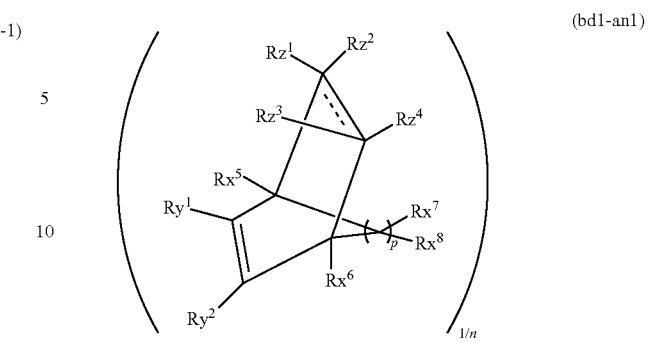

(bd1-an1)

wherein $Rx^5$ and $Rx^6$ each independently represent a hydrocarbon group or a hydrogen atom which may have a substituent; $Rx^7$ and $Rx^8$ each independently represent a hydrocarbon group or a hydrogen atom which may have a substituent, or alternatively, may be mutually bonded to form a ring structure; p is 1 or 2, and when p=2, a plurality of $Rx^7$ and $Rx^8$ may be different from each other; and $Ry^1$ and $Ry^2$ each independently represent a hydrocarbon group or a hydrogen atom which may have a substituent or may be mutually bonded to form a ring structure;

represents a double bond or a single bond; $Rz^1$ to $Rz^4$ each independently represent, where valence allows, a hydrogen atom or a hydrocarbon group which may have a substituent, provided that two or more of $Rz^1$ to $Rz^4$ are mutually bonded to form a ring structure; provided that at least one of $Rx^5$ to $Rx^8$, $Ry^1$, $Ry^2$ and $Rz^1$ to $Rz^4$ has an anion group, and the anion moiety as a whole forms an anion having a valency of n; n represents an integer of 1 or more.

4. The resist composition according to claim 3, wherein the anion moiety in the compound (BD1-1) is an anion represented by the following general formula (bd1-an2):

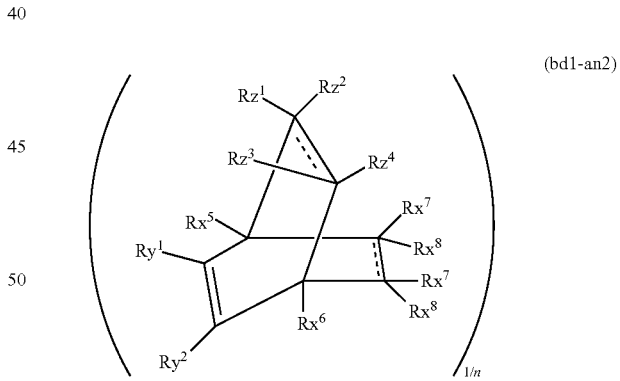

(bd1-an2)

wherein $Rx^5$ and $Rx^6$ each independently represent a hydrocarbon group or a hydrogen atom which may have a substituent; a plurality of $Rx^7$ and $Rx^8$ each independently represent a hydrocarbon group or a hydrogen atom which may have a substituent or two or more thereof may be mutually bonded to form a ring structure; and $Ry^1$ and $Ry^2$ each independently represent a hydrocarbon group or a hydrogen atom which may have a substituent or may be mutually bonded to form a ring structure;

represents a double bond or a single bond; $Rz^1$ to $Rz^4$ each independently represent, where valence allows, a hydrogen atom or a hydrocarbon group which may have a substituent, provided that two or more of $Rz^1$ to $Rz^4$ are mutually bonded to form a ring structure; provided that at least one of $Rx^5$ to $Rx^8$, $Ry^1$, $Ry^2$ and $Rz^1$ to $Rz^4$ has an anion group, and the entire anion moiety may be an n-valent anion; and n represents an integer of 1 or more.

5. The resist composition according to claim 3,
    wherein $Rx^7$ to $Rx^8$ are mutually bonded to form a ring structure.

6. The resist composition according to claim 3,
    wherein at least one of $Rx^5$ and $Rx^6$ has an anion group.

7. The resist composition according to claim 1,
    wherein $Ry^1$ to $Ry^2$ are mutually bonded to form a ring structure.

8. The resist composition according to claim 1,
    wherein at least one of $Rz^1$ to $Rz^4$ has an anion group.

9. The resist composition according to claim 1,
    wherein the sulfonyl group that a cation represented by the general formula (ca-0) has is a bivalent sulfonyl group in which one carbon atom of a ring formed of $R^{b2}$ to $R^{b3}$ that are mutually bonded to form a ring together with a sulfur atom in the formula is substituted.

10. The resist composition according to claim 1,
    wherein the sulfonyl group that a cation represented by the general formula (ca-0) has is a monovalent group represented by $-SO_2-R^{b4}$, wherein $R^{b4}$ is a linear or branched linear alkyl group which may have a substituent, an alicyclic hydrocarbon group which may have a substituent or an aromatic hydrocarbon group which may have a substituent.

11. The resist composition according to claim 1,
    wherein the compound (BD1-1) has only one anionic group,
    wherein $Rx^1$ to $Rx^4$, $Ry^1$ and $Ry^2$ and $Rz^1$ to $Rz^4$ have only one anionic group, and the whole anion moiety is a monovalent anion; n represents an integer of 1; m represents an integer of 1; and $M^{m+}$ represents a monovalent organic cation.

12. A method of forming a resist pattern, comprising:
    forming a resist film on a support using the resist composition according to claim 1;
    exposing the resist film; and
    developing the exposed resist film to form a resist pattern.

13. The method of forming a resist pattern according to claim 12,
    wherein the resist film is exposed with extreme ultraviolet (EUV) or an electron beam (EB).

14. A resist composition which generates an acid upon exposure and exhibits changed solubility in a developing solution under the action of acid, the resist composition comprising:
    a compound having an anion moiety and a cation moiety (BD1-2) and which is represented by the following general formula (bd1-2); and
    a base component (A) that exhibits a changed solubility in a developing solution under the action of acid:

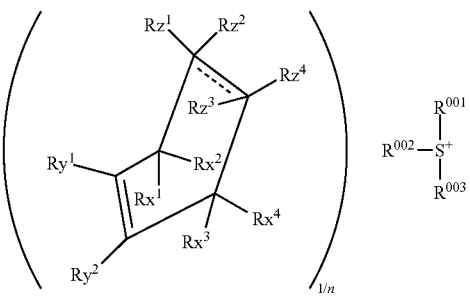

(bd1-2)

wherein $R^{001}$ to $R^{003}$ each independently represent a monovalent organic group; provided that at least one of $R^{001}$ to $R^{003}$ represents an organic group having an acid dissociable group which has a cyclic structure; and two or more of $R^{001}$ to $R^{003}$ may be mutually bonded to form a ring with the sulfur atom; $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

===== represents a double bond or a single bond; $Rz^1$ to $Rz^4$ each independently represent, where valence allows, a hydrogen atom or a hydrocarbon group which may have a substituent, or two or more of $R^{b2}$ and $R^{b3}$ may be mutually bonded to form a ring structure; provided that at least one of $Rz^1$ to $Rz^4$ has an anion group, and the anion moiety as a whole forms an anion having a valency of n; and n represents an integer of 1 or more.

15. The resist composition according to claim 14,
    wherein the acid dissociable group has a tertiary alkyl ester structure having 5 or more carbon atoms.

16. The resist composition according to claim 14,
    wherein the compound (BD1-2) has only one anionic group,
    wherein $Rx^1$ to $Rx^4$, $Ry^1$ and $Ry^2$ and $Rz^1$ to $Rz^4$ have only one anionic group, and the whole anion moiety is a monovalent anion; n represents an integer of 1; m represents an integer of 1; and $M^{m+}$ represents a monovalent organic cation.

17. A method of forming a resist pattern, comprising:
    forming a resist film on a support using the resist composition according to claim 14;
    exposing the resist film; and
    developing the exposed resist film to form a resist pattern.

18. The method of forming a resist pattern according to claim 17,
    wherein the resist film is exposed with extreme ultraviolet (EUV) or an electron beam (EB).

19. A compound having an anion moiety and a cation moiety and which is represented by the following general formula (bd1-2):

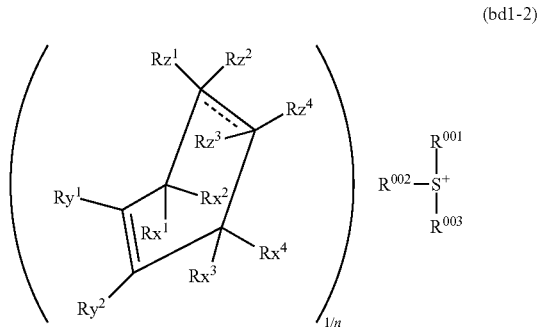

(bd1-2)

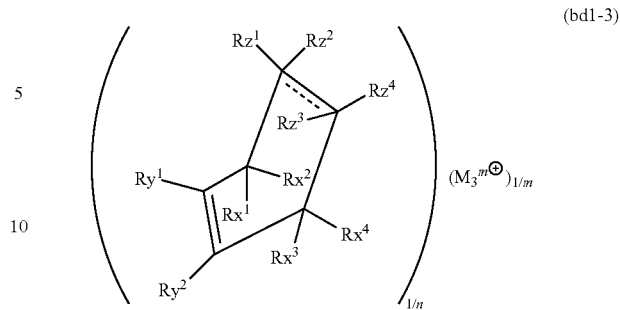

(bd1-3)

wherein $R^{001}$ to $R^{003}$ each independently represent a monovalent organic group; provided that at least one of $R^{001}$ to $R^{003}$ represents an organic group having an acid dissociable group which has a cyclic structure; and two or more of $R^{001}$ to $R^{003}$ may be mutually bonded to form a ring with the sulfur atom; $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

===== represents a double bond or a single bond; $Rz^1$ to $Rz^4$ each independently represent, where valence allows, a hydrogen atom or a hydrocarbon group which may have a substituent, or two or more of $Rz^1$ to $Rz^4$ may be mutually bonded to form a ring structure; provided that at least one of $Rz^1$ to $Rz^4$ has an anion group, and the anion moiety as a whole forms an anion having a valency of n; and n represents an integer of 1 or more.

20. The compound according to claim 19,
wherein the compound has only one anionic group,
wherein $Rx^1$ to $Rx^4$, $Ry^1$ and $Ry^2$ and $Rz^1$ to $Rz^4$ have only one anionic group, and the whole anion moiety is a monovalent anion; n represents an integer of 1; m represents an integer of 1; and $M^{m+}$ represents a monovalent organic cation.

21. An acid generator including the compound according to claim 19.

22. A resist composition which generates an acid upon exposure and exhibits a changed solubility in a developing solution under the action of acid, the resist composition comprising:

a base component (A) that exhibits a changed solubility in a developing solution under the action of acid; and a compound having an anion moiety and a cation moiety (BD1-3) and which is represented by the following general formula (bd1-3):

wherein $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure;

===== represents a double bond or a single bond; $Rz^1$ to $Rz^4$ each independently represent, where valence allows, a hydrogen atom or a hydrocarbon group which may have a substituent, provided that two or more of $Rz^1$ to $Rz^4$ are mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_3^{m+}$ represents an m-valent organic cation having an electron-withdrawing group.

23. The resist composition according to claim 22,
wherein the cation moiety in the compound (BD1-3) is a cation represented by any of the following general formulae (ca0-1) to (ca0-4):

(ca0-1)

(ca0-2)

(ca0-3)

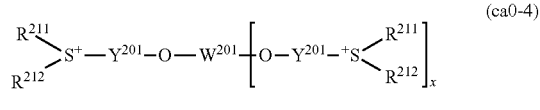

(ca0-4)

wherein $R^{201}$ to $R^{207}$ and $R^{211}$ to $R^{212}$ each independently represent an aryl group which may have a substituent, an alkyl group which may have a substituent, or an alkenyl group which may have a substituent; $R^{201}$ to $R^{203}$, $R^{206}$ to $R^{207}$, $R^{211}$ to $R^{212}$ may be mutually bonded to form a ring together with a sulfur atom in the formula; $R^{208}$ to $R^{209}$ each independently represent a hydrogen atom or an alkyl group having 1 to 5 carbon atoms or may be mutually bonded to form a ring together with a sulfur atom in the formula; $R^{210}$ represents an aryl group which may have a substituent, an alkyl group which may have a substituent, an alkenyl group which may have a substituent, or a —SO$_2$— containing cyclic group which may have a substituent; provided that at least one of one of R$^{201}$ to R$^{203}$, at least one of R$^{204}$ and R$^{205}$, at least one of R$^{206}$ and R$^{207}$, and at least one of R$^{211}$ and R$^{212}$ have an electron-withdrawing group as a substituent; L$^{201}$ represents —C(=O)— or —C(=O)—O—; a plurality of Y$^{201}$'s each independently represent an arylene group, an alkylene group or an alkenylene group; x is 1 or 2; and W$^{201}$ represents an (x+1)-valent linking group.

24. The resist composition according to claim 22, wherein the electron-withdrawing group is a halogen atom or a halogenated alkyl group.

25. The resist composition according to claim 22, wherein at least one of Rx$^1$ to Rx$^2$ and at least one of Rx$^3$ to Rx$^4$ are mutually bonded to form a ring structure.

26. The resist composition according to claim 22, wherein the anion moiety in the compound (BD1-3) is an anion represented by the following general formula (bd1-an1):

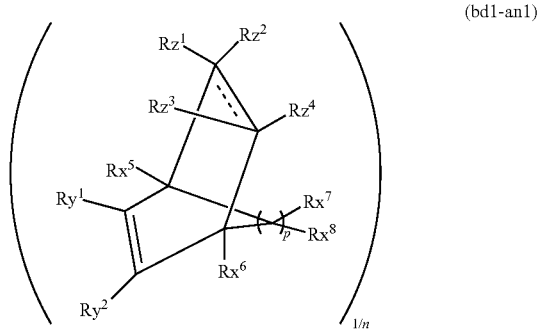

(bd1-an1)

wherein Rx$^5$ to Rx$^6$ each independently represent a hydrocarbon group or a hydrogen atom which may have a substituent; Rx$^7$ to Rx$^8$ each independently represent a hydrocarbon group or a hydrogen atom which may have a substituent, or alternatively, may be mutually bonded to form a ring structure; p is 1 or 2, and when p=2, a plurality of Rx$^7$ to Rx$^8$ may be different from each other; and Ry$^1$ to Ry$^2$ each independently represent a hydrocarbon group or a hydrogen atom which may have a substituent or may be mutually bonded to form a ring structure;

═══ represents a double bond or a single bond; Rz$^1$ to Rz$^4$ each independently represent, where valence allows, a hydrogen atom or a hydrocarbon group which may have a substituent, provided that two or more of Rz$^1$ to Rz$^4$ are mutually bonded to form a ring structure; provided that at least one of Rx$^5$ to Rx$^8$, Ry$^1$, Ry$^2$ and Rz$^1$ to Rz$^4$ has an anion group, the entire anion moiety may be an n-valent anion; and n represents an integer of 1 or more.

27. The resist composition according to claim 26, wherein the anion moiety in the compound (BD1-3) is an anion represented by the following general formula (bd1-an2):

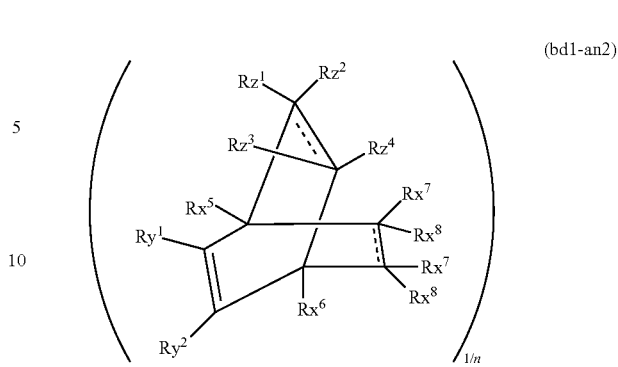

(bd1-an2)

wherein Rx$^5$ to Rx$^6$ each independently represent a hydrocarbon group or a hydrogen atom which may have a substituent; a plurality of Rx$^7$ to Rx$^8$ each independently represent a hydrocarbon group or a hydrogen atom which may have a substituent or two or more thereof may be mutually bonded to form a ring structure; and Ry$^1$ and Ry$^2$ each independently represent a hydrocarbon group or a hydrogen atom which may have a substituent or may be mutually bonded to form a ring structure;

═══ represents a double bond or a single bond; Rz$^1$ to Rz$^4$ each independently represent, where valence allows, a hydrogen atom or a hydrocarbon group which may have a substituent, provided that two or more of Rz$^1$ to Rz$^4$ are mutually bonded to form a ring structure; provided that at least one of Rx$^5$ to Rx$^8$, Ry$^1$, Ry$^2$ and Rz$^1$ to Rz$^4$ has an anion group, the entire anion moiety may be an n-valent anion; and n represents an integer of 1 or more.

28. The resist composition according to claim 26, wherein Rx$^7$ and Rx$^8$ are mutually bonded to form a ring structure.

29. The resist composition according to claim 26, wherein at least one of Rx$^5$ and Rx$^6$ has an anion group.

30. The resist composition according to claim 22, wherein Ry$^1$ and Ry$^2$ are mutually bonded to form a ring structure.

31. The resist composition according to claim 22, wherein at least one of Rz$^1$ to Rz$^4$ has an anion group.

32. The resist composition according to claim 22, wherein the compound (BD1-3) has only one anionic group, wherein Rx$^1$ to Rx$^4$, Ry$^1$ and Ry$^2$ and Rz$^1$ to Rz$^4$ have only one anionic group, and the whole anion moiety is a monovalent anion; n represents an integer of 1; m represents an integer of 1; and M$^{m+}$ represents a monovalent organic cation.

33. A method of forming a resist pattern, comprising:
forming a resist film on a support using the resist composition according to claim 22;
exposing the resist film; and
developing the exposed resist film to form a resist pattern.

34. The method of forming a resist pattern according to claim 33, wherein the resist film is exposed with extreme ultraviolet (EUV) or an electron beam (EB).

35. A compound having an anion moiety and a cation moiety and which is represented by the following general formula (bd1-3):

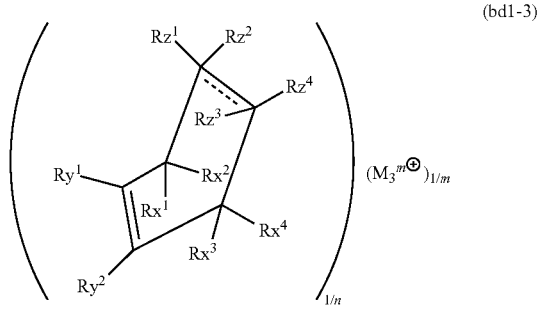

(bd1-3)

wherein $Rx^1$ to $Rx^4$ each independently represent a hydrogen atom or a hydrocarbon group which may have a substituent, or two or more of $Rx^1$ to $Rx^4$ may be mutually bonded to form a ring structure; $Ry^1$ and $Ry^2$ each independently represent a hydrogen atom or a hydrocarbon group which may have a substituent, or $Ry^1$ and $Ry^2$ may be mutually bonded to form a ring structure; ----- represents a double bond or a single bond; $Rz^1$ to $Rz^4$ each independently represent, where valence allows, a hydrogen atom or a hydrocarbon group which may have a substituent, provided that two or more of $Rz^1$ to $Rz^4$ are mutually bonded to form a ring structure; provided that at least one of $Rx^1$ to $Rx^4$, $Ry^1$, $Ry^2$ and $Rz^1$ to $Rz^4$ has an anion group, and the anion moiety as a whole forms an anion having a valency of n; n represents an integer of 1 or more; m represents an integer of 1 or more; and $M_3^{m+}$ represents an m-valent organic cation having an electron-withdrawing group.

36. The compound according to claim 35, wherein the compound has only one anionic group, wherein $Rx^1$ to $Rx^4$, $Ry^1$ and $Ry^2$ and $Rz^1$ to $Rz^4$ have only one anionic group, and the whole anion moiety is a monovalent anion; n represents an integer of 1; m represents an integer of 1; and $M^{m+}$ represents a monovalent organic cation.

37. An acid generator including the compound according to claim 35.

* * * * *